(12) United States Patent
Ingber et al.

(10) Patent No.: US 10,526,399 B2
(45) Date of Patent: *Jan. 7, 2020

(54) ENGINEERED MICROBE-TARGETING MOLECULES AND USES THEREOF

(71) Applicant: PRESIDENT AND FELLOWS OF HARVARD COLLEGE, Cambridge, MA (US)

(72) Inventors: Donald E. Ingber, Boston, MA (US); Michael Super, Lexington, MA (US); Jeffrey Charles Way, Cambridge, MA (US); Mark J. Cartwright, West Newton, MA (US); Julia B. Berthet, Brookline, MA (US); Dinah R. Super, Lexington, MA (US); Martin Rottman, Cambridge, MA (US); Alexander L. Watters, Melrose, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/415,352

(22) Filed: Jan. 25, 2017

(65) Prior Publication Data

US 2017/0362307 A1 Dec. 21, 2017

Related U.S. Application Data

(63) Continuation of application No. 14/233,553, filed as application No. PCT/US2012/047201 on Jul. 18, 2012, now Pat. No. 9,593,160.

(60) Provisional application No. 61/605,052, filed on Feb. 29, 2012, provisional application No. 61/605,081, filed on Feb. 29, 2012, provisional application No. 61/508,957, filed on Jul. 18, 2011.

(51) Int. Cl.

| | | |
|---|---|---|
| *C07K 16/12* | (2006.01) | |
| *G01N 33/543* | (2006.01) | |
| *G01N 33/569* | (2006.01) | |
| *C07K 14/42* | (2006.01) | |
| *A61K 47/68* | (2017.01) | |

(52) U.S. Cl.
CPC ............ *C07K 16/12* (2013.01); *A61K 47/68* (2017.08); *A61K 47/6815* (2017.08); *C07K 14/42* (2013.01); *G01N 33/54353* (2013.01); *G01N 33/56911* (2013.01); *G01N 33/56916* (2013.01); *G01N 33/56938* (2013.01); *G01N 33/56961* (2013.01); *C07K 2319/33* (2013.01); *G01N 2333/42* (2013.01); *G01N 2333/4724* (2013.01); *Y02A 50/53* (2018.01); *Y02A 50/58* (2018.01)

(58) Field of Classification Search
CPC ........ A61K 47/68; C07K 14/42; C07K 16/12; C07K 2319/33
See application file for complete search history.

(56) References Cited

U.S. PATENT DOCUMENTS

| | | |
|---|---|---|
| 4,425,330 A | 1/1984 | Norcross et al. |
| 5,137,810 A | 8/1992 | Sizemore et al. |
| 5,270,199 A | 12/1993 | Ezekowitz |
| 5,273,884 A | 12/1993 | Gale et al. |
| 5,405,832 A | 4/1995 | Potempa |
| 5,474,904 A | 12/1995 | Potempa et al. |
| 5,545,820 A | 8/1996 | Gatehouse et al. |
| 5,585,349 A | 12/1996 | Potempa |
| 5,783,179 A | 7/1998 | Nestor, Jr. et al. |
| 5,874,238 A | 2/1999 | Potempa et al. |
| 5,951,976 A | 9/1999 | Segal |
| 6,057,295 A | 5/2000 | Caretto et al. |
| 6,117,977 A | 9/2000 | Lasky et al. |
| 6,225,046 B1 | 5/2001 | Vesey et al. |
| 6,376,473 B1 | 4/2002 | Audonnet et al. |

(Continued)

FOREIGN PATENT DOCUMENTS

| | | |
|---|---|---|
| EP | 0375736 B1 | 7/1990 |
| EP | 0861667 A2 | 9/1998 |

(Continued)

OTHER PUBLICATIONS

Cooper., "A generic pathogen caputre technology for sepsis diagnosis", retrieved from http://hdl.handle.net/1721.1/83966 (2013).

(Continued)

*Primary Examiner* — Karen Cochrane Carlson
(74) *Attorney, Agent, or Firm* — Nixon Peabody LLP; David S. Resnick; Nicole D. Kling

(57) ABSTRACT

Described herein are engineered microbe-targeting or microbe-binding molecules, kits comprising the same and uses thereof. Some particular embodiments of the microbe-targeting or microbe-binding molecules comprise a carbohydrate recognition domain of mannose-binding lectin, or a fragment thereof, linked to a portion of a Fc region. In some embodiments, the microbe-targeting molecules or microbe-binding molecules can be conjugated to a substrate, e.g., a magnetic microbead, forming a microbe-targeting substrate (e.g., a microbe-targeting magnetic microbead). Such microbe-targeting molecules and/or substrates and the kits comprising the same can bind and/or capture of a microbe and/or microbial matter thereof, and can thus be used in various applications, e.g., diagnosis and/or treatment of an infection caused by microbes such as sepsis in a subject or any environmental surface. Microbe-targeting molecules and/or substrates can be regenerated after use by washing with a low pH buffer or buffer in which calcium is insoluble.

6 Claims, 40 Drawing Sheets

Specification includes a Sequence Listing.

(56) References Cited

U.S. PATENT DOCUMENTS

| | | |
|---|---|---|
| 6,471,968 B1 | 10/2002 | Baker et al. |
| 6,503,761 B1 | 1/2003 | Koenig et al. |
| 6,528,618 B1 | 3/2003 | Fridkin et al. |
| 6,528,624 B1 | 3/2003 | Idusogie et al. |
| 6,562,784 B1 | 5/2003 | Thiel et al. |
| 6,703,219 B1 | 3/2004 | Potempa et al. |
| 6,733,753 B2 | 5/2004 | Boone et al. |
| 6,846,649 B1 | 1/2005 | Thiel et al. |
| 6,900,292 B2 | 5/2005 | Sun et al. |
| 7,182,945 B2 | 2/2007 | Fridkin et al. |
| 7,202,207 B2 | 4/2007 | Thiel et al. |
| 7,211,396 B2 | 5/2007 | Uttenthal |
| 7,226,429 B2 | 6/2007 | Tullis |
| 7,439,224 B2 | 10/2008 | Thiel et al. |
| 7,462,596 B2 | 12/2008 | Larsen et al. |
| 7,566,694 B2 | 7/2009 | Rider |
| 7,629,440 B2 | 12/2009 | Segal et al. |
| 7,695,937 B2 | 4/2010 | Baum |
| 7,763,436 B2 | 7/2010 | Das et al. |
| 8,013,120 B2 | 9/2011 | Du Clos et al. |
| 8,080,245 B2 | 12/2011 | Visintin et al. |
| 8,084,275 B2 | 12/2011 | Hirai et al. |
| 8,088,596 B2 | 1/2012 | Zeng et al. |
| 8,415,118 B2 | 4/2013 | Huang et al. |
| 8,598,324 B2 | 12/2013 | Rider |
| 9,150,631 B2 | 10/2015 | Super et al. |
| 2003/0162248 A1 | 8/2003 | Wakamiya |
| 2003/0166878 A1 | 9/2003 | Nishiya et al. |
| 2003/0180814 A1 | 9/2003 | Hodges et al. |
| 2004/0018611 A1 | 1/2004 | Ward et al. |
| 2004/0229212 A1 | 11/2004 | Thiel et al. |
| 2005/0014932 A1 | 1/2005 | Imboden et al. |
| 2005/0037949 A1 | 2/2005 | O'Brien et al. |
| 2006/0040362 A1 | 2/2006 | Wakamiya |
| 2006/0104975 A1 | 5/2006 | Geijtenbeek et al. |
| 2006/0177879 A1 | 8/2006 | Mayes et al. |
| 2006/0188963 A1 | 8/2006 | Kongerslev et al. |
| 2006/0251580 A1 | 11/2006 | Keppler et al. |
| 2007/0031819 A1 | 2/2007 | Koschwanez et al. |
| 2007/0049532 A1 | 3/2007 | Feige et al. |
| 2007/0072247 A1 | 3/2007 | Wong et al. |
| 2007/0122850 A1 | 5/2007 | Teng |
| 2007/0184463 A1 | 8/2007 | Molho et al. |
| 2007/0224640 A1 | 9/2007 | Dahlgren Caldwell et al. |
| 2007/0231833 A1 | 10/2007 | Arcidiacono et al. |
| 2007/0269818 A1 | 11/2007 | Savage |
| 2007/0269878 A1 | 11/2007 | Gerard et al. |
| 2008/0014576 A1 | 1/2008 | Jovanovich et al. |
| 2008/0056949 A1 | 3/2008 | Lee et al. |
| 2008/0108120 A1 | 5/2008 | Cho et al. |
| 2008/0156736 A1 | 7/2008 | Hirai et al. |
| 2008/0182793 A1 | 7/2008 | Baum |
| 2008/0193965 A1 | 8/2008 | Zeng et al. |
| 2008/0260738 A1 | 10/2008 | Moore |
| 2008/0300188 A1 | 12/2008 | Yang et al. |
| 2009/0078614 A1 | 3/2009 | Varghese et al. |
| 2009/0175797 A1 | 7/2009 | Warren et al. |
| 2009/0181041 A1 | 7/2009 | Holgersson et al. |
| 2009/0220932 A1 | 9/2009 | Ingber et al. |
| 2009/0252729 A1 | 10/2009 | Farrington et al. |
| 2009/0269843 A1 | 10/2009 | Blume et al. |
| 2009/0297516 A1 | 12/2009 | Mayo et al. |
| 2010/0044232 A1 | 2/2010 | Lin et al. |
| 2010/0055675 A1 | 3/2010 | Kumamoto et al. |
| 2010/0266558 A1 | 10/2010 | Zipori |
| 2010/0323342 A1 | 12/2010 | Gomez et al. |
| 2010/0323429 A1 | 12/2010 | Hu et al. |
| 2010/0331240 A1 | 12/2010 | Michelow et al. |
| 2011/0027267 A1 | 2/2011 | Kyneb et al. |
| 2011/0053145 A1 | 3/2011 | Takakura et al. |
| 2011/0053250 A1 | 3/2011 | Takakura et al. |
| 2011/0065095 A1 | 3/2011 | Kida et al. |
| 2011/0159000 A1 | 7/2011 | Silverman |
| 2011/0183398 A1 | 7/2011 | Dasaratha et al. |
| 2011/0281792 A1 | 11/2011 | Zion et al. |
| 2012/0100140 A1 | 4/2012 | Reyes et al. |
| 2012/0164628 A1 | 6/2012 | Duffin et al. |
| 2013/0029428 A1 | 1/2013 | Kim et al. |
| 2013/0035283 A1 | 2/2013 | Super |
| 2013/0072445 A9 | 3/2013 | Du Clos et al. |

FOREIGN PATENT DOCUMENTS

| | | |
|---|---|---|
| EP | 0915970 B1 | 9/2004 |
| EP | 1862541 A1 | 12/2007 |
| EP | 1812459 B1 | 3/2011 |
| JP | S54-18198 A | 2/1979 |
| JP | 2008515389 A | 5/2008 |
| JP | 2010122205 A | 6/2010 |
| JP | 2010268800 A | 12/2010 |
| WO | 2000/006603 A1 | 2/2000 |
| WO | 2001/003737 A1 | 1/2001 |
| WO | 2002/032292 A2 | 4/2002 |
| WO | 2003/014150 A2 | 2/2003 |
| WO | 2003/054164 A2 | 7/2003 |
| WO | 2004/018698 A2 | 3/2004 |
| WO | 2005092925 A2 | 10/2005 |
| WO | 2006/018428 A2 | 2/2006 |
| WO | 2006/044650 A2 | 4/2006 |
| WO | 2007/001332 A1 | 1/2007 |
| WO | 2007/044642 A2 | 4/2007 |
| WO | 2007/111496 A1 | 10/2007 |
| WO | 2008/130618 A1 | 10/2008 |
| WO | 2009/040048 A2 | 4/2009 |
| WO | 2009/062195 A2 | 5/2009 |
| WO | 2009/119722 A1 | 10/2009 |
| WO | 2009/126346 A2 | 10/2009 |
| WO | 2011/084749 A1 | 7/2011 |
| WO | 2011/090954 A2 | 7/2011 |
| WO | 2011/091037 A2 | 7/2011 |
| WO | 2011/103144 A1 | 8/2011 |
| WO | 2012/019178 A2 | 2/2012 |
| WO | 2012/050874 A2 | 4/2012 |
| WO | 2012/100099 A2 | 7/2012 |
| WO | 2012/135834 A2 | 10/2012 |
| WO | 2012142515 A2 | 10/2012 |
| WO | 2013/012924 A2 | 1/2013 |

OTHER PUBLICATIONS

Ilyas et al., "High glucose disrupts oligosaccharide recognition function via competitive inhibition: a potential mechanism for immune dysregulation in diabetes mellitus", Immunobiology 216(1-2) 126-131 (2011).

Kjaer et al., "M-ficolin binds selectively to the capsular polysaccharides of *Streptococcus pneumoniae* serotypes 19B and 19C and of a *Streptococcus mitis* strain", Infect Immun 81(2) 452-459 (2013).

Sheriff et al., "Human mannose-binding protein carbohydrate recognition domain trimerizes through a triple alpha-helical coiled-coil", Nat Struct Biol 1(11) 789-794 (1994).

Zettner et al., "Principles of competitive binding assays (saturation analyses). II. Sequential saturation", Clin Chem 20(1) 5-14 (1974).

Zettner et al., "Principles of competitive binding assays (saturation analysis). 1. Equilibrium techniques", Clin Chem 19(7) 699-705 (1973).

Arakawa et al., "Elution of antibodies froma protein—A column by aqueous arginine solutions." Protein Expression and Purification 36:244-248 (2004).

Armour et al., "Recombinant human IGG molecules lacking Fcgamma receptor I binding and monocyte triggering activities." Eur. J. Immunol. 29:2613-2624 (1999).

Ashkenazi et al., "Immunoadhesins as research tools and therapeutic agents." Curr Opin Immunol. 9(2):195-200 (1997).

Azevedo et al., "Horseradish peroxidase: a valuable tool in biotechnology," Biotechnology Annual Review, 9:199-247 (2003).

Bangs Laboratories, Inc., "Protein Coated Microspheres", Tech. Note #51 (1997).

Bayston et al., "Bacterial endotoxin and current concepts in the diagnosis and treatment of endotoxaemia", J. Med. Microbiol 31:73-83 (1990).

(56) References Cited

OTHER PUBLICATIONS

Bossola et al., "Circulating bacterial-derived DNA fragments and markers of inflammation in chronic hemodialysis patients." Clin J. Am. Soc. Nephrol. 4:379-385 (2009).
Brooks et al., "Expression and secretion of ficolin beta by porcine neutrophils", Biochim. Biophys. Acta 1624(1-3):36-45 (2003).
Brouwer et al., "Mannose-Binding Lectin (MBL) Facilitates Opsonophagocytosis of Yeasts but Not of Bacteria despite MBL Binding", J. Immunol., 180(6):4124-32 (2008).
Chamow et al., "Immunoadhesisn: principles and applications." Trends Biotechnol. 14(2):52-60 (1996).
Chang et al., "Crystallization and preliminary x-ray analysis of a trimeric form of human mannose binding protein." J. Mol. Biol. 241:125-127 (1994).
Chen et al., Angew. Chem. Int. Ed., 47:8627-8630 (2008). "Fabrication of an Oriented Fc-Fused Lectin Microarray through Boronate Formation."
Foster "Immune evasion by staphylococci." Nature 3:948-958 (2005).
Fox et al., "Single amino acid substitutions on the surface of *Escherichia coli* maltose-binding protein can have a profound impact on the solubility of fusion proteins", Protein Sci. 10(3):622-630 (2001).
Frakking et al., "Safety and phamacokinetics of plasma-derived mannose-binding lectin (MBL) substitution in children with chemotherapy-induced neutropaenia", Eur. J. Cancer, 45(4):505-12 (2009).
Garred et al., "Mannose-binding lectin and its genetic variants", Genes and Immunity, 7(2):85-94 (2006).
Gouin et al., "Multimeric Lactoside "Click Clusters" as Tools to Investigate the Effect of Linker Length in Specific Interactions with Peanut Lectin, Galectin-1, and -3", ChemBioChem 11(10):1430-1442 (2010).
Grogl et al., "Leishmania braziliensis: protein, carbohydrate, and antigen differences between log phase and stationary phase promastigotes in vitro", Exp. Parasitol. 63(3):352-359 (1987).
Hinton et al., "Engineered human IgG antibodies with longer serum half-lives in primates." The Journal of Biological Chemistry 279(8):6213-6216 (2004).
Holmskov et al., "Affinity and kinetic analysis of the bovine plasma C-type lectin collectin-43 (CL-43) interacting with mannan", FEBS Lett. 393(2-3):314-316 (1996).
Huang et al., "Porcine DC-SIGN: molecular cloning, gene structure, tissue distribution and binding characteristics", Dev. Comp. Immunol. 33(4)464-480 (2009).
Hwang et al., "The pepper mannose-binding lectin gene CaMBL1 is required to regulate cell death and defense responses to microbial pathogens", Plant Physiol. 155(1):447-463 (2011).
Idusogie et al., "Engineered antibodies with increased activity to recruit complement." The Journal of Immunology 166(4):2571-5 (2001).
Invivo Gen Insight, "IgG-Fc Engineering for Therapeutic Use." Apr./May 2006.
Jack et al., "Mannose-binding lectin: targeting the microbial world for complement attack and opsonophagocytosis", Immunological Reviews, 180:86-99 (2001).
Jarva et al., "*Streptococcus pneumoniae* evades complement attack and opsonophagocytosis by expressing the pspC locus-encoded Hic protein that binds to short consensus repeats 8-11 of factor H", J. Immunol. 168(4):1886-1894 (2002).
Kang et al., "The human macrophage mannose receptor directs *Mycobacterium tuberculosis* lipoarabinomanan-mediated phagosome biogenesis", J. Exp. Med., 202(7):987-99 (2005).
Keen et al., "Interrelationship between pH and surface growth of nitrobacter." Soil Biol. Biochem. 19(6):665-672 (1987).
Kehres, "A kinetic model for binding protein-mediated arabinose transport", Protein Sci. 1(12):1661-1665 (1992).
Krarup et al., "Simultaneous Activation of Complement and Coagulation by MBL-Associated Serine Protease 2", PLoS ONE, 2(7):e623 (2007).
Linehan et al., Eur. J. Immun., 31:1857-1866 (2001). "Endogenous ligands of carbohydrate recognition domains of the mannose receptor in murine macrophages, endothelial cells and secretory cells; potential relevance to inflammation and immunity."
Lo et al., "High level expression and secretion of Fc-X fusion proteins in mammalian cells", Protein Eng., 11(6):495-500 (1998).
Loosdrecht et al., "Influence of interfaces on microbial activity." Microbiological Reviews 54(1):75-87 (1990).
Matsushita et al., "Activation of the Classical Complement Pathway by Mannose-binding Protein in Association with a Novel C1s-like Serine Protease", J. Exp. Med., 176(6):1497-502 (1992).
Michelow et al., "A novel L-ficolin/mannose-binding lectin chimeric molecule with enhanced activity against Ebola virus." Journal of Biological Chemistry 285(32):24729-24739 (2010).
Nadesalingam et al., "Mannose-binding lectin recognizes peptidoglycan via the N-acetyl glucosamine moiety, and inhibits ligand-induced proinflammatory effect and promotes chemokine production by macrophages." Journal of Immunology 175:1785-1794 (2005).
Nakamura et al., "Characterization of the interaction between serum mannan-binding protein and nucleic acid ligands." Journal of Leukocyte Biology 86:737-748 (2009).
Neth et al., "Ehancement of Complement Activation and Opsonophagocytosis by Complexes of Mannose-Binding Lectin with Mannose-Binding Lectin-Associated Serine Protease After Binding to *Staphylococcus aureus*", J. Immunol., 169:4430-4436 (2002).
Neth et al., "Mannose-Binding Lectin Binds to a Range of Clinically Relevant Microorganisms and Promotes Complement Deposition", Infect. Immun., 68(2):688-93 (2000).
Nisnevitch et al., Journal of Biochemical and Biophysical Methods, 49:467-480 (2001). "The solid phase in affinity chromatography: strategies for antibody attachment."
Ogden et al., "C1q and mannose binding lectin engagement of cell surface calreticulin and CD91 initiates macropinocytosis and uptake of apoptotic cells." J. Exp. Med. 194:781-795 (2001).
Perham, "Domains, Motifs, and Linkers in 2-Oxo Acid Dehydrogenase Multienzyme Complexes: A Paradigm in the Design of a Multifunction Protein", Biochem. 30(35):8501-12 (1991).
Product Data Sheet: Human Mannan Binding Lectin peptied (237-248) (Carboxyterminal end) ab45655.
Rutishauser et al., "Amino Acid Sequence of the Fc Region of a Human yG Immunoglobulin", Biochemistry, 61:1414-1421 (1968).
Safarik et al., "The application of magnetic separations in applied microbiology", Journal of Applied Bacteriology, 78:575-585 (1995).
Schmidt "Fusion proteins as bipharmaceutical—applications and challengs." Current Opinion in Drug Discovery & Development 12(2):284-295 (2009).
Shields et al., "High resolution mapping of the binding site on human IgG1 for Fc gamma RI, Fc gamma RII, Fc gamma RIII, and FcRn and design of IgG1 variants with improved binding to the Fc gamma R." The Journal of Biological Chemistry 276(9):6591-6604 (2001).
Sibille et al., "Comparison of serological tests for the diagnosis of feline immunodeficiency virus infection of cats", Veterinary Microbiology 45(2-3):259-267 1995).
Sprong et al., "Mannose-Binding Lectin is a Critical Factor in Systemic Complement Activation during Meningococcal Septic Shock", Clinical Infectious Diseases, 49(9):1380-6 (2009).
Steurer et al., "Ex vivo coating of islet cell allografts with murine CTLA4/Fc promotes graft tolerance." The Journal of Immunology 155(3):1165-1174 (1995).
Stuart et al., "Mannose-binding lectin-deficient mice display defective apoptotic cell clearance but no autoimmune phenotype." Journal of Immunology 174:3220-3226 (2005).
Takahashi et al., "Mannose-binding lectin and its associated proteases (MASPs) mediate coagulation and its deficiency is a risk factor in developing complications from infection, including disseminated intravascular coagulation." Immunobiology 216(1-2):96-102 (2011).
Terai et al., Eur. J. Immunol., 33:2755-2763 (2003). "Relationship between gene polymorphisms of mannose-binding lectin (MBL) and two molecular forms of MBL."

(56) References Cited

OTHER PUBLICATIONS

Thiel et al., "A second serine protease associated with mannan-binding lectin that activates complement", Nature, 386:506-10 (1997).

Vaccaro et al., "Engineering the Fc region of immunoglobulin G to modulate in vivo antibody levels." Nature Biotechnology 23(1):1283-1288 (2005).

Ward et al., "Characterization of Humanized Antibodies Secreted by Apsergillus niger", Applied and Environmental Microbiology, 70(5):2567-2576 (2004).

Warwick et al., "Use of quantitative 16S ribosomal DNA detection for diagnosis of central vascular catheter-associated bacterial infection." Journal of Clinical Microbiology 42:1402-1408 (2004).

Witus et al., J. Am. Chem. Soc. 132:16812-16817 (2010). "Identification of Highly Reactive Sequences for PLP-Mediated Bioconjugation Using a Combinatorial Peptide Library."

Wong et al., "Bioinspired self-repairing slippery surfaces with pressure—stable omniphobicity." Nature 466:443-447 (2011).

Wriggers et al., "Control of Protein Functional Dynamics by Peptide Linkers", Biopolymers, 80(6):736-46 (2005).

Xia et al., "Combined microfluidic-micromagnetic separation of living cells in continuous flow", Biomed Microdevices, 8(4):299-308 (2006).

Ye et al., "Surface display of a glucose binding protein", Journal of Molecular Catalysis B: Enzymatic 28(4-6):201-206 (2004).

Yung et al., "Micromagnetic-microfluidic blood cleansing device", Lab Chip, 9:1171-7 (2009).

Agrawal et al., "C-reactive protein mutant that does not bind to phosphocholine and pneumococcal C-polysaccharide", J. Immunol. 169(6):3217-3222 (2002).

Barnum et al., "Comparative Studies on the Binding Specificities of C-Reactive Protein (CRP) and HOPC 8", Annals of the New York Academy of Sciences 389:431-434 (1982).

Casey et al., "The acute-phase reactant C-Reactive protein binds to phosphorylcholine-expressing Neisseria meningitidis and increased uptake by human phagocytes", Infection and Immunity 76(3):1298-1304 (2008).

Castle et al., "The binding of 125I-labeled concanavalin A to the cell surface of rabbit peritoneal polymorphonuclear leucocytes." Biochemical Medicine 28(1):1-15 (1982).

Choma et al. "Design of a Heme-Binding Four-Helix Bundle" 116:856-865 (1994).

Zhavnerko et al., "Oriented Immobilization of C-Reactive Protein on Solid Surface for Biosensor Applications", Frontiers of Multi-functional Integrated Nanosystems 95-108 (2004).

Culley et al., "C-reactive protein binds to phosphorylated carbohydrates", Glycobiology 10(1):59-65 (2000).

Szalai, "The biological functions of C-reactive protein", Vascular Pharmacology 39:105-107 (2002).

Dumont et al., "Monomeric Fc Fusions: Impact on Pharmacokinetic and Biological Activity of Protein Therapeutics", Biodrugs 20(3):151-160 (2006).

Feng et al., "Identification of carbohydrates on the surface membrane of pathogenic and nonpathogenic piscine haemoflagellates, Cryptobia salmositica, C. bullocki and C. catostomi (Kinetoplastida)." Diseases of Aquatic Organisms 32(3):201-209 (1998).

Shoulders et al., "Collagen structure and stability." Annual Review of Biochemistry 78(1):929-958 (2009).

Huang et al., "Integrated microfluidic system for rapid screening of CRP aptamers utilizing systematic evolution of ligands by exponential enrichment (SELEX)", Biosensors and Bioelectronics 25:1761-1766 (2010).

Rouhandeh et al., "Surface membrane redistribution and stabilization of concanavalin A-specific receptors following Yaba tumor poxvirus infection." Biochimica et Biophysica Acta (BBA)-Biomembranes 600(2):301-312 (1980).

Lee et al., "Carbohydrate-binding properties of human neo-CRP and its relationship to phosphorylcholine-binding site", Glycobiology 13(1):11-21 (2003).

Lin et al. "Synergistic inflammation is induced by blood degradation products with microbial Toll-like receptor agonists and is blocked by hemopexin." The Journal of Infectious Diseases 202:624 (2010).

Mantuano et al., "The hemopexin domain of matrix metalloproteinase-9 activates cell signaling and promotes migration of schwann cells by binding to low-density lipoprotein receptor-related protein.", The Journal of Neuroscience 28(45):11571-11582 (2008).

Mauk et al. "An alternative view of the proposed alternative activities of hemopexin." Protein Science. 20:791 (2011).

Mold et al., "Binding of Human C-Reactive Protein to Bacteria", Infection and Immunity 38(1):392-395 (1982).

Presanis et al., "Biochemistry and genetics of mannan-binding lectin (MBL)", Biochemical Society Transactions 31(4):748-752 (2003).

Tu et al., "Capture of *Escherichia coli* O157:H7 Using Immunomagnetic Beads of Different Size and Antibody Conjugating Chemistry" Sensors 9:717-730 (2009).

ENGINEERED MICROBE-TARGETING MOLECULES AND USES THEREOF

CROSS REFERENCE TO RELATED APPLICATIONS

This Application is a continuation of co-pending U.S. application Ser. No. 14/233,553 filed Apr. 18, 2014 which is a 35 U.S.C. § 371 National Phase Entry Application of International Application No. PCT/US2012/047201 filed Jul. 18, 2012, which designates the U.S., and which claims the benefit under 35 U.S.C § 119(e) of U.S. Provisional Application Nos. 61/508,957 filed Jul. 18, 2011; 61/605,081 filed Feb. 29, 2012; and 61/605,052 filed Feb. 29, 2012, the contents of each of which are herein incorporated by reference in their entirety.

GOVERNMENT SUPPORT

This invention was made with Government support under grant no. N66001-11-1-4180 awarded by DARPA. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 15, 2014, is named 28671233.txt and is 22,557 bytes in size.

TECHNICAL FIELD

Described herein relates generally to molecules, products, kits and methods for detecting and/or removing microbes in a sample or a target area, including bodily fluids such as blood and tissues of a subject, food, water, and environmental surfaces.

BACKGROUND

Sepsis is a major cause of morbidity and mortality in humans and other animals. In the United States, sepsis is the second leading cause of death in intensive care units among patients with non-traumatic illnesses. It is also the leading cause of death in young livestock, affecting 7.5-29% of neonatal calves, and is a common medical problem in neonatal foals. Despite the major advances of the past several decades in the treatment of serious infections, the incidence and mortality due to sepsis continues to rise.

Sepsis results from the systemic invasion of microorganisms into blood and can present two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and, often times, death.

Sepsis is a systemic reaction defined by the American College of Chest Physicians and the Society of Critical Care Medicine by a systemic inflammatory response (SIRS) in response to a confirmed infectious process. SIRS is defined by the presence of two or more of the following: altered body temperature (<36° C. or >38° C.), tachycardia (heart rate>90/min), tachypnea (respiratory rate>20/min) or hypocapnia ($P_aCO_2$ less than 4.3 kPa), leucopenia (white blood cells (WBCs)<4000 cells/mm$^3$ or leucocytosis (>12000 WBC/mm$^3$) or >10% band forms. The confirmation of the infectious process is confirmed by microbiological means (stain, culture, antigenemia or antigenuria, nucleic acid detection) or pathognomonic signs of infection obtained by imaging or clinical examination. The infection can affect any organ system, but the more severe cases present as septicemia (i.e., organisms, their metabolic end-products or toxins in the blood stream), bacteremia (i.e., bacteria in the blood), toxemia (i.e., toxins in the blood), endotoxemia (i.e., endotoxin in the blood). Sepsis can also result from fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by various microorganisms.

There are three major types of sepsis characterized by the type of infecting organism. For example, gram-negative sepsis is the most frequently isolated (with a case fatality rate of about 35%). The majority of these infections are caused by *Escherichia coli, Klebsiella pneumoniae* and *Pseudomonas aeruginosa*. Gram-positive pathogens such as the *Staphylococci* and *Streptococci* are the second major cause of sepsis. The third major group includes fungi, with fungal infections causing a relatively small percentage of sepsis cases, but with a high mortality rate; these types of infections also have a higher incidence in immunocomprised patients.

Some of these infections can be acquired in a hospital setting and can result from certain types of surgery (e.g., abdominal procedures), immune suppression due to cancer or transplantation therapy, immune deficiency diseases, and exposure through intravenous catheters. Sepsis is also commonly caused by trauma, difficult newborn deliveries, and intestinal torsion (especially in dogs and horses). Infections in the lungs (pneumonia), bladder and kidneys (urinary tract infections), skin (cellulitis), abdomen (such as appendicitis), bone (osteomyeltitis) and joints (arthritis) and other areas (such as meningitis) can spread and also lead to sepsis. In some circumstances, ingestion of microbe-contaminated water, fluid or food, or contact with microbe-covered environmental surfaces can cause infections that lead to sepsis, and infection with food-borne and water-borne pathogens such as *Shigella* spp, or certain serotypes of *Escherichichia coli* (such as O157 H7), *Salmonella* spp including *Salmonella enterica serovar typhi* or *Listeria monocytogenes* can also lead to sepsis.

Many patients with septicemia or suspected septicemia exhibit a rapid decline over a 24-48 hour period. It has been reported that patients with septic shock require adapted treatment in less than 6 hours in order to benefit from antimicrobial therapy. Thus, rapid and reliable diagnostic and treatment methods are essential for effective patient care. Unfortunately, a confirmed diagnosis as to the type of infection, e.g., sepsis, traditionally requires microbiological analysis involving inoculation of blood cultures, incubation for 18-24 hours, plating the causative microorganism on solid media, another incubation period, and final identification 1-2 days later. Even with immediate and aggressive treatment, some patients can develop multiple organ dysfunction syndrome and eventually death. Hence, there remains a strong need for improved techniques for diagnosis and treatment of patients with infectious diseases, blood-borne infections, sepsis, or systemic inflammatory response syndrome. The ability to rapidly detect infectious pathogens in food, water, and/or environmental surfaces would also have great value for preventing infections and sepsis in the population.

SUMMARY

Embodiments described herein are based on, at least in part, engineering a microbe-targeting molecule or a microbe-binding molecule. For example, in one embodiment, a microbe-targeting molecule is engineered by fusing the carbohydrate recognition domain and neck region of a carbohydrate-binding protein (e.g., mannose-binding lectin) to the C-terminal of a Fc fragment of human IgG1. Such microbe-targeting molecules can be also modified to reduce the complement activation and coagulation side effects which are present in the wild-type mannose-binding lectin, and can complicate binding and detection. Further, the microbe-targeting molecules described herein can be engineered, e.g., by inserting an AKT tripeptide to the N-terminal of the Fc fragment for site-specific biotinylation, such that their carbohydrate recognition domains orient away from a substrate to which they attach, thus increasing the microbe-binding capacity. The microbe-targeting molecules can be attached to various substrates, e.g., a magnetic microbead, in a multivalent oriented manner to form a microbe-targeting substrate. The term "microbead" as used herein generally refers to a bead or a particle of any material having a size of about 0.001 µm to about 1000 µm or about 0.001 µm to about 100 µm, or about 0.01 µm to about 10 µm. In one embodiment, the microbead is a nanobead. The term "nanobead" as used herein generally refers to a bead or particle having a size ranging from about 1 nm to about 1000 nm, from about 10 nm to about 500 nm, from about 25 nm to about 300 nm, from about 40 nm to about 250 nm, or from about 50 nm to about 200 nm.

In some embodiments, the microbe-targeting molecules can be modified, e.g., to facilitate attachment of the microbe-targeting molecules to a substrate. For example, in one embodiment, the microbe-targeting molecules can be biotinylated, e.g., for attachment to an avidin- or avidin-like coated substrate. Thus, the engineered microbe-targeting molecules described herein provide a valuable building block for various applications, e.g., diagnosis and/or treatment of diseases caused by microbes or pathogens, removal of microbes or pathogens from a sample, including bodily fluids and tissues of a subject, foods, water, or an environmental surface; and development of targeted drug delivery devices.

Accordingly, provided herein is directed to an engineered microbe-targeting molecule comprising: (a) at least one microbe surface-binding domain; (b) a substrate-binding domain adapted for orienting the microbe surface-binding domain away from the substrate; and (c) at least one linker between the microbe surface-binding domain and the substrate-binding domain.

In some embodiments, the microbe-surface binding domain can comprise a carbohydrate recognition domain (CRD) or a fragment thereof. In some embodiments, the microbe-surface binding domain can further comprise a non carbohydrate recognition domain or fragment thereof from the carbohydrate-binding protein, e.g., a neck region of the carbohydrate-binding protein. As used herein, the term "non carbohydrate recognition domain" refers to the portion or fragment of a carbohydrate-binding protein that does not directly bind with the microbe surface.

In some embodiments, the CRD or the carbohydrate-binding protein can be derived from, e.g., mannose-binding lectin. Hence, another aspect provided herein is directed to an engineered mannose-binding lectin molecule comprising: (a) at least one carbohydrate recognition domain (CRD) or a fragment thereof; (b) a substrate-binding domain adapted for orienting the CRD away from the substrate; and (c) at least one linker between the CRD and the substrate-binding domain.

In some embodiments, the microbe-surface binding domain comprises the full amino acid sequence of a carbohydrate-binding protein. In some embodiments, the amino acid sequence of the carbohydrate-binding protein does not include a complement region. In some embodiments, the amino acid sequence of the carbohydrate-binding protein does not include a coagulation activation region.

In some embodiments of any aspects described herein, the linker can comprise a portion of a Fc region of an immunoglobulin, e.g., IgG1. In such embodiments, the portion of the Fc region can be linked, directly or indirectly, to N-terminal of the carbohydrate recognition domain. In some embodiments, the portion of the Fc region can be genetically modified, e.g., to increase half-life of the engineered molecules, or modulate an immune response (e.g., antibody-dependent cell-mediated cytotoxicity and complement-dependent cytotoxicity).

In some embodiments of any aspects described herein, the substrate-binding domain can comprise at least one oligopeptide comprising an amino acid sequence of AKT. In other embodiments, the substrate-binding domain can comprise a biotin molecule. Depending on various applications, e.g., for use as a soluble protein in pharmaceutical compositions, the substrate-binding domain can become non-essential in some embodiments of the engineered microbe-targeting molecules. Otherwise, the engineered microbe-targeting molecules can be used to coat various substrates for a wide variety of applications. In some embodiments, the substrate is a magnetic microbead, resulting in formation of a microbe-targeting magnetic microbead or opsonin. In some embodiments, the microbe-targeting magnetic microbead or opsonin can encompass a microbe-targeting nanobead.

Not only can the microbe-targeting magnetic microbeads be used to remove microbes or pathogens in a sample, e.g., blood and tissues, they can also be used to develop assays for detecting the presence or absence of, and/or differentiating between, different microbes or pathogens. Accordingly, kits and assays for detecting the presence or absence of microbes, and/or differentiating between, different microbes or pathogens in a test sample are also provided herein. In some embodiments, the kits comprise microbe-targeting substrates (e.g., but not limited to, one or more containers each containing a population of magnetic microbeads coated with a plurality of the engineered microbe-targeting molecules); and at least one reagent. In some embodiments, the kits can further comprise one or more containers each containing a population of detectable labels, wherein each of the detectable labels is conjugated to a molecule that binds to the microbes or pathogens. Such kits can be used for analysis, e.g., by an enzyme-linked immunosorbent assay (ELISA), fluorescent linked immunosorbent assay (FLISA), immunofluorescent microscopy, fluorescence in situ hybridization (FISH), or any other radiological, chemical, enzymatic or optical detection assays. In some embodiments, the kits and assays described herein can be adapted for antibiotic susceptibility tests, e.g., to determine susceptibility of a microbe in a test sample to one or more antibiotics, regardless of whether the identity of the microbe is known or not.

Without limitations, in some embodiments, the engineered microbe-targeting molecules can be formulated as an antibiotic or antiseptic for use in various applications, e.g., wound dressings, alone or in combination with other wound dressing protocols, e.g., silver nanoparticles and other wound treatment.

BRIEF DESCRIPTION OF THE DRAWINGS

FIG. 1A is a diagrammatic view of a native (wild-type) mannose-binding lectin (MBL). FIG. 1B shows one or more embodiments of the engineered microbe-targeting molecules or engineered-binding molecules, e.g., engineered MBL molecules. FIG. 1C shows one or more embodiments of the microbe-targeting or microbe-binding molecules conjugated to a substrate, e.g., a magnetic microbead or nanobead, to form a microbe-targeting substrate.

FIG. 6A shows the percentage of microbes bound to microbe-targeting substrates and controls at a low microbe density (e.g., 1500 C. albicans cells). FIG. 6B shows the amount of unbound microbes remained in the microbe samples after treatment with different magnetic microbeads (including the engineered microbe-targeting magnetic microbeads) when the microbe is present at a much higher microbe density (e.g., greater than $10^8$ cells).

FIG. 18A corresponds to FcMBL directly coupled to MYONE™ Tosyl activated beads and FIG. 18B corresponds to biotinylated AKT-FcMBL coupled to Streptavidin MYONE™ T1 microbeads (~1000 nm diameter). Three different dilutions of an *E. coli* overnight culture were captured on FcMBL microbeads, washed with one of four elution buffers and then run through one or more embodiments of the ELISA protocol described herein. A decrease in signal corresponds to fewer *E. coli* bound to the microbeads prior to the ELISA detection.

FIG. 20A shows data for capture efficiency of FcMBL in the clinical isolates of *S. aureus* and methicillin-resistant *S. aureus* (MRSA). FIG. 20B shows data for capture efficiency of FcMBL in the clinical isolates of *S. aureus*, MRSA, *N. meningitidis*, and *P. aeroginosa*.

FIGS. 21A and 21B shows data for capture efficiency of FcMBL in the clinical isolates of *S. aureus* and *E. coli*, respectively, obtained from other body fluids, e.g., urine, cerebrospinal fluid (CSF), and sputum.

FIG. 25A shows the results in OD450 and FIG. 25B shows the results as a percent of bound bacteria remained on the FcMBL-coated substrates after treatment.

FIG. 26A is an image showing colorimetric outcomes of the tube-based ELISA for *S. aureus* and *E. coli* binding to FcMBL-coated substrates (e.g., magnetic microbeads) in the presence or absence of a chelating agent (e.g., EDTA). FIG. 26B is a bar graph showing quantitative measurement of the color developed in FIG. 26A.

FIG. 30A shows that microbial outgrowth is observed when one or more microbe-targeting substrates (e.g., FcMBL-coated fluorescent microbeads) bind(s) to at least one live microbe, e.g., *E. coli*. FIG. 30B is a set of fluorescent images showing that FcMBL-coated fluorescent microbeads bind to microbial matter (left panel) including live microbes (indicated by the middle panel) and fragments or matter derived from microbes. The right panel is an overlay of the first two fluorescent images in addition to a bright-field image.

FIG. 31A shows capture of *E. coli* or fragments thereof on FcMBL-coated microbeads (e.g., magnetic or fluorescent microbeads) from heparinized blood, followed by incubation with an antibody against *E. coli* lipopolysaccharide lipid A (anti-LPS lipid A antibody. FIG. 31B shows capture of *E. coli* or fragments thereof on FcMBL-coated microbeads (e.g., magnetic or fluorescent microbeads) from blood containing EDTA anticoagulation agent, followed by incubation with an antibody against *E. coli* lipopolysaccharide lipid A (anti-LPS lipid A antibody). Both FIGS. 31A-31B show that the anti-LPS lipid A antibody does not bind to FcMBL-coated microbeads in the absence of *E. coli* or fragments thereof.

FIG. 32A shows capture of microbes or fragments thereof on FcMBL-coated microbeads (e.g., magnetic or fluorescent microbeads) from rat blood (upper panel) or pleural (lower panel) fluids after 24-hr infection, followed by incubation with an anti-LPS lipid A antibody. FIG. 32B shows capture of microbes or fragments thereof on FcMBL-coated microbeads (e.g., magnetic or fluorescent microbeads) from rat blood (upper panel) or pleural (lower panel) fluids after 72-hr infection, followed by incubation with an anti-LPS lipid A antibody.

FIG. 34A is a bar graph showing results of anaerobe cultures at Day 4 of blood collected from five rats developed with intra-abdominal abscesses. FIG. 34B is a plot comparing the microbe detection results based on colorimetric ELISA using FcMBL magnetic microbeads and conventional blood cultures and their correlations with morbidity of the rats. FIG. 34C is a line graph showing correlation of pathogen load determined by the ELISA using FcMBL magnetic microbeads with morbidity ranking. FIG. 34D is a bar graph comparing the microbe detection results based on colorimetric ELISA using FcMBL magnetic microbeads and conventional blood cultures in a separate experiment.

DETAILED DESCRIPTION OF THE INVENTION

Figure 1:
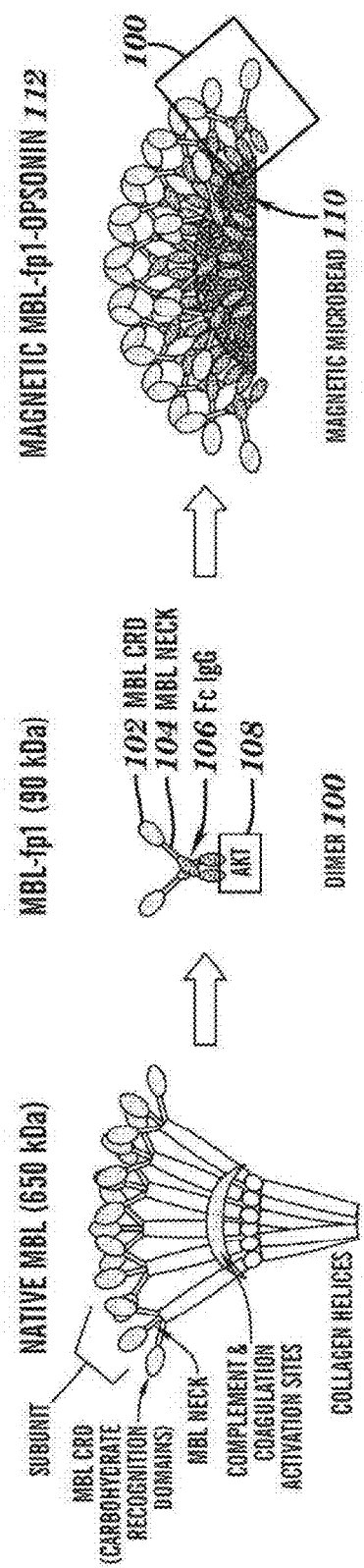
FIGS. 1A-1C shows a general scheme of engineering one or more embodiments of engineered microbe-targeting or microbe-binding molecules and microbe-targeting substrates described herein.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Described herein are engineered microbe-targeting or microbe-binding molecules, compositions comprising the same, processes or assays, and kits for separating microbes from a test sample in vivo, in situ or in vitro, and/or detecting the presence or absence of the microbes in the test sample. The engineered microbe-targeting or microbe-binding molecules can bind or capture at least one microbe, e.g., an intact microbe, and/or "microbial matter." The term "microbial matter" as used herein refers to any matter or component that is derived, originated or secreted from a microbe. For example, microbial matter or a component derived or secreted from a microbe that can bind to an engineered microbe-targeting or microbe-binding molecule can include, but are not limited to, a cell wall component, an outer membrane, a plasma membrane, a ribosome, a microbial capsule, a pili or flagella, any fragments of the aforementioned microbial components, any nucleic acid (e.g., DNA, including 16S ribosomal DNA, and RNA) derived from a microbe, and microbial endotoxin (e.g., lipopolysaccharide). In addition, microbial matter can encompass non-viable microbial matter that can cause an adverse effect (e.g., toxicity) to a host or an environment.

In accordance with various embodiments described herein, the engineered microbe-targeting molecules or microbe-binding molecules comprise a microbe surface-binding domain (e.g., a carbohydrate recognition domain), directly or indirectly, conjugated to a linker (e.g., a Fc fragment), which can further comprise a substrate-binding domain for immobilization. Thus, the engineered microbe-targeting molecules or microbe-binding molecules described herein can be used as soluble proteins, e.g., in therapeutic compositions, or be immobilized to a substrate for various applications ranging from diagnosis and/or treatment of a microbial infection or disease, to microbe-clearing compositions or devices, to drug delivery.

In one aspect, provided herein is an engineered microbe-targeting molecule (or an engineered microbe-binding molecule) comprising at least one microbe surface-binding domain, a substrate-binding domain adapted for orienting the carbohydrate recognition domain away from the substrate, and at least one linker between the microbe surface-binding domain and the substrate-binding domain. In some embodiments, the microbe surface-binding domain can comprise a carbohydrate recognition domain or a fragment thereof. In some embodiments, the microbe surface-binding domain can further comprise at least a portion of mannose-binding lectin (MBL). Accordingly, another aspect provided herein is an engineered MBL molecule comprising at least a fragment of a carbohydrate recognition domain derived from MBL; a substrate-binding domain adapted for orienting the carbohydrate domain away from the substrate; and at least one linker between the fragment of the MBL carbohydrate recognition domain and the substrate-binding domain. The terms "microbe-binding molecule(s)" and "microbe-targeting molecule(s)" are used interchangeably herein.

In some embodiments of any aspects described herein, the substrate-binding domain adapted for orienting the carbohydrate recognition domain away from the substrate is not always necessary and thus can be excluded under certain circumstances, e.g., using the engineered microbe-targeting molecules in a soluble format, e.g., for therapeutic purposes. Further, it should be noted that the engineered microbe-binding molecules excluding the substrate-binding domain adapted for orienting the carbohydrate recognition domain away from the substrate does not necessarily mean that the engineered microbe-binding molecules cannot bind to a substrate surface. In some embodiments, the engineered microbe-binding molecules excluding the substrate-binding domain adapted for orienting the carbohydrate recognition domain away from the substrate can still bind to a substrate surface, but the orientation of the carbohydrate recognition domain relative to the substrate surface can be random.

In some embodiments of any aspects described herein, the engineered microbe-targeting molecule can further comprise a detectable label, e.g., to facilitate detection of the presence or absence of a microbe and/or microbial matter. Detectable labels suitable for conjugation to some embodiments of the engineered microbe-targeting molecule can include any composition detectable by spectroscopic, photochemical, biochemical, immunochemical, electrical, magnetic, optical or chemical means, as well as any examples of detectable labels described herein and any equivalent thereof. In some embodiments, the detectable labels also encompass any imaging agent (e.g., but not limited to, a bubble, a liposome, a sphere, a contrast agent, or any detectable label described herein) that can facilitate imaging or visualization of a tissue or an organ in a subject, e.g., for diagnosis of an infection.

In some embodiments, the detectable label conjugated to the engineered microbe-targeting molecule can include an enzyme of horseradish peroxidase (HRP), alkaline phosphastase (AP), or any combinations thereof. Conjugation of the detectable label (e.g., HRP or AP) to any proteins and antibodies are known in the art. In one embodiment, FcMBL-HRP or FcMBL-AP construct is generated using any art-recognized methods for direct coupling HRP or AP to FcMBL.

In some embodiments, the detectable label conjugated to the engineered microbe-targeting molecule can include a microbial enzyme substrate conjugated to a detectable agent. For example, the detectable agent can be any moiety that, when cleaved from a microbial enzyme substrate by the enzyme possessed or secreted by the microbe, forms a detectable moiety (e.g., a light-emitting signal), but that is not detectable in its conjugated state. The microbial enzyme substrate is a substrate specific for one or more types of microbes to be detected, and it can be selected depending upon what enzymes the microbe possesses or secretes. See, e.g., International Patent Application: WO 2011/103144 for the use of such detectable label in detection of microbes, the content of which is incorporated herein by reference.

General methods of preparing any embodiments of the engineered microbe-targeting molecules are known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60). In one example, an engineered microbe-targeting molecule can be made by cloning into an expression vector such as Fc-X vector as discussed in Lo et al. (1998) 11:495 and Example 1.

The engineered microbe-targeting molecules can contain sequences from the same species or from different species. For example, an interspecies hybrid microbe-targeting molecule can contain a linker, e.g., a peptide linker, from a murine species, and a human sequence from a carbohydrate recognition domain protein, provided that they do not provide unacceptable levels of deleterious effects. The engineered microbe-targeting molecules described herein can also include those that are made entirely from murine-derived sequences or fully human.

Microbe Surface-Binding Domain and Carbohydrate Recognition Domain

As disclosed herein, an engineered microbe-targeting molecule can comprise at least one microbe surface-binding domain, including at least two, at least three, at least four, at least five, at least six, at least seven, at least eight, at least nine, at least ten or more microbe surface-binding domains. The term "microbe surface-binding domain" as used herein refers to any molecule or a fragment thereof that can specifically bind to the surface of a microbe or pathogen, e.g., any component present on a surface of a microbe or pathogen, and/or any microbial matter, e.g., any matter or component/fragment that is derived, originated or secreted from a microbe. Molecules that can be used in the microbe surface-binding domain can include, for example, but are not limited to, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof. In some embodiments, the microbe surface-binding domain can comprise a carbohydrate recognition domain or a fragment thereof. In some embodiments, a microbe surface-binding domain can comprise a peptidomimetic that mimics any molecule or a fragment thereof that can specifically bind to the surface of a microbe or pathogen, and/or any microbial matter. For example, a microbe surface-binding domain can comprise a peptidomimetic that mimics any carbohydrate recognition domain or a fragment thereof, e.g., carbohydrate recognition domain of MBL or a fragment thereof; or any carbohydrate recognition domain that is known in the art or a fragment thereof. In some embodiments, the microbe-surface binding domain comprises the full amino acid sequence of a carbohydrate-binding protein.

In some embodiments, the microbe surface-binding domain can have an amino acid sequence of about 10 to about 300 amino acid residues, or about 50 to about 150 amino acid residues. In some embodiments, the microbe surface-binding domain can have an amino acid sequence of at least about 5, at least about 10, at least about 15, at least about 20, at least about 30, at least about 40, at least about 50, at least about 60, at least about 70, at least about 80, at least about 90, at least about 100 amino acid residues or more. For any known sequences of microbe surface-binding molecules, one of skill in the art can determine the optimum length of amino acid sequence for the microbe surface-binding domain.

In some embodiments, the microbe surface-binding domain can comprise an opsonin or a fragment thereof. The term "opsonin" as used herein refers to naturally-occurring and synthetic molecules which are capable of binding to or attaching to the surface of a microbe or a pathogen, of acting as binding enhancers for a process of phagocytosis. Examples of opsonins which can be used in the engineered molecules described herein include, but are not limited to, vitronectin, fibronectin, complement components such as Clq (including any of its component polypeptide chains A, B and C), complement fragments such as C3d, C3b and C4b, mannose-binding protein, conglutinin, surfactant proteins A and D, C-reactive protein (CRP), alpha2-macroglobulin, and immunoglobulins, for example, the Fc portion of an immunoglobulin.

In some embodiments, the microbe surface-binding domain can comprise a carbohydrate recognition domain. In some embodiments, the microbe surface-binding domain can further comprise at least a portion of a carbohydrate-binding protein or a portion thereof. In some embodiments, the portion of the carbohydrate-binding proteins can activate the complement system. In alternative embodiments, the portion of the carbohydrate-binding protein cannot activate the complement system. In some embodiments, the portion of the carbohydrate-binding protein can be selected or configured such that it cannot activate the complement system, e.g., via modification. Examples of carbohydrate-binding proteins include, but are not limited to, lectin, collectin, ficolin, mannose-binding lectin (MBL), maltose-binding protein, arabinose-binding protein, and glucose-binding protein. Additional carbohydrate-binding proteins that can be included in the microbe surface-binding domain described herein can include, but is not limited to, lectins or agglutinins that are derived from a plant, e.g., *Galanthus nivalis agglutinin* (GNA) from the *Galanthus* (snowdrop) plant, and peanut lectin. In some embodiments, pentraxin family members, e.g., C-reactive protein, can also be used as a carbohydrate-binding protein. Pentraxin family members can generally bind capsulated microbes. The carbohydrate-binding proteins can be wild-type, recombinant or a fusion protein. The respective carbohydrate recognition domains for such carbohydrate-binding proteins are known in the art, and can be modified for various embodiments of the engineered microbe-targeting molecules described herein. In some embodiments, peptidomimetics or any structural mimics mimicking a microbe surface-binding domain (e.g., a carbohydrate recognition domain or a fragment thereof) and capable of binding to a microbe surface can also be used as a microbe surface-binding domain described herein.

The term "lectin" as used herein refers to any molecules including proteins, natural or genetically modified (e.g., recombinant), that interact specifically with saccharides (e.g., carbohydrates). The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and *Galanthus nivalis agglutinin* (GNA) from the *Galanthus* (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the carbohydrate recognition domain can be derived from a C-type lectin, or a fragment thereof. C-type lectin can include any carbohydrate-binding protein that requires calcium for binding. In some embodiments, the C-type lectin can include, but are not limited to, collectin, DC-SIGN, and fragments thereof. Without wishing to be bound by theory, DC-SIGN can generally bind various microbes by recognizing high-mannose-containing glycoproteins on their envelopes and/or function as a receptor for several viruses such as HIV and Hepatitis C.

Collectins are soluble pattern recognition receptors (PRRs) belonging to the superfamily of collagen containing C-type lectins. Exemplary collectins include, without limitations, mannose-binding lectin (MBL) (also known as mannan-binding lectin, mannan-binding protein, or mannose-binding protein), surfactant protein A (SP-A), surfactant protein D (SP-D), collectin liver 1 (CL-L1), collectin placenta 1 (CL-P1), conglutinin, collectin of 43 kDa (CL-43), collectin of 46 kDa (CL-46), and a fragment thereof.

Mannose-binding lectin (MBL), also known as mannose binding protein (MBP), or mannan-binding lectin or mannan-binding protein, is a calcium-dependent serum protein that can play a role in the innate immune response by binding to carbohydrates on the surface of a wide range of microbes or pathogens (viruses, bacteria, fungi, protozoa) where it can activate the complement system. MBL can also serve as a direct opsonin and mediate binding and uptake of pathogens by tagging the surface of a pathogen to facilitate recognition and ingestion by phagocytes.

MBL is a member of the collectin family of proteins. A native MBL is a multimeric structure (e.g., about 650 kDa) composed of subunits, each of which contains three identical polypeptide chains (FIG. 1A). Each MBL polypeptide chain (containing 248 amino acid residues in length with a signal sequence: SEQ ID NO. 1) comprises a N-terminal cysteine rich region, a collagen-like region, a neck region, and a carbohydrate recognition domain (CRD). The sequence of each region has been identified and is well known in the art. SEQ ID NO. 2 shows a full-length amino acid sequence of MBL without a signal sequence.

The surface or carbohydrate recognition function of a native MBL is mediated by clusters of three C-type carbohydrate-recognition domains (CRDs) held together by coiled-coils of a-helices. The N-terminal portion collagen-like domain is composed of Gly-X-Y triplets. The short N-terminal domain contains several cysteine residues that form interchain disulfide bonds. Serum MBLs assemble into larger forms containing 2-4 trimeric subunits in rodents and as many as six subunits in humans. All three oligomeric forms of rat serum MBP, designated MBPA, can fix complement, although the larger oligomers have higher specific activity. Many species express a second form of MBP. In rats, the second form, MBP-C, is found in the liver. MBP-C does not form higher oligomers beyond the simple subunit that contains three polypeptides.

When a native MBL interacts with carbohydrates on the surface of microbes or pathogens, e.g., calcium-dependent binding to the carbohydrates mannose, N-acetylglucosamine, and/or fucose, it can form the pathogen recognition component of the lectin pathway of complement activation. The MBL binds to surface arrays containing repeated mannose or N-acetylglucosamine residues. It circulates as a complex with one or more MBP-associated serine proteases (MASPs) that autoactivate when the complex binds to an appropriate surface. The MBL and associated MASP proteins can activate C2/C4 convertase leading to the deposition of C4 on the pathogen surface and opsonization for phagocytosis. The native MBL can also activate coagulation function through MASP proteins.

While native MBL can detect microbes or pathogens and act as opsonins for tagging the microbes for phagocytosis, native MBLs may not be desirable for use in treatment of microbe-induced inflammatory diseases or infections, e.g., sepsis, because native MBLs can activate complement system and induce an inflammatory response. Provided herein is an engineered MBL molecule that binds to microbes or pathogens, comprising at least one carbohydrate recognition domain or a fragment thereof, e.g., derived from MBL. In some embodiments, the engineered MBL molecule can comprises at least two, at least three or at least four carbohydrate recognition domains or a fragment thereof. In some embodiments, the engineered MBL molecules do not activate complement system or coagulation side effects that are present in a native MBL. Such embodiments can be used as dominant-negative inhibitors of downstream responses in vivo or as microbe-binding proteins that do not induce coagulation or complement fixation in vitro. For example, the engineered MBL molecules that do not have complement fixation and/or coagulation domains can act as a dominant negative protein in terms of activating cytokine and/or inflammatory cascades, and thus reduce system inflammatory syndrome and/or sepsis symptons.

FIG. 1B shows a diagrammatic view of a dimeric engineered MBL molecule 100 according to one or more embodiments of the engineered MBL molecules described herein. The dimeric molecule 100 comprises at least two carbohydrate recognition domains 102 (e.g., MBL CRD) connected, directly or indirectly, to a linker, e.g., a Fc region 106. The N-terminal of the Fc region 106 can further comprise an oligopeptide 108, e.g., comprising an amino acid sequence AKT. In some embodiments, the carbohydrate recognition domains 102 can further comprise neck regions 104 such as MBL neck to provide flexibility of the CRD interacting with microbes.

The full-length amino acid sequence of carbohydrate recognition domain (CRD) of MBL is shown in SEQ ID NO. 4. The carbohydrate recognition domain of an engineered MBL described herein can have an amino acid sequence of about 10 to about 300 amino acid residues, or about 50 to about 160 amino acid residues. In some embodiments, the microbe surface-binding domain can have an amino acid sequence of at least about 5, at least about 10, at least about 15, at least about 20, at least about 30, at least about 40, at least about 50, at least about 60, at least about 70, at least about 80, at least about 90, at least about 100, at least about 150 amino acid residues or more. Accordingly, in some embodiments, the carbohydrate recognition domain of the engineered MBL molecule can comprise SEQ ID NO. 4. In some embodiments, the carbohydrate recognition domain of the engineered MBL molecule can comprise a fragment of SEQ ID NO. 4. Exemplary amino acid sequences of such fragments include, but are not limited to, ND (SEQ ID NO. 10), EZN (SEQ ID NO. 11: where Z is any amino acid, e.g., P), NEGEPNNAGS (SEQ ID NO. 12) or a fragment thereof comprising EPN, GSDEDCVLL (SEQ ID NO. 13) or a fragment thereof comprising E, and LLLKNGQWND-VPCST (SEQ ID NO. 14) or a fragment thereof comprising ND. Modifications to such CRD fragments, e.g., by conservative substitution, are also within the scope described herein. In some embodiments, the MBL or a fragment thereof used in the microbe surface-binding domain of the engineered microbe-targeting molecules described herein can be a wild-type molecule or a recombinant molecule.

The exemplary sequences provided herein for the carbohydrate recognition domain of the engineered microbe-targeting molecules are not construed to be limiting. For example, while the exemplary sequences provided herein are derived from a human species, amino acid sequences of the same carbohydrate recognition domain in other species such as mice, rats, porcine, bovine, feline, and canine are known in the art and within the scope described herein.

In some embodiments, the nucleic acid encodes a carbohydrate recognition domain having greater than 50% homology, including greater than 60%, greater than 70%, greater than 80%, greater than 90% homology or higher, to a fragment of at least 50, at least 60, at least 70, at least 80, at least 90, at least 100, at least 150 contiguous amino acids or more, of any known carbohydrate-binding molecules (e.g., mannose-binding lectins).

The term "carbohydrate recognition domain" as used herein refers to a region, at least a portion of which, can bind to carbohydrates on a surface of microbes or pathogens. For example, as shown in FIG. 1B, the carbohydrate recognition domain, in some embodiments, can encompass MBL CRD 102. However, in some embodiments, the carbohydrate recognition domain can be also construed to encompass a neck region 104 in addition to MBL CRD 102. In some embodiments, the carbohydrate recognition domain can comprise at least about 50% of its domain, including at least about 60%, at least about 70%, at least about 80%, at least about 90% or higher, capable of binding to carbohydrates on a microbe surface. In some embodiments, 100% of the carbohydrate recognition domain can be used to bind to microbes or pathogens. In other embodiments, the carbohydrate recognition domain can comprise additional regions that are not capable of carbohydrate binding, but can have other characteristics or perform other functions, e.g., to provide flexibility to the carbohydrate recognition domain when interacting with microbes or pathogens.

Figure 2:
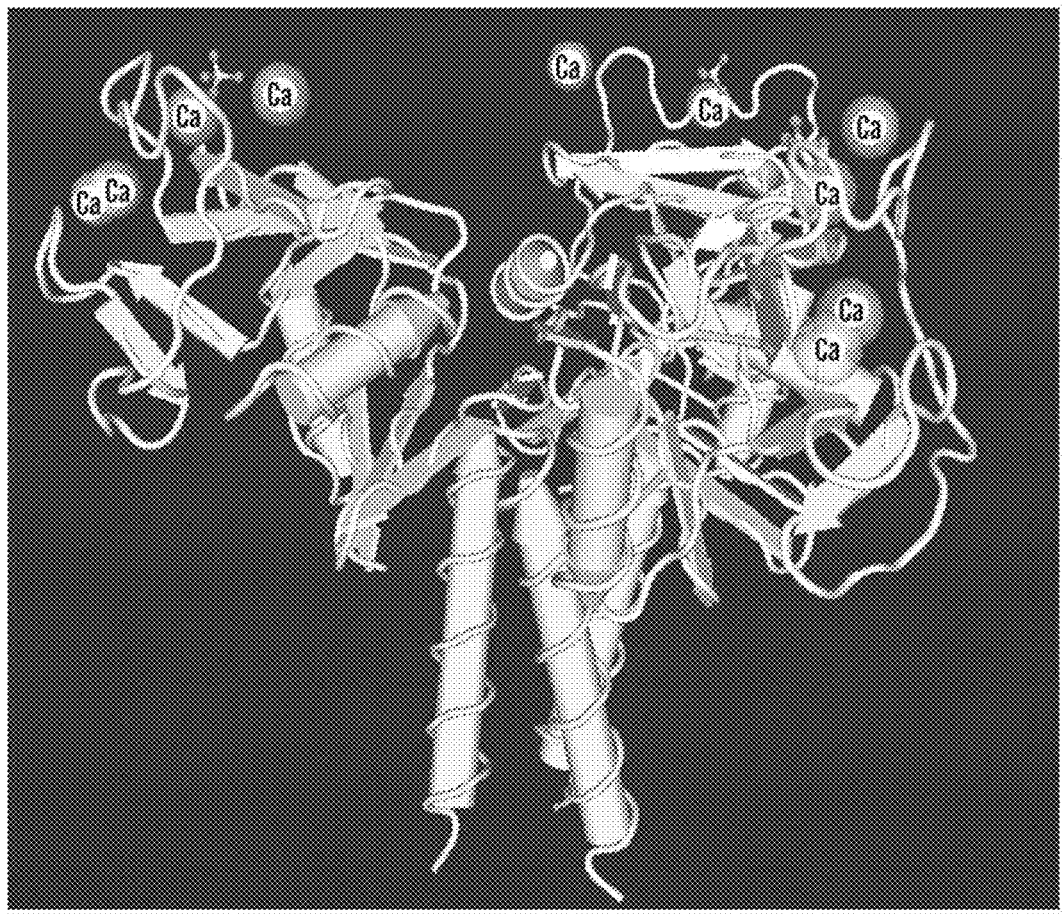
FIG. 2 shows a crystal structure of a portion of a wild-type MBL, which is the "neck and carbohydrate recognition domain (CRD) head." The crystal structure depicts three MBL heads, and calcium binding sites (Chang et al. (1994) J Mol Biol. 241:125-7).

Accordingly, in some embodiments, the carbohydrate recognition domain can further comprise a neck region of the MBL with an amino acid sequence pdgdsslaaserkalqtema rikkwltfslgkq (SEQ ID NO. 15) or a fragment thereof. Without wishing to be bound by theory, the neck region can provide flexibility and proper orientation of the CRD to bind to a microbe surface. In some embodiments, the carbohydrate recognition domain can comprises a full-length CRD of MBL (SEQ ID NO. 4; termed as "CRD head" 102) and the neck region thereof 104, as shown in FIG. 1B. The amino acid sequence encoding a full-length CRD of MBL and the neck region thereof is shown in SEQ ID NO. 5. The crystal structure of a native MBL "neck and CRD head" has been previously shown in Chang et al. (1994) *J Mol Biol.* 241:125-7 (FIG. 2). A skill artisan can readily modify the identified CRD and fragments thereof to modulate its orientation and binding performance to carbohydrates on a microbe surface, e.g., by theoretical modeling and/or in vitro carbohydrate-binding experiments. In addition, based on the crystal structure of the native MBL "neck and CRD head", peptidomimetics that can effectively mimic at least a fragment of the CRD head and optionally the neck region can be also used as a carbohydrate recognition domain of the engineered microbe-targeting molecule or MBL molecule described herein. One of skill in the art can readily determine such peptidomimetic structure without undue experimentations, using any methods known in the art and the known crystal structure.

In some embodiments, the carbohydrate recognition domain of the microbe-targeting molecule can further comprise a portion of a carbohydrate-binding protein. However, in some circumstances, complement or coagulation activation induced by a carbohydrate-binding protein or a fragment thereof can be undesirable depending on various applications, e.g., in vivo administration for treatment of sepsis. In such embodiments, the portion of the carbohydrate-binding protein can exclude at least one of complement and coagulation activation regions. By way of example, when the carbohydrate-binding protein is mannose-binding lectin or a fragment thereof, the mannose-binding lectin or a fragment thereof can exclude at least one of the complement and coagulation activation regions located on the collagen-like region. In such embodiments, the mannose-binding lectin or a fragment thereof can exclude at least about one amino acid residue, including at least about two amino acid residues, at least about three amino acid residues, at least about four amino acid residues, at least about five amino acid residues, at least about six amino acid residues, at least about seven amino acid residues, at least about eight amino acid residues, at least about nine amino acid residues, at least about ten amino acid residues or more, around amino acid residue K55 or L56 of SEQ ID NO. 2. Exemplary amino sequences comprising K55 or L56 of SEQ ID NO. 2 that can be excluded from the engineered MBL molecule include, but are not limited to, EPGQGLRGLQGPPGKLGPPGNPGPSGS (SEQ ID NO. 16), GKLG (SEQ ID NO. 17), GPPGKLGPPGN (SEQ ID NO. 18), RGLQGPPGKL (SEQ ID NO. 19), GKLGPPGN-PGPSGS (SEQ ID NO. 20), GLRGLQGPPGKLGPPGN-PGP (SEQ ID NO. 21), or any fragments thereof.

Further regarding the carbohydrate recognition domain (CRD) or a fragment thereof, its binding characteristics can be manipulated by directed evolution for altered binding specificity. By way of example only, MBL can be modified so that it binds to a more limited set of sugars or other molecular features, with the result that the modified MBL will bind to a more limited set of microbes to provide a capability for pathogen class identification (e.g., one of virus, bacteria, fungi, or protozoan), subclass typing (e.g., gram negative or gram positive bacteria) or specific species determination. Numerous strategies of directed evolution are available in the art.

For example, a straightforward directed evolution strategy visually examines an atomic structure of MBL complexed with a sugar, and then mutates appropriate amino acids that make contact in a sugar-specific manner, so that distinctive contacts are lost or particular types of steric hindrance are created. The three dimensional structure of rat MBL has been solved in a complex with a high-mannose oligosaccharide and with N acetylglucosamine, a methylated fucose, and so on. His189Val and Ile207Val are examples of substitutions that modifications alter specificity.

In another strategy of directed evolution, the protein is subjected to random mutagenesis and the resulting proteins are screened for desired qualities. This is a particularly useful technology for affinity maturation of phage display antibodies, where the antibody complementary determining regions (CDRs) are mutated by saturation mutagenesis and successful variants of the six CDRs are shuffled together to form the highest affinity antibodies.

The directed evolution paradigm can be applied to MBL in order to select MBL variants with specific binding to, e.g., but not limited to, yeast, gram-positive bacteria, gram-negative, coagulase negative, and aerobic bacteria. For this to work, however, the pattern and nature of the target sugars or related surface features on these target microorganisms can differ between the classes or species.

MBL is known to bind strongly to mannose and N-acetylglucosamine sugars on fungi, gram-positive, and gram-negative bacteria. For example, MBL binds strongly to *Candida* spp., *Aspergillus fumigatus, Staphylococcus aureus*, and β hemolytic group A streptococci. MBL has intermediate affinity to *Escherichia coli, Klebsiella* spp., and *Haemophilus* influenzae type b. MBL binds weakly to β hemolytic group B *streptococci, Streptococcus pneumoniae*, and *Staphylococcus epidermidis*. Neth et al., 68 *Infect. & Immun.* 688 (2000). The capsular polysaccharide of *Neisseria meningitides* serogroup B, *H. influenzae* type b and *Cryptococcus neoformans* are thought to decrease MBL binding, as does bacterial endotoxin. Id.; Van Emmerik et al., 97 *Clin. Exp. Immunol.* 411 (1994); Schelenz et al., 63 *Infect. Immun.* 3360 (1995).

Others have reported that MBL facilitates opsonophagocytosis of yeasts but not of bacteria, despite MBL binding: MBL (Lectin) pathway of complement was critical for the opsonophagocytosis of yeast, but the classical complement pathway was critical for opsonophagocytosis of bacteria. Brouwer et al., 180 *J. Immunol.* 4124 (2008). It was not reported that MBL bound to the bacterial species tested, however, only that MBL binding did not promote significant complement activation and opsonophagocytosis.

Derivatives of MBL with a particular specificity can be isolated, e.g., by the following approach, which is a standard phage display strategy: First, express a set of MBL variants from a phagemid vector; then bind this library to a target of interest (e.g., *E. coli*) and perform one or two rounds of selection; and then perform a round of negative selection against a related target (e.g., *Candida*), taking those phagemids that fail to bind. These cycles of positive and negative selection are then repeated until a population of phages that generally bind to the target and do not bind to the non-target is generated. This method can be applied to any pair of microbial strains against which differential binding is desired, such as bacteria that are resistant and sensitive to a given antibiotic. This positive/negative enrichment strategy can also be used with an antibody-phage display library, which is an even more standard way to isolate such specific binders.

The directed evolution and selection approach described above also can potentially be used to generate human antibody fragments or peptides that provide the class, subclass and species specificity described above.

In some embodiments, at least two microbe surface-binding domains (e.g., carbohydrate recognition domains), including at least three, at least four, at least five, at least six, at least seven, at least eight, at least nine, at least ten or more microbe surface-binding domains, can be linked together to form a multimeric microbe surface-binding domain or carbohydrate recognition domain. In such embodiments, the distances between microbe surface-binding domains (e.g., carbohydrate recognition domains) can be engineered to match with the distance between the binding sites on the target microbe surface.

A multimeric microbe surface-binding domain can have each of the individual microbe surface-binding domains the same. Alternatively, a multimeric microbe surface-binding domain can have at least one, at least two, or at least three microbe surface-binding domains different from the rest. In such embodiments, microbe surface-binding domains that share a common binding specificity for carbohydrates on a microbe surface can be used. By way of example only, the fibrinogen-like domain of several lectins has a similar function to the CRD of C-type lectins including MBL, and function as pattern-recognition receptors to discriminate pathogens from self. One of such lectins comprising the fibrinogen-like domain is serum ficolins.

Serum ficolins have a common binding specificity for GlcNAc (N-acetyl-glucosamine), elastin or GalNAc (N-acetyl-galactosamine). The fibrinogen-like domain is responsible for the carbohydrate binding. In human serum, two types of ficolin, known as L-ficolin (also called P35, ficolin L, ficolin 2 or hucolin) and H-ficolin (also called Hakata antigen, ficolin 3 or thermolabile b2-macroglycoprotein), have been identified, and both of them have lectin activity. L-ficolin recognises GlcNAc and H-ficolin recognises GalNAc. Another ficolin known as M-ficolin (also called P3 5-related protein, ficolin 1 or ficolin A) is not considered to be a serum protein and is found in leucocytes and in the lungs. L-ficolin and H-ficolin activate the lectin-complement pathway in association with MASPs. M-Ficolin, L-ficolin and H-ficolin has calcium-independent lectin activity. Accordingly, in some embodiments, an engineered microbe-targeting, e.g., an engineered MBL molecule, can comprise MBL and L-ficolin carbohydrate recognition domains, MBL and H-ficolin carbohydrate recognition domains, or a combination thereof.

Any art-recognized recombinant carbohydrate-binding proteins or carbohydrate recognition domains can also be used in the engineered microbe-targeting molecules. For example, recombinant mannose-binding lectins, e.g., but not limited to, the ones disclosed in the U.S. Pat. Nos. 5,270,199; 6,846,649; and U.S. Patent Application No. US 2004/0229212, the contents of which are incorporated herein by reference, can be used in constructing the engineered MBL molecules described herein.

In one embodiment, the microbe-binding molecule comprises an MBL, a carbohydrate recognition domain of an MBL, or a genetically engineered version of MBL (FcMBL) as described in International Application No. WO 2011/090954, filed Jan. 19, 2011, the content of both of which is incorporated herein by reference. Amino acid sequences for MBL and engineered MBL include, but are not limited to:

```
(i) MBL full length (SEQ ID NO. 1):
MSLFPSLPLL LLSMVAASYS ETVTCEDAQK TCPAVIACSS

PGINGFPGKD GRDGTKGEKG EPGQGLRGLQ GPPGKLGPPG

NPGPSGSPGP KGQKGDPGKS PDGDSSLAAS ERKALQTEMA

RIKKWLTFSL GKQVGNKFFL TNGEIMTFEK VKALCVKFQA

SVATPRNAAE NGAIQNLIKE EAFLGITDEK TEGQFVDLTG

NRLTYTNWNE GEPNNAGSDE DCVLLLKNGQ WNDVPCSTSH

LAVCEFPI (ii) MBL without the signal sequence
(SEQ ID NO. 2):
ETVTCEDAQK TCPAVIACSS PGINGFPGKD GRDGTKGEKG

EPGQGLRGLQ GPPGKLGPPG NPGPSGSPGP KGQKGDPGKS

PDGDSSLAAS ERKALQTEMA RIKKWLTFSL GKQVGNKFFL

TNGEIMTFEK VKALCVKFQA SVATPRNAAE NGAIQNLIKE

EAFLGITDEK TEGQFVDLTG NRLTYTNWNE GEPNNAGSDE

DCVLLLKNGQ WNDVPCSTSH LAVCEFPI (iii) Truncated MBL (SEQ ID NO. 3):
AASERKALQT EMARIKKWLT FSLGKQVGNK FFLTNGEIMT

FEKVKALCVK FQASVATPRN AAENGAIQNL IKEEAFLGIT

DEKTEGQFVD LTGNRLTYTN WNEGEPNNAG SDEDCVLLLK

NGQWNDVPCS TSHLAVCEFP I (iv) Carbohydrate recognition domain (CRD) of MBL
(SEQ ID NO. 4):
VGNKFFLTNG EIMTFEKVKA LCVKFQASVA TPRNAAENGA

IQNLIKEEAF LGITDEKTEG QFVDLTGNRL TYTNWNEGEP

NNAGSDEDCV LLLKNGQWND VPCSTSHLAV CEFPI (v) Neck + Carbohydrate recognition domain
of MBL (SEQ ID NO. 5):
PDGDSSLAAS ERKALQTEMA RIKKWLTFSL GKQVGNKFFL

TNGEIMTFEK VKALCVKFQA SVATPRNAAE NGAIQNLIKE

EAFLGITDEK TEGQFVDLTG NRLTYTNWNE GEPNNAGSDE

DCVLLLKNGQ WNDVPCSTSH LAVCEFPI (vi) FcMBL.81 (SEQ ID NO. 6):
EPKSSDKTHT CPPCPAPELL GGPSVFLFPP KPKDTLMISR

TPEVTCVVVD VSHEDPEVKFNWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTPPVLDSDGSFF LYSKLTVDKS

RWQQGNVFSC SVMHEALHNH YTQKSLSLSP

GAPDGDSSLAASERKALQTE MARIKKWLTF SLGKQVGNKF

FLTNGEINITF EKVKALCVKF QASVATPRNA AENGAIQNLI

KEEAFLGITD EKTEGQFVDL TGNRLTYTNW NEGEPNNAGS

DEDCVLLLKN GQWNDVPCST SHLAVCEFPI (vii) AKT-FcMBL (SEQ ID NO. 7):
AKTEPKSSDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GAPDGDSSLA

ASERKALQTE MARIKKWLTF SLGKQVGNKF FLTNGEIMTF

EKVKALCVKF QASVATPRNA AENGAIQNLI KEEAFLGITD

EKTEGQFVDL TGNRLTYTNW NEGEPNNAGS DEDCVLLLKN

GQWNDVPCST SHLAVCEFPI (viii) FcMBL.111 (SEQ ID NO. 8):
EPKSSDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GATSKQVGNKF

FLTNGEEVITF EKVKALCVKF QASVATPRNA AENGAIQNLI

KEEAFLGITD EKTEGQFVDL TGNRLTYTNW NEGEPNNAGS

DEDCVLLLKN GQWNDVPCST SHLAVCEFPI
```

In some embodiments, a microbe-binding molecule comprises an amino acid sequence selected from SEQ ID NO. 1-SEQ ID NO. 8.

Without wishing to be bound by a theory, microbe-binding molecules comprising lectins or modified versions thereof can act as broad-spectrum pathogen binding molecules. Accordingly, microbes and/or microbial matter present in a test sample can be captured using lectin-based microbe-binding molecules without identifying the microbe.

Linkers

As used herein, the term "linker" generally refers to a molecular entity that can directly or indirectly connect at two parts of a composition, e.g., at least one microbe surface-binding domain and at least one substrate-binding domain. In some embodiments, the linker can directly or indirectly connect to one or more microbe surface-binding domains. Without limitations, in some embodiments, the linker can also provide binding sites to one or more microbes and/or microbial matter. In such embodiments, the microbe-binding sites on the linker can bind to the same types and/or species of microbes as the microbes bind to a microbe-surface-binding domain. Alternatively or additionally, the microbe-binding sites on the linker can capture different types and/or species of microbes than the ones that bind to a microbe surface-binding domain described herein.

Linkers can be configured according to a specific need, e.g., based on at least one of the following characteristics. By way of example only, in some embodiments, linkers can be configured to have a sufficient length and flexibility such that it can allow for a microbe surface-binding domain to orient accordingly with respect to at least one carbohydrate on a microbe surface. In some embodiments, linkers can be configured to allow multimerization of at least two engineered microbe-targeting molecules (e.g., to from a di-, tri-, tetra-, penta-, or higher multimeric complex) while retaining biological activity (e.g., microbe-binding activity). In some embodiments, linkers can be configured to facilitate expression and purification of the engineered microbe-targeting molecule described herein. In some embodiments, linkers can be configured to provide at least one recognition site for proteases or nucleases. In addition, linkers are preferably non-reactive with the functional components of the engineered molecule described herein (e.g., minimal hydrophobic or charged character to react with the functional protein domains such as a microbe surface-binding domain or a substrate-binding domain).

In some embodiments, a linker can be configured to have any length in a form of a peptide, peptidomimetic, an aptamer, a protein, a nucleic acid (e.g., DNA or RNA), or any combinations thereof. In some embodiments, the peptidyl or nucleic acid linker can vary from about 1 to about 1000 amino acids long, from about 10 to about 500 amino acids long, from about 30 to about 300 amino acids long, or from about 50 to about 150 amino acids long. Longer or shorter linker sequences can be also used for the engineered microbe-targeting molecules described herein. In one embodiment, the peptidyl linker has an amino acid sequence of about 200 to 300 amino acids in length.

In some embodiments, a peptide or nucleic acid linker can be configured to have a sequence comprising at least one of the amino acids selected from the group consisting of glycine (Gly), serine (Ser), asparagine (Asn), threonine (Thr), methionine (Met) or alanine (Ala), or at least one of codon sequences encoding the aforementioned amino acids (i.e., Gly, Ser, Asn, Thr, Met or Ala). Such amino acids and corresponding nucleic acid sequences are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp), or nucleic acid sequences encoding the amino acids thereof can also be included in a linker sequence. In alternative embodiments, polar amino acids or nucleic acid sequence thereof can be added to modulate the flexibility of a linker. One of skill in the art can control flexibility of a linker by varying the types and numbers of residues in the linker. See, e.g., Perham, 30 *Biochem.* 8501 (1991); Wriggers et al., 80 *Biopolymers* 736 (2005).

In alternative embodiments, a linker can be a chemical linker of any length. In some embodiments, chemical linkers can comprise a direct bond or an atom such as oxygen or sulfur, a unit such as NH, C(O), C(O)NH, SO, $SO_2$, $SO_2$NH, or a chain of atoms, such as substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{12}$ aryl, substituted or unsubstituted $C_5$-$C_{12}$ heteroaryl, substituted or unsubstituted $C_5$-$C_{12}$ heterocyclyl, substituted or unsubstituted $C_3$-$C_{12}$ cycloalkyl, where one or more methylenes can be interrupted or terminated by O, S, S(O), $SO_2$, NH, or C(O). In some embodiments, the chemical linker can be a polymer chain (branched or linear).

Figure 3:
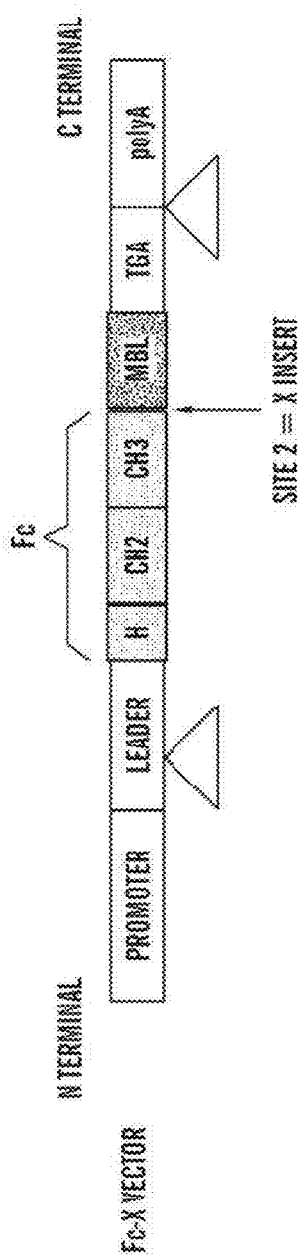
FIG. 3 is a schematic diagram showing an exemplary Fc-X vector construct for one or more embodiments of the engineered microbe-targeting or microbe-binding molecules described herein.

In some embodiments where the linker is a peptide, such peptidyl linker can comprise at least a portion of an immunoglobulin, e.g., IgA, IgD, IgE, IgG and IgM including their subclasses (e.g., IgG1), or a modified molecule or recombinant thereof. In some embodiments, the peptide linker can comprise a portion of fragment crystallization (Fc) region of an immunoglobulin or a modified thereof. In such embodiments, the portion of the Fc region that can be used as a linker can comprise at least one region selected from the group consisting of a hinge region, a CH2 region, a CH3 region, and any combinations thereof. By way of example, in some embodiments, a CH2 region can be excluded from the portion of the Fc region as a linker. In one embodiment, Fc linker comprises a hinge region, a CH2 domain and a CH3 domain, e.g., Fc IgG 106 as shown in FIG. 1B and FIG. 3. Such Fc linker can be used to facilitate expression and purification of the engineered microbe-targeting molecules described herein. The N terminal Fc has been shown to improve expression levels, protein folding and secretion of the fusion partner. In addition, the Fc has a staphylococcal protein A binding site, which can be used for one-step purification protein A affinity chromatography. See Lo K M et al. (1998) *Protein Eng.* 11: 495-500. Further, the protein A binding site can be used to facilitate binding of protein A-expressing or protein G-expressing microbes in the absence of calcium ions. Such binding capability can be used to develop methods for distinguishing protein A-expressing microbes (e.g., *S. aureus*) from non-protein A-expressing or non-protein G-expressing microbes (e.g., *E. coli*) present in a test sample, and various embodiments of such methods will be described in detail later. Further, such Fc linker have a molecule weight above a renal threshold of about 45 kDa, thus reducing the possibility of engineered microbe-targeting molecules being removed by glomerular filtration. Additionally, the Fc linker can allow dimerization of two engineered microbe-targeting molecules to form a dimer, e.g., the dimeric engineered MBL molecule 100 as shown in FIG. 1B.

In some embodiments where the linker comprises a Fc region or a fragment thereof, the Fc region or a fragment thereof can comprise at least one mutation, e.g., to modify the performance of the engineered microbe-targeting molecules. For example, in some embodiments, a half-life of the engineered microbe-targeting molecules described herein can be increased, e.g., by mutating an amino acid lysine (K) at the residue 232 of SEQ ID NO. 9 to alanine (A). Other mutations, e.g., located at the interface between the CH2 and CH3 domains shown in Hinton et al (2004) *J Biol Chem.*

279:6213-6216 and Vaccaro C. et al. (2005) *Nat Biotechnol.* 23: 1283-1288, can be also used to increase the half-life of the IgG1 and thus the engineered microbe-targeting molecules.

In some embodiments, the linker can be albumin, transferrin or a fragment thereof. Such linkers can be used to extend the plasma half-life of the engineered microbe-targeting molecules and thus are good for in vivo administration. See Schmidt S R (2009) *Curr Opin Drug Discov Devel.* 12: 284.

When the engineered microbe-targeting molecules are used as therapeutics in vivo, the linker can be further modified to modulate the effector function such as antibody-dependent cellular cytotoxicity (ADCC) and complement-dependent cytotoxicity (CDC). By way of example only, the Fc region for use as a linker can mediate ADCC and CDC. In ADCC, the Fc region can generally bind to Fc receptors on the surface of immune effector cells such as natural killers and macrophages, leading to the phagocytosis or lysis of a targeted cell. In CDC, the Fc region can generally trigger the complement cascade at the cell surface to kill the targeted cell. Accordingly, modulating effector functions can be achieved by engineering the Fc region to either increase or decrease their binding to the Fc receptors on the surface of the immune effector cells or the complement factors. For example, numerous mutations within a Fc region for modulating ADCC and CDC are well known to a skilled artisan, e.g., see Armour K L. et al. (1999) *Eur J Immmunol* 29: 2613-2624; Shields R L. et al. (2001) *J Biol Chem.* 276: 6591-6604; Idusogie E E. et al. (2001) *J Immunol.* 166: 2571-2575; Idusogie E E. et al. (2000) *J Immunol.* 155: 1165-1174; and Steurer W. et al. (1995) *J Immunol.* 155: 1165-1674. In one embodiment, the amino acid asparagine (N) at the residue 82 of the SEQ ID NO. 6 can be mutated to aspartic acid (D), e.g., to remove the glycosylation of Fc and thus, in turn, reduce ADCC and CDC functions.

In various embodiments, the N-terminus or the C-terminus of the linker, e.g., the portion of the Fc region, can be modified. By way of example only, the N-terminus or the C-terminus of the linker can be extended by at least one additional linker described herein, e.g., to provide further flexibility, or to attach additional molecules. In some embodiments, the N-terminus of the linker can be linked directly or indirectly (via an additional linker) with a substrate-binding domain adapted for orienting the carbohydrate recognition domain away from the substrate.

In some embodiments, the linker can be embodied as part of the microbe surface-binding domain, or part of the carbohydrate-binding protein (e.g., MBL and/or the neck region thereof).

In some embodiments, the linker can be a physical substrate, e.g., microparticles or magnetic microbes, to which a plurality of microbe surface-binding domains (including carbohydrate recognition domain) can bind, provided that there is at least a certain distance between the microbe surface-binding domain and the substrate surface sufficient for the microbe surface-binding domain to interact effectively with microbes. In some embodiments, the distance between the microbe surface-binding domain and the substrate can range from about 50 angstroms to about 5000 angstroms, from about 100 angstroms to about 2500 angstroms, or from about 200 angstroms to about 1000 angstroms.

The linkers can be of any shape. In some embodiments, the linkers can be linear. In some embodiments, the linkers can be folded. In some embodiments, the linkers can be branched. For branched linkers, each branch of a microbe surface-binding domain can comprise at least one microbe surface-binding domain. In other embodiments, the linker adopts the shape of the physical substrate.

In some embodiments provided herein, the linker can further comprise a detectable label. In some embodiments, the detectable label can be a chromogenic or fluorogenic microbe enzyme substrate so that when a microbe binds to the engineered microbe-targeting molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-deoxyglucopyranoside, and any other art-recognized microbe enzyme substrates. Such embodiments can act as an indicator for the presence of a microbe or pathogen.

Conjugation of Engineered Microbe-Targeting Molecules to a Substrate

The engineered microbe-targeting molecules can be immobilized on any substrate for various applications and/or purposes. For example, when the affinity of a single microbe surface-binding domain for a target molecule (e.g., a carbohydrate recognition domain for a sugar/carbohydrate molecule) is relatively low, and such binding is generally driven by avidity and multivalency, multivalency of such engineered microbe-targeting molecules can be effectively increased by attachment of a plurality of the engineered microbe-targeting molecules (e.g., each with one or two or more carbohydrate recognition domains) to a solid substrate (e.g., a nanometer- or micrometer-sized bead) at a high density, which can be varied to provide optimal functionality. Alternatively, the engineered microbe-targeting molecules can be immobilized on a solid substrate for easy handling during usage, e.g., for isolation, observation or microscopic imaging.

The attachment of the engineered microbe-binding molecule (e.g., FcMBL) to a substrate surface (e.g., membrane surface, glass surface, tubing surface) can be performed with multiple approaches, for example, by direct cross-linking the engineered microbe-binding molecule (e.g., FcMBL) to the substrate surface; cross-linking the engineered microbe-binding molecule (e.g., FcMBL) to the substrate surface via a nucleic acid matrix (e.g., DNA matrix or DNA/oligonucleotide origami structures) for orientation and concentration to increase detection sensitivity; cross-linking FcMBL to the substrate surface via a dendrimer-like structure (e.g., PEG/Chitin-structure) to increase detection sensitivity; attracting FcMBL-coated magnetic microbeads to the substrate surface with a focused magnetic field gradient applied to the substrate surface, attaching an engineered microbe-binding molecule (e.g., FcMBL) to a substrate via biotin-avidin or biotin-avidin-like interaction, or any other art-recognized methods.

For engineered microbe-targeting molecules or mannose-binding lectin molecules to be immobilized on or conjugated to a substrate, the engineered molecules described herein can further comprise at least one (e.g., one, two, three, four, five, six, seven, eight, nine, ten, eleven, twelve, thirteen, fourteen, fifteen, sixteen, seventeen, eighteen, nineteen, twenty or more) substrate-binding domain, e.g., adapted for orienting the carbohydrate recognition domain away from the substrate. Without limitations, exemplary types of substrates can be a nucleic acid scaffold, a biological molecule (e.g., a living cell), or a solid surface. In some embodiments, the solid surface can be functionalized with a coupling molecule, e.g., an amino group, to facilitate the conjugation of engineered microbe surface-binding domains to the solid surface.

As used herein, the term "substrate-binding domain" refers to any molecule that facilitates the conjugation of the engineered molecules described herein to a substrate or a functionalized substrate. In some embodiments, the substrate-binding domain can comprise at least one amino group that can non-convalently or covalently coupled with functional groups on the surface of the substrate. For example, the primary amines of the amino acid residues (e.g., lysine or cysteine residues) at the N-terminus or in close proximity to the N-terminus of the engineered microbe surface-binding domains (e.g., engineered mannose-binding lectins) can be used to couple with functional groups on the substrate surface.

In some embodiments, the substrate-binding domain can comprise at least one, at least two, at least three or more oligopeptides. The length of the oligonucleotide can vary from about 2 amino acid residues to about 10 amino acid residues, or about 2 amino acid residues to about 5 amino acid residues. Determination of an appropriate amino acid sequence of the oligonucleotide for binding with different substrates is well within one of skill in the art. For example, as shown in FIG. 1B, according to one or more embodiments, the substrate-binding domain 108 can comprise an oligopeptide comprising an amino acid sequence of AKT, which provides a single biotinylation site for subsequent binding to streptavidin-coated substrate, e.g., a magnetic microbead 110. Such single biotinylation site can also enable the carbohydrate recognition domain of an engineered microbe surface-binding domain to orient away from the substrate, and thus become more accessible to microbes or pathogens. See, e.g., Witus et al. (2010) *JACS* 132: 16812.

In some embodiments, the substrate-binding domain can comprise at least one oligonucleotide. The sequence and length of the oligonucleotides can be configured according to the types of the substrate, binding density, and/or desired binding strength. For example, if the substrate is a nucleic acid scaffold, e.g., a DNA scaffold, the oligonucleotide sequence of the substrate-binding domain can be designed such that it is complementary to a sub-sequence of the nucleic acid scaffold to where the substrate-binding domain can hybridize.

In some embodiments, the oligonucleotides can include aptamers. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art. The oligonucleotides including aptamers can be of any length, e.g., from about 1 nucleotide to about 100 nucleotides, from about 5 nucleotides to about 50 nucleotides, or from about 10 nucleotides to about 25 nucleotides. Generally, a longer oligonucleotide for hybridization to a nucleic acid scaffold can generate a stronger binding strength between the engineered microbe surface-binding domain and substrate.

Alternatively or additionally, the surface of a substrate can be functionalized to include coupling molecules described herein. As used herein, the term "coupling molecule" refers to any molecule or any functional group that is capable of selectively binding with an engineered microbe surface-binding domain described herein. Representative examples of coupling molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The coupling molecules need not comprise an entire naturally occurring molecule but may consist of only a portion, fragment or subunit of a naturally or non-naturally occurring molecule, as for example the Fab fragment of an antibody. The coupling molecule can further comprise a detectable label. The coupling molecule can also encompass various functional groups that can couple the substrate to the engineered microbe surface-binding domains. Examples of such functional groups include, but are not limited to, an amino group, a carboxylic acid group, an epoxy group, and a tosyl group.

In some embodiments, the engineered microbe-targeting molecule can be conjugated to a substrate surface through a covalent or non-covalent interaction. The engineered microbe-targeting molecule and/or coupling molecule can be conjugated to the surface of a solid substrate covalently or non-covalently using any of the methods known to those of skill in the art. For example, covalent immobilization can be accomplished through, for example, silane coupling. See, e.g., Weetall, 15 *Adv. Mol. Cell Bio.* 161 (2008); Weetall, 44 *Meths. Enzymol.* 134 (1976). The covalent interaction between the engineered microbe-targeting molecule and/or coupling molecule and the surface can also be mediated by other art-recognized chemical reactions, such as NHS reaction or a conjugation agent. The non-covalent interaction between the engineered microbe-targeting molecule and/or coupling molecule and the surface can be formed based on ionic interactions, van der Waals interactions, dipole-dipole interactions, hydrogen bonds, electrostatic interactions, and/or shape recognition interactions.

Without limitations, conjugation can include either a stable or a labile (e.g. cleavable) bond or conjugation agent. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, cyclodextrin/adamantly host guest interaction) and the like.

As used herein, the term "conjugation agent" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, $C(O)N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

Without limitations, any conjugation chemistry known in the art for conjugating two molecules or different parts of a composition together can be used for linking at least one engineered microbe-targeting molecule to a substrate. Exemplary coupling molecules and/or functional groups for conjugating at least one engineered microbe-targeting molecule to a substrate include, but are not limited to, a polyethylene glycol (PEG, $NH_2$-$PEG_X$-COOH which can have a PEG spacer arm of various lengths X, where 1<X<100, e.g., PEG-2K, PEG-5K, PEG-10K, PEG-12K, PEG-15K, PEG-20K, PEG-40K, and the like), maleimide conjugation agent, PASylation, HESylation, Bis(sulfosuccinimidyl) suberate conjugation agent, DNA conjugation agent, peptide conjugation agent, silane conjugation agent, polysaccharide conjugation agent, hydrolyzable conjugation agent, and any combinations thereof.

In alternative embodiments, the engineered microbe surface-binding domains or the engineered microbe-targeting molecule can be conjugated onto the surface of the solid substrate by a coupling molecule pair. The terms "coupling molecule pair" and "coupling pair" as used interchangeably herein refer to the first and second molecules that specifically bind to each other. One member of the binding pair is conjugated with the solid substrate while the second member is conjugated with the substrate-binding domain of an engineered microbe surface-binding domain. As used herein, the phrase "first and second molecules that specifically bind to each other" refers to binding of the first member of the coupling pair to the second member of the coupling pair with greater affinity and specificity than to other molecules.

Exemplary coupling molecule pairs include, without limitations, any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One example of using coupling pair conjugation is the biotin-avidin or biotin-streptavidin conjugation. In this approach, one of the members of the coupling pair (e.g., a portion of the engineered microbe-targeting molecule such as substrate-binding domain, or a substrate) is biotinylated and the other (e.g., a substrate or the engineered microbe-targeting molecule) is conjugated with avidin or streptavidin. Many commercial kits are also available for biotinylating molecules, such as proteins. For example, an aminooxy-biotin (AOB) can be used to covalently attach biotin to a molecule with an aldehyde or ketone group. In one embodiment, AOB is attached to the substrate-binding domain (e.g., comprising AKT oligopeptide) of the engineered microbe-targeting molecule.

One non-limiting example of using conjugation with a coupling molecule pair is the biotin-sandwich method. See, e.g., Davis et al., 103 PNAS 8155 (2006). The two molecules to be conjugated together are biotinylated and then conjugated together using tetravalent streptavidin. In addition, a peptide can be coupled to the 15-amino acid sequence of an acceptor peptide for biotinylation (referred to as AP; Chen et al., 2 Nat. Methods 99 (2005)). The acceptor peptide sequence allows site-specific biotinylation by the E. coli enzyme biotin ligase (BirA; Id.). An engineered microbe surface-binding domain can be similarly biotinylated for conjugation with a solid substrate. Many commercial kits are also available for biotinylating proteins. Another example for conjugation to a solid surface would be to use PLP—mediated bioconjugation. See, e.g., Witus et al., 132 JACS 16812 (2010). As described earlier, an AKT sequence on the N terminal of the engineered microbe-targeting molecule (e.g., N terminal of the linker between the substrate binding domain and the carbohydrate-binding molecule such as Fc region as described earlier) can allow the substrate binding domain to be biotinylated at a single site and further conjugated to the streptavidin-coated solid surface.

Still another example of using coupling pair conjugation is double-stranded nucleic acid conjugation. In this approach, one of the members of the coupling pair (e.g., a portion of the engineered microbe-targeting molecule such as substrate-binding domain, or a substrate) can be conjugated with a first strand of the double-stranded nucleic acid and the other (e.g., a substrate, or an engineered microbe-targeting molecule) is conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges.

In some embodiments, the linker can comprise at least one cleavable linking group. A cleavable linking group is one which is sufficiently stable under one set of conditions, but which is cleaved under a different set of conditions to release the two parts the linker is holding together. In some embodiments, the cleavable linking group is cleaved at least 10 times or more, e.g., at least 100 times faster under a first reference condition (which can, e.g., be selected to mimic or represent a microbe-infected condition, such as a microbe-infected tissue or body fluid, or a microbial biofilm occurring in an environment) than under a second reference condition (which can, e.g., be selected to mimic or represent non-infected conditions, e.g., found in the non-infected blood or serum, or in an non-infected environment).

Cleavable linking groups are susceptible to cleavage agents, e.g., hydrolysis, pH, redox potential or the presence of degradative molecules. Generally, cleavage agents are more prevalent or found at higher levels or activities at a site of interest (e.g. a microbial infection) than in non-infected area. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell, organ, or tissue to be targeted. In some embodiments, cleavable linking group is cleaved at least 1.25, 1.5, 1.75, 2, 3, 4, 5, 10, 25, 50, or 100 times faster under a first reference condition (or under in vitro conditions selected to mimic a microbe-infected condition, such as a microbe-infected tissue or body fluid, or a microbial biofilm occurring in an environment or on a working surface) than under a second reference condition (or under in vitro conditions selected to mimic non-infected conditions, e.g., found in the non-infected blood or serum, or in an non-infected environment). In some embodiments, the cleavable linking group is cleaved by less than 90%, 80%, 70%, 60%, 50%, 40%, 30%, 20%, 10%, 5%, or 1% in the non-infected conditions, e.g., found in the non-infected blood or serum, or in an non-infected environment, as compared to a microbe-infected condition, such as a microbe-infected tissue or body fluid, or a microbial biofilm occurring in an environment or on a working surface.

Exemplary cleavable linking groups include, but are not limited to, hydrolyzable linkers, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—S—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease. In some embodiments, an acid cleavable linking group is cleavable in an acidic environment with a pH of about 6.5 or lower (e.g., about 6.5, 6.0, 5.5, 5.0, or lower), or by agents such as enzymes that can act as a general acid.

Activation agents can be used to activate the components to be conjugated together (e.g., surface of a substrate). Without limitations, any process and/or reagent known in the art for conjugation activation can be used. Exemplary surface activation method or reagents include, but are not limited to, 1-Ethyl-3-[3-dimethylaminopropyl]carbodiimide hydrochloride (EDC or EDAC), hydroxybenzotriazole (HOBT), N-Hydroxysuccinimide (NHS), 2-(1H-7-Azabenzotriazol-1-yl)-1,1,3,3-tetramethyl uronium hexafluorophosphate methanaminium (HATU), silanization, surface activation through plasma treatment, and the like.

Again, without limitations, any art known reactive group can be used for coupling. For example, various surface reactive groups can be used for surface coupling including, but not limited to, alkyl halide, aldehyde, amino, bromo or iodoacetyl, carboxyl, hydroxyl, epoxy, ester, silane, thiol, and the like.

Exemplary Microbe-Targeting Substrates or Products and Applications Thereof

Some embodiments of the engineered microbe-targeting molecules described herein can be immobilized or conjugated to a surface of various substrates. Accordingly, a further aspect provided herein is a "microbe-targeting substrate" or product for targeting or binding microbes comprising a substrate and at least one engineered microbe-targeting molecule described herein, wherein the substrate comprises on its surface at least one, including at least two, at least three, at least four, at least five, at least ten, at least 25, at least 50, at least 100, at least 250, at least 500, or more engineered microbe-targeting molecules. In some embodiments, the substrate can be conjugated or coated with at least one engineered microbe-targeting molecule, e.g., an engineered mannose-binding lectin as described herein, using any of conjugation methods described earlier or any other art-recognized methods. The terms "microbe-targeting substrate" and "microbe-binding substrate" are used interchangeably herein.

The solid substrate can be made from a wide variety of materials and in a variety of formats. For example, the solid substrate can be utilized in the form of beads (including polymer microbeads, magnetic microbeads, and the like), filters, fibers, screens, mesh, tubes, hollow fibers, scaffolds, plates, channels, other substrates commonly utilized in assay formats, and any combinations thereof. Examples of substrates include, but are not limited to, nucleic acid scaffolds, protein scaffolds, lipid scaffolds, dendrimers, microparticles or microbeads, nanotubes, microtiter plates, medical apparatuses (e.g., needles or catheters) or implants, dipsticks or test strips, microchips, filtration devices or membranes, diagnostic strips, hollow-fiber reactors, microfluidic devices, living cells and biological tissues or organs, extracorporeal devices, mixing elements (e.g., spiral mixers).

The solid substrate can be made of any material, including, but not limited to, metal, metal alloy, polymer, plastic, paper, glass, fabric, packaging material, biological material such as cells, tissues, hydrogels, proteins, peptides, nucleic acids, and any combinations thereof.

The particular format and/or material of the solid substrate depend on the assay application such as separation/detection methods employed in the assay. In some embodiments, the format and/or material of the solid substrate can be chosen or modified to maximize signal-to-noise ratios, e.g., to minimize background binding, and/or for ease of separation of reagents and cost. For example, the surface of the solid substrate can be treated or modified with surface chemistry to minimize chemical agglutination and non-specific binding. In some embodiments, at least a portion of the substrate surface that is in contact with a test sample can be treated to become less adhesive to any molecules (including microbes, if any) present in the test sample. By way of example only, the substrate surface in contact with a test sample can be silanized or coated with a polymer such that the substrate surface is inert to the molecules present in the test sample, including but not limited to, cells or fragments thereof (including blood cells and blood components), proteins, nucleic acids, peptides, small molecules, therapeutic agents, microbes, microorganisms and any combinations thereof. In other embodiments, a substrate surface can be treated with an omniphobic layer, which can allow binding of a microbe by the engineered microbe-targeting molecule without a subsequent hydrophobic binding between the microbe and the substrate surface. See, e.g., Wong T S et al., "Bioinspired self-repairing slippery surfaces with pressure-stable omniphobicity." (2011) *Nature* 477 (7365): 443-447, and International Application No.: PCT/US12/21928, the content of which is incorporated herein by reference, for methods to produce a slippery substrate surface. Accordingly, non-specific binding of molecules from the test sample (including microbes and/or microbial matter) to a substrate surface can be reduced, thus increasing the sensitivity of the microbial detection.

In some embodiments, the solid substrate can be fabricated from or coated with a biocompatible material. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include, for example, derivatives and copolymers of polyimides, poly(ethylene glycol), polyvinyl alcohol, polyethyleneimine, and polyvinylamine, polyacrylates, polyamides, polyesters, polycarbonates, and polystyrenes. In some embodiments, biocompatible materials can include metals, such as titanium and stainless steel, or any biocompatible metal used in medical implants. In some embodiments, biocompatible materials can include paper substrate, e.g., as a substrate for a diagnostic strip. In some embodiments, biocompatible materials can include peptides or nucleic acid molecules, e.g., a nucleic acid scaffold such as a 2-D DNA sheet or 3-D DNA scaffold.

Additional material that can be used to fabricate or coat a solid substrate include, without limitations, polydimethylsiloxane, polyimide, polyethylene terephthalate, polymethylmethacrylate, polyurethane, polyvinylchloride, polystyrene polysulfone, polycarbonate, polymethylpentene, polypropylene, polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

In various embodiments, the substrate can be functionalized with various coupling molecules as described earlier.

As used herein, by the "coating" or "coated" is generally meant a layer of molecules or material formed on an outermost or exposed layer of a substrate surface. With respect to a coating of engineered microbe-targeting molecules on a substrate, the term "coating" or "coated" refers to a layer of engineered microbe-targeting molecules formed on an outermost or exposed layer of a substrate surface. In some embodiments, the substrate surface can encompass an outer substrate surface and/or an inner substrate surface, e.g., with respect to a hollow structure. For example, the inner surface of a needle or catheter can be coated with the engineered microbe-targeting molecules described herein, e.g., for removing any potential microbe contaminants from a fluid before administering the fluid to a subject.

The amount of the engineered microbe-targeting molecules conjugated to or coating on a substrate surface can vary with a number of factors such as a substrate surface area, conjugation/coating density, types of engineered microbe-targeting molecules, and/or binding performance. A skilled artisan can determine the optimum density of engineered microbe-targeting molecules on a substrate surface using any methods known in the art. By way of example only, for magnetic microbeads (including nanobeads) as a substrate (as discussed in detail later), the amount of the engineered microbe-targeting molecules used for conjugating to or coating magnetic microbeads can vary from about 1 wt % to about 30 wt %, or from about 5 wt % to about 20 wt %. In some embodiments, the amount of the engineered microbe-targeting molecules used for conjugating to or coating magnetic microbeads can be higher or lower, depending on a specific need. However, it should be noted that if the amount of the engineered microbe-targeting molecules used for conjugating to or coating the magnetic microbeads is too low, the magnetic microbeads can show a lower binding performance with a pathogen/microbe. On the contrary, if the amount of the engineered microbe-targeting molecules used for conjugating to or coating the magnetic microbeads is too high, the dense layer of the engineered microbe-targeting molecules can exert an adverse influence on the magnetic properties of the magnetic microbeads, which in turn can degrade the efficiency of separating the magnetic microbeads from a fluid utilizing the magnetic field gradient.

Microbe-Targeting Microparticles:

Some embodiments described herein provide a microbe-targeting microparticle comprising at least one engineered microbe-targeting molecule on its surface. The term "microparticle" as used herein refers to a particle having a particle size of about 0.001 µm to about 100 µm, about 0.005 µm to about 50 µm, about 0.01 µm to about 25 µm, about 0.05 µm to about 10 µm, or about 0.05 µm to about 5 µm. In one embodiment, the microparticle has a particle size of about 0.05 µm to about 1 µm. In one embodiment, the microparticle is about 0.09 µm—about 0.2 µm in size. It will be understood by one of ordinary skill in the art that microparticles usually exhibit a distribution of particle sizes around the indicated "size." Unless otherwise stated, the term "size" as used herein refers to the mode of a size distribution of microparticles, i.e., the value that occurs most frequently in the size distribution. Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

The microparticles can be of any shape, e.g., a sphere. In some embodiments, the term "microparticle" as used herein can encompass a microsphere. The term "microsphere" as used herein refers to a microparticle having a substantially spherical form. A substantially spherical microparticle is a microparticle with a difference between the smallest radii and the largest radii generally not greater than about 40% of the smaller radii, and more typically less than about 30%, or less than 20%. In one embodiment, the term "microparticle"

as used herein encompasses a microcapsule. The term "microcapsule" as used herein refers to a microscopic capsule that contains an active ingredient, e.g., a therapeutic agent.

Accordingly, in some embodiments, the microparticles comprising on their surface engineered microbe-targeting molecules can encapsulate at least one active ingredient therein, e.g., a therapeutic agent to treat an infection, and be used as a cell-targeted drug delivery device. In such embodiments, the microparticles can comprise biocompatible polymers as described herein. In some embodiments, the microparticles can further comprise biodegradable polymers, e.g., for releasing the encapsulated drugs.

As used herein, the term "biodegradable" refers to the ability of a composition to erode or degrade in vivo to form smaller chemical fragments. Degradation can occur, for example, by enzymatic, chemical or physical processes. Non-limiting examples of biodegradable polymers that can be used in aspects provided herein include poly(lactide)s, poly(glycolide)s, poly(lactic acid)s, poly(glycolic acid)s, poly (lactide-co-glycolide), polyanhydrides, polyorthoesters, polycaprolactone, polyesteramides, polycarbonate, polycyanoacrylate, polyurethanes, polyacrylate, blends and copolymers thereof.

Other additional biodegradable polymers include biodegradable polyetherester copolymers. Generally speaking, the polyetherester copolymers are amphiphilic block copolymers that include hydrophilic (for example, a polyalkylene glycol, such as polyethylene glycol) and hydrophobic blocks (for example, polyethylene terephthalate). An exemplary block copolymer is, but is not limited to, poly(ethylene glycol)-based and poly(butylene terephthalate)-based blocks (PEG/PBT polymer). PEG/PBT polymers are commercially available from OctoPlus Inc, under the trade designation PolyActive™. Non-limiting examples of biodegradable copolymers or multiblock copolymers include the ones described in U.S. Pat. Nos. 5,980,948 and 5,252,701, the contents of which are incorporated herein by reference.

Other biodegradable polymer materials include biodegradable terephthalate copolymers that include a phosphorus-containing linkage. Polymers having phosphoester linkages, called poly(phosphates), poly(phosphonates) and poly (phosphites), are known in the art. See, for example, Penczek et al., *Handbook of Polymer Synthesis*, Chapter 17: "Phosphorus-Containing Polymers," 1077-1 132 (Hans R. Kricheldorf ed., 1992), as well as U.S. Pat. Nos. 6,153,212; 6,485,737; 6,322,797; 6,600,010; 6,419,709; 6,419,709; 6,485,737; 6,153,212; 6,322,797 and 6,600,010, the contents of which are incorporated herein by reference.

Biodegradable polyhydric alcohol esters can also be used as a material of a substrate (e.g., a microparticle) (See U.S. Pat. No. 6,592,895, which is incorporated herein by reference). In some embodiments, the biodegradable polymer can be a three-dimensional crosslinked polymer network containing hydrophobic and hydrophilic components which forms a hydrogel with a crosslinked polymer structure, such as the one described in U.S. Pat. No. 6,583,219. In yet further embodiments, the biodegradable polymer can comprise a polymer based upon α-amino acids (such as elastomeric copolyester amides or copolyester urethanes, as described in U.S. Pat. No. 6,503,538, which is incorporated herein by reference).

In general, any biocompatible material well known in the art for fabrication of microparticles can be used in embodiments of the microparticle described herein. Accordingly, a microparticle comprising a lipidic microparticle core is also within the scope described herein. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art, e.g., Szoka and Papahadjopoulos (1980) *Ann. Rev. Biophys. Bioeng.* 9: 467, Deamer and Uster (1983) Pp. 27-51 In: *Liposomes*, ed. M. J. Ostro, Marcel Dekker, New York.

Microbe-Targeting Magnetic Microbeads:

In some particular embodiments, provided herein is a "microbe-targeting magnetic microbead" wherein a magnetic microbead comprising on its surface at least one engineered microbe-targeting molecule, e.g., an engineered mannose-binding lectin as described herein. By way of example only, a microbe targeting magnetic microbead 112, as shown in FIG. 1C, can comprise a magnetic microbead 110 coated with a plurality of the microbe-targeting molecules, e.g., dimeric microbe-targeting molecules 100. Such microbe-targeting magnetic microbeads can be used to separate microbes or pathogens from a test sample, e.g., but not limited to, any fluid, including a biological fluid such as blood. In some embodiments, the microbe-targeting magnetic microbeads can be used to remove living microbes or pathogens. Using magnetic microbeads as a substrate can be advantageous because the microbe-bound magnetic microbeads can be easily separated from a sample fluid using a magnetic field gradient, be examined for the presence of the microbe, and/or be used to transfer the collected microbes to conventional pathogen culture and sensitivity testing assays. Thus, in some embodiments, the microbe-targeting magnetic microbeads can be used to remove microbe contaminants from any source or in any fluid, e.g., a biological fluid (e.g., blood sample), environmental fluid or surface (e.g., wastewater, building or machine surface), or an edible substance or fluid (e.g., food, water). In some embodiments where the fluid is blood, after removal of the microbe/pathogen from the blood collected from a subject with the microbe-targeting magnetic microbeads, the blood can be circulated back to the same subject as a therapeutic intervention. In some embodiments, the microbe-targeting magnetic microbeads can be used in diagnostics as a means of collecting potential pathogens for identification; not only in the diagnosis of disease, but in the identification of water- or food-borne pathogens, particulates or other contaminants. Alternatively, the solid substrate can comprise a hollow-fiber reactor or any other blood filtration membrane or flow device (e.g., a simple dialysis tube, spiral mixer or static mixer) or other resins, fibers, or sheets to selective bind and sequester the biological pathogens.

The magnetic microbeads can be of any shape, including but not limited to spherical, rod, elliptical, cylindrical, and disc. In some embodiments, magnetic beads having a substantially spherical shape and defined surface chemistry can be used to minimize chemical agglutination and non-specific binding. As used interchangeably herein, the terms "magnetic microbeads" and "magnetic beads" can refer to a nano- or micro-scale particle that is attracted or repelled by a magnetic field gradient or has a non-zero magnetic susceptibility. The magnetic microbeads can be ferromagnetic, paramagnetic or super-paramagnetic. In some embodiments, magnetic microbeads can be super-paramagnetic. In some embodiments, magnetic microbeads can have a polymer shell for protecting the microbe-targeting molecule from exposure to iron provided that the polymer shell has no adverse effect on the magnetic property. For example, biocompatible polymer-coated magnetic microbeads can be used to remove microbes/pathogens from a test sample, e.g., a biological fluid, such as blood.

The magnetic microbeads can range in size from 1 nm to 1 mm. For example, magnetic microbeads can be about 2.5 nm to about 500 µm, or about 5 nm to about 250 µm in size. In some embodiments, magnetic microbeads can be about 5 nm to about 100 µm in size. In some embodiments, magnetic microbeads can be about 0.01 µm to about 10 µm in size. In some embodiments, magnetic microbeads can be about 0.05 µm to about 5 µm in size. In some embodiments, magnetic microbeads can be about 0.08 µm to about 1 µm in size. In one embodiment, magnetic microbeads can be about 10 nm to about 10 µm in size. In some embodiments, the magnetic microbeads can be magnetic nanobeads, e.g., with a size ranging from about 1 nm to about 1000 nm, from about 10 nm to about 500 nm, from about 25 nm to about 300 nm, from about 40 nm to about 250 nm, or from about 50 nm to about 200 nm. In one embodiment, the magnetic microbeads can be magnetic nanobeads with a size of about 50 nm to about 200 nm. Magnetic microbeads can be manipulated using magnetic field or magnetic field gradient. Such particles commonly consist of magnetic elements such as iron, nickel and cobalt and their oxide compounds. Magnetic microbeads are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199, the contents of which are incorporated herein by reference.

Magnetic microbeads are also widely and commercially available, with or without functional groups capable of binding to coupling molecules. Magnetic microbeads functionalized with various functional groups, e.g., amino groups, carboxylic acid groups, epoxy groups, tosyl groups, or silica-like groups, are also widely and commercially available. Suitable magnetic microbeads are commercially available such as from AdemTech, Miltenyi, PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic microbeads that can be used herein can be any DYNABEADS® magnetic microbeads (Invitrogen Inc.), depending on the substrate surface chemistry.

Microbe-Targeting Cells:

In some embodiments, the substrate to which the engineered microbe-targeting molecule binds can be a living cell, or a biological tissue or organ. For example, the living cells can be associated with an immune response, and such cells include, but are not limited to, a phagocyte (macrophage, neutrophil, and dendritic cell), mast cell, eosinophil, basophil, and/or natural killer cell. Alternatively, the living cell can be the cell of biological tissues or organs of the immune system, such as spleen, lymph nodes, lymphatic vessels, tonsils, thymus, bone marrow, Peyer's patches, connective tissues, mucous membranes, the reticuloendothelial system, etc. In some embodiments, the surface to which the engineered microbe-targeting molecules bind can also be the extracellular matrix of one or more of these tissues or organs.

Microbe-Binding Microtiter Plates:

In some embodiments, the bottom surface of microtiter wells can be coated with the engineered microbe-targeting molecules described herein, e.g., for detecting and/or determining the amount of microbes in a sample. After microbes or pathogens in the sample binding to the engineered microbe-targeting molecules bound to the microwell surface, the rest of the sample can be removed. Detectable molecules that can also bind to microbes or pathogens (e.g., an engineered microbe-targeting molecule conjugated to a detectable molecule as described herein) can then be added to the microwells with microbes/pathogens for detection of microbes/pathogens. Various signal detection methods for determining the amount of proteins, e.g., using enzyme-linked immunosorbent assay (ELISA), with different detectable molecules have been well established in the art, and those signal detection methods can also be employed herein to facilitate detection of the signal induced by microbes/pathogens binding on the engineered microbe-targeting molecules.

Microbe-Binding Dipsticks/Test Strips:

In some embodiments, the engineered microbe-targeting molecules can be adapted for use in a dipstick and/or a test strip for detection of microbes or pathogens. For example, a dipstick and/or a test strip can include at least one test area containing one or more engineered microbe-targeting molecules described herein. In some embodiments, the engineered microbe-targeting molecules can be conjugated or attached to a test area surface of the dipstick and/or a test strip. Methods for conjugating a protein to a substrate surface are known in the art, including, but not limited to direct cross-linking, indirect cross-linking via a coupling agent (e.g., a functional group, a peptide, a nucleic acid matrix such as DNA matrix), absorption, or any other art-recognized methods known in the art.

In one embodiment, about 1 µg to about 100 µg microbe-binding molecules can be coated on or attached to a dipstick or membrane surface. In another embodiment, about 3 µg to about 60 µg microbe-binding molecules can be coated on or attached to a dipstick or membrane surface. In some embodiments, about 0.1 mg/mL to about 50 mg/mL, about 0.5 mg/mL to about 40 mg/mL, about 1 mg/mL to about 30 mg/mL, about 5 mg/mL to about 20 mg/mL microbe-binding molecules can be coated on or attached to a dipstick or membrane surface. In one embodiment, about 11.5 mg/mL microbe-binding molecules can be coated on or attached to a dipstick or membrane surface.

In some embodiments, the engineered microbe-targeting molecule(s) conjugated to the dipstick and/or a test strip can further comprise a detectable label as described herein. In one embodiment, the detectable label can include a microbial enzyme substrate conjugated to a detectable moiety. Such detectable moiety is undetectable when conjugated to the microbial enzyme substrate, but becomes a detectable entity (e.g., a light-emitting signal) in the presence of an enzyme possessed or secreted by the microbe. See, e.g., WO 2011/103144, for the use of such detectable label in detection of microbes, the content of which is incorporated herein by reference.

In some embodiments, the dipstick and/or a test strip can further comprise at least one reference area or control area for comparison with a readout signal determined from the test area. The reference area generally excludes the engineered microbe-targeting molecules, e.g., to account for any background signal. In some embodiments, the reference area can include one or more known amounts of the detectable label that the engineered microbe-targeting molecules in the test area encompass. In such embodiments, the reference area can be used for calibration such that the amount of microbes in a test sample can be estimated or quantified.

The dipstick and/or a test strip can be in any shape and/or in any format, e.g., a planar shape such as a rectangular strip or a circular disk, or a curved surface such as a stick.

Alternatively, a continuous roll can be utilized, rather than discrete test strips, on which the test area(s) and optionally reference area(s) are present in the form of continuous lines or a series of spots.

The dipstick and/or a test strip can be made of any material, including, without limitations, paper, nitrocellulose, glass, plastic, polymer, membrane material, nylon, and any combinations thereof. In one embodiment, the dipstick and/or a test strip can include paper. In one embodiment, the dipstick and/or a test strip can include nylon.

The microbe-binding dipsticks and/or test strips described herein can be used as point-of-care diagnostic tools for microbe or pathogen detection. By way of example only, a microbe-binding dipstick or test strip (e.g., made of membrane material such as nylon) can be brought into contact with a test sample (e.g., a blood sample) from a patient or a subject, and incubated for a period of time, e.g., at least about 15 seconds, at least about 30 seconds, at least about 1 min, at least about 2 mins, at least about 5 mins, at least about 10 mins, at least about 15 mins, at least about 30 mins, at least about 1 hour or more. In some embodiments, the incubated dipstick or test strip can then be incubated in a blocking agent (e.g., BSA, normal serum, casesin, non-fat dry milk, and/or any commercially-available blocking agents to minimize non-specific binding). Depending on different embodiments of the engineered microbe-targeting molecules, in some embodiments, the microbe-binding dipstick or test strip after contact with a test sample (e.g., a blood sample) can be further contacted with at least one additional agent to facilitate detection of pathogen, and/or to increase specificity of the pathogen detection. For example, some embodiments of the dipstick or test strip after contact with a test sample (e.g., a blood sample) can be further contacted with a detectable label that is conjugated to a molecule that binds to a microbe and/or microbial matter. Examples of such molecules can include, but are not limited to, one or more embodiments of the engineered microbe-targeting molecule described herein, an antibody specific for the microbes or pathogens to be detected, a protein, a peptide, a carbohydrate or a nucleic acid that is recognized by the microbes or pathogens to be detected, and any combinations thereof.

In some embodiments, the readout of the microbe-binding dipsticks and/or test strips can be performed in a system or device, e.g., a portable device. The system or device can display a signal indicating the presence or the absence of a microbial infection in a test sample, and/or the extent of the microbial infection.

Generally, the diagnosis of infection relies on indirect or direct evidence. The indirect evidence relies on the detection of an adapted and specific host response directed against the pathogen. The direct evidence relies on the culture of the microorganism from the infected site, amplification and detection of pathogen-specific nucleic acids or the detection of a specific antigen in blood or urine; however, existing technologies only allow detection of living pathogens and not non-living microbial matter, such as endotoxins, that can have devastating effects on patient survival.

Specific antigen detection is widely used for a variety of infectious diseases, most commonly for legionellosis (*Legionella pneumophila* serotype 1 in urine), malaria (*Plasmodium falciparum* in blood) and with less success with *Streptococcus pneumonia* infection (in urine). However, direct antigen detection can only be used to rule in or rule out a specific etiology and cannot identify most bacteria.

As described herein, engineered microbe-binding molecules or substrates (e.g., FcMBL molecules or FcMBL-bound magnetic microbeads) can bind to the surface of a wide array of microbes including pathogens, e.g., but not limited to, bacterial, fungal, parasitic or viral. For example, in some embodiments, blood or urine or any other biological fluid can be subjected to microbial capture by the engineered microbe-binding molecules or substrates (e.g., FcMBL molecules or FcMBL-bound magnetic microbeads) and adequate controls (e.g., non-specific binding control by non-relevant protein coated magnetic microbeads). Accordingly, engineered microbe-binding molecules or substrates (e.g., FcMBL or FcMBL-coated magnetic microbeads) can be used to bind microbes such as bacteria for diagnostic or therapeutic applications.

Not only can the engineered microbe-binding molecules or substrates bind to at least a portion of a cell surface of a microbe, the engineered microbe-binding molecules or substrates can also capture microbial matter (e.g., microbe-originating cell fragments or matter derived from microbes circulating in biological fluids including endotoxins, e.g., during the course of an infection, even in the absence of bacteremia, or found on an environmental surface, food or water, a pharmaceutical product or a medical device). The presence of such microbial cell fragments or microbe-derived matter can be used, alone or in combination with detection of an intact microbe, for diagnostic applications, e.g., the presence of pathogen-originating cell fragments or matter derived from pathogens can be diagnostic of an infectious disease in a subject, or a microbial contamination on an environmental surface, food or water, a pharmaceutical product, or a medical device. Moreover, the biochemical/proteomic (MALDI-TOF, multiple mass spectrometry (e.g., MSn) or specific antibody or aptamer based) analysis of the bound products (e.g., microbial matter or microbes bound onto an engineered microbe-binding molecule or substrate) can allow recognition of elements pathognomonic for microbes.

Accordingly, provided herein also include methods for detection of the presence or absence of a microbe and/or microbial matter in an organ, a tissue, and/or a cell in a subject (including blood, normally sterile fluids or virtual cavities). For example, the presence or absence of a microbe and/or microbial matter can be detected by capture of a microbe and/or non-viable microbial matter or particles circulating in the subject's body fluid, e.g., blood, or found in other fluids such as urine, or in any other organ sampled by any appropriate means (e.g., but not limited to, biopsy, puncture, aspiration, and lavage).

The inventors have discovered that, in some embodiment, FcMBL captured not only whole bacteria for concentration and direct analysis but also non-viable microbial matter. Such binding can be quantified by a microbe binding assay based on the capture of this microbial matter on the engineered microbe-binding molecules or substrates (e.g., FcMBL-coated microbeads). The detection of this material can be performed using enzyme-linked engineered microbe-binding molecules described herein (e.g., FcMBL) or fluorescent-linked engineered microbe-binding molecules described herein (e.g., FcMBL). The engineered microbe-binding molecules (e.g., FcMBL) can be multimerized on the surface of a desired substrate (e.g., a magnetic bead) to form a microbe-binding substrate for enhanced avidity. Examples 16-17 show that engineered microbe-binding molecules described herein (e.g., FcMBL) can detect live and dead microbes as well as microbial matter (including, but not limited to, fragments of a microbe and endotoxins)

in a biological sample (e.g., blood sample), and the detection results correlate with clinical symptons or morbidity of an infection.

Accordingly, in some embodiments, the presence of intact microbes and/or microbial matter (including microbe cell fragments or matter derived from a microbe) bound on the engineered microbe-binding molecules or substrates can be used as a marker for infection or contamination. Current generic biomarkers for infection include molecules, for example, cytokines; acute phase proteins such as CRP, procalcitonin, and fibrinogen; erythrocyte sedimentation rate (ESR), and elevated or diminished leukocyte counts. However, these generic biomarkers are not specific to infection, but are also involved in non-infectious inflammation.

In contrast, binding of microbes or fragments thereof (including matter derived from microbes) on an engineered microbe-binding molecule and/or substrate can not only be used for infection of a sampled organ or tissue or cell(s) (blood or otherwise) but also to any major infectious process ongoing anywhere in the body where sufficient microbial destruction or catabolism results in the presence of microbial matter in the bloodstream, urine or any other conveniently accessed fluid. There is currently no biological marker for infection that does not cross-react with generic non-infectious inflammation. Thus, this is a major breakthrough in the management of patients suspected of infection. Without wishing to be bound, not only can the engineered microbe-binding molecules and/or substrates be used to detect an infection in a subject (e.g., a mammalian subject), but they can also be used to detect the presence or absence of a microbe in any environment or on any device where a microbe can be present, including but are not limited to, biomedical devices, clinics or hospitals, ponds or water reservoirs, wastewater, water farms (including hydroponics), and/or food processing plants or machines.

Indeed, the inventors have collected blood from de-identified, hospitalized patients and demonstrated, in some embodiments, that the FcMBL assay is positive in patients with negative blood cultures and correlates strongly with the diagnosis of infection. Thus, in some embodiments, the FcMBL assay is more sensitive than conventional blood cultures for detection of an infection. In some embodiments, the FcMBL assay can be used for early diagnosis of an infection. In some embodiments, the engineered microbe-binding molecules and/or substrates and/or diagnosis/detection processes described herein can detect presence of a microbe and/or microbial matter in a test sample which previously yielded a negative result in a traditional diagnosis method (e.g., a blood culture). Accordingly, the engineered microbe-binding molecules and/or substrates and/or diagnosis/detection process described herein can enable a more sensitive and faster diagnosis than the traditional diagnostic method (e.g., a blood culture).

Further, in some embodiments, the wide spectrum of the engineered microbe-binding molecules or substrates (e.g., FcMBL molecules or FcMBL-coated magnetic microbeads) can enable the capture of most clinically relevant bacterial species. The presence of microbial matter or fragments of microbes can reflect deep tissue infection as they generally find its way into the bloodstream and most likely the urine. The capture and characterization of this microbial matter or fragments of microbes can be used as evidence markers specific for a given microbial species, thus allowing the diagnosis and/or identification of a microbe causing infection anywhere in an organism.

For example, the use of one or more specific antibodies can allow characterization of the nature and/or types of the microbial material bound to the engineered microbe-binding molecules or substrates. Specific detection of certain molecules (e.g., proteins, carbohydrates, lipids) present on a microbe surface, such as Lipid A on $E.$ $coli$ or any other molecules on a microbe of interest, can allow further discrimination of samples or identification of microbes present in the samples. Without wishing to be limiting, as shown in Example 16 and FIG. 33, in order to determine if the captured microbes and/or fragments thereof were associated with $E.$ $coli$, FcMBL-coated magnetic beads with captured microbes and/or fragments thereof can be further contacted with a specific antibody raised against $Escherichia$ $coli$ lipopolysaccharide Lipid A (anti-LPS Lipid A antibody). As shown in the bottom panel of FIG. 33, the microbes and/or fragments thereof captured on the FcMBL-coated magnetic beads did not bind to anti-LPS antibodies, indicating that the microbes and/or microbial fragments bound to the FcMBL-coated microbeads were unlikely associated with $E.$ $coli$. In contrast, the microbes and/or fragments thereof captured on the FcMBL-coated magnetic microbeads bound to anti-LPS antibodies, indicating that the microbes and/or microbial fragments bound to the FcMBL-coated microbeads were likely associated with $E.$ $coli$. Accordingly, the screening of a library of antibodies directed against a plurality of microbes (including pathogens) can allow direct diagnosis of microbe-specific infections, e.g., anywhere in the body of a subject by a simple blood or urine test available in less than three hours in any microbiology laboratory equipped for magnetic separation.

Figure 13:
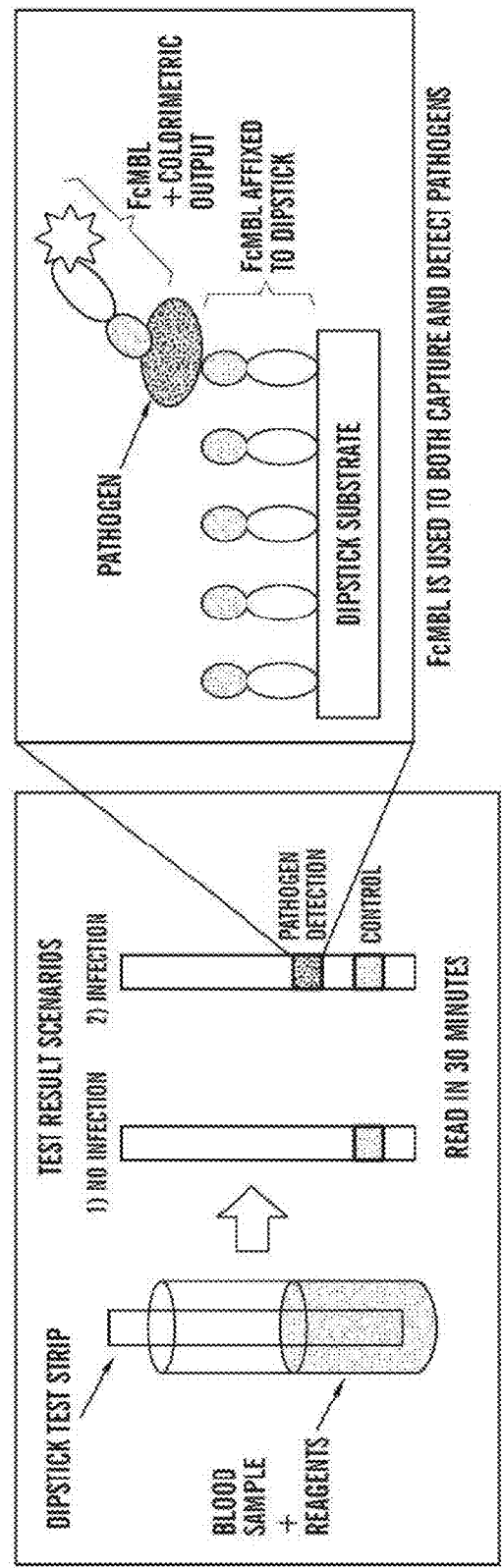
FIG. 13 is a schematic diagram showing one or more embodiments of a dipstick assay for microbial detection. The FcMBL can be attached to a membrane (for example Biodyne membrane). The membrane can be mixed with a test sample (e.g., blood sample), washed, incubated with a desired detecting protein (e.g., AP-labeled FcMBL or specific antibody for certain microbes, e.g., bacteria or fungus), washed and added with a readout reagent for colorimetric development. The dipstick assay can be performed manually or modified for automation.

In a different embodiment, a rapid test can be performed using a "dipstick" format. For example, a membrane spotted with lines of microbial species-specific antibodies (instead of FcMBL molecules as shown in FIG. 13) can be incubated with the microbe-binding substrates (e.g., FcMBL-coated microbeads) previously incubated with a fluid test sample. The microbe-binding substrates (e.g., FcMBL-coated microbeads) captured by proper antibodies on the membrane can form a detectable band (e.g., rust-colored for FcMBL-coated magnetic microbeads) on the membrane, indicating the species (one or many) of which microbial matter or microbes was captured.

Other than antibody-based characterization methods, other known methods such as mass spectrometric characterization methods or PCR analysis can also be used to characterize and/or identify the species of a microbe captured on the engineered microbe-binding molecules and/or substrates. In some embodiments, the microbe-binding molecules and/or substrates with captured microbes and/or microbial matter/fragments can be washed prior to any further characterization methods such as mass spectrometric characterization methods.

In some embodiments, the engineered microbe-binding molecules and/or substrates with captured microbes and/or microbial matter/fragments can be subjected to direct analysis for characterization and/or identification of species of microbes and/or microbial matter bound thereon. For example, the engineered microbe-binding molecules and/or substrates with captured microbial materials can be directly subjected to MALDI-TOF analysis (e.g., without separation of the captured microbial materials from the engineered microbe-binding molecules and/or substrates).

Alternatively, any art-recognized protocols or methods described herein can be applied on the engineered microbe-binding molecules and/or substrates to isolate bound microbes and/or microbial compounds/fragments from the engineered microbe-binding molecules and/or substrates prior to any characterization analysis. Exemplary methods to recover or isolate bound microbes and/or microbial compounds/fragments from the engineered microbe-binding molecules and/or substrates, prior to any characterization analysis, include, but are not limited to, $Ca^{2+}$ chelation to release captured materials from the engineered microbe-binding molecules and/or substrates; lowering pH to release binding mediated by Fc-protein A interaction; protein extraction using formic acid and acetonitrile, and any combinations thereof. The control microbeads (e.g., microbeads coated with molecules that do not react to microbes) can be treated similarly for baseline determination.

In some embodiments, the extracted captured material from the engineered microbe-binding molecules and/or substrates and/or non-specific control-bound material can be subjected to PCR analysis. For example, the identity of the extracted captured material can be determined by detecting the presence or absence of a gene encoding a protein specific to a microbe species. Thus, the presence of one or more microbe species-specific genes (s) can be indicative of the corresponding microbe species bound on the engineered microbe-binding molecules.

In some embodiments, extracted captured material from the engineered microbe-binding molecules and/or substrates, and/or non-specific control-bound material can be subjected to mass spectrometric analysis, including but not limited to, MALDI-TOF or MALDI-TOF-TOF. The non-specific control-bound material can establish a baseline for the composition of the medium tested. This profile can be used as reference for the analysis of the material bound to the engineered microbe-binding molecules and/or substrates. Peaks present in the control-bound samples can be subtracted from the profile obtained from the material bound to the engineered microbe-binding molecules and/or substrates. The specific profile of the material that was bound to the microbe-binding molecules and/or substrates (e.g., after subtraction of the reference profile) can constitute a microbe/microbial fragment signature. Both positive and/or negative charge analysis can be performed to identify informative peaks.

Recognition of a microbe signature can be analyzed by any known methods in the art. For example, a microbe/microbial fragment signature can be recognized by comparing the specific profile of the material that was bound to the microbe-binding molecules and/or substrates to one or more microbe/microbial fragment signature libraries, e.g., using matching comparison algorithms based on the previously accumulated profiles.

For identification of microbe species, depending on origins of microbes, a microbe/microbial fragment signature library can be established by in vivo or in situ samples such as clinical-trial derived samples and/or environment derived samples (e.g., samples collected from a clinical setting, culture medium, food processing plant, water source). For example, blood (or other biological fluids) of patients infected with known microbes, e.g., pathogens, can be analyzed and a microbial material signature can be characterized. Recognition of the signature in the same clinical context can establish the family/genus/species diagnosis.

Additionally or alternatively, another microbe/microbial fragment library can be established from in vitro analysis of microbes' binding moieties to engineered microbe-binding molecule(s) described herein, wherein the microbes can be subjected to mechanical or chemical or antibiotic lysis or autolysis. The microbial material can be captured in different media, buffer, urine, blood or any appropriate medium.

The diagnostic profiles can be matched to any reference profiles, e.g., specific in vivo or in situ derived microbe profiles and/or specific in-vitro derived microbes profiles for identification with a probability score for generic infection, clades level, family level, genus level or species level identification.

Further, methods for detection of the presence or absence of a microbe and/or microbial matter on an environmental surface, food or water, a pharmaceutical product, or a medical device by capture of a microbe and/or non-viable microbial matter or particles present thereon are also within the scope described herein. In some embodiments, the methods of any aspect described herein can be used to screen pharmaceutical products (e.g., drugs, therapeutic agents or imaging agents), and/or medical devices (e.g., fluid delivery devices, or implantable devices) for the presence or absence of a microbe and/or microbial matter (including but not limited to endotoxin produced by a microbe, e.g., a gram-negative microbe such as *E. coli* and/or a gram-positive microbe such as *S. aureus*). In one embodiment, the method can be used to screen pharmaceutical products (e.g., drugs, therapeutic agents or imaging agents), and/or medical devices (e.g., fluid delivery devices, or implantable devices) for the presence or absence of endotoxin produced by a microbe, e.g., a gram-negative microbe such as *E. coli* and/or a gram-positive microbe such as *S. aureus*.

Exemplary Optimization or Modifications of Microbe-Targeting Substrates

In accordance with at least some embodiments described herein, engineered microbe-binding molecules and/or substrates (e.g., FcMBL-bound paramagnetic microbeads) can bind to a surface of a variety of microbes and/or microbial matter described herein, e.g., but not limited to, bacterial, fungal, parasitic or viral. In some embodiments, a number of factors such as the orientation of engineered microbe-binding molecules (e.g., FcMBL) conjugated to or coated on a substrate (e.g., a paramagnetic microbead), size of a substrate (e.g., a microbead), selection of linkers and microbe surface-binding domains used in constructing an engineered microbe-targeting molecule, microbial assay condition, and any combinations thereof, can be optimized for binding of the microbe-targeting substrates to microbes.

Optimization of Substrate Size and Densities of Engineered Microbe-Targeting Molecules on the Substrate:

Additionally or alternatively, the density of engineered microbe-binding molecules (e.g., FcMBL) conjugated to or coated on a substrate (e.g., a microbead) can be optimized to capture microbes.

In some embodiments where the engineered microbe-binding molecule is FcMBL, the FcMBL differs from recombinant wild-type MBL in that the FcMBL is a dimeric protein with two Carbohydrate Recognition Domain (CRD) heads whereas wild-type MBL has 9-18 heads in groups of 3. The affinity of the individual heads is $10^{-3}$ and MBL binding to microbe surfaces requires binding of multiple CRD heads to give high avidity binding. In order to achieve this high avidity with the dimeric FcMBL protein, in some embodiments, a plurality of (e.g., at least about 2, at least about 5, at least about 10, at least about 25, at least about 50, at least about 100, at least about 1000, at least about $10^4$, at least about $10^5$, at least about $10^6$, at least about $10^7$) engineered microbe-binding molecules (e.g., FcMBL) can be multiplexed on a surface of a substrate (e.g. magnetic microbeads such as the MYONE™ Streptavidin microbeads from Life Technologies). The number of the engineered microbe-binding molecules conjugated to a substrate can vary with available surface area of a substrate.

Accordingly, a number of factors, including density of engineered microbe-binding molecules on a substrate, size of the substrate, and/or size of the engineered microbe-binding molecules, can be varied to optimize binding of microbes to the engineered microbe-binding substrates (e.g., but not limited to, FcMBL-coated beads). Some exemplary optimizations/modifications can include, but are not limited to, using a substrate (e.g., but not limited to, a microbead) of different sizes; varying the density of engineered microbe-binding molecules (e.g., but not limited to, FcMBL) on the substrate (e.g., but not limited to, a microbead) by binding the engineered microbe-binding molecules (e.g., but not limited to, FcMBL) to a substrate scaffold in various oriented arrays, e.g., but not limited to DNA, aptamers, or extracellular matrix (e.g., fibronectin); producing fusion proteins of microbe-binding domain(s) (e.g., but not limited to, MBL CRD head and neck regions) bound to a linker described herein or fusion partner (or linker described herein) of different sizes (e.g., between about 100 kDa to about 1000 kDa or between about 250 kDa to about 750 kDa. An exemplary fusion partner can include, but is not limited to, the Fc portion of IgM, which is about 500 kDa); producing fusion proteins of microbe-binding domain(s) (e.g., but not limited to, MBL CRD head and neck regions) with multimeric (e.g., at least dimeric, at least trimeric) linkers described herein or fusion partners (or linkers described herein); and any combinations thereof. As used herein, the term "multimeric linker" or "multimeric fusion partner" refers to a linker or fusion partner comprising two or more identical linker units for providing attachment of microbe-binding domains. By way of example only, a trimeric linker or fusion partner is a linker or fusion partner comprising three identical linker units for attachement of microbe-binding domains.

The binding of any microbe to a microbe-binding substrate described herein can be determined by any methods known in the art and/or described herein, such as by ELISA-colorimetric assay or antibody-based imaging methods described in the Examples. Accordingly, the microbe-binding substrate can be optimized for detection of a microbe, e.g., by varying its density and/or size of engineered microbe-binding molecules, its substrate structure and/or size, and then determining their effects on the binding of the microbe to the microbe-binding substrate.

For example, Example 18 shows an exemplary method to evaluate the microbe-capture efficiency of microbe-targeting magnetic microbeads (e.g., FcMBL-coated magnetic microbeads) having different sizes. In some embodiments, a microbead (e.g., a magnetic microbead or a non-magnetic microbead) as a substrate for attachment of engineered microbe-binding molecules can have a size of about 10 nm to 10 μm, about 20 nm to about 5 μm, about 40 nm to about 1 μm, about 50 nm to about 500 nm, or about 50 nm to about 200 nm. Without wishing to be bound by theory, the size of a microbead can be smaller than the size of a microbe so that more than one microbead (e.g., at least 2, at least 3, at least 4, at least 5, at least 10 or more) can bind to the same microbe for enhanced capture and increased detection sensitivity.

Additionally, the density of the engineered microbe-binding molecules on a surface of the microbe-targeting substrate can be optimized for microbial binding. In order to enhance binding of a specific microbe to the microbe-targeting substrate, the distance between any two microbe-binding molecules on a surface of the microbe-targeting substrate can be less than the size of a microbe. Therefore, a microbe can bind to more than one microbe-binding molecules (e.g., at least 2, at least 3, at least 4, at least 5, at least 6, at least 7, at least 8, at least 9, at least 10, or more) present on the microbe-targeting substrate with a greater combined binding strength.

In some embodiments, the microbe-targeting substrates can comprise on their surfaces a saturating amount of the engineered microbe-binding molecules described herein. As used herein, the term "saturating amount" refers to the maximum number or amount of engineered microbe-binding molecules that can be conjugated to and/or coated on a surface of a substrate. The saturating amount of the engineered microbe-binding molecules that can be present on a surface of a substrate is dependent on a number of factors such as size and/or structure of the engineered microbe-binding molecules, size and/or structure of the substrate, orientation of the engineered microbe-binding molecules present on the substrate, and any combinations thereof.

Selection of Linkers and Microbe Surface-Binding Domain Used in Constructing an Engineered Microbe-Targeting Molecule and Microbial Assay Condition:

In some embodiments, a linker can be selected to provide binding sites of a microbe, wherein the binding interaction of the microbe to the linker is different from the interaction of the microbe to the microbe surface-binding domain. For example, in an engineered microbe-binding molecule where the linker is a Fc molecule and the microbe surface-binding domain is derived from MBL or a fragment thereof, the Fc linker allows protein A or protein G binding, which is calcium-independent, while the MBL binding domain requires calcium ions for binding with a microbe. Accordingly, a protein A-expressing (e.g., *S. aureus*) or protein G-expressing microbe can bind to both MBL binding domain and Fc linker in the presence of calcium ions, but can bind to only Fc linker in the absence of calcium ions. In contrast, a protein A- and protein G-negative microbe (e.g., *E. coli*) generally binds to neither MBL binding domain nor Fc linker in the absence of calcium ions. In such embodiments, by controlling the amount of calcium ions present in a microbial assay, one can distinguish protein A- or protein G-expressing microbes (e.g., *S. aureus*) from protein A- and protein G-negative microbes (e.g., *E. coli*). Additional details of such embodiments can be found in later sections "Exemplary Process for Capture and/or Detection of a Microbe and/or Microbial Matter in a Test Sample" and "Exemplary Embodiments of Methods for Diagnosing a Microbial Infection."

Figure 17:
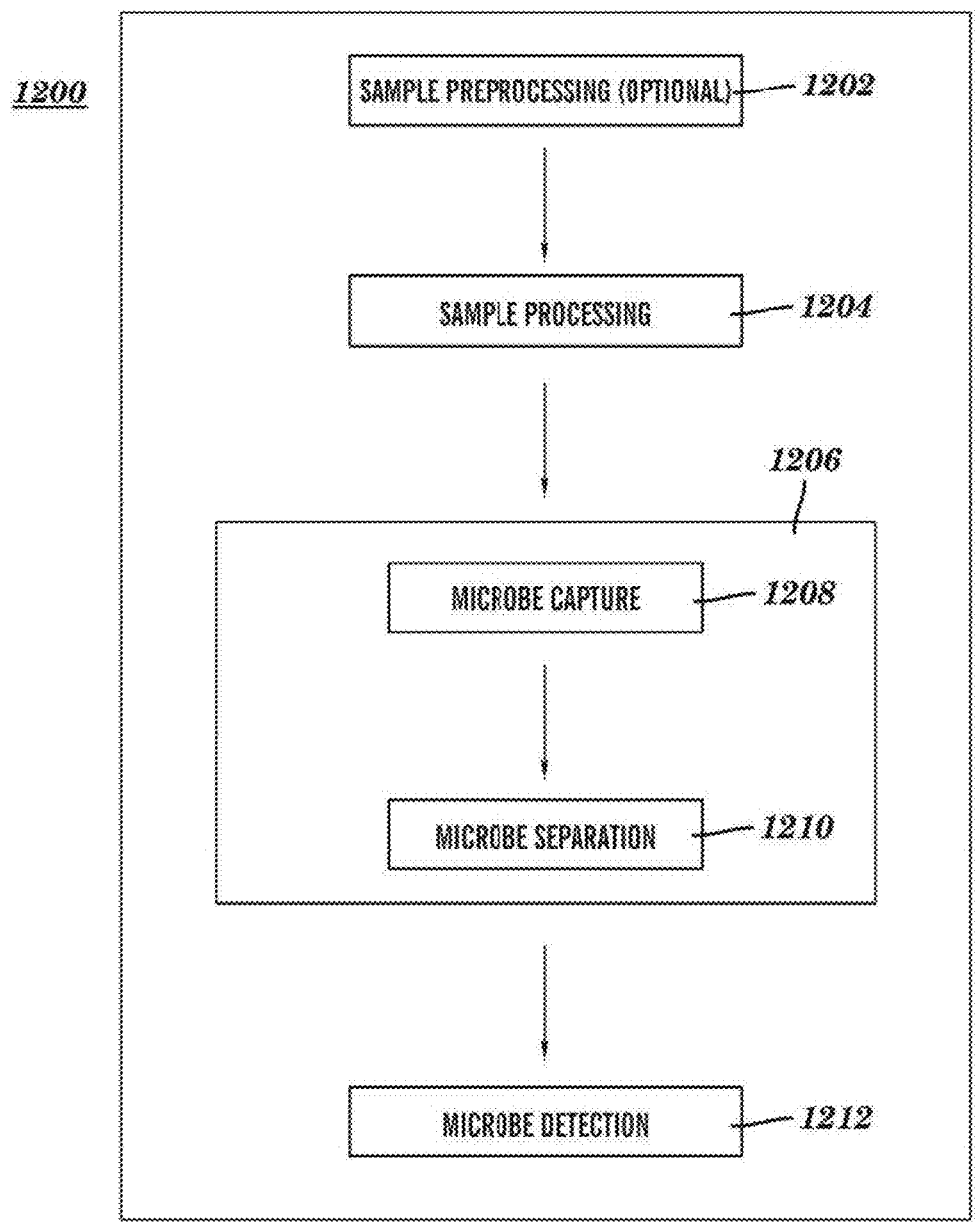
FIG. 17 is a schematic of an exemplary microbial detection process or diagnosis process.

Exemplary Process for Capture and/or Detection of a Microbe and/or Microbial Matter in a Test Sample In one aspect, a process for detecting a microbe and/or microbial matter in a test sample is described herein. As shown in FIG. 17, the process 1200 comprises the optional step 1202 (preprocessing of the sample), step 1204 (processing of the sample), step 1206 comprising 1208 (microbe capture) and 1210 (microbe separation), and 1212 (microbe detection). While these are discussed as discrete processes, one or more of the preprocessing, processing, capture, microbe separation, and detection can be performed in a microfluidic device. Use of a microfluidic device can automate the analysis process and/or allow analysis of multiple samples at the same time. One of skill in the art is well aware of methods in the art for collecting, handling and processing biological fluids which can be used in the practice of the present disclosure. The process described herein can allow sample analysis at in short time periods. For example, the process can be completed in less than 6 hours, less than 5 hours, less than 4 hours, less than 3 hours, less than 2 hours, less than 1 hour, less than 30 minutes. In some embodiments, presence and identity of a microbe in the sample can be done within 10 minutes to 60 minutes of starting the process.

In some embodiments, the sample can be a biological fluid, e.g., blood, plasma, serum, lactation products, amniotic fluids, sputum, saliva, urine, semen, cerebrospinal fluid, bronchial aspirate, perspiration, mucus, liquefied stool sample, synovial fluid, lymphatic fluid, tears, tracheal aspirate, and any mixtures thereof. For example, the sample can be a whole blood sample obtained from a subject.

The process described herein can be utilized to detect the presence of a microbe in a sample of any given volume. In some embodiments, sample volume is about 0.25 ml to about 50 ml, about 0.5 ml to about 25 ml, about 2 ml to about 15 ml, about 2 ml to about 10 ml. In some embodiments, sample volume is about 5 ml. In one embodiment, sample volume is 8 ml.

1202 (Sample Preprocessing):

It can be necessary or desired that a test sample, such as whole blood, be preprocessed prior to microbe detection as described herein, e.g., with a preprocessing reagent. Even in cases where pretreatment is not necessary, preprocessing can be optionally done for mere convenience (e.g., as part of a regimen on a commercial platform). A preprocessing reagent can be any reagent appropriate for use with the assays or processes described herein.

The sample preprocessing step generally comprises adding one or more reagent to the sample. This preprocessing can serve a number of different purposes, including, but not limited to, hemolyzing blood cells, dilution of sample, etc. The preprocessing reagents can be present in the sample container before sample is added to the sample container or the preprocessing reagents can be added to a sample already present in the sample container. When the sample is a biological fluid, the sample container can be a VACUTAINER®, e.g., a heparinized VACUTAINER®.

The preprocessing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions.

In some embodiments, a preprocessing reagent is a surfactant or a detergent. In one embodiment, the preprocessing reagent is Triton X100.

Amount of preprocessing reagent to be added can depend on a number of factors. Generally, the preprocessing reagent is added to a final concentration of about 0.1 mM to about 10 mM. If a liquid, the preprocessing reagent can be added so as to dilute the sample at least 10%, at least 20%, at least 30%, at least 40%, at least 50%, at least 60%, at least 60%, at least 80%, at least 90%, at least 1-fold, at least 2-fold, at least 3-fold, or at least 5-fold.

After addition of the preprocessing reagent, the reagent can be mixed into the sample. This can be simply accomplished by agitating the sample, e.g., shaking or vortexing the sample and/or moving the sample around, if it is in a microfluidic device.

After addition of the preprocessing reagent, the sample mixture can be incubated for a period of time, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature. In some embodiments, incubation is for about 5 seconds to about 60 seconds. In some embodiments, there is no incubation and the sample mixture is used directly in the sample processing step.

1204 (Sample Processing):

After the optional preprocessing step, the sample can be optionally processed by adding one or more processing reagents to the sample. These processing reagents can serve to lyse cells, degrade unwanted molecules present in the sample and/or dilute sample for further processing. These processing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions. Amount of the processing reagent to be added can depend on the particular sample to be analyzed, the time required for the sample analysis, identity of the microbe to be detected or the amount of microbe present in the sample to be analyzed.

It is not necessary, but if one or more reagents are to be added they can present in a mixture (e.g., in a solution, "processing buffer") in the appropriate concentrations. Amount of the various components of the processing buffer can vary depending upon the sample, microbe to be detected, concentration of the microbe in the sample, or time limitation for analysis.

Generally, addition of the processing buffer can increase the volume of the sample by 5%, 10%, 15%, 20% or more. In some embodiments, about 50 µl to about 5000 µl of the processing buffer are added for each ml of the sample. In some embodiments, about 100 µl to about 250 µl of the processing buffer are added for each ml of the sample. In one embodiment, about 800 µl of the processing buffer are added for each 200 µl of the sample.

In some embodiments, a detergent or surfactant comprises about 5% to about 20% of the processing buffer volume. In some embodiment, a detergent or surfactant comprises about 5% to about 15% of the processing buffer volume. In one embodiment, a detergent or surfactant comprises about 10% of the processing buffer volume.

Exemplary surfactants and detergents include, but are not limited to, sulfates, such as, ammonium lauryl sulfate, sodium dodecyl sulfate (SDS), and sodium lauryl ether sulfate (SLES) sodium myreth sulfate; sulfonates, such as, dioctyl sodium sulfosuccinate (Docusates), perfluorooctanesulfonate (PFOS), perfluorobutanesulfonate, alkyl benzene sulfonates, and 3-[(3-Cholamidopropyl)dimethylammonio]-1-propanesulfonate (CHAPS); 3-[(3-cholamidopropyl)dimethylammonio]-2-hydroxy-1-propanesulfonate (CHAPSO); phosphates, such as alkyl aryl ether phosphate and alkyl ether phosphate; carboxylates, such as fatty acid salts, sodium stearate, sodium lauroyl sarcosinate, perfluorononanoate, and perfluorooctanoate (PFOA or PFO); octenidine dihydrochloride; alkyltrimethylammonium salts, such as cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; dioctadecyldimethylammonium bromide (DODAB); sultaines, such as cocamidopropyl hydroxysultaine; cetyl alcohol; stearyl alcohol; cetostearyl alcohol (consisting predominantly of cetyl and stearyl alcohols); oleyl alcohol; polyoxyethylene glycol alkyl ethers (Brij) such as, octaethylene glycol monododecyl ether and pentaethylene glycol monododecyl ether; polyoxypropylene glycol alkyl ethers; glucoside alkyl ethers, such as decyl glucoside, lauryl glucoside and octyl glucoside; polyoxyethylene glycol octylphenol ethers, such as Triton X-100; polyoxyethylene glycol alkylphenol ethers, such as Nonoxynol-9; glycerol alkyl esters, such as glyceryl laurate; polyoxyethylene glycol sorbitan alkyl esters, such as Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate); cocamide ME; cocamide DEA; dodecyldimethylamine oxide; poloxamers; DOC; nonyl phenoxypolyethoxylethanol NP-40 (Tergitol-type NP-40); octyl phenoxypolyethoxylethanol (Noidet P-40); cetyltrimethylammonium bromide; and any mixtures thereof.

In some embodiments, one ml of the processing buffer can comprise about 1 U to about 100 U of a degradative enzyme. In some embodiments, one ml of the processing buffer comprises about 5 U to about 50 U of a degradative enzyme. In one embodiment, one ml of the processing buffer comprises about 10 U of a degradative enzyme. Enzyme unit (U) is an art known term for the amount of a particular enzyme that catalyzes the conversion of 1 mol of substrate per minute.

In some embodiments, one ml of the processing buffer can comprise about 1 µg to about 10 µg of an anti-coagulant. In some embodiment, one ml of the processing buffer can comprise about 1 µg to about 5 µg of an anti-coagulant. In one embodiment, one ml of the processing buffer comprises about 4.6 µg of an anti-coagulant.

In some embodiments, one ml of the processing buffer can comprise about 1 mg to about 10 mg of anti-coagulant. In some embodiment, one ml of the processing buffer can comprise about 1 mg to about 5 mg of anti-coagulant. In one embodiment, one ml of the processing buffer comprises about 4.6 mg of anti-coagulant.

Exemplary anti-coagulants include, but are not limited to, heparin, heparin substitutes, salicylic acid, D-phenylalanyl-L-prolyl-L-arginine chloromethyl ketone (PPACK), Hirudin, Ancrod (snake venom, Vipronax), tissue plasminogen activator (tPA), urokinase, streptokinase, plasmin, prothrombopenic anticoagulants, platelet phosphodiesterase inhibitors, dextrans, thrombin antagonists/inhibitors, ethylene diamine tetraacetic acid (EDTA), acid citrate dextrose (ACD), sodium citrate, citrate phosphate dextrose (CPD), sodium fluoride, sodium oxalate, potassium oxalate, lithium oxalate, sodium iodoacetate, lithium iodoacetate and mixtures thereof.

Suitable heparinic anticoagulants include heparins or active fragments and fractions thereof from natural, synthetic, or biosynthetic sources. Examples of heparin and heparin substitutes include, but are not limited to, heparin calcium, such as calciparin; heparin low-molecular weight, such as enoxaparin and lovenox; heparin sodium, such as heparin, lipo-hepin, liquaemin sodium, and panheprin; heparin sodium dihydroergotamine mesylate; lithium heparin; and ammonium heparin.

Suitable prothrombopenic anticoagulants include, but are not limited to, anisindione, dicumarol, warfarin sodium, and the like.

Examples of phosphodiesterase inhibitors suitable for use herein include, but are not limited to, anagrelide, dipyridamole, pentoxifyllin, and theophylline.

Suitable dextrans include, but are not limited to, dextran70, such as HYSKON™ (CooperSurgical, Inc., Shelton, Conn., U.S.A.) and MACRODEX™ (Pharmalink, Inc., Upplands Vasby, Sweden), and dextran 75, such as GENTRAN™ 75 (Baxter Healthcare Corporation).

Suitable thrombin antagonists include, but are not limited to, hirudin, bivalirudin, lepirudin, desirudin, argatroban, melagatran, ximelagatran and dabigatran.

As used herein, anticoagulants can also include factor Xa inhibitors, factor IIa inhibitors, and mixtures thereof. Various direct factor Xa inhibitors are known in the art including, those described in Hirsh and Weitz, *Lancet*, 93:203-241, (1999); Nagahara et al. *Drugs of the Future*, 20: 564-566, (1995); Pinto et al, 44: 566-578, (2001); Pruitt et al, *Biorg. Med. Chem. Lett.*, 10: 685-689, (2000); Quan et al, *J. Med. Chem.* 42: 2752-2759, (1999); Sato et al, *Eur. J. Pharmacol*, 347: 231-236, (1998); Wong et al, *J. Pharmacol. Exp. Therapy*, 292:351-357, (2000). Exemplary factor Xa inhibitors include, but are not limited to, DX-9065a, RPR-120844, BX-807834 and SEL series Xa inhibitors. DX-9065a is a synthetic, non-peptide, propanoic acid derivative, 571 D selective factor Xa inhibitor. It directly inhibits factor Xa in a competitive manner with an inhibition constant in the nanomolar range. See for example, Herbert et al, *J. Pharmacol. Exp. Ther.* 276:1030-1038 (1996) and Nagahara et al, *Eur. J. Med. Chem.* 30(suppl):140s-143s (1995). As a non-peptide, synthetic factor Xa inhibitor, RPR-120844 (Rhone-Poulenc Rorer), is one of a series of novel inhibitors which incorporate 3-(S)-amino-2-pyrrolidinone as a central template. The SEL series of novel factor Xa inhibitors (SEL1915, SEL-2219, SEL-2489, SEL-2711: Selectide) are pentapeptides based on L-amino acids produced by combinatorial chemistry. They are highly selective for factor Xa and potency in the pM range.

Factor IIa inhibitors include DUP714, hirulog, hirudin, melgatran and combinations thereof. Melagatran, the active form of pro-drug ximelagatran as described in Hirsh and Weitz, *Lancet*, 93:203-241, (1999) and Fareed et al. *Current Opinion in Cardiovascular, pulmonary and renal investigational drugs*, 1:40-55, (1999).

Generally, salt concentration of the processing buffer can range from about 10 mM to about 100 mM. In some embodiments, the processing buffer comprises a salt at a concentration of about 25 mM to about 75 mM. In some embodiment, the processing buffer comprises a salt at a concentration of about 45 mM to about 55 mM. In one embodiment, the processing buffer comprises a salt at a concentration of about 43 mM to about 45 mM.

The processing buffer can be made in any suitable buffer solution known the skilled artisan. Such buffer solutions include, but are not limited to, TBS, PBS, BIS-TRIS, BIS-TRIS Propane, HEPES, HEPES Sodium Salt, MES, MES Sodium Salt, MOPS, MOPS Sodium Salt, Sodium Chloride, Ammonium acetate solution, Ammonium formate solution, Ammonium phosphate monobasic solution, Ammonium tartrate dibasic solution, BICINE buffer Solution, Bicarbonate buffer solution, Citrate Concentrated Solution, Formic acid solution, Imidazole buffer Solution, MES solution, Magnesium acetate solution, Magnesium formate solution, Potassium acetate solution, Potassium acetate solution, Potassium acetate solution, Potassium citrate tribasic solution, Potassium formate solution, Potassium phosphate dibasic solution, Potassium phosphate dibasic solution, Potassium sodium tartrate solution, Propionic acid solution, STE buffer solution, STET buffer solution, Sodium acetate solution, Sodium formate solution, Sodium phosphate dibasic solution, Sodium phosphate monobasic solution, Sodium tartrate dibasic solution, TNT buffer solution, TRIS Glycine buffer solution, TRIS acetate-EDTA buffer solution, Triethylammonium phosphate solution, Trimethylammonium acetate solution, Trimethylammonium phosphate solution, Tris-EDTA buffer solution, TRIZMA® Base, and TRIZMA® HCL. Alternatively, the processing buffer can be made in water.

In some embodiments, the processing buffer comprises a mixture of Trirton-X, DNAse I, human plasmin, $CaCl_2$ and Tween-20. In one embodiment, the processing buffer consists of a mixture of Trirton-X, DNAse I, human plasmin, $CaCl_2$ and Tween-20 in a TBS buffer.

In one embodiment, one ml of the processing buffer comprises 100 µl of Triton-X100, 10 µl of DNAse (1 U/1 µl), 10 µl of human plasmin at 4.6 mg/ml and 870 µl of a mixture of TBS, 0.1% Tween-20 and 50 mM $CaCl_2$.

Reagents and treatments for processing blood before assaying are also well known in the art, e.g., as used for assays on Abbott TDx, AxSYM®, and ARCHITECT® analyzers (Abbott Laboratories), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, and U.S. Pat. App. Pub. No. 2008/0020401, content of all of which is incorporated herein by reference. It is to be understood that one or more of these known reagents and/or treatments can be used in addition to or alternatively to the sample treatment described herein.

In some embodiments, after addition of the processing buffer, the sample comprises 1% Triton-X, 10 U of DNase, 4.6 mg/ml of plasmin, 5 mM Calcium, 0.01% of Tween 20, 2.5 mM of Tris, 150 mM of NaCl and 0.2 mM of KCl in addition to the components already present in the sample.

After addition of the processing buffer, the sample can undergo mixing. This can be simply accomplished by agitating the sample, e.g., shaking or vortexing the sample and/or moving the sample around, if it is in a microfluidic device. In other embodiments where the microbe-targeting substrate is in a form of a dipstick or a membrane, the microbe-targeting dipstick or membrane can be dipped in a volume of a test sample and gently agitated with a rocking motion.

After addition of the processing reagents, the sample can be incubated for a period of time, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature.

1206 (1208 (Microbe Capture) and 1210 (Microbe Separation)):

After processing of the sample, the sample can be subjected to a microbe capture process. During the microbe capture process, a microbe-targeting substrate added into a test sample can capture one or more microbes present in the test sample. In some embodiments, the microbe capture process can be repeated and/or performed for a sufficient amount of time to allow for concentrating and/or cleaning up the test sample before microbe detection. Thus, microbe capture and separation process described herein can be used for concentrating and/or cleaning up a sample before analysis for a target component in the sample.

In some embodiments, the microbe capture process can comprise mixing nano- and/or micron-sized beads or particles coated with affinity molecules (e.g., FcMBL or engineered microbe-binding molecules described herein) which can bind to a microbe in the sample. These affinity molecule coated nano- and/or micron-sized beads or particles are also referred to as "coated-microbeads" herein. These coated-microbeads can be magnetic microbeads or non-magnetic microbeads (e.g., fluorescent microbeads).

In some embodiments, the coated-microbeads can be microbe-targeting magnetic microbeads described herein.

Amount of coated-microbeads added to the sample can be dependent on a number of different factors, such as, number of affinity molecules on each microbead, size of the microbead, binding affinity of the affinity molecule to the microbe, and concentration of the microbe in the sample. Additionally, amount of coated-microbeads added to the sample can be adjusted to optimize the capture of microbes. In some embodiments, amount of coated-microbeads added to the sample is such that a microbead binds with one microbe. However, each microbe can be bound to more than one coated-microbeads. This can reduce cross-linking of multiple microbes together which can lead to coagulation and/or precipitation of such cross-linked microbes from the sample. Generally, about 100 to about $10^9$ coated-microbeads can be added to each ml of the sample. In some embodiments, about $10^4$ to about $5 \times 10^6$ coated-microbeads can be added for each ml of sample. Stated another way, in some embodiments, the total amount of the microbe-binding molecules contacted with the test sample can range from about 0.01 µg to about 1 mg, about 0.1 µg to about 500 µg, about 0.5 µg to about 250 µg, about 1 µg to about 100 µg, or about 3 µg to about 60 µg. In some embodiments, the total amount of the microbe-binding molecules contacted with the test sample can range from about 500 µg to about 1000 mg, about 1 mg to about 750 mg, about 5 mg to about 500 mg, about 10 mg to about 250 mg, or about 25 mg to about 100 mg.

In some embodiments, a plurality of coated-microbeads can be contacted with a test sample. The plurality of coated-microbeads can comprise at least two subsets (e.g., 2, 3, 4, 5, or more subsets), wherein each subset of coated-microbeads have a pre-determined dimension. In some embodiments, the plurality of coated-microbeads can comprise a first subset of the coated-microbeads and a second subset of the coated-microbeads. In such embodiments, the first subset of the coated-microbeads each has a first pre-determined dimension; and the second subset of the coated-microbeads each has a second pre-determined dimension.

The pre-determined dimension of a coated-microbead depends, in part, on the dimension of a microbead described herein to which the engineered microbe-binding molecules are conjugated. For example, the microbead can have a size of about 10 nm to 10 µm, about 20 nm to about 5 µm, about 40 nm to about 1 µm, about 50 nm to about 500 nm, or about 50 nm to about 200 nm.

Additionally, each subset of the coated-microbeads can comprise on their surfaces substantially the same density or different densities of the affinity molecules (e.g., FcMBL or engineered microbe-binding molecules described herein).

Different subsets of the plurality of the coated-microbeads can be brought into contact with a test sample in any manner. For example, in some embodiments, the plurality of coated-microbeads can be provided as a single mixture comprising at least two subsets of the coated-microbeads to be added into a test sample. In some embodiments, in order to distinguish among different subsets of the coated-microbeads, the coated-microbeads in each subset can have a distinct detection label, e.g., a distinctly-fluorescent label that can be sorted afterward, for example, by flow cytometry.

In other embodiments, the plurality of the coated-microbeads can be brought into contact with a test sample in a sequential manner. For example, a test sample can be contacted with a first subset of the coated-microbeads, followed by a contact with at least one more subsets of the coated-microbeads. The previous subset of the coated-microbeads can be removed from the test sample before addition of another subset of the coated-microbeads into the test sample.

In some embodiments, the coated-microbeads are or a microbe-targeting substrate is present in the processing buffer. In one embodiment, one ml of the processing buffer comprises 100 µl of Triton-X100, 10 µl of a solution comprising about 25 million microbeads (AKT-FC-MBL on 1 µm MYONE™ C1 streptavidin microbeads), 10 µl of DNAse (1 U/1 µl), 10 µl of human plasmin at 4.6 mg/ml and 870 µl of a mixture of TBS, 0.1% Tween-20. In some embodiments, the processing buffer can include a calcium salt, e.g., $CaCl_2$ (e.g., ~50 mM $CaCl_2$). In some embodiments, the processing or capture buffer can include no calcium salt, e.g., $CaCl_2$.

After addition of the coated-microbeads, the coated-microbeads can be mixed in the sample to allow microbes to bind with the microbeads. This can be simply accomplished by agitating the sample, e.g., shaking or vortexing the sample and/or moving the sample around in a microfluidic device. In other embodiments where the microbe-targeting substrate is in a form of a dipstick or a membrane, the microbe-targeting dipstick or membrane can be dipped in a volume of a test sample and gently agitated with a rocking motion.

The volume of a test sample required for contacting the microbe-targeting substrate can vary with, e.g., the selection of the microbe-targeting substrate (e.g., microbeads, fibers, filters, filters, fibers, screens, mesh, tubes, hollow fibers), the concentration of microbes present in a test sample, and/or the platform used to carry out the assay (e.g., a microfluidic device or a blood collection tube, a microtiter plate). In some embodiments, the test sample volume used to perform the assay described herein, e.g., in a microfluidic platform, can range from about 1 µL to about 500 µL, from about 5 µL to about 250 µL, or from about 10 µL to about 100 µL. In other embodiments, the test sample volume used to perform the assay described herein, e.g., in a tube platform, can range from about 0.05 mL to about 50 mL, from about 0.25 ml to about 50 ml, about 0.5 ml to about 25 ml, about 1 ml to about 15 ml, or about 2 ml to about 10 ml. In some embodiments, the test sample volume used to perform the assay described herein can be about 1 mL to about 5 ml. In one embodiment, the test sample volume used to perform the assay described herein is about 5 ml to about 10 mL.

After addition of the microbe-targeting substrate (e.g., coated-microbeads) into a test sample (containing a processing buffer), the sample mixture can be incubated for a period of time to allow the microbe of interest to bind onto the microbe-targeting substrate, e.g., incubation for at least one minute, at least two minutes, at least three minutes, at least four minutes, at least five minutes, at least ten minutes, at least fifteen minutes, at least about twenty minutes, at least thirty minutes, at least forty-five minutes, or at least one hour. In one embodiment, the sample mixture can be incubated for a period of about 10-20 minutes. Such incubation can be performed at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the incubation can be performed at a temperature ranging from about room temperature to about 37° C. In some embodiments, the sample can be incubated for about 10 mins to about 20 mins at room temperature. In some embodiments, the sample is incubated for about fifteen minutes at room temperature.

To prevent or reduce agglutination (or non-specific binding) during separation of the microbes from the sample, additional reagents can be added to the sample mixture. Such reagents are also referred to as blocking reagents herein. For example, these blocking reagents can comprise a ligand of the affinity molecules on the coated-microbeads. Addition of such blocking reagents can reduce agglutination by binding with any empty ligand binding sites on the affinity molecules. Accordingly, when microbe-targeting magnetic microbeads are used for capturing the microbes, the blocking reagent can be a carbohydrate, such as mannose. Amount of additional reagent can depend on the amount of microbeads added to the sample. Generally, about the reagent is added to a final concentration of about 0.1 mM to about 10 mM. The amount of the blocking agent required can vary, at least partly, with the amount and/or surface area of the microbe-targeting substrate that is in contact with a test sample. In some embodiments, the blocking reagent can be added to a final concentration of about 0.1% (w/v) to about 10% (w/v), about 0.5% (w/v) to about 7.5% (w/v), or about 1% (w/v) to about 5% (w/v). In some embodiments, about 1% casein can be used as a blocking agent in the assay described herein.

After addition of the blocking reagent, the sample mixture can be incubated for a period of time to allow the blocking reagent to bind to with the affinity molecules, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature. In some embodiments, incubation is for about 5 seconds to about 60 seconds. In some embodiments, the incubation can be performed at a temperature ranging from about room temperature to about 37° C. In some embodiments, the sample is incubated for about fifteen minutes at room temperature.

To prevent or reduce non-specific binding during the contact between a microbe-targeting substrate and a test sample, in some embodiments, the microbe-targeting substrate (e.g., coated-microbeads) and/or the test sample can be pre-treated with a blocking agent that does not react with microbes, e.g., casein, normal serum, BSA, non-fat dry milk powder and any art-recognized block agent, before contacting each other. Optionally, microbe-targeting substrate after blocking can be washed with any art-recognized buffer to remove any leftover blocking agent. The number of wash steps can range from 1 to many, e.g., 1, 2, 3, 4, 5, 6, 7, 8, 9, 10 or more wash steps. In one embodiment, the microbe-targeting substrate after blocking can be washed with a buffer, e.g., TBST, for about at least 1-3 times.

Exemplary Optional Modifications to 1208 (Microbe Capture):

In accordance with one aspect described herein, the test sample can be contacted with a microbe-targeting substrate in the presence of a chelating agent. Without wishing to be bound by theory, the addition of a chelating agent to a test sample and/or processing buffer can reduce the likelihood of any protein A- and protein G-negative microbe (e.g., *E. coli*), but not protein A- or protein G-expressing microbe (e.g., *S. aureus*) in the test sample, to bind with at least one microbe-binding molecule. Accordingly, detection of any microbes bound on the microbe-targeting substrate described herein in the presence of a chelating agent can determine the presence or absence of a protein A- or protein G-expressing microbe in a test sample.

The chelating agent can be added into the processing buffer comprising the test sample. The amount of the chelating agent is sufficient to chelate free calcium ions and thus prevent or reduce calcium-dependent carbohydrate recognition domain binding (e.g., mannose-binding lectin) with a microbe. The amount of the chelating agent needed to prevent or reduce calcium-dependent carbohydrate recognition domain binding (e.g., mannose-binding lectin) with a microbe can depend on, e.g., the concentration of free calcium ions present in a test sample and optionally a capture buffer, e.g., used to dilute a chelating agent and/or a test sample. Thus, in some embodiments, the concentration of the chelating agent can be higher than the total concentration of free calcium ions present in the combined solution of a test sample and a capture buffer. For example, in some embodiments, the concentration of the chelating agent can be at least about 30% higher, including at least about 40%, at least about 50%, at least about 60%, at least about 70%, at least about 80%, at least about 90%, at least about 95%, at least about 98%, up to and including 100%, or any percent between about 30% and about 100%, higher than the total concentration of free calcium ions present in the combined solution of a test sample and a capture buffer. In other embodiments, the concentration of the chelating agent can be at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 75-fold, at least about 100-fold or more, higher than the total concentration of free calcium ions present in the combined solution of a test sample and a capture buffer. In one embodiment, the concentration of the chelating agent can be at least about 5-fold to about 50-fold, or at least about 7-fold to about 25-fold, higher than the total concentration of free calcium ions present in the combined solution of a test sample and a capture buffer.

In some embodiments, the concentration of a chelating agent present in the test sample and optionally a processing or capture buffer, e.g., used to dilute the chelating agent and/or the test sample, can range from about 0.1 mM to about 1 M, about 10 mM to about 500 mM, about 20 mM to about 250 mM, or about 25 mM to about 125 mM. In one embodiment, the concentration of a chelating agent present in the test sample and optionally a capture buffer can be about 25 mM to about 125 mM.

In some embodiments, the concentration of a chelating agent present in the test sample containing the microbe-targeting substrate can be sufficient to reduce the likelihood of a protein A- and protein G-negative microbe (e.g., *E. coli*), if present in the test sample, to bind with at least one microbe-binding molecule. For example, the concentration of a chelating agent present in the test sample with the microbe-targeting substrate can be sufficient to reduce the number of protein A- and protein G-negative microbes (e.g., *E. coli*), if present in the test sample, to bind with at least one microbe-binding molecule, by at least about 30%, at least about 40%, at least about 50%, at least about 60%, at least about 70%, at least 80% or higher, as compared to the number of protein A- and protein G-negative microbes (e.g., *E. coli*) bound on the microbe binding molecules in the absence of the chelating agent. In some embodiments, the concentration of a chelating agent present in the test sample with the microbe-targeting substrate can be sufficient to reduce the number of protein A- and protein G-negative microbes (e.g., *E. coli*), if present in the test sample, to bind with at least one microbe-binding molecule, by at least about 85%, at least about 90%, at least about 95%, at least about 98%, at least about 99%, up to and including 100%, or any values between about 85% and about 100%, as compared to the number of protein A- and protein G-negative microbes (e.g., *E. coli*) bound on the microbe-binding molecules in the absence of the chelating agent.

The protein A-expressing and protein G-expressing microbes can generally bind to microbe-binding molecules via two independent (but additive) mechanisms: Fc-mediated binding and microbe surface-binding domain (e.g., MBL)-mediated binding. Without wishing to be bound by theory, while the protein A-expressing and protein G-expressing microbes can still be captured on the microbe-targeting substrate in the presence of a chelating agent, the presence of free calcium ions can further increase the number of protein A-expressing and protein G-expressing microbes bound to the microbe-targeting substrate, because the overall binding in the presence of calcium ions can be almost twice as strong as in the absence of calcium ions.

Figure 29:
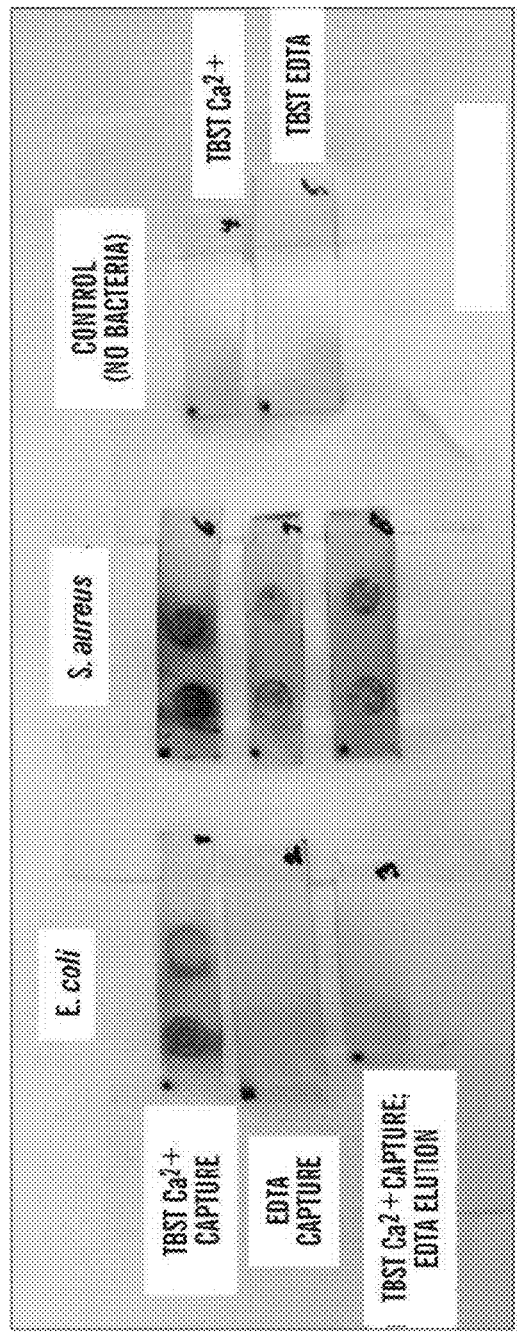
FIG. 29 is an image showing dot blot determination of *E. coli* and *S. aureus* with or without EDTA in the capture and/or wash buffer.

Accordingly, in some embodiments, the concentration of a chelating agent present in the test sample containing the microbe-targeting substrate can reduce the number of protein A-expressing microbes and/or protein G-expressing microbes bound onto the microbe-targeting substrate, but such effect as compared to that on the protein A- and protein G-negative microbes (e.g., *E. coli*) is much smaller, e.g., at least about 30% smaller, at least about 40% smaller, at least about 50%, at least about 60% smaller, at least about 70% smaller, or at least about 80% smaller. For example, as shown in FIG. 29, while the concentration of a chelating agent (e.g., 100 mM EDTA) is sufficient to reduce the binding of protein A- and protein G-negative microbes (e.g., *E. coli*) with a microbe-targeting substrate (e.g., a microbe-targeting membrane) to an undetectable level, there is still a detectable level of protein A-expressing microbes (e.g., *S. aureus*) binding to the microbe-targeting membrane. Therefore, in some embodiments, the concentration of a chelating agent used in the assay described herein should be high enough to prevent at least about 80% or higher, including at least about 90%, at least about 95%, up to and including 100%, of the protein A- and protein G-negative microbes (e.g., *E. coli*) from binding to be microbe-targeting substrate, but low enough to allow at least about 30% or higher, including at least about 40%, at least about 50%, at least about 60%, at least about 70% or higher, of the protein A-expressing microbes (e.g., *S. aureus*) or protein G-expressing microbes to bind with the microbe-targeting substrate. In one embodiment, the concentration of a chelating agent used in the assay described herein should be high enough to prevent at least about 90% or higher, of the protein A- and protein G-negative microbes (e.g., *E. coli*), if any present in the test sample, from binding to be microbe-targeting substrate, but low enough to allow at least about 50% of the protein A-expressing microbes (e.g., *S. aureus*) or protein G-expressing microbes, if any present in the test sample, to bind with the microbe-targeting substrate.

Examples of calcium ion-chelating agents can include, but are not limited to, 1,2-bis(2-aminophenoxy)ethane-N,N,N',N'-tetraacetic acid, ethylenediaminetetraacetic acid (EDTA); ethylene glycol-bis(2-aminoethylether)-N,N,N',N'-tetraacetic acid; ethylene glycol-bis(β-aminoethyl ether)-N,N,N',N'-tetraacetic acid (EGTA), 1,2-bis(o-aminophenoxy)ethane-N,N,N',N'-tetraacetic acid (BAPTA), a buffer containing citrate, N,N-Bis(2-(bis-(carboxymethyl)amino)ethyl)-glycine (DTPA), nitrilo-2,2',2"-triacetic acid (NTA), a buffer that precipitates a calcium ion from the test sample, including, e.g., a phosphate buffer, a carbonate buffer and a bicarbonate buffer, a low pH buffer (e.g., a pH buffer less than pH 7 or less than pH 6), citric acids and its salts, gluconic acid and its salts, alkali metal pyrophosphates, alkali metal polyphosphates, sodium hexametaphosphate, triethylene tetramine, diethylene triamine, o-phenanthroline, oxalic acid and any combinations thereof.

The chelating agent can be directly added to the test sample or prepared in a processing or capture buffer, which is then added to the test sample in contact with the microbe-targeting substrate. The processing or capture buffer can be any buffered solutions, e.g., with a pH ranging from about 6 to about 10. In some embodiments, the processing or capture buffer can include, but is not limited to, a tris-buffered saline, a phosphate buffered saline or a combination thereof. In some embodiments, the processing or capture buffer can include a surfactant, e.g., to prevent non-specific binding of a microbe to a microbe-surface-binding domain of the microbe-targeting substrate, and/or to saturate non-specific binding sites, if any, present in the microbe-targeting substrate. A surfactant or detergent, e.g., as described earlier, can be dissolved in a buffered solution in any amount, e.g., ranging from about 0.001% (v/v) to about 5% (v/v), from about 0.01% (v/v) to about 2.5% (v/v), or from about 0.05% (v/v) to about 1% (v/v). In some embodiments, the surfactant added to the processing or capture buffer can include Tween 80 or polysorbate 80 at a concentration of about 0.01% to about 0.1%. In one embodiment, the surfactant added to the processing or capture buffer can include Tween 80 or polysorbates 80 at a concentration of about 0.05%.

After incubation, the microbe-targeting substrate can then be analyzed, as described below, for the presence or absence of a bound microbe. In the absence of a microbe-targeting substrate-bound microbe, in some embodiments, the previous volume of the test sample or a new fresh volume of the test sample can be contacted with a fresh microbe-targeting substrate in the presence of free calcium ions, e.g., to determine the presence or absence of protein A- and protein G-negative microbes (e.g., *E. coli*). In some embodiments, the free calcium ions can be produced adding a sufficient amount of calcium salts in the test sample. If there has been a chelating agent present in the test sample, a higher amount of calcium salts is generally needed in order to obtain free calcium ions.

As used herein, the term "free calcium ions" refers to calcium ions that are not complexed with any molecule or compound, e.g., a chelating agent, which can hinder its reaction with other molecules or ions to mediate binding of carbohydrate patterns on a microbial cell surface to a microbe surface-binding domain (e.g., MBL) of the engineered microbe-binding molecule. Accordingly, in some embodiments, free calcium ions can be present in the absence of chelating agent. In some embodiments, free calcium ions can be present in a solution comprising a chelating agent and calcium ions, wherein the amount of calcium ions present in the solution is at least about 30% more than an amount sufficient to interact with substantially all the chelating agent molecules present in the solution to form chelate complexes. For example, in some embodiments, in order to obtain free calcium ions, the amount of calcium ions present in the solution can be at least about 30%, including at least about 40%, at least about 50%, at least about 60%, at least about 70%, at least about 80%, at least about 90%, at least about 95%, at least about 98%, up to and including 100% and any percent between 30% and 100%, more than an amount sufficient to interact with substantially all the chelating agent molecules present in the solution to form chelate complexes. In some embodiments, in order to obtain free calcium ions, the amount of calcium ions present in the solution can be at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 100-fold, at least about 500-fold, at least about 1000-fold, more than an amount sufficient to interact with substantially all the chelating agent molecules present in the solution to form chelate complexes. In some embodiments, free calcium ions can be present in a solution when the concentration of calcium ions in the solution is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, or higher than the concentration of a chelating agent present in the same solution.

In some embodiments, calcium ions can be obtained from a water-soluble calcium salt. By the term "water-soluble calcium salt" is meant a calcium salt which has significant solubility in water at room temperature, for example at least 1 gram per 100 ml water, at least 10 grams per 100 ml water, or at least 25 grams per 100 ml water or higher. Examples of calcium salts include, without limitations, calcium chloride, calcium fluoride, calcium bromide, calcium iodide, calcium nitrate, calcium citrate, calcium formate, calcium acetate, calcium gluconate, calcium ascorbate, calcium lactate, calcium glycinate and mixtures thereof. In some embodiments, calcium chloride can be used as a source of calcium ions.

Free calcium ions can be present at a concentration or an amount sufficient to mediate binding of calcium-dependent carbohydrate recognition domain with a microbe surface. In some embodiments, free calcium ions can be present at a concentration of at least about 1 μM, at least about 10 μM, at least about 25 μM, at least about 50 μM, at least about 100 μM, at least about 250 μM, at least about 500 μM, or at least about 1 mM or higher. In some embodiments, the free calcium ions can be present at a concentration of at least about 1 mM, at least about 2.5 mM, at least about 5 mM, at least about 10 mM, at least about 25 mM, at least about 50 mM, at least about 75 mM, at least about 100 mM or higher. In other embodiments, the free calcium ions can be present at a concentration of at least about 100 mM, at least about 150 mM, at least about 200 mM, at least about 300 mM, at least about 400 mM, at least about 500 mM, at least about 600 mM, at least about 700 mM, at least about 800 mM, at least about 900 mM, at least about 1 M or higher. In one embodiment, the free calcium ions can be present at a concentration of about 1 mM to about 10 mM. In one embodiment, the free calcium ions can be present at a concentration of at least about 5 mM.

While a chelating agent can be added during an initial capture of a microbe on a microbe-targeting substrate, the chelating agent can also be first excluded to allow the initial capture of any microbe, including protein A- and protein G-negative microbes, on a microbe-targeting substrate in the presence of free calcium ions, but added after the capture to remove any captured protein A- or protein G-negative microbes from the microbe-targeting substrate.

Accordingly, in some embodiments, the microbe capture can comprise (i) contacting at least a first volume of a test sample with a microbe-targeting substrate described herein in the presence of free calcium ions, and (ii) contacting the microbe-binding molecule of the microbe-targeting substrate described herein, upon the contact with the test sample, with a solution comprising a chelating agent.

When the microbe-targeting substrate is contacted with a test sample in the presence of free calcium ions as described herein, microbes that primarily depend on calcium-dependent MBL-mediated binding such as protein A- and protein G-negative microbes, e.g., E. coli can bind to the microbe-target substrate, in addition to microbes associated with Fc-mediated binding such as protein A-expressing microbes (e.g., S. aureus), and protein G-expressing microbes.

To elute off or remove from the microbe-targeting substrate the captured microbes that primarily depend on calcium-dependent MBL-mediated binding such as protein A- and protein G-negative microbes, e.g., E. coli, the microbe-binding molecules on the microbe-targeting substrates can be contacted with a solution comprising a sufficient amount of a chelating agent as described herein. The solution comprising the chelating agent can be same as a capture buffer described above. In such embodiments, the microbe-targeting substrate can be incubated with the solution comprising a chelating agent for a period of time to allow microbes that primarily bind to microbe-binding molecules via calcium-dependent MBL-mediated binding to elute off the microbe-targeting substrate, e.g., incubation for at least one minute, at least two minutes, at least three minutes, at least four minutes, at least five minutes, at least ten minutes, at least fifteen minutes, at least thirty minutes, at least forty-five minutes, or at least one hour. Such incubation can be performed at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the microbe-targeting substrate can be incubated with the solution comprising a chelating agent for at least about 5 mins to about 15 mins at room temperature.

In these embodiments, the concentration of a chelating agent used in the assay described herein is sufficient to elute off or remove from the microbe-targeting substrate at least about 30% of the bound protein A- and protein G-negative microbes (e.g., E. coli). For example, the concentration of a chelating agent used in the assay described herein is sufficient to elute off or remove from the microbe-targeting substrate at least about 30% of the bound protein A- and protein G-negative microbes (e.g., E. coli), including at least about 40%, at least about 50%, at least about 60%, at least about 70%, at least 80% or higher, of the bound protein A- and protein G-negative microbes (e.g., E. coli). In some embodiments, the concentration of a chelating agent used in the assay described herein is sufficient to elute off or remove from the microbe-targeting substrate at least about 85% of the bound protein A- and protein G-negative microbes (e.g., E. coli), including at least about 85%, at least about 90%, at least about 95%, at least about 98%, up to and including 100%, or any values between about 85% and about 100%, of the bound protein A- and protein G-negative microbes (e.g., E. coli).

As noted above, the protein A-expressing and protein G-expressing microbes can bind to microbe-binding molecules via Fc-mediated and calcium ion-dependent MBL-mediated binding. Without wishing to be bound by theory, the concentration of a chelating agent used in the assay described herein can also elute off or remove at least a portion of the protein A-expressing and/or protein G-expressing microbes from the microbe-targeting substrate. For example, the concentration of a chelating agent used to elute off or remove protein A- and protein G-negative microbes from the microbe-targeting substrate can be sufficient to elute off or remove no more than 60%, no more than 50%, no more than 40%, no more than 30%, no more than 20%, no more than 10% or lower, of the bound protein A-expressing and/or protein G-expressing microbes. In some embodiments, the concentration of a chelating agent used to elute off or remove from the microbe-targeting substrate at least about 80% or more, including at least about 90% or more, of the bound protein A- and protein G-negative microbes can be sufficient to elute off or remove no more than 50%, or more than 40% of the bound protein A-expressing and/or protein G-expressing microbes. As shown in FIG. 29, while the concentration of a chelating agent (e.g., 100 mM EDTA) is sufficient to elute off or remove substantially all protein A- and protein G-negative microbes (e.g., E. coli) from a microbe-targeting substrate to an undetectable level, there is still a detectable level of protein A-expressing microbes (e.g., S. aureus) remained bound to the microbe-targeting membrane.

As a person having ordinary skill in the art can appreciate, the assay described herein can further comprise isolating the microbe-targeting substrate from the test sample, e.g., as described below, before contacting microbe-binding molecules on its substrate surface with the solution comprising the chelating agent described herein.

1210 (Microbe Separation from Sample):

The sample mixture is then subjected to a microbe separation process. In some embodiments, because microbes are bound with one or more magnetic microbeads, a magnet can be employed to separate the bound microbes from the test sample. The skilled artisan is well aware of methods for carrying out magnetic separations. Generally, a magnetic field gradient can be applied to direct the capture of magnetic microbeads. Optionally, the bound microbe can be washed with a buffer to remove any leftover sample and unbound components. Number of wash steps can range from 1 to many, e.g., 1, 2, 3, 4, 5, 6, 7, 8, 9, 10 or more wash steps. Without wishing to be bound by a theory, capture and separation of the bound microbes from the sample can concentrate the microbes and also remove components, which can interfere with the assay or process, from the test sample.

The magnetic field source can be any magnet device positioned to generate the magnetic field gradient that is used to pull the captured microbe out from the sample. An electromagnetic controller can be used to control and adjust the magnetic field and gradients thereof, and to control the migration, separation and orientation of the magnetically bound microbes. The magnetic field gradient can be generated by a permanent magnet or by an electromagnetic signal generator. The electromagnetic signal generator can include an electromagnet or electrically-polarizable element, or at least one permanent magnet. The magnetic field gradient can be produced at least in part according to a pre-programmed pattern. The magnetic field gradient can have a defined magnetic field strength and/or spatial orientation. In some embodiments, the magnetic field gradient has a defined magnetic field strength. The term "magnetic field gradient" as used herein refers to a variation in the magnetic field with respect to position. By way of example only, a one-dimensional magnetic field gradient is a variation in the magnetic field with respect to one direction, while a two-dimensional magnetic field gradient is a variation in the magnetic field with respect to two directions.

As used herein, the term "magnetic field" refers to magnetic influences which create a local magnetic flux that flows through a composition and can refer to field amplitude, squared-amplitude, or time-averaged squared-amplitude. It is to be understood that magnetic field can be a direct-current (DC) magnetic field or alternating-current (AC) magnetic field. The magnetic field strength can range from about 0.00001 Tesla per meter (T/m) to about $10^5$ T/m. In some embodiments, the magnetic field strength can range from about 0.0001 T/m to about $10^4$ T/m. In some other embodiments, the magnetic field strength can range from about 0.001 T/m to about $10^3$ T/m.

In some embodiments, microbe capture and/or microbe-targeting substrate separation can be performed by a rapid microbe diagnostic device as described in Int. Pat. App. No. WO 2011/091037, filed Jan. 19, 2011, the content of which is incorporated herein by reference. A rapid microbe diagnostic device as described in Int. Pat. App. No. WO 2011/091037, filed Jan. 19, 2011, can be modified to replace the capture chamber or capture and visualization chamber with an s-shaped flow path. A magnet can then be used to capture bound microbe against the flow path wall; separating the bound microbe from rest of the sample.

In some embodiments, microbe capture and/or separation is by a device or method as described in U.S. Pat. App. Pub. No. 2009/0220932, No. 2009/007861, No. 2010/0044232, No. 2007/0184463, No. 2004/0018611, No. 2008/0056949, No. 2008/0014576, No. 2007/0031819, No. 2008/0108120, and No. 2010/0323342, the contents of which are all incorporated herein by reference.

Without limitations, if a microbe-targeting substrate does not possess a magnetic property, isolation of a microbe-targeting substrate (e.g., particles, posts, fibers, dipsticks, membrane, filters, capillary tubes, etc.) from the test sample can be carried out by non-magnetic means, e.g., centrifugation, and filtration. In some embodiments where the microbe-targeting substrate is in a form a dipstick or membrane, the microbe-targeting dipstick or membrane can be simply removed from the test sample, where microbes, if any, in the test sample, remained bound to the engineered microbe-binding molecules conjugated to the dipstick or membrane substrate.

Optionally, the microbe-targeting substrate after isolated from the test sample or processing buffer can be washed with a buffer (e.g., TBST) to remove any residues of test sample, solution comprising the chelating agent or any unbound microbes. The number of wash steps can range from 1 to many, e.g., 1, 2, 3, 4, 5, 6, 7, 8, 9, 10 or more wash steps. In one embodiments, the microbe-targeting substrate after isolated from the solution comprising the chelating agent and/or the test sample can be washed with a buffer (e.g., TBST) for about at least 1-3 times.

1212 (Microbe Detection/Analysis):

A detection component, device or system can be used to detect and/or analyze the presence of the separated microbe, for example, by spectroscopy, electrochemical detection, polynucleotide detection, fluorescence anisotropy, fluorescence resonance energy transfer, electron transfer, enzyme assay, magnetism, electrical conductivity, isoelectric focusing, chromatography, immunoprecipitation, immunoseparation, aptamer binding, filtration, electrophoresis, use of a CCD camera, immunoassay, ELISA, Gram staining, immunostaining, microscopy, immunofluorescence, western blot, polymerase chain reaction (PCR), RT-PCR, fluorescence in situ hybridization, sequencing, mass spectroscopy, or substantially any combination thereof. The separated microbe can remain bound on the microbe-targeting substrate during detection and/or analysis, or be isolated form the microbe-targeting substrate prior to detection and/or analysis.

In some embodiments, labeling molecules that can bind with the microbe can also be used to label the microbes for detection. As used herein, a "labeling molecule" refers to a molecule that comprises a detectable label and can bind with a target microbe. Labeling molecules can include, but are not limited to, MBL or a portion thereof, FcMBL, AKT-FcMBL, wheat germ agglutinin, lectins, antibodies (e.g., gram-negative antibodies or gram-positive antibodies, antibiotics to specific microbial strains or species), antigen binding fragments of antibodies, aptamers, ligands (agonists or antagonists) of cell-surface receptors and the like. The labeling molecule can also be a non-specific labeling molecule that non-specifically stains all viable cells in a sample.

As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein.

A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO- TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CFDA; CFP-Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydrorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments, the detectable label is a fluorophore or a quantum dot. Without wishing to be bound by a theory, using a fluorescent reagent can reduce signal-to-noise in the imaging/readout, thus maintaining sensitivity. Accordingly, in some embodiments, prior to detection, the microbes isolated from or remained bound on the microbe-targeting substrate can be stained with at least one stain, e.g., at least one fluorescent staining reagent comprising a microbe-binding molecule, wherein the microbe-binding molecule comprises a fluorophore or a quantum dot. Examples of fluorescent stains include, but are not limited to, any microbe-targeting element (e.g., microbe-specific antibodies or any microbe-binding proteins or peptides or oligonucleotides) typically conjugated with a fluorophore or quantum dot, and any fluorescent stains used for detection as described herein.

In some embodiments, a labeling molecule can be configured to include a "smart label", which is undetectable when conjugated to the microbe-binding molecules, but produces a color change when released from the engineered molecules in the presence of a microbe enzyme. Thus, when a microbe binds to the engineered microbe-binding molecules, the microbe releases enzymes that release the detectable label from the engineered molecules. An observation of a color change indicates presence of the microbe in the sample.

In some embodiments, the microbe-targeting substrate can be conjugated with a label, such as a detectable label or a biotin label.

In some embodiments, the labeling molecule can comprise MBL or a microbe-binding molecule described herein. In one embodiment, the labeling molecule comprises FcMBL. Without wishing to be bound by a theory, labeling molecules based on MBL, and FcMBL in particular, attach selectively to a broad range of microbes, and so they enable the method described herein to detect the majority of blood-borne microbes with high sensitivity and specificity.

Any method known in the art for detecting the particular label can be used for detection. Exemplary methods include, but are not limited to, spectrometry, fluorometry, microscopy imaging, immunoassay, and the like. While the microbe capture step can specifically capture microbes, it can be beneficial to use a labeling molecule that can enhance this specificity. If imaging, e.g., microscopic imaging, is to be used for detecting the label, the staining can be done either prior to or after the microbes have been laid out for microscopic imaging. Additionally, imaging analysis can be performed via automated image acquisition and analysis.

For optical detection, including fluorescent detection, more than one stain or dye can be used to enhance the detection or identification of the microbe. For example, a first dye or stain can be used that can bind with a genus of microbes, and a second dye or strain can be used that can bind with a specific microbe. Colocalization of the two dyes then provides enhanced detection or identification of the microbe by reducing false positive detection of microbes.

In some embodiments, microscopic imaging can be used to detect signals from label on the labeling agent. Generally, the microbes in the subsample are stained with a staining reagent and one or more images taken from which an artisan can easily count the number of cells present in a field of view.

In particular embodiments, microbe can be detected through use of one or more enzyme assays, e.g., enzyme-linked assay (ELISA). Numerous enzyme assays can be used to provide for detection. Examples of such enzyme assays include, but are not limited to, beta-galactosidase assays, peroxidase assays, catalase assays, alkaline phosphatase assays, and the like. In some embodiments, enzyme assays can be configured such that an enzyme will catalyze a reaction involving an enzyme substrate that produces a fluorescent product. Enzymes and fluorescent enzyme substrates are known and are commercially available (e.g., Sigma-Aldrich, St. Louis, Mo.). In some embodiments, enzyme assays can be configured as binding assays that provide for detection of microbe. For example, in some embodiments, a labeling molecule can be conjugated with an enzyme for use in the enzyme assay. An enzyme substrate can then be introduced to the one or more immobilized enzymes such that the enzymes are able to catalyze a reaction involving the enzyme substrate to produce a detectable signal.

In some embodiments, an enzyme-linked assay (ELISA) can be used to detect signals from the labeling molecule. In ELISA, the labeling molecule can comprise an enzyme as the detectable label. Each labeling molecule can comprise one or more (e.g., 1, 2, 3, 4, 5, 6, 7, 8, 9, 10 or more) enzymes. Additionally, each labeling molecule can comprise one or more (e.g., 1, 2, 3, 4, 5, 6, 7, 8, 9, 10 or more) sites for binding with a microbe. Without wishing to be bound by a theory, presence of multimeric probe molecules can enhance ELISA signal.

For ELISA, any labeling molecule conjugated to an enzyme can be used. Exemplary labeling molecule include those comprising MBL, FcMBL, AKT-FcMBL, wheat germ agglutinin, lectins, antibodies (e.g., gram-negative antibodies or gram-positive antibodies), antigen binding fragments of antibodies, aptamers, ligands (agonists or antagonists) of cell-surface receptors and the like.

In some embodiments, the labeling molecule can comprise MBL or FcMBL labeled with a detectable label.

Similarly, a variety of enzymes can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like.

In some embodiments, the enzyme is a horseradish peroxidase (HRP).

In some embodiments, the enzyme is an alkaline peroxidase (AP).

A microbe-binding molecule and the enzyme can be linked to each other by a linker. In some embodiments, the linker between the microbe-binding molecule and the enzyme is an amide bond. In some embodiments, the linker between the microbe-binding molecule and the enzyme is a disulfide (S—S) bond.

When the microbe-binding molecule is a peptide, polypeptide or a protein, the enzyme can be linked at the N-terminus, the C-terminus, or at an internal position of the microbe-binding molecule. Similarly, the enzyme can be linked by its N-terminus, C-terminus, or an internal position.

In one embodiment, the ELISA probe molecule can comprise a MBL or a portion there of or a FcMBL molecule linked to a HRP. Conjugation of HRP to any proteins and antibodies are known in the art. In one embodiment, FcMBL-HRP construct is generated by direct coupling HRP to FcMBL using any commercially-available HRP conjugation kit. In some embodiments, the microbes isolated from or remained bound on the microbe-targeting substrate can be incubated with the HRP-labeled microbe-binding molecules, e.g., MBL or a portion thereof, or a FcMBL molecule linked to a HRP for a period of time, e.g., at least about 5 mins, at least about 10 mins, at least about 15 mins, at least about 20 mins, at least about 25 mins, at least about 30 mins. The typical concentrations of HRP-labeled molecules used in the ELISA assay can range from about 1:500 to about 1:20,000 dilutions. In one embodiment, the concentration of HRP-labeled microbe-binding molecules, e.g., MBL or a portion thereof, or a FcMBL molecule linked to a HRP molecule, can be about 1:1000 to about 1:10000 dilutions.

In one embodiment, the ELISA probe molecule can comprise a MBL or a portion thereof, or a FcMBL molecule linked to a AP. Conjugation of AP to any proteins and antibodies are known in the art. In one embodiment, FcMBL-AP construct is generated by direct coupling AP to FcMBL using any commercially-available AP conjugation kit. In some embodiments, the microbes isolated from or remained bound on the microbe-targeting substrate can be incubated with the AP-labeled microbe-binding molecule, e.g., MBL or a portion thereof, or a FcMBL molecule linked to a AP for a period of time, e.g., at least about 5 mins, at least about 10 mins, at least about 15 mins, at least about 20 mins, at least about 25 mins, at least about 30 mins. The typical concentrations of AP-labeled molecules used in the ELISA assay can range from about 1:1000 to about 1:20,000 dilutions. In one embodiment, the concentration of AP-labeled microbe-binding molecules, e.g., MBL or a portion thereof, or a FcMBL molecule linked to a AP molecule, can be about 1:5000 to about 1:10000 dilutions.

Following incubation with the ELISA probe molecules, the sample can be washed with a wash buffer one or more (e.g., 1, 2, 3, 4, 5 or more) times to remove any unbound probes. An appropriate substrate for the enzyme (e.g., HRP or AP) can be added to develop the assay. Chromogenic substrates for the enzymes (e.g., HRP or AP) are known to one of skill in the art. A skilled artisan can select appropriate chromogenic substrates for the enzyme, e.g., TMB substrate for the HRP enzyme, or BCIP/NBT for the AP enzyme. In some embodiments, the wash buffer used after incubation with an ELISA probe molecule can contain calcium ions at a concentration of about at least about 0.01 mM, at least about 0.05 mM, at least about 0.1 mM, at least about 0.5 mM, at least about 1 mM, at least about 2.5 mM, at least about 5 mM, at least about 10 mM, at least about 20 mM, at least about 30 mM, at least about 40 mM, at least about 50 mM or more. In alternative embodiments, the wash buffer used after incubation with an ELISA probe molecule can contain no calcium ions. In some embodiments, the wash buffer used after incubation with an ELISA probe molecule can contain a chelating agent. A wash buffer can be any art-recognized buffer used for washing between incubations with antibodies and/or labeling molecules. An exemplary wash buffer can include, but is not limited to, TBST.

In some embodiments, without wishing to be bound by theory, it can be desirable to use a wash buffer without a surfactant or a detergent for the last wash before addition of a chromogenic substrate, because a surfactant or detergent may have adverse effect to the enzymatic reaction with a chromogenic substrate.

One advantage of the ELISA-based approach is that the solid substrate does not need to be dispersed or dissociated from the microbe before binding the secondary reagents. This is in contrast to microscopic techniques, in which excess residual solid substrate may obscure the microbe during imaging. Furthermore, the optical readout components for ELISA are likely cheaper than in the microscopy case, and there is no need for focusing or for demanding that the sample be on the same focal plane. A further advantage of the ELISA-based approach is that it can take advantage of commercially available laboratory equipment. In particular, when the solid substrate is magnetic, magnetic separation can be automated using the KINGFISHER® system, the brief culture can be performed using an airlift fermenter, and the colorimetric/fluorescent readout can be attained using a standard plate reader.

Further amplification of the ELISA signal can be obtained by multimerizing the recognition molecule (e.g., the microbe-binding molecule) or by multimerizing the detection enzyme (HRP, etc.). For instance, phage expression can be used to yield multimerized MBL and provide a scaffold to increase the concentration of HRP (either through direct coupling of HRP to the phage particles or using an HRP-antiM13 conjugated antibody).

In some embodiments, microbe can be detected through use of immunoassay. Numerous types of detection methods may be used in combination with immunoassay based methods.

Without limitations, detection of microbes in a sample can also be carried out using light microscopy with phase contrast imaging based on the characteristic size (5 um diameter), shape (spherical to elliptical) and refractile characteristics of target components such as microbes that are distinct from all normal blood cells. Greater specificity can be obtained using optical imaging with fluorescent or cytochemical stains that are specific for all microbes or specific subclasses (e.g. calcofluor (1 $\mu$M to 100 $\mu$M) for chitin in fungi, fluorescent antibodies directed against fungal surface molecules, gram stains, acid-fast stains, fluorescent MBL, fluorescent Fc-MBL, etc.).

Microbe detection can also be carried out using an epifluorescent microscope to identify the characteristic size (5 um diameter), shape (spherical to elliptical) and staining characteristics of microbes. For example, fungi stain differently from all normal blood cells, strongly binding calcofluor (1 $\mu$M to 100 $\mu$M) and having a rigid ellipsoid shape not found in any other normal blood cells.

In some embodiments, a microbe can be detected through use of spectroscopy. Numerous types of spectroscopic methods can be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., *Clinical Chemistry*, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, a microbe can be detected through use of fluorescence anisotropy. Fluorescence anisotropy is based on measuring the steady state polarization of sample fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy can be coupled to numerous fluorescent labels as have been described herein and as have been described in the art.

In some embodiments, microbe can be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect captured microbe. For example, in some embodiments, a first labeling molecule can be labeled with a fluorescent donor and second labeling molecule can be labeled with a fluorescent acceptor. Accordingly, such labeled first and second labeling molecules can be used within competition assays to detect the presence and/or concentration of microbe in a sample. Numerous combinations of fluorescent donors and fluorescent acceptors can be used for detection.

In some embodiments, a microbe can be detected through use of polynucleotide analysis. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described, for example, in U.S. Pat. Nos. 7,118,910 and 6,960,437; herein incorporated by reference). Such methods can be adapted to provide for detection of one or more microbe nucleic acids. In some embodiments, fluorescence quenching, molecular beacons, electron transfer, electrical conductivity, and the like can be used to analyze polynucleotide interaction. Such methods are known and have been described, for example, in Jarvius, *DNA Tools and Microfluidic Systems for Molecular Analysis*, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al, *Proc. Natl. Acad. Sci,* 100:7605-7610 (2003); Wang et al. *Anal. Chem,* 75:3941-3945 (2003); and Fan et al, *Proc. Natl. Acad. Sci,* 100:9134-9137 (2003) and in U.S. Pat. Nos. 6,958,216; 5,093,268; and 6,090,545, the content of all of which is incorporated herein by reference. In some embodiments, the polynucleotide analysis is by polymerase chain reaction (PCR). The fundamentals of PCR are well-known to the skilled artisan, see, e.g. McPherson, et al., *PCR, A Practical Approach*, IRL Press, Oxford, Eng. (1991), hereby incorporated by reference.

In some embodiments, a metabolic assay is used to determine the relative number of microbes in a sample compared to a control. As will be apparent to one of ordinary skill in the art any metabolic indicator that can be associated with cells can be used, such as but not limited to, turbidity, fluorescent dyes, and redox indicators such as, but not limited to, Alamar Blue, MTT, XTT, MTS, and WST. Metabolic indicators can be components inherent to the cells or components added to the environment of the cells. In some embodiments, changes in or the state of the metabolic indicator can result in alteration of ability of the media containing the sample to absorb or reflect particular wavelengths of radiation.

Exemplary metabolic assays include, but are not limited to, ATP Luminescence, reactive oxygen species (ROS) assays, Resazurin assays, Luminol, MTT-metabolic assays, and the like. Further, as one of skill in the art is well aware, kits and methods for carrying out metabolic assays are commercially available. For example, 2-(N-(7-Nitrobenz-2-oxa-1,3-diazol-4-yl)Amino)-2-Deoxyglucose (2-NBDG), ATP Determination Kit, AMPLEX® Red Galactose/Galactose Oxidase Assay Kit, AMPLEX® Red Glucose/Glucose Oxidase Assay Kit, AMPLEX® Red Glutamic Acid/Glutamate Oxidase Assay Kit, AMPLEX® Red Hydrogen Peroxide/Peroxidase Assay Kit, AMPLEX® Red Monoamine Oxidase Assay Kit, AMPLEX® Red Neuraminidase (Sialidase) Assay Kit, AMPLEX® Red Phosphatidylcholine-Specific Phospholipase C Assay Kit, AMPLEX® Red Sphingomyelinase Assay kit, AMPLEX® Red Uric Acid/Uricase Assay Kit, AMPLEX® Red Xanthine/Xanthine Oxidase Assay Kit, THIOLTRACKER™ Violet (Glutathione Detection Reagent), THIOLTRACKER™ Violet (Glutathione Detection Reagent), and VYBRANT® Cell Metabolic Assay Kit from Invitrogen; Adenosine 5'-triphospahte (ATP) Luminescence Assay Kit (ENLITEN® from Promega; ATPLITE™ from PerkinElmer Life Sciences; ATP Bioluminescence Assay kit HS II from Boehringer Mannheim, Germany; Adenosine 5'-triphosphate (ATP) Luminescence Assay Kit from EMD Millipore; Reactive Oxygen Species (ROS) Assays from Cell BioLabs, Inc.; Cellular Reactive Oxygen Species Detection Assay Kit from ABCAM®; hROS Detection Kit from Cell Technology, Inc.; and ABTS Antioxidant Assay Kit, ORAC Antioxidant Assay Kit, OxiSelect HORAC Activity Assay Kit, OxiSelect In vitro ROS/RNS Assay Kit (Green Fluorescence), OxiSelect Intracellular ROS Assay Kit (Green Fluorescence), OxiSelect ORAC Activity Assay Kit, OxiSelect Total Antioxidant Capacity (TAC) Assay Kit, and Total Antioxidant Capacity Assay Kit from BioCat.

In some embodiments, microbes isolated from or remained bound on microbe-targeting substrate can be labeled with nucleic acid barcodes for subsequent detection and/or multiplexing detection. Nucleic acid barcoding methods for detection of one or more analytes in a sample are well known in the art.

In other embodiments, the captured microbe can be analyzed and/or detected in the capture chamber or capture and visualization chamber of a rapid microbe diagnostic device described in the Int. Pat. App. No. Int. Pat. App. No. WO 2011/091037, filed Jan. 19, 2011. Alternatively, the captured microbe can be recovered (i.e., removed) and analyzed and/or detected.

In some embodiments, the captured microbe is recovered and analyzed and/or detected using a particle on membrane assay as described in U.S. Pat. No. 7,781,226, content of which is incorporated herein by reference. A particle on membrane assay as described in U.S. Pat. No. 7,781,226 can be operably linked with a rapid microbe diagnostic device of the Int. Pat. App. No. Int. Pat. App. No. WO 2011/091037 to reduce the number of sample handling steps, automate the process and/or integrate the capture, separation and analysis/detection steps into a microfluidic device.

In some embodiments, microbe capture, separation and analysis can be done using a hybrid microfluidic SPR and molecular imagining device as described in U.S. Pat. App. Pub. No. US 2011/0039280.

In some embodiments, the processes or assays described herein can detect the presence or absence of a microbe and/or identify a microbe in a test sample in less than 24 hours, less than 12 hours, less than 10 hours, less than 8 hours, less than 6 hours, less than 4 hours, less than 3 hours, less than 2 hours, less than 1 hour, or lower. In some embodiments, the processes or assays described herein can detect the presence or absence of a microbe and/or identify a microbe in a test sample in less than 6 hours, less than 4 hours, less than 3 hours, less than 2 hours, less than 1 hour, or lower.

Optional Additional Analyses or Treatment—Culturing:

In some embodiments of any aspects described herein, the assay or process can further comprise culturing any microbe bound on the microbe-targeting substrate (e.g., microbe-targeting magnetic microbeads) for a period of time. In such embodiments, the microbe bound on the microbe-targeting substrate can expand in population by at least about 10% after culturing for a period of time.

In some embodiments, the microbe bound on the microbe-targeting substrate (e.g., microbe-targeting magnetic microbeads) can be cultured for a period of time, e.g., at least about 15 mins, at least about 30 mins, at least about 1 hour, at least about 2 hours, at least about 3 hours, at least about 6 hours, at least about 9 hours, at least about 12 hours, at least about 18 hours, at least about 24 hours or longer. In some embodiments, the microbe bound on the microbe-targeting substrate (e.g., microbe-targeting magnetic microbeads) can be cultured for at least about 30 mins to at least about 3 hours.

In some embodiments, the number of microbes bound on the microbe-targeting substrate (e.g., microbe-targeting magnetic microbeads) after culturing for a certain period of time can be increased or expanded by at least about 30%, at least about 40%, at least about 50%, at least about 60%, at least about 70%, at least about 80%, at least about 90%, at least about 100%, as compared to the number of the microbes originally bound on the microbe-targeting substrate. In some embodiments, the number of microbes bound on the microbe-targeting substrate (e.g., microbe-targeting magnetic microbeads) after culturing for a certain period of time can be increased or expanded by at least about 1.5-fold, at least about 2-fold, at least about 3-fold, at least about 4-fold, at least about 5-fold, at least about 10-fold, at least about 50-fold, at least about 100-fold, at least about 500-fold, at least about 1000-fold, at least about 10000-fold, at least about 100000-fold, as compared to the number of the microbes originally bound on the microbe-targeting substrate.

In some embodiments, the microbes bound on the microbe-targeting substrates (e.g., microbe-targeting magnetic microbeads) can be cultured on a microbe-compatible culture medium, e.g., plated on an agar plate or cultured in LB broth. One of skill in the art will readily recognize microbial culture techniques, including, but not limited to, the use of incubators and/or equipment used to provide a gentle agitation, e.g., rotator platforms, and shakers, if necessary, e.g., to prevent the cells from aggregation without subjecting them to a significant shear stress and provide aerial agitation.

The microbes can remain bound on the microbe-targeting substrate (e.g., microbe-targeting magnetic microbeads) during detection and/or additional analyses described herein or they can be detached, eluted off or removed from a microbe-targeting substrate prior to detection or additional analyses described herein. In some embodiments where the bound microbes are desired to be detached, eluted off or removed from a microbe-targeting substrate, the microbe-binding molecules of the microbe-targeting substrate can be further contacted with a low pH buffer, e.g., a pH buffer less than 6, less than 5, less than 4, less than 3, less than 2, less than 1 or lower. In some embodiments, a low pH buffer that does not cause precipitation of a chelating agent, if present, can be used. In one embodiment, a low pH buffer can be arginine. In another embodiment, a low pH buffer can be pyrophosphate.

In some embodiments of any aspects described herein, the microbe-binding molecules of the microbe-targeting substrate can be further contacted with a low pH buffer and a chelating agent. In some embodiments, the contact of the microbe-binding molecules of the microbe-targeting substrate with the low pH buffer and the chelating agent can be concurrent or sequentially. In one embodiment, the microbe-binding molecules of the microbe-targeting substrate can be further contacted with arginine (e.g., 2 M) with EDTA or EGTA at pH 4.4.

The isolated microbes can then be used for analyses described earlier or additional treatment, e.g., expansion in culture, antibiotic sensitivity testing, sequencing and/or DNA or RNA analysis.

Optional Additional Analyses or Treatment—Antibiotic Sensitivity or Susceptibility Testing:

In some embodiments of any aspects described herein, the process or assay described herein can further comprise subjecting the microbes bound on the microbe-targeting substrate (e.g., microbe-targeting magnetic microbeads) and/or the expanded cultures of microbes isolated from the microbe-targeting substrate (e.g., microbe-targeting magnetic microbeads) to one or more antibiotics. The response of the microbe to an antibiotic can then be evaluated with any known methods in the art, e.g., by measuring the viability of microbes. Thus, an appropriate antibiotic can be identified for treatment of an infection caused by a microbe, even though the specific species of the microbe bound onto the microbe-targeting substrate is initially unknown. Additional details for use of engineered microbe-targeting molecules described herein in antibiotic sensitivity testings can be found, e.g., in U.S. Prov. App. Nos. 61/604,878 filed Feb. 29, 2012 and 61/647,860 filed May 16, 2012.

Any processes or steps described herein can be performed by a module or device. While these are discussed as discrete processes, one or more of the processes or steps described herein can be combined into one system for carrying out the assays of any aspects described herein.

Exemplary Embodiments of Methods for Diagnosing or Locating a Microbial Infection or Contamination In general, embodiments of the assays or processes of any aspects described herein can be used to detect the presence or absence of a microbe and/or microbial matter in a test sample or in situ (e.g., where the microbe actually resides, e.g., in a water reservoir or on a working surface). For example, in some embodiments, a test sample, e.g., obtained from a subject or an environmental source, or an environmental surface can be contacted with engineered microbe-binding molecules or engineered microbe-binding substrates described herein, such that any microbes, if present, in the test sample or environmental surface can be captured by the engineerd microbe-binding molecules or engineered microbe-binding substrates e.g., using any embodiments of the exemplary process described above. In some embodiments, the captured microbes bound on the engineered microbe-binding molecules and/or microbe-binding substrates can then be subjected to different analyses as described above, e.g., for identifying a microbe genus or species such as by immunoassay (e.g., using antibodies to a specific microbe), mass spectrometry, PCR, etc. In alternative embodiments where the engineered microbe-binding molecules comprise an imaging agent (e.g., a bubble, a liposome, a sphere, a diagnostic contrast agent or a detectable label described herein), the binding of the microbes to the engineered microbe-binding molecules can be detected in situ for identification of localized microbial infection or contamination, and also allow localized treatment of the infection or contamination.

In some embodiments, the assays or processes described herein can be used to diagnose or locate a microbial infection in situ in a subject. For example, engineered microbe-targeting microbeads comprising an imaging agent (e.g., the engineered microbe-targeting microbeads can be linked to an imaging agent, e.g., a bubble, a liposome, a sphere, a diagnostic contrast agent or a detectable label described herein) can be administered to a subject, either systemically (e.g., by injection), or locally. In such embodiments, the engineered microbe-targeting microbeads comprising an imaging agent can be used to identify and/or localize pockets of localized microbial infection (e.g., in a tissue) in the subject and optionally allow localized treatment of the microbial infection, which is described in the section "Exemplary Compositions and Methods for Treating and/or Preventing a Microbial Infection" below.

While an engineered microbe-binding molecule described herein (e.g., FcMBL) can bind to a broad spectrum of microbes, in certain embodiments, a microbe species (e.g., S. aureus) can be isolated and/or differentiated from another species (E. coli) based on their distinct abilities of binding to the engineered microbe-binding molecules or substrates described herein. For example, the inventors have demonstrated that S. aureus can bind to FcMBL via both calcium-dependent MBL-mediated interaction and calcium-independent Fc-mediated interaction, while E. coli can bind to FcMBL primarily via calcium-dependent MBL-mediated interaction. Without wishing to be limiting, an exemplary method for diagnosing an infection caused by S. aureus based on such unique ability of S. aureus binding to an engineered microbe-binding molecule (e.g., FcMBL) is described below for illustration purposes. One of skill in the art can readily make any necessary modifications to the exemplary illustration and/or adopt any embodiments of the assays or processes described herein to detect the presence or absence of any microbe in a test sample or in situ and/or diagnosing different kinds of microbial infections in a subject.

For example, there is a strong need for more rapid and/or effective diagnostic methods for distinguishing at least S. aureus from other bacteria, e.g., E. coli, which can permit physicians to initiate an appropriate drug therapy early on, rather than starting with a sub-optimal or a completely ineffective antibiotic. A delay in treatment of a microbial infection, e.g., S. aureus, can significantly affect the treatment outcome, and can be sometimes fatal.

Accordingly, in some embodiments, the assays or processes described herein can be used to distinguish a protein A-expressing microbe or a protein G-expressing microbe from a protein A- and protein G-negative microbe (e.g., E. coli) in a test sample. In particular, the inventors have demonstrated that S. aureus can be differentiated from E. coli using some embodiments of the assays or processes described herein. In some embodiments, a microbe-targeting substrate comprises a substrate coupled to a fusion protein between the Fc portion of human IgG1 and the neck and carbohydrate recognition domain (CRD) of human Mannose Binding Lectin (MBL) can be used for such microbial differentiation.

Accordingly, exemplary methods of determining the presence or absence of Staphylococcus aureus infection in a subject are also provided herein. For example, the method can comprise contacting at least a first volume of a test sample with a microbe-targeting substrate described herein in the presence of a chelating agent. Alternatively, the method can comprise (i) contacting at least a first volume of a test sample with a microbe-targeting substrate described herein in the presence of free calcium ions, and (ii) contacting the microbe-binding molecule of the microbe-targeting substrate described herein, upon the contact with the test sample, with a solution comprising a chelating agent. In some embodiments described herein, the method can further comprise analyzing the microbe-targeting substrate for the presence or absence of a bound microbe. The presence of a microbe bound onto the microbe-targeting substrate indicates the presence of a protein-A expressing microbe or a protein G-expressing microbe in the test sample; and the absence of a microbe bound onto the microbe-targeting substrate indicates the absence of a protein-A expressing or a protein G-expressing microbe in the test sample.

In some embodiments, the method can further comprise administering or prescribing to the subject an antimicrobial agent when the subject is detected with S. aureus. Non-limiting examples of an antimicrobial agent can include any therapeutic agent for treatment of S. aureus. In some embodiments, an antimicrobial agent can be an antibiotic commonly indicated for treatment of S. aureus, including, but not limited to, penicillin, methicillin, nafcillin, oxacillin, cloxacillin, dicloxacillin, flucloxacillin, vancomycin, and any combinations thereof.

In some embodiments where a microbe is absent on the microbe-targeting substrate, the method can further comprise analyzing the test sample or the solution comprising the chelating agent after removal of the microbe-targeting substrate to determine the presence or absence of a protein A- and protein G-negative microbe. For example, additional calcium ions (e.g., calcium salts) can be added to the test sample or the solution comprising the chelating agent in an amount more than what is needed to react with substantially all of the chelating agent molecules such that there are free calcium ions available to mediate carbohydrate recognition domain (e.g., MBL)-mediated binding between a microbe and the microbe-targeting substrate. A fresh microbe-targeting substrate can then be contacted with the treated test sample or the solution comprising the chelating agent in the presence of free calcium ions to detect the presence or absence of a protein A- and protein G-negative microbe (e.g., E. coli). Alternatively, a fresh microbe-targeting substrate can be contacted with a fresh volume of the test sample in the presence of free calcium ions (e.g., addition of a calcium salt at a concentration, e.g., of at least about 1 mM, at least about 5 mM, or higher) to detect the presence or absence of a protein A- and protein G-negative microbe (e.g., E. coli). Detection methods described above for a protein A-expressing or protein G-expressing microbe bound on a microbe-targeting substrate can be used for such purposes as well. Detection methods described in the International Application No. WO 2011/090954, the content of which is incorporated herein by reference, can also be employed herein to determine the presence or absence of protein A- and protein G-negative microbes (e.g., E. coli).

In those embodiments, when a microbe (e.g., protein A- and protein G-negative microbe (e.g., E. coli)) is detected in a subject, the method can further comprise administering or prescribing to the subject an appropriate antimicrobial agent described herein to treat the corresponding microbe (e.g., the protein A- and protein G-negative microbe, e.g., E. coli).

Without wishing to be bound by theory, some embodiments of the engineered microbe-binding molecules can be used to opsonize a microbe, which is then cleared out by an innate immune response. In some embodiments, FcMBL protein can be a more potent opsonin of a microbe, g., S. aureus than Fc or wild-type MBL. Accordingly, in some embodiments, when the subject is diagnosed with a microbial infection using the methods described herein, the subject can be administered or prescribed with a composition comprising at least one engineered microbe-binding molecule described herein.

Without limitations, the methods of any aspects described herein can be used to diagnose a microbe that is resistant to at least one, at least two, at least three, at least four or more antibiotics. For example, in one embodiment, the methods described herein can be used to diagnose methicillin-resistant *S. aureus*. In another embodiment, the methods described herein can be used to diagnose vancomycin-resistant *S. aureus*.

Exemplary Compositions and Methods for Treating and/or Preventing a Microbial Infection The binding of microbes to engineered microbe-targeting molecules can facilitate isolation and removal of microbes and/or microbial matter from an infected area. Accordingly, another aspect provided herein relate to compositions for treating and/or preventing a microbial infection or microbial contamination comprising one or more engineered microbe-targeting molecules or microbe-targeting substrates (e.g., microbe-targeting magnetic microbeads) described herein.

In some embodiments, the composition can be formulated for treating and/or preventing a microbial infection or a microbial contamination present in an environmental surface. The term "environmental surface" as used herein refers to any surface and/or body of an environment or an object. The environmental object can be a non-living object or a living object, e.g., a botanical plant. Examples of an environmental surface can include, but is not limited to, a medical device, an implantable device, a surface in a hospital or clinic (e.g., an operating room or an intensive-care unit), a machine or working surface for manufacturing or processing food or pharmaceutical products (e.g., drugs, therapeutic agents or imaging agents), a cell culture, a water treatment plant, a water reservoir and a botanical plant.

In some embodiments, the composition can be formulated for treating and/or preventing microbial infection in a body fluid of a subject, e.g., blood. While in some embodiments, the engineered microbe-targeting molecules of the composition described herein can capture microbes and/or microbial matter in a circulating body fluid, e.g., blood, in other embodiments, the engineered microbe-targeting molecules can opsonize a microbe and/or microbial matter such that the microbe and/or microbial matter can be recognized by an innate immune system for clearance.

Unlike wild-type MBL that can induce systemic complement activation (see, e.g., Sprong T. (2009) *Clin Infect Dis.* 49: 1380-1386), in some embodiments, the engineered microbe-targeting molecules can act as dominant negative molecules by binding microbes and/or microbial matter without stimulating downstream inflammatory cascades, and thus reduce system inflammatory syndromes and/or sepsis symptons in vivo, e.g., reduction of disseminated intravascular coagulation (DIC).

Alternatively, the engineered microbe-targeting molecules can localize a microbe and can thus prevent it from spreading, e.g., deeper into a wound. In particular, the inventors have demonstrated that *S. aureus* can strongly bind to some embodiments of the engineered microbe-targeting molecules (e.g., microbe-binding magnetic microbeads) due to the presence of both carbohydrate patterns and protein A on its microbial surface capable of independent binding to the engineered microbe-targeting molecules. Thus, in some embodiments, the engineered microbe-targeting molecules can be used to localize a microbe load, which can then be easily removed from an infected area. In some embodiments, the microbead can be labeled for specific imaging of infected sites. For SPECT imaging the tracer radioisotopes typically used such as iodine-123, technetium-99m, xenon-133, thallium-201, and fluorine-18 can be used. Technetium 99m can be used for scintigraphic assay. Iodine-derived or other radioopaque contrast agents can also be incorporated in the beads for radiographic or CT-scan imaging. The use of paramagnetic or superparamagnetic microbeads can be used for magnetic resonance imaging as contrast agents to alter the relaxation times of atoms within a nidus of infection. In another embodiment, the microspheres can be fluorescently dyed and applied to a surgical wound to determine the extension of an infectious process. This can be useful for assisting the surgeon in distinguishing between infected and healthy tissues during debridment surgeries for osteomyelitis, cellulitis or fasciitis.

Accordingly, another aspect provided herein related to compositions for treating and/or preventing a microbial infection in a tissue of a subject. In some embodiments, the composition comprises at least one engineered microbe-targeting molecule as described herein. In some embodiments, the amount of the engineered microbe-targeting molecules and/or microbe-targeting substrates present in the composition is sufficient to reduce the growth and/or spread of the microbe in the tissue of the subject. The phrase "reducing the growth and/or spread of the microbe in the tissue" as used herein refers to reducing the number of colonies of the microbe and/or movement of the microbe in the tissue. In some embodiments, the engineered microbe-targeting molecule can capture and localize a microbe present in a tissue such that the number of colonies of the microbe in the tissue can be reduced by at least about 30%, at least about 40%, at least about 50%, at least about 60%, at least about 70%, at least about 80%, at least about 90%, at least about 95%, at least about 98%, up to and including 100%, as compared to in the absence of the engineered microbe-targeting molecule. In some embodiments, the engineered microbe-targeting molecule can capture and localize a microbe present in a tissue such that the number of colonies of the microbe in the tissue can be reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more, as compared to in the absence of the engineered microbe-targeting molecules. In one embodiment, the binding of the engineered microbe-targeting molecules with a microbe (e.g., *S. aureus*) reduces the number of colonies by at least about 4-fold to at least about 6-fold (e.g., at least about 5-fold), as compared to in the absence of the engineered microbe-targeting molecules, after a period of at least about 12 hours, at least about 16 hours or at least about 24 hours.

In other embodiments, the engineered microbe-targeting molecule can capture and localize a microbe present in a tissue such that the movement of the microbe within the tissue (e.g., in terms of a distance travelled deeper into the tissue and/or area of spread from the infected site) can be reduced by at least about 30%, at least about 40%, at least about 50%, at least about 60%, at least about 70%, at least about 80%, at least about 90%, at least about 95%, at least about 98%, up to and including 100%, as compared to in the absence of the engineered microbe-targeting molecule. In some embodiments, the engineered microbe-targeting molecule can capture and localize a microbe present in a tissue such that the movement of the microbe within the tissue (e.g., in terms of a distance travelled deeper into the tissue and/or area of spread from the infected site) can be reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more, as compared to in the absence of the engineered microbe-targeting molecule.

In some embodiments, the composition can further comprise at least one of an antimicrobial agent and a drug delivery vehicle. For example, in some embodiments, the composition can further comprise at least 1, at least 2, at least 3, at least 4, at least 5 or more antimicrobial agents. In some embodiments, the composition can further comprise one or a plurality of (e.g., 2, 3, 4, 5, 6, 7, 8, 9, 10, 20, 30, 40, 50, 60, 70, 80, 90, 100, 500, 1000 or more) delivery vehicles. In some embodiments, the composition can further comprise a combination of at least one (including at least 2, at least 3, at least 4, at least 5 or more) antimicrobial agent and at least one (including 1, 2, 3, 4, 5, 6, 7, 8, 9, 10, 20, 30, 40, 50, 60, 70, 80, 90, 100, 500, 1000 or more) drug delivery vehicle. As used herein, the term "drug delivery vehicle" generally refers to any material that can be used to carry an active agent to a target site. Examples of drug delivery vehicles includes, but are not limited to, a cell, a peptide particle, a polymeric particle, a dendrimer, a vesicle, a liposome, a hydrogel, a nucleic acid scaffold, an aptamer, and any combinations thereof, In some embodiments where a drug delivery vehicle is included, an engineered microbe-targeting molecule and/or an antimicrobial agent can be dispersed within (e.g., encapsulated or embedded in) a drug delivery vehicle and/or coated on a surface of the drug delivery vehicle.

In some embodiments where the composition includes at least one antimicrobial agent, the antimicrobial agent can be present as a separate entity from the engineered microbe-targeting molecule and/or it can be fused with at least one engineered microbe-targeting molecule, e.g., by genetic modification and/or chemical conjugation.

The term "antimicrobial agent" as used herein refers to any entity with antimicrobial activity, i.e. the ability to inhibit or reduce the growth and/or kill a microbe, e.g., by at least about 30%, at least about 40%, at least about 50%, at least about 75%, at least about 90% or more, as compared to in the absence of an antimicrobial agent. An antimicrobial agent can be, for example, but not limited to, a silver nanoparticle, a small molecule, a peptide, a peptidomimetics, an antibody or a fragment thereof, a nucleic acid, an enzyme (e.g., an antimicrobial metalloendopeptidase such as lysostaphin), an aptamer, a drug, an antibiotic, a chemical or any entity that can inhibit the growth and/or kill a microbe. Examples of an antimicrobial peptide that can be included in the composition described herein, include, but are not limited to, mefloquine, venturicidin A, antimycin, myxothiazol, stigmatellin, diuron, iodoacetamide, potassium tellurite hydrate, aDL-vinylglycine, N-ethylmaleimide, L-allyglycine, diaryquinoline, betaine aldehyde chloride, acivcin, psicofuraine, buthionine sulfoximine, diaminopemelic acid, 4-phospho-D-erythronhydroxamic acid, motexafin gadolinium and/or xycitrin or modified versions or analogues thereof.

In some embodiments, an antimicrobial agent included in the composition can be an antibiotic. As used herein, the term "antibiotic" is art recognized and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Substances of similar structure and mode of action can be synthesized chemically, or natural compounds can be modified to produce semi-synthetic antibiotics. Exemplary classes of antibiotics include, but are not limited to, (1) β-lactams, including the penicillins, cephalosporins monobactams, methicillin, and carbapenems; (2) aminoglycosides, e.g., gentamicin, kanamycin, neomycin, tobramycin, netilmycin, paromomycin, and amikacin; (3) tetracyclines, e.g., doxycycline, minocycline, oxytetracycline, tetracycline, and demeclocycline; (4) sulfonamides (e.g., mafenide, sulfacetamide, sulfadiazine and sulfasalazine) and trimethoprim; (5) quinolones, e.g., ciprofloxacin, norfloxacin, and ofloxacin; (6) glycopeptides (e.g., vancomycin, telavancin, teicoplanin); (7) macrolides, which include for example, erythromycin, azithromycin, and clarithromycin; (8) carbapenems (e.g., ertapenem, doripenem, meropenem, and imipenem); (9) cephalosporins (e.g., cefadroxil, cefepime, and ceftobiprole); (10) lincosamides (e.g., clindamycin, and lincomycin); (11) monobactams (e.g., aztreonam); (12) nitrofurans (e.g., furazolidone, and nitrofurantoin); (13) Penicillins (e.g., amoxicillin, and Penicillin G); (14) polypeptides (e.g., bacitracin, colistin, and polymyxin B); and (15) other antibiotics, e.g., ansamycins, polymycins, carbacephem, chloramphenicol, lipopeptide, and drugs against mycobacteria (e.g., the ones causing diseases in mammals, including tuberculosis (*Mycobacterium tuberculosis*) and leprosy (*Mycobacterium leprae*), and any combinations thereof.

Additional exemplary antimicrobial agent can include, but are not limited to, antibacterial agents, antifungal agents, antiprotozoal agents, antiviral agents, and any mixtures thereof.

Exemplary antibacterial agents include, but are not limited to, Acrosoxacin, Amifioxacin, Amoxycillin, Ampicillin, Aspoxicillin, Azidocillin, Azithromycin, Aztreonam, Balofloxacin, lc Benzylpenicillin, Biapenem, Brodimoprim, Cefaclor, Cefadroxil, Cefatrizine, Cefcapene, Cefdinir, Cefetamet, Cefmetazole, Cefprozil, Cefroxadine, Ceftibuten, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafloxacin, Tetracycline, Tetroxoprim, Tinidazole, Tosufloxacin, Trimethoprim, and phramceutically acceptable salts or esters thereof.

Exemplary antifungal agents include, but are not limited to, Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid, and pharmaceutically acceptable salts or esters thereof.

Exemplary antiprotozoal agents include, but are not limited to, Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole, and pharmaceutically acceptable salts or esters thereof.

Exemplary antiviral agents include, but are not limited to, Acyclovir, Brivudine, Cidofovir, Curcumin, Desciclovir, 1-Docosanol, Edoxudine, gQ Fameyclovir, Fiacitabine, Ibacitabine, Imiquimod, Lamivudine, Penciclovir, Valacyclovir, Valganciclovir, and pharmaceutically acceptable salts or esters thereof.

In some embodiments, the antimicrobial agent can include silver present in any form, e.g., a nanoparticle, a colloid, a suspension, powder, and any combinations thereof.

In some embodiments, the composition can be used to treat and/or prevent an infection caused by any microbe described herein. In one embodiment, the composition can be used to treat and/or prevent an infection caused by *S. aureus*.

In some embodiments, the composition can be used to treat and/or prevent an infection caused by a microbe that is resistant to at least one, at least two, at least three, at least four or more antimicrobial agents described herein. In one embodiment, the composition can be used to treat and/or prevent an infection caused by a microbe that is resistant to at least one, at least two, at least three, at least four or more antibiotics described herein. For example, in one embodiment, the composition can be used to treat and/or prevent an infection caused by methicillin-resistant *S. aureus*. In another embodiment, the composition can be used to treat and/or prevent an infection caused by vancomycin-resistant *S. aureus*.

Exemplary antimicrobial applications and/or products: The compositions described herein can be formulated or configured for different applications and/or products such antimicrobial products. In some embodiments, the composition described herein can be formulated as pharmaceutical compositions as described below, e.g., for therapeutic treatment as an antibiotic or antiseptic.

Wound dressings: In some embodiments, the composition described herein can be formulated for topical application, e.g., in wounds, lesions or abscesses. By way of example only, in some embodiments, a plurality of engineered microbe-targeting molecules can be blended with, attached to or coated on a wound dressing, for example, but not limited to, a bandage, an adhesive, a gauze, a film, a gel, foam, hydrocolloid, alginate, hydrogel, paste (e.g., polysaccharide paste), a spray, a granule and a bead.

In some embodiments, the wound dressing can include an additional antimicrobial agent described herein and/or an antiseptic chemical, e.g., boracic lint and/or medicinal castor oil.

In one embodiment, a plurality of engineered microbe-targeting molecules (e.g., microbe-targeting microparticles or microbe-targeting magnetic microbeads) can be attached or coated onto a wound dressing such as a bandage or an adhesive. When such wound dressing is applied to a wound or a lesion, any microbe (e.g., *S. aureus*) and/or microbial matter present in the wound or lesion can bind and localized to the wound dressing. Thus, regular replacement of the wound dressing can remove the microbe from the wound or lesion and thus prevent the microbe from moving deeper into the wound or lesion for further infection.

In one embodiment, a plurality of engineered microbe-targeting molecules (e.g., microbe-targeting microparticles or microbe-targeting magnetic microbeads) can be formulated into a wound dressing spray, which can be handy and used anywhere, e.g., during a transportation on an emergency vehicle. When the wound dressing spray containing the microbe-targeting magnetic microbeads, the microbe-targeting magnetic microbeads with bound microbes (e.g., *S. aureus*) can be removed from the wound with a magnetic field gradient before re-application of the spray.

Debridement Fluids or Sprays:

In some embodiments, the composition described herein can be formulated as part of a debridement fluid (optionally with suspended particulates that are abrasive to a lesion area). In some embodiments, the composition described herein can be formulated as part of a debridement spray. As used herein, the term "debridement" generally refers to complete or partial removal of a subject's dead, damaged, and/or infected tissue to improve the healing potential of the remaining healthy and/or non-infected tissue. By way of example only, a plurality of engineered microbe-targeting molecules (e.g., microbe-targeting microparticles or magnetic microbeads) can be suspended in a debridement fluid or spray, e.g., for use in an orthopedic procedure. The debridement fluid or spray containing the engineered microbe-targeting molecules can be applied to a lesion, an abscess or a wound, where the engineered microbe-targeting microparticles or magnetic microbeads can capture a microbe (e.g., *S. aureus*) and/or microbial matter from the lesion, abscess or wound. The debridement fluid or spray can then be removed from the applied site by vacuum, or suction. In some embodiments, the debridement fluid or spray containing the engineered microbe-targeting magnetic microbeads can be also removed from the applied site by exposing the applied site to a magnetic field gradient, which can pull or attract the applied microbe-targeting magnetic microbeads out from the applied site.

Medical Device Coating:

In some embodiments, the composition described herein can be coated on a surface of a medical device, e.g., a fluid delivery device such as hollow fibers, tubing or a spiral mixer in an extracorporeal device, or an implantable device such as an indwelling catheter, chip or scaffold. By way of example only, a plurality of engineered microbe-targeting molecules can be coated or conjugated to a surface of a fluid delivery device such that when a fluid (e.g., blood) flows through the fluid delivery device coated with engineered microbe-targeting molecules, any microbe (e.g., *S. aureus*) and/or microbial matter present in the fluid (e.g., blood) can be extracted therefrom, thus reducing the chance of a microbial infection. In another embodiment, a plurality of engineered microbe-targeting molecules coated on a medical device can comprise a detectable label, e.g., a "smart label" described herein, which can provide a detectable signal when any microbe (e.g., *S. aureus*) binds to a surface of the medical device, indicating that the medical device has been contaminated and/or infected, and thus is not appropriate for use or implantation.

Provided herein are also methods for removing a microbe and/or microbial matter from a target area comprising contacting the target area with at least one composition described herein. As removal of a microbe and/or microbial matter from an infected area can treat and/or prevent a microbial infection or microbial contamination, provided herein also include methods for treating and/or preventing a microbial infection or microbial contamination in a target area. An exemplary method comprises contacting the target area with a composition. The target area can be anywhere, e.g., an environmental surface or in a body of a subject (e.g., body fluid, and/or tissue). In some embodiments, the method comprises contacting the tissue of the subject with any embodiments of the composition described herein. In some embodiments, the tissue can have an open wound, a lesion or an abscess.

In one embodiment, the composition can be formulated for use as a wound dressing described herein.

As the engineered microbe-targeting molecules can localize a microbe (e.g., *S. aureus*) for easier removal of the microbe from the tissue, in some embodiments, the method can further comprise replacing the previously-applied composition in contact with the tissue with a fresh composition after a period of time. For example, depending on the condition of the microbial infection and/or specific compositions, the previously-applied composition can be replaced every 1 hour, every 2 hours, every 3 hours, every 4 hours, every 5 hours, every 6 hours, every 8 hours, every 10 hours, every 12 hours, every 16 hours, every 24 hours or longer.

In some embodiments, the method can further comprise administering an additional treatment to the tissue. Exemplary additional treatments can include, but are not limited to, a negative-pressure treatment, a vacuum-assisted debridement, administration of an antimicrobial agent, or any combinations thereof.

Without limitations, the compositions and/or methods of any aspects described herein can be used to treat and/or prevent a microbial infection or contamination in vitro, in situ or in vivo. In some embodiments, the compositions and/or methods of any aspects described herein can be used to treat and/or prevent a microbal infection or contamination in a fluid or on any surface, including, but not limited to, a tissue surface, a solid substrate surface, e.g., a medical device surface, an environmental surface, or food.

Additionally, in some embodiments where the composition comprises at least one engineered microbe-targeting molecule conjugated to a detectable label described herein or an imaging agent, can be used to image an infection in situ, e.g., in a subject or on an environmental surface.

Figure 22:
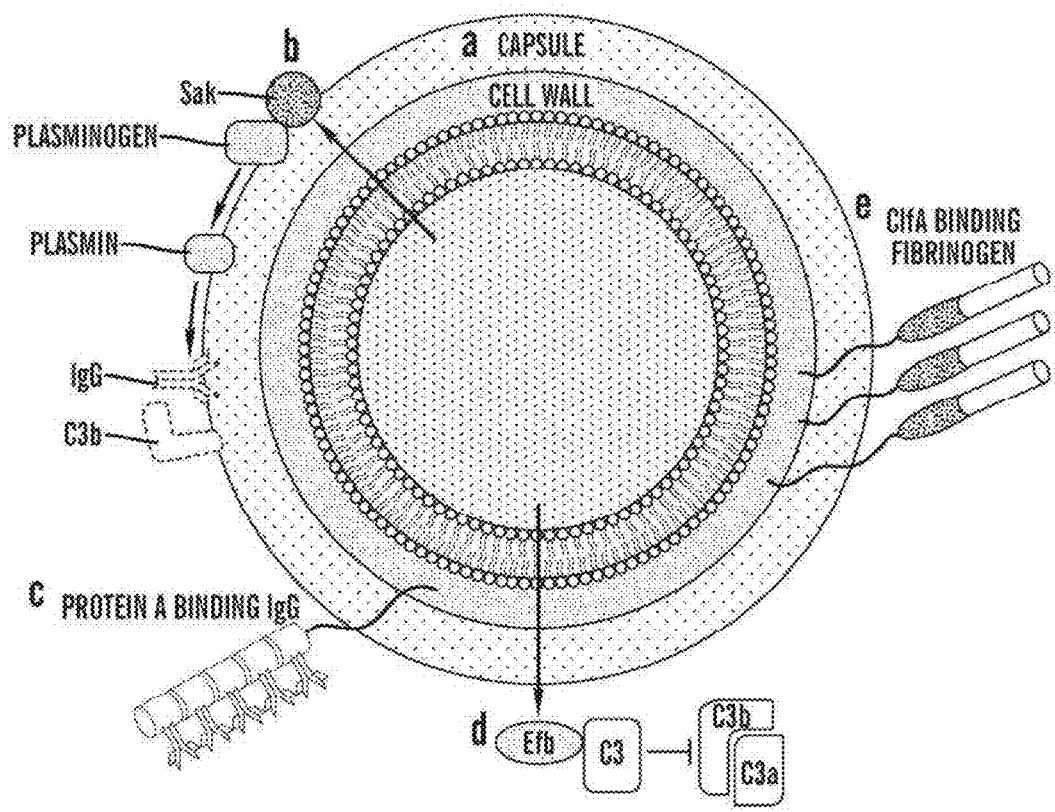
FIG. 22 is a schematic diagram showing mechanism by which *S. aureus* avoids opsonophagocytosis. See additional details in Fraser T., *Nature Reviews Microbiology* 2005: 3(12):948-58.

S. aureus infections can sometimes be difficult to treat as S. aureus has protein A on its cell surface. Protein A is a wall-anchored protein with either four or five domains, each of which can bind to the Fc region of IgG. The X-ray structure of protein A IgG-binding domains in complex with the Fc region of IgG has been reported, and residues from helix I that are involved in the interaction have been identified and evaluated by site directed mutagenesis. The interaction between protein A and IgG can coat the surface of the cell with IgG molecules that are in an orientation incorrect to be recognized by the neutrophil Fc receptor (FIG. 22). This can indicate the anti-phagocytic effect of protein A and its role in pathogenesis of S. aureus infections. Protein-A-deficient mutants of S. aureus are reported to be phagocytosed more efficiently by neutrophils in vitro and show decreased virulence in several animal infection models (See, e.g., Fraser T., Nature Reviews Microbiology 2005: 3(12): 948-58). In accordance with some aspects provided herein, the compositions and/or methods described herein can be used to treat or prevent S. aureus microbial infection.

Pharmaceutical Compositions

Some embodiments of the engineered microbe-targeting molecules can be used for therapeutic purposes. For administration to a subject in need thereof, engineered microbe-targeting molecules described herein can be provided in pharmaceutically acceptable compositions. Accordingly, in yet another aspect, provided herein is a pharmaceutical composition comprising at least one engineered microbe-targeting molecule described herein, and a pharmaceutically acceptable carrier.

Depending on the selected administration route, the compositions or preparations can be in any form, e.g., a tablet, a lozenge, a suspension, a free-flowing powder, an aerosol, and a capsule. The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a pharmaceutically-acceptable material, composition or vehicle for administration of an active agent described herein. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) C2-C12 alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation. For compositions or preparations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a preparation described herein, depending on the administration route and formulation. The compositions and preparations described herein can be delivered via any administration mode known to a skilled practitioner. For example, the compositions and preparations described herein can be delivered in a systemic manner, via administration routes such as, but not limited to, oral, and parenteral including intravenous, intramuscular, intraperitoneal, intradermal, and subcutaneous. In some embodiments, the compositions and preparations described herein are in a form that is suitable for injection. In other embodiments, the compositions and preparations described herein are formulated for oral administration.

When administering parenterally, a composition and preparation described herein can be generally formulated in a unit dosage injectable form (solution, suspension, emulsion). The compositions and preparations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

An oral composition can be prepared in any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Liquid preparations for oral administration can also be prepared in the form of a dry powder to be reconstituted with a suitable solvent prior to use.

The compositions can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions described herein, however, any vehicle, diluent, or additive used should have to be biocompatible with the active agents described herein. Those skilled in the art will recognize that the components of the compositions should be selected to be biocompatible with respect to the active agent. This will present no problem to those skilled in chemical and pharmaceutical principles, or problems can be readily avoided by reference to standard texts or by simple experiments (not involving undue experimentation).

In some embodiments, the compositions and preparations described herein can be formulated in an emulsion or a gel. Such gel compositions and preparations can be implanted locally to a diseased tissue region of a subject.

For in vivo administration, the compositions or preparations described herein can be administered with a delivery device, e.g., a syringe. Accordingly, an additional aspect described herein provides for delivery devices comprising at least one chamber with an outlet, wherein the at least one chamber comprises a pre-determined amount of any composition described herein and the outlet provides an exit for the composition enclosed inside the chamber. In some embodiments, a delivery device described herein can further comprise an actuator to control release of the composition through the outlet. Such delivery device can be any device to facilitate the administration of any composition described herein to a subject, e.g., a syringe, a dry powder injector, a nasal spray, a nebulizer, or an implant such as a microchip, e.g., for sustained-release or controlled release of any composition described herein.

In some embodiments of the products described herein, the microbe-targeting microparticles described herein itself can be modified to control its degradation and thus the release of active agents. In some embodiments, the engineered microbe-targeting molecules, microbe-targeting microparticles and/or microbe-targeting cells described herein can be combined with other types of delivery systems available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations thereof. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neukal fats such as mono-, di- and triglycerides; hydrogel release systems; liposome-based systems; phospholipid based-systems; silastic systems; peptide based systems; or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and—29 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system can be used to deliver one or more embodiments of the compositions or preparations described herein. Use of a long-term sustained release formulations or implants can be particularly suitable for treatment of some infections. Long-term release, as used herein, means that a formulation or an implant is made and arranged to deliver compositions or preparations described herein at a therapeutic level for at least 30 days, or at least 60 days. In some embodiments, the long-term release refers to a formulation or an implant being configured to deliver an active agent at a therapeutic level over several months.

Regeneration of Microbe-Binding Substrates (e.g., Microbe-Binding Microbeads)

In some applications, an artisan may want to detach or release a pathogen captured by or bound to an engineered microbe-targeting molecule. As discussed herein, calcium ions are involved in binding interactions of the engineered microbe-targeting molecules described herein with microbe surface. A skilled artisan will appreciate that detaching the pathogen from support bound microbe-targeting molecule also regenerates the support bound microbe-targeting molecule.

Accordingly, disclosed herein are methods for inhibiting $Ca^{2+}$ assisted interactions between two components, e.g., in a complex, by reducing the amount of $Ca^{2+}$ ions available for the interactions. This can be accomplished by contacting or incubating the complex with a buffer or solution comprising a chelating agent which chelates calcium ions. Exemplary chelating agents include, but are not limited to, 1,2-Bis(2-Aminophenoxy)ethane-N,N,N',N'-tetraacetic acid; Ethylenediaminetetraacetic acid (EDTA); Ethylene glycol-bis(2-aminoethylether)-N,N,N',N'-tetraacetic acid; and Ethylene glycol-bis(β-aminoethyl ether)-N,N,N',N'-tetraacetic acid.

For some uses, chelating agents can be problematic. For example, chelating agents such as EDTA and EGTA can be harsh or dangerous to biological samples. Accordingly, the inventors have also discovered alternative methods for reducing the amount of $Ca^{2+}$ ions available for assisting in complex formation. In one example, the complex can be contacted or incubated with a low pH buffer. Without wishing to be bound by a theory, low pH buffer protonates the negatively charged carboxyl groups (glutamate side chains) on the engineered microbe-targeting molecules that are responsible for binding calcium. Protonating these side chains can remove their negative charge, can remove their ability to bind to positively charged calcium ions. In some embodiments, the low pH buffer is of about pH 6.75, about pH 6.5, about pH 6.25, about pH 6, about pH 5.75, about pH 5.5, about pH 5.25, about pH 5, about pH 4.5, about pH 4, about pH 3.5, about pH 3, about pH 2.5 or lower. In one embodiment, buffer is of pH about 2.8. In some embodiments, the low pH buffer can further comprise a chelating agent.

Alternatively or in addition to a low pH buffer, one can also use a buffer in which calcium is not soluble. For example, calcium can interact with one or more components of the buffer and can precipitate out of the buffer solution. Thus, contacting or incubating the complex in such a buffer can lead to precipitation of the calcium ions making them unavailable for the necessary interaction with the targeting molecule—microbe interface. Generally, buffers in which calcium is not soluble include an anion which forms a salt with the $Ca^{2+}$ ion. Thus formed salt is less soluble in the solvent of the buffer. Exemplary anion which produce insoluble salts with $Ca^{2+}$ include, but are not limited to, phosphates, oxalates, carbonates, sulfates, fluorides, gluconic acid, oxido-trioxo-manganese, stearic acid, and the like. In some embodiments, the buffer can further comprise a chelating agent.

In some embodiments, the buffer is a 0.2M glycine buffer of pH 2.8. In some embodiments, the buffer is a 0.1M sodium phosphate buffer of pH 6.0.

Many of the calcium salts become more insoluble at elevated temperature. Accordingly, during detachment of the pathogen, temperature of the buffer can be increased or decrease. In some embodiments, the buffer is heated during detachment of the pathogen. In some other embodiments, the buffer is cooled during detachment of the pathogen. Temperature of the buffer can be increased or decreased by at least 5° C., at least 10° C., at least 15° C., at least 20° C., at least 25° C. or more relative to room temperature.

The method described herein for inhibiting $Ca^{2+}$ assisted interactions between two components can also be used for detaching a pathogen from an engineered microbe-targeting molecule. For example, the pathogen—targeting molecule complex can be contacted or incubated with a low pH buffer or with a buffer in which calcium is not soluble.

In one embodiment, a bound pathogen can be detached from a targeting molecule using a 0.2M glycine buffer at pH 2.8. In another embodiment, a bound pathogen can be detached from a targeting molecule using a 0.1M sodium phosphate buffer at pH 6.0.

If the targeting molecule with the bound pathogen is attached to a support surface, e.g., a microparticle or a magnetic microparticle, the pathogen can be detached by incubating or contacting the support with a low pH buffer or a buffer in which calcium is not soluble. Thus provided herein is also a method for detaching a microbe from a support bound microbe-targeting molecule. The method comprising contacting, washing, or incubating the support bound pathogen with a low pH buffer or a buffer in which calcium in insoluble. After a predetermined time (e.g., 5 mins, 10 mins, 15 mins, 30 mins, 25 mins, 30 mins, 35 mins, 40 mins, 45 mins, 50 mins, 55 mins, 1 hour, 1.25 hours, 1.5 hours, 2 hours, 3 hours, 4 hours, 5 hours, 6 hours or more) has passed, the buffer can be removed and the support optionally washed one or more times. Without wishing to be bound by a theory, this regenerates the support bound targeting molecules for binding with pathogens in sample. In other words, detaching the microbes allows one to re-use the support bound targeting molecules. The detached pathogens can be used for analysis, detection or for any other use.

Kits

Kits for capturing, detecting and/or determining the presence or absence of a microbe and/or microbial matter in a sample are also provided herein. In some embodiments, the kit can comprise: (a) one or more containers containing a population of engineered microbe-targeting molecules described herein; and (b) at least one reagent. In these embodiments, a user can generate their own microbe-targeting substrates by conjugating the provided engineered microbe-targeting molecules to their desired substrate, e.g., using any art-recognized conjugation chemistry and/or methods described herein. In such embodiments, the reagent can include, but is not limited to, a coupling agent for conjugation of engineered microbe-targeting molecules to a substrate. In some embodiments, the kit can further comprise one or more substrates (e.g., microbeads such as magnetic microbeads) to which the engineered microbe-targeting molecules described herein are conjugated. In such embodiments, a user can further modify the surface chemistry of the provided substrate prior to conjugation of the engineered microbe-targeting molecules to the substrate.

In other embodiments, the kit can provide microbe-targeting substrates that are ready for use. Accordingly, in these embodiments, the kit can comprise: (a) one or more microbe-targeting substrates described herein; and (b) at least one reagent. In some embodiments, the microbe-targeting substrate can include one or more microbe-binding dipsticks, e.g., as described herein. In other embodiments, the microbe-targeting substrate can include a population of microbe-targeting microbeads (including, but not limited to, polymeric microbeads and magnetic microbeads). In some embodiments, the microbe-targeting substrate can include a population of microbe-targeting magnetic microbeads. The microbe-targeting microbeads or microbe-targeting magnetic microbeads can be provided in one or more separate containers, if desired. In some embodiments, the population of the microbe-targeting microbeads or magnetic microbeads contained in one or more containers can be lyophilized.

In some embodiments of any aspects of the kits described herein, the population of the microbeads or microbe-targeting microbeads can comprise at least one distinct subset of the microbeads or microbe-targeting microbeads, respectively. For example, each distinct subset of the microbeads or microbe-targeting microbeads can be provided in a separate container. In some embodiments, the distinct subset of the microbeads or microbe-targeting microbeads can have a size. In some embodiments, the distinct subset of microbe-targeting microbeads can comprise on their surfaces a different density of engineered microbe-targeting molecules from the rest of the population. In these embodiments, two or more subsets of the microbe-targeting microbes having different sizes and/or different coating density of the engineered microbe-binding molecules can be used to detect and differentiate microbes of different classes and/or sizes, e.g., employing the methods described herein. In some embodiments, the distinct subset of microbe-targeting substrates, e.g., microbe-targeting microbeads, can comprise a different carbohydrate recognition domain from the others.

In some embodiments of any aspects of the kits described herein, the substrates (e.g., microbeads) or microbe-targeting substrates (e.g., microbe-targeting microbeads) can further comprise a detection label. By way of example only, depending on the choice of detection methods, each distinct subset of the microbeads can comprise a unique detection label or the same detection label. For example, if each distinct subset of the microbe-targeting microbeads is used in a different sampling well, the same detection label can be used on the microbe-targeting microbeads. However, if it is desirable to detect multiple different microbe-targeting microbeads in the same well, it is preferably to have each distinct subset of microbe-targeting microbeads comprising a distinct detection label.

Detectable labels suitable for use in any kits provided herein include any composition detectable by spectroscopic, photochemical, biochemical, immunochemical, electrical, optical or chemical means. Any art-recognized detectable labels or the ones described herein can be included in the kits described herein.

Means of detecting such labels are well known to those of skill in the art and exemplary detection methods are described herein. For example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments of any aspects described herein, the kits can further comprise one or more containers containing a population of detectable labels, wherein the detectable label is conjugated to a molecule. In some embodiments, at least one of the containers can contain a distinct population of detectable labels.

The molecule conjugated to a detectable label can be any molecule that binds to a microbe of interest. For example, in some embodiments, the molecule conjugated to a detectable label can comprise the same carbohydrate recognition domains as used in the microbe-targeting substrates (e.g., microbe-targeting magnetic microbeads). In such embodiments, at least one population of the molecule-detectable label conjugate can comprise at least one carbohydrate recognition domain or a fragment thereof, e.g., derived from mannose-binding lectin or at least a portion of the CRD domain, e.g., encoded by SEQ ID NO. 4, or a fragment thereof. In some embodiments, the molecule conjugated to a detectable label can further comprise a Fc region of an immunoglobulin. In alternative embodiments, the molecule conjugated to a detectable label can comprise an antibody specific to at least one genus, species, or type/class of microbes (e.g., gram-positive vs. gram-negative microbes; protein A-expressing or protein G-expressing microbes vs. protein A- or protein G-negative microbes) recognized by the microbe-targeting molecules described herein, or an antibody specific to at least one type of carbohydrate recognition domain (e.g., C-type lectins vs. S-type lectins) employed in the microbe-targeting molecules described herein. However, the antibody can also be a common antibody that binds to all the microbes or pathogens recognized by the microbe-targeting molecules provided in the kit. Without limitations, a molecule attached to a detectable label can also include any ligand targeting microbial cell surface proteins or receptors, including carbohydrates, lipids, lectins, aptamers, protein, peptides, nucleic acid, polynucleotides, antibody or a portion thereof, an antibody-like molecule, peptidomimetic, and any combinations thereof.

In some embodiments, at least one of the containers can contain a distinct population of the molecule-detectable label conjugate as described earlier. The distinct population of the molecule-detectable label conjugate can contain a unique molecule with the detectable label same as others, or a conjugate comprising a distinct detectable label (e.g., a unique fluorescent molecule) and a distinct molecule. As each distinct detectable label can identify the associated protein, conjugates comprising a distinct detectable label associated with a distinct molecule can allow detecting in a single sample at least two or more distinct populations of the engineered microbe-targeting substrates (e.g., microbe-targeting magnetic microbeads); for example, each distinct population of the engineered microbe-targeting magnetic microbeads can bind to a distinct genus or species or type/size of a microbe. In alternative embodiments, the molecule-detectable label conjugates in each of the containers can comprise the same detectable label. For example, the detectable label can comprise an enzyme (e.g., horseradish peroxidase or alkaline phosphatase) that produces a color change in the presence of an enzyme substrate. In such embodiments, the kit can further comprise one or more containers containing an enzyme substrate that changes color in the presence of the enzyme.

In one embodiment, the microbe-targeting substrate provided in the kit can include a dipstick or test strip or membrane containing one or more engineered microbe-targeting molecules, e.g., microbe-binding dipstick or membrane described herein. In this embodiment, the kit can comprise 1, 2, 3, 4, 5, 6, 7, 8, 9, 10, 15, 20, 25, 50, 75, 100, 150, 200 or more microbe-binding dipsticks or test strips described herein. These kits comprising the microbe-binding dipsticks or test strips can be used as a diagnostic or probe for a microbe anywhere, e.g., at home, in clinics or hospitals, on emergency vehicles, in outdoor environments, in food processing plants, and anywhere in need of microbe capture and/or detection.

In some embodiments, each microbe-targeting substrate or product described herein, e.g., each microbe-binding dipstick or membrane, can be individually packaged to maintain their sterility. In some embodiments, two or more products (e.g., 2, 3, 4, 5, 6, 7, 8, 9, 10, 15, 20, 25, 50, or more products such as microbe-binding dipsticks or membranes) can be packaged into one single unit. In such embodiments, users can sterilize any unused products after opening, e.g., with UV radiation, high temperature, gamma-radiation, ethylene oxide sterilization or any other known methods that would not significantly affect the activity of the engineered microbe-targeting molecules for microbe detection.

In other embodiments, the microbe-targeting substrate provided in the kit can include a population of microbe-targeting microbeads or magnetic microbeads. In some embodiments, the microbe-targeting microbeads or magnetic microbeads can be lyophilized.

Depending on the configuration/combination of the molecule-detectable label conjugates provided in the kit, different populations of the microbe-targeting microbeads or magnetic microbeads can be mixed together with a test sample in a single reaction, or different populations each can be applied separately to different aliquots of the same test sample. After contacting the test sample with the microbe-targeting microbeads or magnetic microbeads, any microbes or pathogens recognized by the microbe-targeting molecules will bind to the microbe-targeting microbeads or magnetic microbeads.

Figure 14:
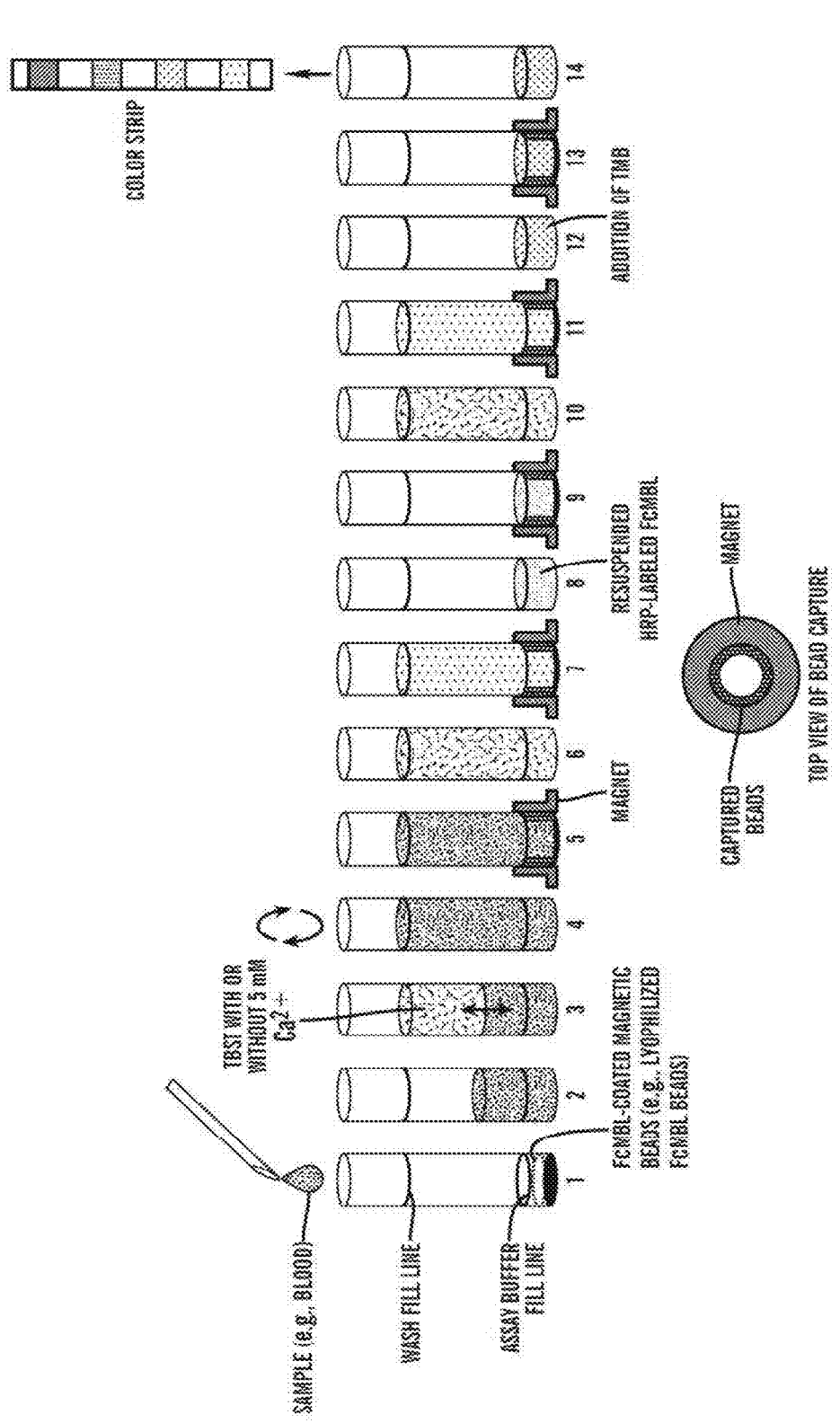
FIG. 14 is a schematic diagram showing one or more embodiments of an ELISA-based test for microbial detection. A test sample (e.g., blood sample) can be added into a single tube (e.g., a blood collection container such as EDTA VACUTAINER®) containing lyophilized FcMBL magnetic microbeads or FcMBL-coated magnetic microbeads. An exemplary protocol for microbial capture and detection is described in Example 10. The ELISA-based test can be performed manually or modified for automation. In some embodiments, the single-tube based ELISA assay can be used to detect microbes or pathogens such as S. aureus and E. coli.

In some embodiments, the kit can further comprise at least one blood collection container or any equivalent sample container or chamber, including at least 1, at least 2, at least 3, at least 4, at least 5, at least 6, at least 7, at least 8, at least 9, at least 10, at least 15, at least 20 blood collection containers or equivalent sample containers or chambers. In some embodiments, the population of the microbe-targeting microbeads or magnetic microbeads can be pre-loaded in at least one blood collection container. In some embodiments, the blood collection container can further comprise an anti-coagulant agent described herein. In some embodiments, a blood sample can be directly added to such blood collection container containing a population of the microbe-targeting and/or microbe-binding microbeads or magnetic microbeads for carrying out a microbe detection assay, e.g., as described in Example 10 and FIG. 14. While Example 10 and FIG. 14 illustrates the use of microbe-targeting magnetic microbeads for capture of microbes, an ordinary artisan will readily appreciate that some embodiments of the microbe-targeting microbeads (without magnetic properties) described herein can also be applicable for the assay. For example, instead of using a magnet to collect the microbe-targeting magnetic microbeads after contact with a test sample (e.g., a blood sample), the microbe-targeting microbeads (without magnetic properties) can also be collected, e.g., by filtration, centrifugation or any other methods known in the art.

In some embodiments where the kits comprise microbe-targeting magnetic microbeads, the kits can further comprise a magnet adapted for use with the assay for isolation of the microbe-targeting magnetic microbeads from a test sample. For example, if the assay is carried out in a blood collection tube, the magnet can be adapted for use with the blood collection tube, e.g., a magnet can be designed to be a magnet collar surrounding the blood collection tube to immobilize or isolate the microbe-targeting magnetic microbeads from a test sample or an assay buffer.

In any aspects of the kits provided herein, the kits can further comprise a portable readout machine or device, e.g., to determine and display the signal produced from the assay performed with the kit. For example, the readout machine or device can detect a colorimetric signal and/or a fluorescent signal produced from the assay of pathogen detection performed with the kits described herein.

In any aspects of the kits described herein, the kits can further include a reference for comparison with a readout determined from a test sample. An exemplary reference can be a strip or a chart showing different colors corresponding to various extents or degrees of a microbial infection.

Depending on different embodiments of the engineered microbe-targeting molecules and/or products provided in the kits, some embodiments of any aspects of the kits described herein can further comprise an additional agent. For example, in some embodiments where the engineered microbe-targeting molecules present on the substrate are unlabeled, the kit can further comprise one or more containers containing a population of detectable labels described earlier, each of which is conjugated to a targeting agent specific for a microbe, e.g., without limitations, one or more embodiments of an engineered microbe-targeting molecule or a fragment thereof, an antibody specific for at least one microbe (e.g., antibodies specific for Gram-positive microbes such as anti-LTA antibodies, antibodies specific for Gram-negative microbes such as anti-LPS antibodies, or antibodies specific for fungus, and any combinations thereof). The use of an additional targeting agent specific for a microbe conjugated to a detectable label can not only facilitate the detection of microbes or pathogens, but can also increase the specificity of the detection for a microbe or a pathogen.

In any aspects of the kits provided herein, when the detection label includes an enzyme (e.g., horseradish peroxidase, alkaline phosphatase and any others commonly used for colorimetric detection), the kits can further comprise one or more containers containing an enzyme substrate that produces a color change in the presence of the enzyme. One of skill in the art can readily recognize an appropriate enzyme substrate for any art-recognized enzymes used for colorimetric detection. By way of example only, an exemplary substrate for alkaline phosphatase can include BCIP/NBT or PNPP (p-Nitrophenyl Phosphate, Disodium Salt); an exemplary substrate for horseradish peroxidase can include TMB.

In any aspects of the kits provided herein, the at least one reagent can be a wash buffer, a dilution buffer, a stop buffer, e.g., to stop the color development, a buffer solution containing a chelating agent described herein, or any combinations thereof. In one embodiment, at least one of the reagents provided in the kit can include at least one buffered solution containing a chelating agent. The chelating agent can be used to chelate any ions (e.g., divalent ions) present in the test samples or assay buffer, e.g., for inhibiting calcium-dependent binding of certain microbes, but not others, to some embodiments of the microbe-binding molecules described herein. Accordingly, such kit can be used to distinguish one microbe (e.g., *S. aureus*) from another (e.g., *E. coli*) in a test sample, e.g. employing some embodiments of the method described herein.

In any aspects of the kits provided herein, the kits can further comprise at least one microtiter plate, e.g., for performing the reaction and the detection.

In addition to the above mentioned components, any embodiments of the kits described herein can include informational material. The informational material can be descriptive, instructional, marketing or other material that relates to the methods described herein and/or the use of the aggregates for the methods described herein. For example, the informational material can describe methods for using the kits provided herein to perform an assay for pathogen or microbe capture and/or detection. The kit can also include an empty container and/or a delivery device, e.g., which can be used to deliver a test sample to a test container.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the kit can contain separate containers, dividers or compartments for each component and informational material. For example, each different component can be contained in a bottle, vial, or syringe, and the informational material can be contained in a plastic sleeve or packet. In other embodiments, the separate elements of the kit are contained within a single, undivided container. For example, a collection of the magnetic microbeads is contained in a bottle, vial or syringe that has attached thereto the informational material in the form of a label.

In general, the kits described herein can be used to separate, remove, and/or detect a microbe present in a test sample. In some embodiments, the kits can be used to differentiate between different microbe species, classes, and/or sizes, by employing the methods and/or assays described herein. By way of example only, some embodiments of the kits can be used to detect the presence or absence of any protein A-expressing microbe or any protein G-expressing microbe in a test sample. Accordingly, some embodiments of the kits described herein can be used to detect or determine the presence or absence of at least one staphylococcus species, excluding *S. epidermidis*, in a test sample. In one embodiment, the assays, methods, and kits described herein can be used to detect or determine the presence or absence of *S. aureus* in a test sample. In some embodiments, the assays, methods, and kits described herein can be used to detect or determine the presence or absence of at least one streptococci species in a test sample.

In some embodiments, the kits described herein can be used to screen a pharmaceutical product (e.g., a drug, a therapeutic agent, or an imaging agent), and/or a medical device (including, but not limited to, implantable devices) for the presence or absence of microbial matter (including, but not limited to, endotoxins secreted by a microbe).

Test Sample

In accordance with various embodiments described herein, a test sample or sample, including any fluid or specimen (processed or unprocessed), that is suspected of comprising a microbe and/or microbial matter can be subjected to an assay or method, kit and system described herein. The test sample or fluid can be liquid, supercritical fluid, solutions, suspensions, gases, gels, slurries, and combinations thereof. The test sample or fluid can be aqueous or non-aqueous.

In some embodiments, the test sample can be an aqueous fluid. As used herein, the term "aqueous fluid" refers to any flowable water-containing material that is suspected of comprising a microbe and/or microbial matter.

In some embodiments, the test sample can include a biological fluid obtained from a subject. Exemplary biological fluids obtained from a subject can include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In some embodiments, a biological fluid can include a homogenate of a tissue specimen (e.g., biopsy) from a subject.

In some embodiments, the biological fluid sample obtained from a subject, e.g., a mammalian subject such as a human subject or a domestic pet such as a cat or dog, can contain cells from the subject. In other embodiments, the biological fluid sample can contain non-cellular biological material, such as non-cellular fractions of blood, saliva, or urine, which can be used to measure plasma/serum biomarker expression levels.

The biological fluid sample can be freshly collected from a subject or a previously collected sample. In some embodiments, the biological fluid sample used in the assays and/or methods described herein can be collected from a subject no more than 24 hours, no more than 12 hours, no more than 6 hours, no more than 3 hours, no more than 2 hours, no more than 1 hour, no more than 30 mins or shorter.

In some embodiments, the biological fluid sample or any fluid sample described herein can be treated with a chemical and/or biological reagent described herein prior to use with the assays and/or methods described herein. In some embodiments, at least one of the chemical and/or biological reagents can be present in the sample container before a fluid sample is added to the sample container. For example, blood can be collected into a blood collection tube such as VACUTAINER®, which has already contained heparin. Examples of the chemical and/or biological reagents can include, without limitations, surfactants and detergents, salts, cell lysing reagents, anticoagulants, degradative enzymes (e.g., proteases, lipases, nucleases, collagenases, cellulases, amylases), and solvents such as buffer solutions.

In some embodiments, the test sample can include a fluid or specimen obtained from an environmental source, e.g., but not limited to, water supplies (including wastewater), ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the test sample can include a fluid (e.g., culture medium) from a biological culture. Examples of a fluid (e.g., culture medium) obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the test sample can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

As used herein, the term "reagent" refers to any solution used in a laboratory or clinical setting for biomedical and molecular biology applications. Reagents include, but are not limited to, saline solutions, PBS solutions, buffered solutions, such as phosphate buffers, EDTA, Tris solutions, and any combinations thereof. Reagent solutions can be used to create other reagent solutions. For example, Tris solutions and EDTA solutions are combined in specific ratios to create "TE" reagents for use in molecular biology applications.

In some embodiments, the test sample can be a non-biological fluid. As used herein, the term "non-biological fluid" refers to any fluid that is not a biological fluid as the term is defined herein. Exemplary non-biological fluids include, but are not limited to, water, salt water, brine, buffered solutions, saline solutions, sugar solutions, carbohydrate solutions, lipid solutions, nucleic acid solutions, hydrocarbons (e.g. liquid hydrocarbons), acids, gasoline, petroleum, liquefied samples (e.g., liquefied samples), and mixtures thereof.

Exemplary Microbes or Pathogens

As used herein, the term "microbes" or "microbe" generally refers to microorganism(s), including bacteria, fungi, protozoan, archaea, protists, e.g., algae, and a combination thereof. The term "microbes" encompasses both live and dead microbes. The term "microbes" also includes pathogenic microbes or pathogens, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis.

Microbe-Induced Diseases:

In some other embodiments, the engineered microbe-targeting molecules or substrates, products and kits described herein can be used to detect or bind to the following microbes that causes diseases and/or associated microbial matter: Bartonella henselae, Borrelia burgdorferi, Campylobacter jejuni, Campylobacterfetus, Chlamydia trachomatis, Chlamydia pneumoniae, Chylamydia psittaci, Simkania negevensis, Escherichia coli (e.g., O157:H7 and K88), Ehrlichia chafeensis, Clostridium botulinum, Clostridium perfringens, Clostridium tetani, Enterococcus faecalis, Haemophilus influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum, Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi, among other viruses, bacteria, archaea, protozoa, and fungi).

In some embodiments, the engineered microbe-targeting molecules or substrates, products and kits described herein can be used to differentiate a protein A-expressing or protein G-expressing microbe from protein A- and protein G-negative microbes (e.g., E. coli) by employing the methods or assays described herein.

In some embodiments, a protein A-expressing microbe includes Staphylococcus species. Examples of Staphylococcus species include, but are not limited to, S. aureus group (e.g., S. aureus, S. simiae), S. auricularis group (e.g., S. auricularis), S. carnosus group (e.g., S. carnosus, S. condimenti, S. massiliensis, S. piscifermentans, S. simulans), S. epidermidis group (e.g., S. capitis, S. caprae, S. epidermidis, S. saccharolyticus), S. haemolyticus group (e.g., S. devriesei, S. haemolyticus, S. hominis), S. hyicus-intermedius group (e.g., S. chromogenes, S. felis, S. delphini, S. hyicus, S. intermedius, S. lutrae, S. microti, S. muscae, S. pseudintermedius, S. rostri, S. schleiferi), S. lugdunensis group (e.g., S. lugdunensis), S. saprophyticus group (e.g., S. arlettae, S. cohnii, S. equorum, S. gallinarum, S. kloosii, S. leei, S. nepalensis, S. saprophyticus, S. succinus, S. xylosus), S. sciuri group (e.g., S. fleurettii, S. lentus, S. sciuri, S. stepanovicii, S. vitulinus), S. simulans group (e.g., S. simulans), and S. warneri group (e.g., S. pasteuri, S. warneri).

In some embodiments, S. aureus can be differentiated from a protein A- and protein G-negative microbe (e.g., E. coli) using the assays and/or methods described herein.

In some embodiments, S. aureus can be differentiated from S. epidermidis using the assays and/or methods described herein.

In some embodiments, S. epidermidis cannot be differentiated from a protein A- and protein G-negative microbe (e.g., E. coli) using the assays and/or methods described herein.

In some embodiments, a protein G-expressing microbe includes Streptococcus species. Examples of Streptococcus species can include, but are not limited to, alpha-hemolytic including Pneumococci (e.g., S. pneumonia), and the Viridans group (e.g., S. mutans, S. mitis, S. sanguinis, S. salivarius, S. salivarius ssp. thermophilus, S. constellatus); and beta-hemolytic including Group A (e.g., S. pyogenes), Group B (e.g., S. agalactiae), Group C (e.g., S. equi, and S. zooepidemicus), Group D (e.g., enterococci, Streptococcus bovis and Streptococcus equinus), Group F streptococci, and Group G streptococci.

In some embodiments, a protein G-expressing microbe includes Group C and Group G streptococci.

One skilled in the art can understand that the engineered microbe-targeting molecules or substrates, products and kits described herein can be used to target any microorganism with a microbe surface-binding domain described herein modified for each microorganism of interest. A skilled artisan can determine the cell-surface proteins or carbohydrates for each microorganism of interest using any microbiology techniques known in the art.

Biofilm:

Accordingly, in some embodiments, the microbe-targeting molecules or substrates, products and kits herein can be used to detect microbes and/or assocatied microbial matter present in a biofilm or to treat equipment surfaces to prevent or inhibit formation of a biofilm. For example, Listeria monocytogenes can form biofilms on a variety of materials used in food processing equipment and other food and non-food contact surfaces (Blackman, J Food Prot 1996; 59:827-31; Frank, J Food Prot 1990; 53:550-4; Krysinski, J Food Prot 1992; 55:246-51; Ronner, J Food Prot 1993; 56:750-8). Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et al., Annu Rev Microbiol 1995; 49:711-45). In some embodiments, the engineered microbe-targeting microparticles, e.g., encapsulating a drug or a chemical for treatment of a biofilm, can be sprayed on contaminated equipment surfaces. The bacteria present in the biofilm bind to the microbe-targeting microparticles, which release the drug to treat the bacteria for targeted drug delivery.

In addition, *L. monocytogenes* attached to surfaces such as stainless steel and rubber, materials commonly used in food processing environments, can survive for prolonged periods (Helke and Wong, J Food Prot 1994; 57:963-8). This would partially explain their ability to persist in the processing plant. Common sources of *L. monocytogenes* in processing facilities include equipment, conveyors, product contact surfaces, hand tools, cleaning utensils, floors, drains, walls, and condensate (Tomkin et al., Dairy, Food Environ Sanit 1999; 19:551-62; Welbourn and Williams, Dairy, Food Environ Sanit 1999; 19:399-401). In some embodiments, the engineered microbe-targeting molecules can be configured to include a "smart label", which is undetectable when conjugated to the engineered microbe-targeting molecules, but produces a color change when released from the engineered molecules in the presence of a microbe enzyme. Thus, when a microbe binds to the engineered microbe-targeting molecules, the microbe releases enzymes that release the detectable label from the engineered molecules. An observation of a color change indicates a risk for bacteria contamination on a particular surface, and thus some embodiments of the engineered microbe-targeting molecules and products can be used for early detection of biofilm formation.

Plant Microbes:

In still further embodiments, the engineered microbe-targeting molecules or substrates and products described herein can be used to target plant microbes and/or associated microbial matter. Plant fungi have caused major epidemics with huge societal impacts. Examples of plant fungi include, but are not limited to, *Phytophthora infestans*, *Crimpellis perniciosa*, frosty pod (*Moniliophthora roreri*), oomycete *Phytophthora capsici*, *Mycosphaerella fijiensis*, *Fusarium Ganoderma* spp fungi and *Phytophthora*. An exemplary plant bacterium includes *Burkholderia cepacia*. Exemplary plant viruses include, but are not limited to, soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

Military and Bioterrorism Applications:

In yet other embodiments, the engineered microbe-targeting molecules and product comprising thereof can be used to detect or combat bioterror agents (e.g., *B. Anthracis*, and smallpox).

In accordance with some embodiments described herein, an engineered microbe-binding molecule or microbe-binding substrate can be modified to bind to any of the microbes, e.g., the ones described herein, including the associated microbial matter (e.g., but not limited to, fragments of cell wall, microbial nucleic acid and endotoxin).

Embodiments of the various aspects described herein can be illustrated by the following numbered paragraphs.

1. An engineered microbe-targeting molecule comprising:
   a. at least one microbe surface-binding domain;
   b. a substrate-binding domain adapted for orienting the microbe surface-binding domain away from a substrate; and
   c. at least one linker between the microbe surface-binding domain and the substrate-binding domain.
2. The engineered molecule of paragraph 1, wherein the microbe-surface binding domain comprises a carbohydrate recognition domain (CRD) or a fragment thereof.
3. The engineered molecule of paragraph 1 or 2, wherein the CRD or a fragment thereof further comprises at least a portion of a carbohydrate-binding protein.
4. The engineered molecule of paragraph 3, wherein the portion of the carbohydrate-binding protein excludes at least one of complement and coagulation activation region.
5. The engineered molecule of any of paragraphs 2-4, wherein the CRD or the carbohydrate-binding protein is derived from a lectin, a ficolin, or a fragment thereof
6. The engineered molecule of paragraph 5 wherein the lectin is C-type lectin, or a fragment thereof
7. The engineered molecule of paragraph 6, wherein the C-type lectin is collectin, or a fragment thereof
8. The engineered molecule of paragraph 7, wherein the collectin is mannose-binding lectin (MBL) or a fragment thereof.
9. The engineered molecule of any of paragraphs 2-8, wherein the CRD is of SEQ ID NO. 4 or a fragment thereof.
10. The engineered molecule of any of paragraphs 2-9, wherein the CRD or a fragment thereof further comprises a neck region of the carbohydrate-binding protein or a fragment thereof.
11. The engineered molecule of any of paragraphs 1-10, wherein the substrate-binding domain comprises at least one amine.
12. The engineered molecule of any of paragraphs 1-11, wherein the substrate-binding domain comprises at least one oligopeptide comprising an amino acid sequence of AKT.
13. The engineered molecule of any of paragraphs 1-12, wherein the linker is adapted to provide flexibility and orientation of the carbohydrate recognition domain to bind to the microbe surface.
14. The engineered molecule of any of paragraphs 1-13, wherein the linker is adapted to facilitate expression and purification.
15. The engineered molecule of any of paragraphs 1-14, wherein the linker comprises a portion of a Fc region of an immunoglobulin.
16. The engineered molecule of paragraph 15, wherein the immunoglobulin is selected from the group consisting of IgA, IgD, IgE, IgG, and IgM.

17. The engineered molecule of paragraph 15 or 16, wherein the immunoglobulin is IgG1.
18. The engineered molecule of any of paragraphs 15-17, wherein the portion of the Fc region comprises at least one region selected from the group consisting of a hinge region, a CH2 region, a CH3 region, and any combinations thereof
19. The engineered molecule of any of paragraphs 15-18, wherein the portion of the Fc region comprises at least one hinge region, at least one CH2 region and at least one CH3 region.
20. The engineered molecule of any of paragraphs 15-19, wherein the portion of the Fc region comprises at least one mutation.
21. The engineered molecule of paragraph 20, wherein the at least one mutation is selected to increase half-life of the engineered molecule.
22. The engineered molecule of any of paragraphs 20-21, wherein the mutation is selected to modulate antibody-dependent cell-mediated cytotoxicity.
23. The engineered molecule of any of paragraphs 20-22, wherein the mutation is selected to modulate complement-dependent cytotoxicity.
24. The engineered molecule of any of paragraphs 20-23, wherein the mutation occurs at amino acid residue 82 of SEQ ID NO. 9 from asparagine to aspartic acid.
25. The engineered molecule of any of paragraphs 15-24, wherein N-terminus of the Fc region is adapted for linking to the substrate-binding domain.
26. The engineered molecule of any of paragraphs 1-25, wherein the linker is part of the carbohydrate-binding protein, the neck region, the Fc region, or any combinations thereof.
27. The engineered molecule of any of paragraphs 1-26, wherein the engineered molecule is a dimer.
28. The engineered molecule of paragraph 27, wherein the dimer is formed by dimerizing the Fc region of two engineered molecules.
29. The engineered molecule of any of paragraphs 1-28, further comprising a detectable label.
30. The engineered molecule of paragraph 29, wherein the detectable label is selected from the group consisting of biotin, a fluorescent dye or particle, a luminescent or bioluminescent marker, a radiolabel, an enzyme, a microbial enzyme substrate, a quantum dot, an imaging agent, and any combinations thereof
31. The engineered molecule of paragraph 30, wherein the enzyme causes a color change in the presence of an enzyme substrate.
32. The engineered molecule of paragraph 31, wherein the enzyme is a horseradish peroxidase or alkaline phosphatase.
33. An engineered mannose-binding lectin molecule comprising:
    a. at least one carbohydrate recognition domain (CRD) or a fragment thereof
    b. a substrate-binding domain adapted for orienting the CRD away from a substrate; and
    c. at least one linker between the CRD and the substrate-binding domain.
34. The engineered lectin of paragraph 33, wherein the CRD is of SEQ ID NO. 4.
35. The engineered lectin of paragraph 33 or 34, wherein the CRD or a fragment thereof further comprises at least a portion of mannose-binding lectin (MBL).
36. The engineered lectin of any of paragraphs 33-35, wherein the portion of the MBL excludes at least one of complement and coagulation activation region.
37. The engineered lectin of any of paragraphs 33-36, wherein the CRD further comprises a neck region of the MBL.
38. The engineered lectin of any of paragraphs 33-37, wherein the substrate-binding domain comprises at least one amine.
39. The engineered lectin of any of paragraphs 33-38, wherein the substrate-binding domain comprises at least one oligopeptide comprising an amino acid sequence of AKT.
40. The engineered lectin of any of paragraphs 33-39, wherein the linker is adapted to provide flexibility and orientation of the carbohydrate recognition domain to bind to the microbe surface.
41. The engineered lectin of any of paragraphs 33-40, wherein the linker is adapted to facilitate expression and purification.
42. The engineered lectin of any of paragraphs 33-41, wherein the linker comprises a portion of a Fc region of an immunoglobulin.
43. The engineered lectin of paragraph 42, wherein the immunoglobulin is selected from the group consisting of IgA, IgD, IgE, IgG, and IgM.
44. The engineered lectin of paragraph 42 or 43, wherein the immunoglobulin is IgG1.
45. The engineered lectin of any of paragraphs 42-44, wherein the portion of the Fc region comprises at least one region selected from the group consisting of a hinge region, a CH2 region, a CH3 region, and any combinations thereof
46. The engineered lectin of any of paragraphs 42-45, wherein the portion of the Fc region comprises at least one hinge region, at least one CH2 region and at least one CH3 region.
47. The engineered lectin of any of paragraphs 42-46, wherein the portion of the Fc region comprises at least one mutation.
48. The engineered lectin of paragraph 47, wherein the mutation is selected to increase half-life of the engineered molecule.
49. The engineered lectin of paragraph 48, wherein the mutation occurs at an amino acid residue 232 of SEQ ID NO. 9 from lysine to alanine.
50. The engineered lectin of any of paragraphs 47-49, wherein the mutation is selected to modulate antibody-dependent cell-mediated cytotoxicity.
51. The engineered lectin of any of paragraphs 47-50, wherein the mutation is selected to modulate complement-dependent cytotoxicity.
52. The engineered lectin of any of paragraphs 47-51, wherein the mutation occurs at amino acid site 82 of SEQ ID NO. 9 from asparagine to aspartic acid.
53. The engineered lectin of any of paragraphs 47-52, wherein N-terminus of the Fc region is adapted for linking to the substrate-binding domain.
54. The engineered lectin of any of paragraphs 47-53, wherein the linker is part of the mannose-binding lectin, the neck region, the Fc region, or any combinations thereof
55. The engineered lectin of any of paragraphs 33-54, wherein the engineered molecule is a dimer.
56. The engineered lectin of paragraph 55, wherein the dimer is formed by dimerizing the Fc region of two engineered lectin molecules.

57. The engineered lectin of any of paragraphs 33-56, further comprising a detectable label.
58. The engineered lectin of paragraph 57, wherein the detectable label or imaging agent is selected from the group consisting of biotin, a fluorescent dye or particle, a luminescent or bioluminescent marker, a radiolabel, an enzyme, a microbial enzyme substrate, a quantum dot, an imaging agent, and any combinations thereof.
59. The engineered lectin of paragraph 58, wherein the enzyme causes a color change in the presence of an enzyme substrate.
60. The engineered lectin of paragraph 59, wherein the enzyme is a horseradish peroxidase or alkaline phosphatase.
61. An engineered microbe-targeting molecule comprising:
   a. at least one microbe surface-binding domain; and
   b. at least a portion of a Fc region of an immunoglobulin.
62. The engineered molecule of paragraph 61, wherein the portion of the Fc region is linked to N-terminal of the microbe surface-binding domain.
63. The engineered molecule of paragraph 61 or 62, wherein the microbe surface-binding domain comprises a carbohydrate recognition domain (CRD) or a fragment thereof.
64. The engineered molecule of paragraph 63, wherein the CRD or a fragment thereof further comprises at least a portion of a carbohydrate-binding protein.
65. The engineered molecule of paragraph 64, wherein the portion of the carbohydrate-binding protein excludes at least one of complement and coagulation activation region.
66. The engineered molecule of any of paragraphs 63-65, wherein the CRD or the carbohydrate-binding protein is derived from a lectin, a ficolin, or a fragment thereof
67. The engineered molecule of paragraph 66, wherein the lectin is C-type lectin, or a fragment thereof.
68. The engineered molecule of paragraph 67, wherein the C-type lectin is collectin, or a fragment thereof.
69. The engineered molecule of paragraph 68, wherein the collectin is mannose-binding lectin (MBL) or a fragment thereof.
70. The engineered molecule of any of paragraphs 63-69, wherein the CRD is of SEQ ID NO. 4 or a fragment thereof.
71. The engineered molecule of any of paragraphs 63-70, wherein the CRD or a fragment thereof further comprises a neck region of a carbohydrate-binding protein.
72. The engineered molecule of any of paragraphs 61-71, wherein said at least a portion of the Fc region of the immunoglobulin further comprises a substrate-binding domain.
73. The engineered molecule of paragraph 72, wherein the substrate-binding domain comprises at least one amine.
74. The engineered molecule of any of paragraphs 61-73, wherein the substrate-binding domain comprises at least one oligopeptide comprising an amino acid sequence of AKT.
75. The engineered molecule of any of paragraphs 61-74, wherein the immunoglobulin is selected from the group consisting of IgA, IgD, IgE, IgG, and IgM.
76. The engineered molecule of any of paragraphs 61-75, wherein the immunoglobulin is IgG1.
77. The engineered molecule of any of paragraphs 61-76, wherein the portion of the Fc region comprises at least one region selected from the group consisting of a hinge region, a CH2 region, a CH3 region, and any combinations thereof
78. The engineered molecule of any of paragraphs 61-77, wherein the portion of the Fc region comprises at least one hinge region, at least one CH2 region and at least one CH3 region.
79. The engineered molecule of any of paragraphs 61-78, wherein the portion of the Fc region comprises at least one mutation.
80. The engineered molecule of paragraph 79, wherein the at least one mutation is selected to increase half-life of the engineered microbe-binding molecule.
81. The engineered molecule of any of paragraphs 61-80, wherein the mutation is selected to modulate antibody-dependent cell-mediated cytotoxicity.
82. The engineered molecule of any of paragraphs 61-81, wherein the mutation is selected to modulate complement-dependent cytotoxicity.
83. The engineered molecule of any of paragraphs 61-82, wherein the mutation occurs at amino acid residue 82 of SEQ ID NO. 9 from asparagine to aspartic acid.
84. The engineered molecule of any of paragraphs 61-83, wherein the engineered molecule is a dimer.
85. The engineered molecule of paragraph 84, wherein the dimer is formed by dimerizing the Fc region of two engineered molecules.
86. The engineered molecule of any of paragraphs 61-85, further comprising a detectable label.
87. The engineered molecule of paragraph 86, wherein the detectable label is selected from the group consisting of biotin, a fluorescent dye or particle, a luminescent or bioluminescent marker, a radiolabel, an enzyme, a microbial enzyme substrate, a quantum dot, an imaging agent, and any combinations thereof
88. The engineered molecule of paragraph 87, wherein the enzyme causes a color change in the presence of an enzyme substrate.
89. The engineered molecule of paragraph 88, wherein the enzyme is a horseradish peroxidase or alkaline phosphatase.
90. A microbe-targeting substrate or a product comprising a substrate, and at least one engineered microbe-targeting molecule of any of paragraphs 1-32 and 61-89 or at least one engineered mannose-binding lectin molecule of any of paragraphs 33-60, wherein the substrate comprises on its surface said at least one engineered microbe-targeting molecule or at least one engineered mannose-binding lectin molecule.
91. The microbe-targeting substrate or the product of paragraph 90, wherein the substrate-binding domain of the engineered microbe-targeting molecule or mannose-binding lectin molecule is adapted for binding to the substrate.
92. The microbe-targeting substrate or the product of paragraph 90 or 91, wherein the substrate is selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a spiral mixer, and a hollow-fiber reactor.
93. The microbe-targeting substrate or the product of any of paragraphs 90-92, wherein the substrate is a microparticle.
94. The microbe-targeting substrate or the product of paragraph 93, wherein the microparticle is a magnetic microparticle.
95. The microbe-targeting substrate or the product of paragraph 93, wherein the microparticle is a fluorescent microparticle or a quantum dot.

96. The microbe-targeting substrate or the product of paragraph 93, wherein the microparticle is a drug delivery vehicle.

97. The microbe-targeting substrate or the product of any of paragraphs 90-96, wherein the substrate is a dipstick.

98. The microbe-targeting substrate or the product of any of paragraphs 90-96, wherein the substrate is a membrane.

99. The microbe-targeting substrate or the product of paragraph 97 or 98, wherein the dipstick or the membrane comprises on its surface at least an area adapted for use as a reference area.

100. The microbe-targeting substrate or the product of any of paragraphs 90-99, wherein the substrate is a living cell, or a biological tissue or organ.

101. The microbe-targeting substrate or the product of any of paragraphs 90-100, wherein the substrate is functionalized.

102. The microbe-targeting substrate or the product of any of paragraphs 90-101, wherein the substrate is treated to become less adhesive to a biological molecule.

103. The microbe-targeting substrate or the product of paragraph 102, wherein the biological molecule is selected from the group consisting of blood cells and components, proteins, nucleic acids, peptides, small molecules, therapeutic agents, cells or fragments thereof, and any combinations thereof.

104. A pharmaceutical composition comprising at least one engineered microbe-targeting molecule of any of paragraphs 1-32 and 61-89 or at least one engineered mannose-binding lectin molecule of any of paragraphs 33-60 or at least one microbe-targeting substrate of any of paragraphs 90-103, and a pharmaceutically acceptable carrier.

105. A kit comprising:
   a. one or more containers containing a population of engineered microbe-targeting molecules of any of paragraphs 1-32 and 61-89 or a population of engineered mannose-binding lectin molecules of any of paragraphs 33-60; and
   b. at least one reagent.

106. The kit of paragraph 105, further comprising one or more substrates to which the engineered microbe-targeting molecules or engineered mannose-binding lectin molecules are conjugated.

107. The kit of paragraph 105 or 106, wherein the substrates are selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a spiral mixer, and a hollow-fiber reactor.

108. The kit of any of paragraphs 105-107, wherein the substrates include a population of the microbeads.

109. The kit of paragraph 108, wherein the microbeads are magnetic microbeads.

110. A kit comprising:
   a. one or more microbe-targeting substrates of any of paragraphs 90-104; and
   b. at least one reagent.

111. The kit of any of paragraphs 105-108, wherein the one or more microbe-targeting substrates include dipsticks.

112. The kit of any of paragraphs 105-109, wherein the one or more microbe-targeting substrates include a population of microbe-targeting microbeads.

113. The kit of paragraph 108, 109 or 112, wherein the population of microbes or microbe-targeting microbeads is provided in one or more separate containers.

114. The kit of any of paragraphs 108, 109, and 112-113, wherein the population of the microbeads or microbe-targeting microbeads comprises at least one distinct subset, the distinct subset comprising microbeads or microbe-targeting microbeads having a dimension different from the rest of the population.

115. The kit of any of paragraphs 110-114, wherein the microbe-targeting microbeads each further comprises a detection label.

116. The kit of any of paragraphs 105-115, further comprising one or more containers each containing a population of detectable labels, wherein each of the detectable label is conjugated to a molecule.

117. The kit of paragraph 116, wherein at least one of the containers contains a distinct population of detectable labels.

118. The kit of any of paragraphs 116-117, wherein the molecule is an engineered microbe-targeting molecule of any of paragraphs 1-32 and 61-89 or an engineered mannose-binding lectin molecules of any of paragraphs 33-60.

119. The kit of paragraph 118, wherein the molecule comprises at least a carbohydrate recognition domain (CRD) or a fragment thereof.

120. The kit of paragraph 119, wherein at least one population of the molecule comprises SEQ ID NO.4 or a fragment thereof.

121. The kit of any of paragraphs 116-120, wherein the molecule further comprises a Fc region of an immunoglobulin.

122. The kit of any of paragraphs 116-120, wherein the molecule includes an antibody specific to the microbe.

123. The kit of any of paragraphs 116-122, wherein the detectable label comprises an enzyme that produces a color change in the presence of an enzyme substrate.

124. The kit of paragraph 123, wherein the enzyme is a horseradish peroxidase, an alkaline phosphatase, or any combinations thereof.

125. The kit of any of paragraphs 105-124, further comprising one or more containers containing an enzyme substrate that changes color in the presence of the enzyme.

126. The kit of any of paragraphs 116-125, wherein the detectable label comprises a fluorescent molecule.

127. The kit of any of paragraphs 105-126, wherein the at least one reagent is a wash buffer, a dilution buffer, a stop buffer, a buffered solution containing a chelating agent, a coupling agent used for conjugation of the engineered molecule to the substrate, or any combinations thereof 128. The kit of any of paragraphs 105-127, further comprising at least one microtiter plate.

129. The kit of any of paragraphs 108-128, wherein the population of microbeads or microbe-targeting microbeads is lyophilized.

130. The kit of any of paragraphs 105-129, further comprising at least one blood collection container.

131. The kit of paragraph 130, wherein the population of the microbe-targeting microbeads is pre-loaded into said at least one blood collection container.

132. The kit of paragraph 130 or 131, wherein the blood collection container further comprises an anti-coagulant agent.

133. The kit of any of paragraphs 112-132, wherein the engineered microbe-targeting microbeads are microbe-targeting magnetic microbeads.

134. The kit of paragraph 133, further comprising a magnet adapted for collecting the microbe-targeting magnetic microbeads in the blood collection container.
135. The kit of any of paragraphs 105-134, further comprising a reference for comparison with a readout determined from a test sample.
136. The kit of any of paragraphs 110-135, wherein one or more microbe-targeting substrates are individually packaged.
137. A method of detaching a microbe and/or microbial matter from a microbe-targeting molecule, the method comprising incubating the substrate with buffer having an acidic pH.
138. The method of paragraph 137, wherein the buffer has a pH about 6.5 or lower.
139. The method of paragraph 137 or 138, wherein the buffer comprises 0.2M glycine and has a pH of about 2.8.
140. A method of detaching a microbe and/or microbial matter from a microbe-targeting molecule, the method comprising incubating the substrate with a buffer comprising an ion which forms a salt with Ca2+ ion and wherein the said salt is insoluble in the buffer.
141. The method of paragraph 140, wherein said ion is selected from the group consisting of phosphate, oxalate, carbonate, sulfate, fluoride, gluconic acid, oxido-trioxo-manganese, stearic acid, and any combinations thereof.
142. The method of paragraph 140 or 141, wherein said ion is present at a concentration of about 0.05M to about 5M.
143. The method of any of paragraphs 140-142, wherein the buffer comprises about 0.1M sodium phosphate and has pH of about 6.8.
144. The method of any of paragraphs 140-143, wherein the interaction between the microbe and the microbe-targeting molecule is mediated by a Ca2+ ion.
145. The method of any of paragraphs 140-144, wherein the aqueous solution further comprises a chelating agent.
146. The method of paragraph 145, wherein the chelating agent is selected from the group consisting of 1,2-bis(2-Aminophenoxy)ethane-N,N,N',N'-tetraacetic acid; ethylenediaminetetraacetic acid (EDTA); ethylene glycol-bis(2-aminoethylether)-N,N,N',N'-tetraacetic acid (EGTA); ethylene glycol-bis($\beta$-aminoethyl ether)-N,N,N',N'-tetraacetic acid, 1,2-bis(o-aminophenoxy)ethane-N,N,N',N'-tetraacetic acid (BAPTA), nitrile-2,2',2"-triacetic acid (NTA), and any combinations thereof.
147. The method of any of paragraphs 137-146, wherein the substrate is microparticle.
148. The method of any of paragraphs 137-147, wherein the substrate is a magnetic microparticle.
149. The method of any of paragraphs 137-148, wherein the microbe-targeting molecule is an engineered microbe-targeting molecule of any of paragraphs 1-32 or 61-89, or an engineered mannose-binding ligand of any of paragraphs 33-60.
150. The method of any of paragraphs 137-149, further comprising heating or cooling the buffer during said contacting.
151. The method of any of paragraphs 137-150, further comprising shaking the substrate in the buffer.
152. The method of any of paragraphs 137-151, wherein said incubation is for at least 5 minutes.
153. The method of any of paragraphs 137-152, further comprising washing the substrate with after detachment of the microbe.
154. The method of any of paragraphs 137-153, wherein the microbe-targeting molecule binds to a substrate.
155. A composition for treating and/or preventing a microbial infection or a microbial contamination comprising at least one engineered microbe-targeting molecule of any of paragraphs 1-32 or 61-89 or at least one engineered mannose-binding lectin molecule of any of paragraphs 33-60 or at least one microbe-targeting substrate of any of paragraphs 90-103.
156. The composition of paragraph 155, wherein the composition is formulated for treating and/or preventing a microbial infection or a microbial contamination present in an environment surface.
157. The composition of paragraph 156, wherein the environmental surface includes a medical device, an implantable device, a surface in a hospital or clinic (e.g., an operating room or an intensive-care unit), a machine or working surface for manufacturing or processing food or pharmaceutical products, a cell culture, a water treatment plant, a water reservoir or a botanical plant.
158. The composition of any of paragraphs 155-157, wherein the composition is formulated for treating and/or preventing a microbial infection in a body fluid of a subject.
159. The composition of any of paragraphs of 155-158, wherein the composition is formulated for treating and/or preventing a microbial infection in a tissue of a subject.
160. The composition of paragraph 158 or 159, wherein the subject is a mammalian subject.
161. The composition of any of paragraphs 155-160, wherein said at least one engineered microbe-targeting molecule is present in an amount effective to reduce the growth and/or spread of the microbe.
162. The composition of any of paragraphs 155-161, further comprising at least one of an antimicrobial agent and a drug delivery vehicle.
163. The composition of paragraph 162, wherein at least one of the engineered microbe-targeting molecule and the antimicrobial agent is coated on a surface of the drug delivery vehicle.
164. The composition of paragraph 162 or 163, wherein the drug delivery vehicle is selected from the group consisting of a peptide particle, a polymeric particle, a dendrimer, a vesicle, a liposome, a hydrogel, a nucleic acid scaffold, an aptamer, and any combinations thereof,
165. The composition of any of paragraphs 162-164, wherein the antimicrobial agent is fused with said at least one engineered microbe-targeting molecule.
166. The composition of any of paragraphs 162-165, wherein the antimicrobial agent is selected from the group consisting of silver nanoparticle, an antimicrobial metalloendopeptidase, an antimicrobial peptide, an antibiotic, and any combinations thereof.
167. The composition of any of paragraphs 155-166, wherein a microbe causing the microbial infection or microbial contamination is a protein A-expressing microbe, a protein G-expressing microbe or any combinations thereof.
168. The composition of paragraph 167, wherein the protein A-expressing microbe includes *Staphylococcus* or the protein G-expressing microbe includes *Streptococcus*.
169. The composition of paragraph 167 or 168, wherein the protein A-expressing microbe includes *Staphylococcus aureus*.
170. The composition of any of paragraphs 167-169, wherein the microbe is resistant to at least one antimicrobial agent.
171. The composition of paragraph 170, wherein the antimicrobial agent is an antibiotic.

172. The composition of paragraph 171, wherein the antibiotic is selected from the group consisting of aminoglycosides, ansamycins, carbacephem, carbapenems, cephalosporins, glycopeptides, lincosamides, lipopeptide, macrolides, monobactams, nitrofurans, penicillins, polypeptides, quinolones, sulfonamides, tetracyclines, methicillin, vancomycin, and any combinations thereof 173. The composition of any of paragraphs 167-172, wherein the protein A-expressing microbe includes methicillin-resistant *Staphylococcus aureus*.

174. The composition of any of paragraphs 167-173, wherein the protein A-expressing microbe includes vancomycin-resistant *Staphylococcus aureus*.

175. The composition of any of paragraphs 155-174, wherein the composition is adapted for use as a wound dressing.

176. The composition of any of paragraphs 155-175, wherein the immunoglobulin is a human immunoglobulin.

177. A method for removing a microbe and/or microbial matter from a target area comprising contacting the target area with a composition of any of paragraphs 155-176.

178. A method for treating and/or preventing a microbial infection or microbial contamination in a target area comprising contacting the target area with a first composition of any of paragraphs 155-176.

179. The method of paragraph 177 or 178, wherein the target area includes an environmental surface.

180. The method of paragraph 179, wherein the environmental surface includes a medical device, an implantable device, a surface in a hospital or clinic (e.g., an operating room or an intensive-care unit), a machine or working surface for manufacturing or processing food or pharmaceutical products, a cell culture, a water treatment plant, a water reservoir or a botanical plant.

181. The method of paragraph 177 or 178, wherein the target area is present in a body fluid of a subject.

182. The method of paragraph 177 or 178, wherein the target area is present in a tissue of a subject.

183. The method of paragraph 182, further comprising replacing the first composition in contact with the tissue with a second composition of any of paragraphs 157-178 after a period of time.

184. The method of paragraph 182 or 183, further comprising administering an additional treatment to the tissue.

185. The method of paragraph 184, wherein the additional treatment includes a negative-pressure treatment, a vacuum-assisted debridement, administration of an antimicrobial agent, or any combinations thereof 186. An assay for determining the presence or absence of a microbe and/or microbial matter in a test sample, the assay comprising: contacting a test sample with a microbe-targeting substrate of any of paragraphs 90-103.

187. An assay of determining the presence or absence of a microbe and/or microbial matter in a test sample, the method comprising:
    contacting a test sample with a plurality of microbe-targeting substrates of any of paragraphs 90-103, wherein the plurality of microbe-targeting substrates comprises a first subset of microbe-targeting substrates and a second subset of microbe-targeting substrates; and
    wherein the first subset of microbe-targeting substrates each has a first pre-determined dimension; and
    wherein the second subset of microbe-targeting substrates each has a second pre-determined dimension.

188. The assay of paragraph 187, wherein the first subset and the second subset are added to the test sample to form a single mixture.

189. The assay of paragraph 187, wherein the second subset is added to the test sample after isolation of the first subset previously added to the test sample.

190. The assay of any of paragraph 186-189, wherein the microbe-targeting substrate is in a form of a microbead.

191. The assay of paragraph 190, wherein the first pre-determined dimension and the second pre-determined dimension of the microbead range from about 10 nm to about 10 μm.

192. The assay of paragraph 190, wherein the first pre-determined dimension and the second pre-determined dimension of the microbead range from about 50 nm to about 200 nm.

193. The assay of any of paragraphs 190-192, wherein the microbead is a magnetic microbead.

194. The assay of any of paragraphs 186-193, further comprising analyzing the microbe-targeting substrate for the presence or absence of a bound microbe and/or microbial matter, wherein the presence of a microbe-targeting substrate-bound microbe and/or microbial matter indicates that the test sample is infected with a microbe; and the absence of a microbe-targeting substrate-bound microbe and/or microbial matter indicates the test sample contains no detectable microbes or microbial matter.

195. The assay of any of paragraphs 186-194, wherein the microbial matter includes endotoxin.

196. An assay for determining the presence or absence of a protein-A expressing microbe, a protein-G expressing microbe, or microbial matter thereof, in a test sample, the assay comprising:
    contacting a test sample with a microbe-targeting substrate of any of paragraphs 90 to 103 in the presence of a chelating agent.

197. The assay of paragraph 196, further comprising analyzing the microbe-targeting substrate for the presence or absence of a bound microbe, wherein the presence of a microbe-targeting substrate-bound microbe indicates the presence of a protein-A expressing microbe or a protein G-expressing microbe in the test sample; and the absence of a microbe-targeting substrate-bound microbe indicates the absence of a protein-A expressing or a protein G-expressing microbe in the test sample.

198. The assay of paragraph 197, wherein in the absence of a microbe-targeting substrate-bound microbe, the test sample is further contacted with the microbe-targeting substrate in the presence of free calcium ions.

199. An assay for detecting a protein-A expressing microbe, a protein-G expressing microbe, or microbial matter thereof, in a test sample, the assay comprising:
    i. contacting a test sample with a microbe-targeting substrate of any of paragraphs 90 to 103;
    ii. contacting the microbe-binding molecule with a solution comprising a chelating agent; and
    iii. analyzing the microbe-targeting substrate for the presence or absence of a bound microbe, wherein the presence of a microbe-targeting substrate-bound microbe indicates the presence of a protein A-expressing microbe or a protein G-expressing microbe in the test sample; and the absence of a microbe-targeting substrate-bound microbe indicates the absence of a protein A-expressing microbe or a protein G-expressing microbe in the test sample.

200. The assay of paragraph 199, further comprising isolating the microbe-targeting substrate from the test sample before contacting with the solution comprising the chelating agent.
201. The assay of any of paragraphs 186-200, further comprising isolating the microbe-targeting substrate from the test sample or the solution comprising the chelating agent before the analyzing step.
202. The assay of paragraph 201, wherein the analyzing comprises an immunoassay, ELISA, Gram staining, immunostaining, microscopy, spectroscopy, immunofluorescence, western blot, PCR, RT-PCR, fluorescence in situ hybridization, sequencing, mass spectroscopy, and any combinations thereof
203. The assay of any of paragraphs 186-202, further comprising culturing the microbe bound on the microbe-targeting substrate.
204. The assay of any of paragraphs 186-203, further comprising subjecting the microbe bound on the microbe-targeting substrate to an antibiotic.
205. The assay of any of paragraphs 186-204, wherein the microbe-targeting substrate is preformed from at least a substrate and said at least one engineered microbe-binding molecule before the contacting.
206. The assay of any of paragraphs 186-204, wherein the microbe-targeting substrate is formed from at least said substrate and said at least one engineered microbe-binding molecule during the contacting.
207. The assay of any of paragraphs 196-206, wherein the presence of the chelating agent reduces the likelihood of a protein A- and protein G-negative microbe, if present, in the test sample, to bind with said at least one engineered microbe-binding molecule.
208. The assay of any of paragraphs 186-207, further comprising detaching the bound microbe from the microbe-targeting substrate.
209. The assay of paragraph 208, further comprising contacting the isolated microbe-targeting substrate with a low pH buffer.
210. The assay of any of paragraphs 196-209, wherein the chelating agent is a metal-ion chelating agent.
211. The assay of any of paragraphs 196-210, wherein the chelating agent chelates a calcium ion.
212. The assay of paragraph 211, wherein the calcium-chelating agent is selected from the group consisting of 1,2-bis(2-aminophenoxy)ethane-N,N,N',N'-tetraacetic acid, ethylenediaminetetraacetic acid (EDTA); ethylene glycol-bis(2-aminoethylether)-N,N,N',N'-tetraacetic acid; ethylene glycol-bis(□-aminoethyl ether)-N,N,N?,N?-tetraacetic acid (EGTA), 1,2-bis(o-aminophenoxy)ethane-N,N,N',N'-tetraacetic acid (BAPTA), a buffer containing citrate, N,N-Bis(2-(bis-(carboxymethyl)amino)ethyl)-glycine (DTPA), nitrilo-2,2',2"-triacetic acid (NTA), a buffer that precipitates a calcium ion from the test sample, a low pH buffer, any derivatives thereof, and any combinations thereof.
213. The assay of any of paragraphs 209-212, wherein the low pH buffer has a pH less than 7.
214. The assay of any of paragraphs 209-213, wherein the low pH buffer is selected from the group consisting of arginine and pyrophosphate.
215. The assay of any of paragraphs 196-214, wherein the protein A-expressing microbe includes *Staphylococcus*, or the protein G-expressing microbe includes *Streptococcus*.
216. The assay of paragraph 215, wherein the protein A-expressing microbe includes *Staphylococcus aureus*.
217. The assay of paragraph 215, wherein the *Staphylococcus* species excludes *Staphylococcus epidermidis*.
218. The assay of any of paragraphs 186-217, further comprising analyzing at least one microbe-targeting substrate upon contact with the test sample before contacting the microbe-binding molecule with the solution comprising the chelating agent.
219. The assay of paragraph 186-218, wherein the microbe-targeting substrate is in a form of a microbead.
220. The assay of paragraph 219, wherein the microbead is a magnetic microbead.
221. A method of determining the presence or absence of *Staphylococcus aureus* infection in a subject, comprising performing the assay of any of paragraphs 190-214, wherein the binding of a microbe to said at least one engineered microbe-targeting substrate in the presence of a chelating agent is indicative of *Staphylococcus aureus* infection in the subject.
222. The method of paragraph 221, further comprising administering or prescribing to the subject a first antimicrobial agent when the subject is detected with *Staphylococcus aureus*.
223. The method of paragraph 221 or 222, further comprising analyzing the test sample or the solution comprising the chelating agent after isolating the engineered microbe-targeting substrate therefrom to determine the presence or absence of a protein A-negative or a protein G-negative microbe.
224. The method of paragraph 223, further comprising administering or prescribing to the subject a second antimicrobial agent when the subject is detected with a protein A-negative or a protein G-negative microbe.
225. The method of paragraph 224, wherein the protein A-negative or the protein G-negative microbe include *E. coli*.
226. The method of any of paragraphs 221-225, further comprising administering or prescribing to the subject a composition comprising at least one engineered microbe-targeting molecule of any of paragraphs 1-32 or 61-89, or at least one engineered mannose-binding lectin molecule of any of paragraphs 33-60.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially" of refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "microbe-binding" and "microbe-targeting" as used interchangeably herein refers to an ability of a molecule or composition to bind and/or capture a microbe and/or microbial matter.

The term "FcMBL microbead" as used herein refers to a microbead comprising on its surface at least one FcMBL molecule. In some embodiments, the microbead comprises on its surface a saturating amount of the FcMBL molecules. A microbead can be magnetic or non-magnetic.

The term "FcMBL magnetic microbead" as used herein refers to a magnetic microbead comprising on its surface at least one FcMBL molecule. In some embodiments, the magnetic microbead comprises on its surface a saturating amount of the FcMBL molecules.

The term "antibody" as used herein refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, humanized antibodies, human antibodies, and single chain antibodies (scFvs).

The term "peptide" refers to a polymer of amino acids, or amino acid analogs, regardless of its size or function. In some embodiments, the term "peptide" refers to small polypeptides, e.g., a polymer of about 15-25 amino acids.

The term "oligonucleotide" as used herein refers to a short nucleic acid polymer, typically with twenty or fewer bases.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein.

In some embodiments, the subject is a mammal. The mammal can be a human, non-human primate, mouse, rat, dog, cat, horse, or cow, but are not limited to these examples. Mammals other than humans can be advantageously used as subjects that represent animal models of disorders.

A subject can be one who has been previously diagnosed with or identified as suffering from or having a disease or disorder caused by any microbes or pathogens described herein. By way of example only, a subject can be diagnosed with sepsis, inflammatory diseases, or infections.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

As used here in, the term "peptidomimetic" means a peptide-like molecule that has the activity of the peptide on which it is structurally based. Such peptidomimetics include chemically modified peptides, peptide-like molecules containing non-naturally occurring amino acids, and peptoids, and have an activity such as the cardiac specificity of the peptide upon which the peptidomimetic is derived (see, for example, Goodman and Ro, Peptidomimetics for Drug Design, in "Burger's Medicinal Chemistry and Drug Discovery", Vol. 1 (ed. M. E. Wolff; John Wiley & Sons 1995), pages 803-861).

A variety of peptidomimetics are known in the art and can be encompassed within embodiments described herein including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an Nα-Cacyclized amino acid;

an Nα-methylated amino acid; αβ- or γ-amino cycloalkane carboxylic acid; an αβ-unsaturated amino acid; a ββ-dimethyl or β-methyl amino acid; αβ-substituted-2,3-methano amino acid; an N-Cδ or Cα-Cδcyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; transolefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide described herein, as well as potential geometrical and chemical complementarity to a cognate receptor. Where no crystal structure of a peptide described herein is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide described herein, for example, having specificity for the microbes.

The terms "homology" as used herein refers to sequence similarity between two peptides or between two nucleic acid molecules. Homology can be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology refers to a function of the number of identical or similar amino acids at positions shared by the compared sequences. A sequence which is "unrelated" or "non-homologous" shares less than 40% identity. Determination of homologs of the genes or peptides described herein may be easily ascertained by the skilled artisan.

The term "conservative substitution," when describing a polypeptide, refers to a change in the amino acid composition of the polypeptide that does not substantially alter the polypeptide's activity, fore examples, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions." Insertions or deletions are typically in the range of about 1 to 5 amino acids.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Expression and Purification of Exemplary Engineered MBL Molecules

Engineered MBL for optimized binding to pathogens without the complement activation and coagulation side effects which are present in WT MBL were constructed. The MBL carbohydrate recognition domain & various lengths of the neck domain were cloned and fused to the Fc fragment of human IgG1 comprising the hinge, CH2 and CH3 regions to form the fusion proteins. In one embodiment, the MBL carbohydrate recognition domain and at least a portion of the neck domain was cloned and fused to the Fc fragment of human IgG1 to form the fusion protein FcMBL.81 (SEQ ID NO. 6). In one embodiment, the MBL carbohydrate recognition domain without a neck region was cloned and fused to the Fc fragment of human IgG1 to form the fusion protein FcMBL.111 (SEQ ID NO.8). The complement and coagulation activation regions of the MBL (e.g., the collagen triple helix and hinge MASP binding regions) was removed from the fusion proteins.

In some embodiments, the AKT tripeptide was inserted into the N terminus of Fc (at the hinge region: H of the Fc-X vector shown in FIG. 3) for single-site biotinylation of the FcMBL.81 (The amino acid sequence for such embodiment with the AKT tripeptide fused to the N terminal portion of the Fc, designated as AKTFcMBL.81, is shown in SEQ ID NO. 7). The mono-biotin engineered MBL molecules AKT-FcMBL.81 were then conjugated to streptavidin-coated beads and the carbohydrate binding MBL heads were oriented away from the substrate for optimized binding to pathogens.

In some embodiments, the asparagine N82 (N297 in Kabat numbering) of SEQ ID NO. 6 was mutated to aspartic acid (D) to remove the glycosylation of Fc to remove antibody dependent cellular cytotoxicity (ADCC) and Complement Dependent Cytotoxicity (CDC) functionality.

Four different engineered MBL fusion protein construct were produced:
(1) Fc MBL.111 (SEQ ID NO. 8) consists of the Fc portion of IgG (Kabat numbering 216-447) fused to the MBL CRD head (amino acids 111 to 228).
(2) Fc MBL.81 (SEQ ID NO. 6) consists of the Fc portion of IgG (Kabat numbering 216-447) fused to the MBL CRD head AND neck region (amino acids 81-228).
(3) AKT-Fc MBL.81 (SEQ ID NO. 7) consists of the Fc portion of IgG (Kabat numbering 216-447) fused to the MBL CRD head AND neck region (amino acids 81-228). The 3 amino acid fragment AKT is fused to the N terminal portion of the Fc.
(4) Fc MBL.81 D consists of the Fc portion of IgG (Kabat numbering 216-447) fused to the MBL CRD head AND neck region (amino acids 81-228), in addition, the Fc glycosylation site has been removed by substituting aspartic acid (D) for asparagine (N) at position 82 (297 in Kabat numbering)

A major advantage of the Fc fusion technology is the ease of expression and purification of fusion proteins (Lo et al. (1998) *Protein Engineering*. 11: 495-500). The N terminal Fc has been shown to improve expression levels, protein folding and secretion of the fusion partner. In addition, the Fc has a staphylococcal protein A binding site, which is extremely useful for one-step purification on protein A affinity chromatography. Thus, in some embodiments, different engineered MBL nucleic acid sequences encoding the amino acid sequences discussed above can be inserted in the Fc-X vector disclosed in the Lo et al. Id. Human U 293 cells were then transfected with Fc MBL DNA using the lipofectamine reagent (Invitrogen). The engineered MBL fusion proteins can be purified on a 5 ml HiTrap Protein A column using the GE Akta Avant 25 system.

For protein purification, an exemplary loading buffer is 100 mM Phosphate 150 mM NaCl pH 7, and an exemplary elution buffer is 100 mM Phosphate 150 mM NaCl pH 3. Following elution, the protein was immediately neutralized with 1 N NaOH and Tween 80 (Pierce SurfactAmp) was added to a final concentration of 0.01%. The engineered MBL fusion proteins were then sterile-filtered through a 0.22 micron nylon filter and stored at 4° C. This one-step purification gave a recovery of at least about 90% (data not shown).

Figure 4:
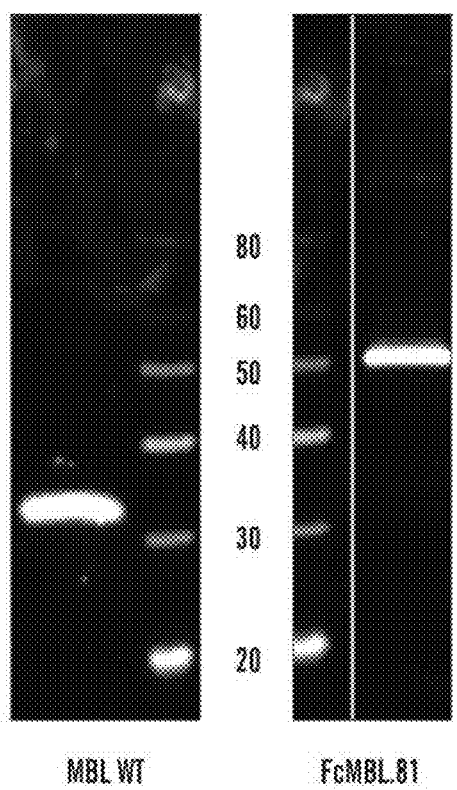
FIG. 4 shows a Western blot image indicating expression of the purified wild-type MBL (MBL WT) proteins and one or more embodiments of the engineered microbe-targeting or microbe-binding molecules described herein (FcMBL.81: SEQ ID NO. 6).

To analyze the purified proteins, a reduced SDS-PAGE was performed using the Invitrogen System. Western blotting was then performed onto PVDF membranes using an iBlot system (Invitrogen) and the PVDF membranes were then probed with biotinylated anti-human MBL antibodies (R&D Systems). The results of the purified proteins FcMBL.81 and MBL wild-type (WT) are shown in FIG. 4.

Example 2: Testing the Potency/Biological Activity of the MBL Constructs

To determine calcium-dependent binding of the Fc MBL proteins to a mannan-coated ELISA plate, 96-well ELISA plate was first coated with 0.5 mg/ml mannan (M3640, Sigma). The purified Fc MBL.81 and Fc MBL.111 fusion proteins (supernatant from 293 cell expression purified using recombinant protein A using the AKTA system & confirmed>90% pure by SDS-PAGE) were diluted and added to the mannan-coated ELISA plate. In some sample wells, EDTA was also added to chelate calcium. A secondary antibody anti-human Fc HRP (109-036-098 Jackson Lab) was then added to all sample wells. The O.D. values of each sample were measured at 450 nm.

Figure 5:
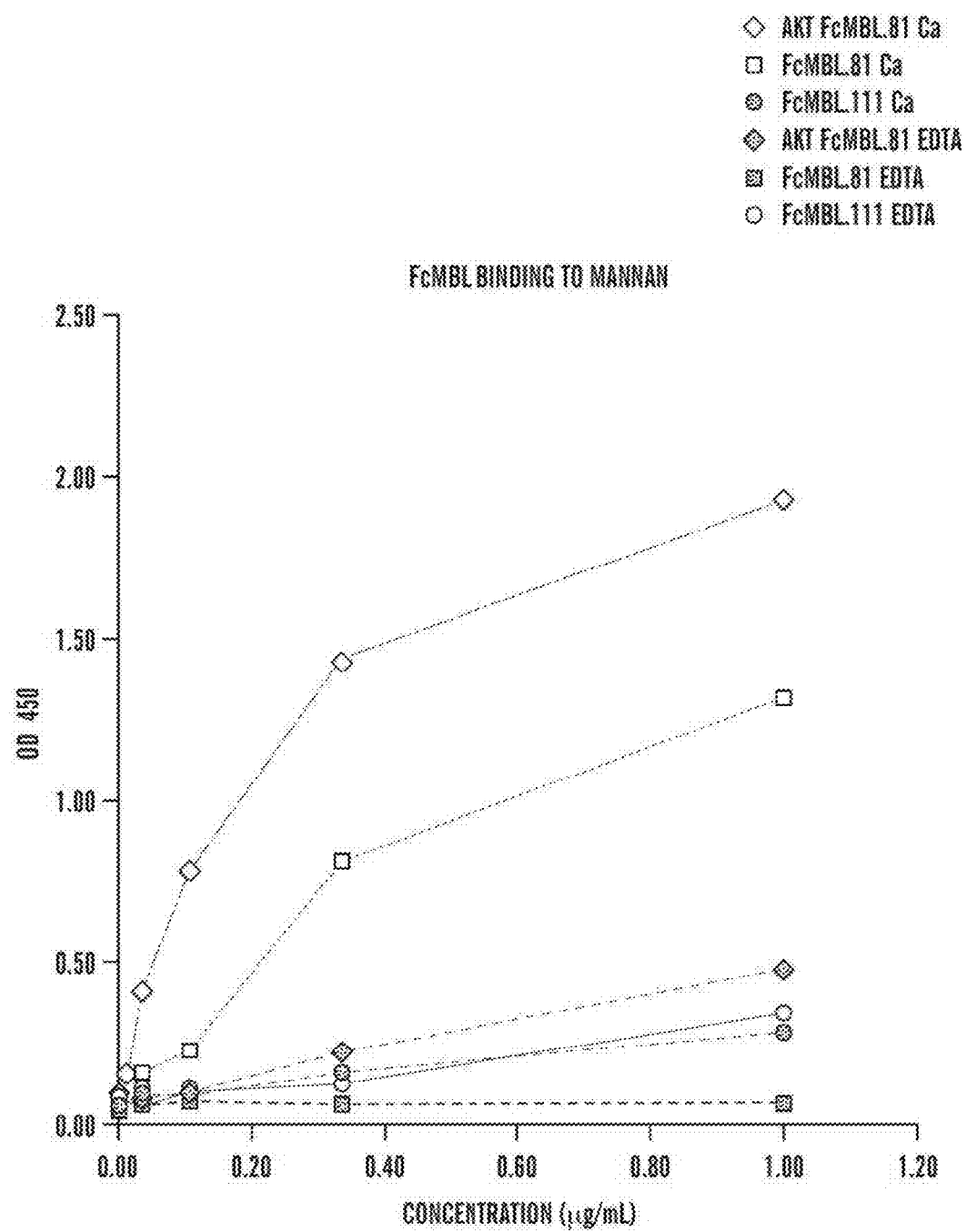
FIG. 5 shows the mannan-binding results of various embodiments of the engineered microbe-targeting or microbe-binding molecules described herein in the presence or absence of calcium ions. A chelating agent (e.g., EDTA) can be added to the sample to remove calcium ions.

Presented herein indicated that the Fc MBL.81 fusion protein binds to mannan in the presence of calcium, but such binding is reduced by ~100 fold in the presence of EDTA (FIG. 5). These assays can be repeated and compared with the WT MBL from SinoBiologicals. As shown in FIG. 5, the FcMBL.111 fusion protein is inactive in the mannan binding, regardless of the presence of calcium. Without wishing to be bound by theory, the neck regions are needed in some embodiments provided herein to provide flexibility and orientation of the engineered microbe-targeting molecules (e.g., engineered MBL molecules) for binding to the carbohydrates on pathogens. The findings presented herein indicate that both the Fc MBL.81 and WT MBL binding to mannan is calcium-dependent and can be reversed by EDTA chelation. Further, the findings indicated that Fc MBL.111 (the MBL CRD head fused to Fc) appears to be a relatively poor binder to mannan, as compared to Fc MBL.81.

The AKT-FcMBL.81 fusion protein appears to show a higher background binding to mannan in the presence of EDTA than the Fc MBL.81 fusion protein. This can be, not being bound by theory, due to the AKT binding site on the N terminus of the fusion protein, which is designed for aminoxy biotinylation for oriented binding on streptavidin beads. Thus, the AKT-FcMBL.81 fusion protein can be a bit sticky. In some embodiments, the AKT-FcMBL.81 may not be ideal for the mannan binding assay.

Example 3: Activity in Complement and Coagulation Assays with MBL Null Serum

WT MBL activates complement and coagulation through the MASP proteins. In this example provided herein, MBL null serum was used as a source of complement and coagulation proteins, while the WT MBL and the FcMBL.81 were used as the sources of MBL to activate complement activation of clotting function.

Assays to measure complement activation has been discussed in Michelow et al. (2010) *JBC* 285: 24729. Briefly, triplicate samples of diluted chimeric proteins were added to mannan-coated microtiter plates with 1% MBL-null human serum as a source of MASP. Normal human serum complement standard (Quidel, San Diego, Calif.) containing native MBL was used to generate a standard curve. After incubation at 37° C. and rinsing, deposited human C4 fragments (Sigma-Aldrich) were detected with anti-human C4c antibodies (Dako Denmark A/S), followed by addition of biotinylated secondary antibodies (JacksonImmunoResearch Laboratories, West Grove, Pa.), avidin-containing Vectastain ABC-alkaline phosphatase reagent (VectorLaboratories, Burlingame, Calif.), and p-nitrophenyl phosphate, and measurement at A405 nm.

Methods to determine coagulation and search for thrombin-like activity have been previously established, e.g., discussed in Takahashi et al. (2011) *Immunobiology* 216: 96). Briefly, the assay was designed to detect MBL-MASP complex-mediated activities by using plates that were coated with Mannan in carbonate binding buffer, pH 9.5. After rinsing the prepared mannan-coated plates with TBS, pH 7.4, supplemented with 10 mMCaCl$_2$ (TBS-CaCl$_2$), the wells were incubated with diluted MBL proteins with or without 1% MBL null serum as a MASP source. The wells were incubated at room temperature for 1 h and then rinsed thoroughly to wash off endogenous prothrombin and thrombin. Thrombin-like activity of MBL/MASP complex was measured by incubating the wells with a rhodamine 110 based thrombin substrate (tosyl Gly-Phe-Arg-amide, R22124, Invitrogen).

The findings presented herein indicate that no C4 deposition on mannan-coated plates from Fc MBL.81 activation of MBL null serum, but C4 was deposited from the WT MBL control (Data not shown). Further, no coagulation activation (thrombin-like activity) by the Fc MBL.81 fusion protein was determined (data not shown). Thus, unlike the WT MBL, the Fc MBL.81 does not activate complement or coagulation.

Example 4: Exemplary Methods for Production of MBL Magnetic Microbeads

Different microbe-targeting molecules (e.g., engineered MBL molecules) can be coupled to magnetic microbeads using different sizes or types of microbeads and surface chemistries. Examples of magnetic microbeads that can be used for the microbe-targeting magnetic microbeads include, but are not limited to, 1 micron MYONE™ T1 streptavidin microbeads (streptavidin coupled via tosyl groups) from Invitrogen (DYNABEADS®), 1 micron Tosylactivated microbeads from Invitrogen (DYNABEADS®), and 100 nm (128 nm average diameter) Streptavidin Plus microbeads (streptavidin coupled via carboxyl groups) from Ademtech.

For binding to the MYONE™ and Ademtech streptavidin microbeads, the MBL can be biotinylated (~4 biotins per molecule) using Thermo EZ-Link Sulfo-NHS-LC-Biotin, which reacts with primary amines (lysine residues). For single-site biotinylation, for example, using the method described in Witus et al. (2010) *JACS*. 132: 16812, the AKT-FcMBL.81 fusion protein is biotinylated only at the N-terminal amine for oriented binding to Streptavidin microbeads. Briefly, the PLP-mediated bioconjugation is a two-step process, in which an aldehyde is first added to the N-terminal amine in a PLP-mediated transamination reaction, followed by the addition of aminooxy-biotin to the aldehyde.

For the Tosylactivated microbeads, the MBL can be directly and covalently coupled to the surface of the microbeads by replacing the tosyl groups with its primary amines (lysine residues). Alternatively, aminooxy chemistries can be used to allow for oriented binding to the Tosylactivated DYNABEADS® microbeads without using biotin-streptavidin. This should lead to a more stable system and reduce non-specific binding to sticky streptavidin.

Example 5: Comparison of *C. albicans* Capture by Fc MBL.81-Coated Magnetic Microbeads with WT MBL-coated Magnetic Microbeads It was sought to determine whether the small ~90 kDa AKT-FcMBL dimers assembled on the surface of the DYNABEADS® microbeads with the CRD heads oriented away from the microbead substrate, and whether the AKT-FcMBL.81 conjugated to the magnetic microbeads (via biotin-streptavidin coupling) has the same avidity of binding as the large (~650 kDa) multimeric wild-type biotinylated MBL, which is randomly attached to the streptavidin microbead.

Briefly, the 650 kDa MBL from Sino Biological was biotinylated and then coupled to MYONE™ Streptavidin microbeads described in Example 4. The wide-type MBL coupled to such microbeads was designated as "Sino MBL microbeads" below. AKT-FcMBL.81 was also coupled to MYONE™ Streptavidin microbeads. Equivalent masses of the two proteins were coupled to equal numbers of microbeads.

To perform the MBL microbead capture experiments, 1500 *Candida* were incubated for 10 minutes with either 1 ul of the AKT FcMBL microbeads or 1 ul of the Sino MBL microbeads in TBS-Tween buffer supplemented with 5 mM Calcium. Microbeads with bound *Candida* were removed by capturing them on a magnet for 2 minutes. Then, about 1/10 of the captured material was plated on YEPD Agar plates and incubated at 30° C. for 1-2 days, followed by counting and comparing with the total counts from an equivalent dilution of the 1500 *Candida* starting culture.

Figure 6A:
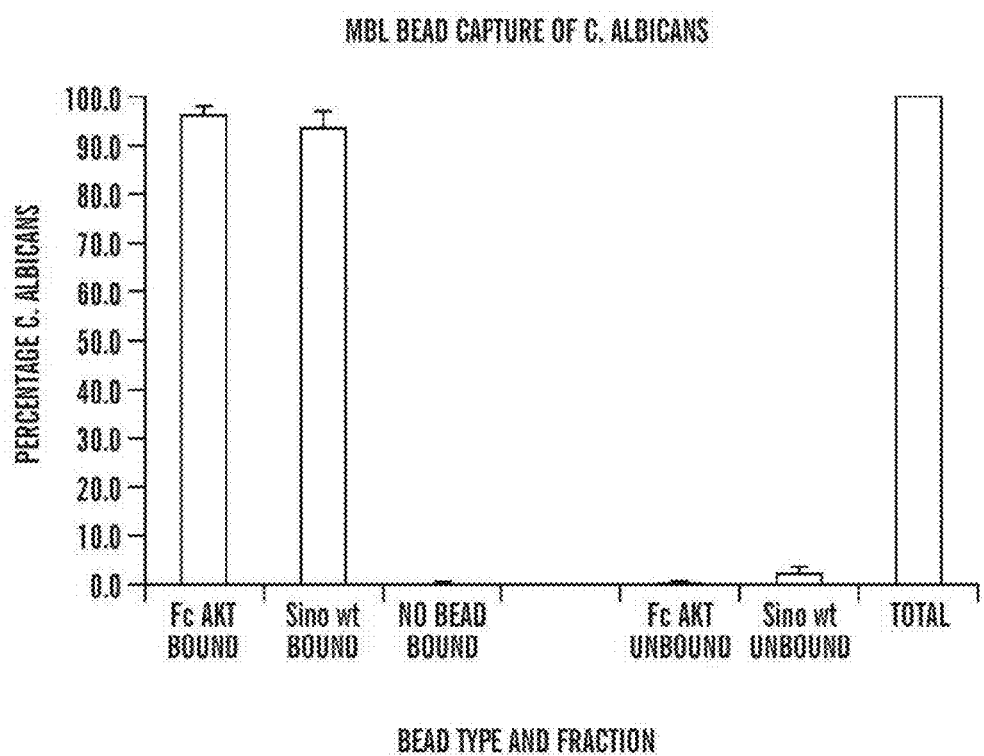
FIGS. 6A and 6B are bar graphs showing the results of capturing microbes, e.g., C. albicans, with one or more embodiments of the microbe-targeting substrates (e.g., AKT-FcMBL.81 conjugated to magnetic microbeads having a size of about 1 µm at various microbe densities.

FIG. 6A shows that greater than 95% of the *Candida* was bound to the AKT Fc MBL.81 microbeads, while greater than 92% was bound to the Sino MBL microbeads. There were no significant differences in the results using these two types of microbeads, indicating that the engineered MBL magnetic microbeads described herein showed at least comparable, or indeed better, binding than the WT MBL magnetic microbeads at the indicated pathogen density.

Next, it was sought to evaluate the performance of the engineered MBL magnetic microbeads at higher pathogen densities, e.g., above $10^8$ yeast cells. First, *C. albicans* was cultured overnight for 2 days, and then washed 2 times with PBS. The final pellet of *C. albicans* was resuspended in T-TBS w/ Calcium [TBS, 0.1% Tween-20, 5 mM CaCl$_2$] with a reading of OD600 around 0.5-0.7. The unlabeled MYONE™ T1 streptavidin microbeads were washed 2 times in PBS 0.1% BSA and diluted in original volume of PBS 0.1% BSA. To a 1.5 mL tube, about 1 mL of above *C. albicans* mixture was first added, followed by either 2 µl of unlabeled microbeads, 2 µl of FcMBL labeled microbeads, or 2 ul of WT MBL labeled microbeads. A *C. albicans* mixture was used as a no-bead control. All the mixtures were then mixed on a Hula mixer for about 10 minutes, followed by capturing the microbeads on a magnet for 2 minutes. The OD of unbound fraction (supernatant) was measured at 600 nm.

Alternatively, *Candida* were cultured until the OD600 reached a value of ~0.6. The yeast were incubated for 10 minutes with either 1 ul of the AKT FcMBL microbeads or 1 ul of the WT MBL microbeads in TBS-Tween buffer supplemented with 5 mM Calcium. The microbeads and captured yeast were removed by magnetic capture for 2 minutes. The OD (600 nm) of the remaining supernatant was measured to determine the unbound fraction.

Figure 6B:
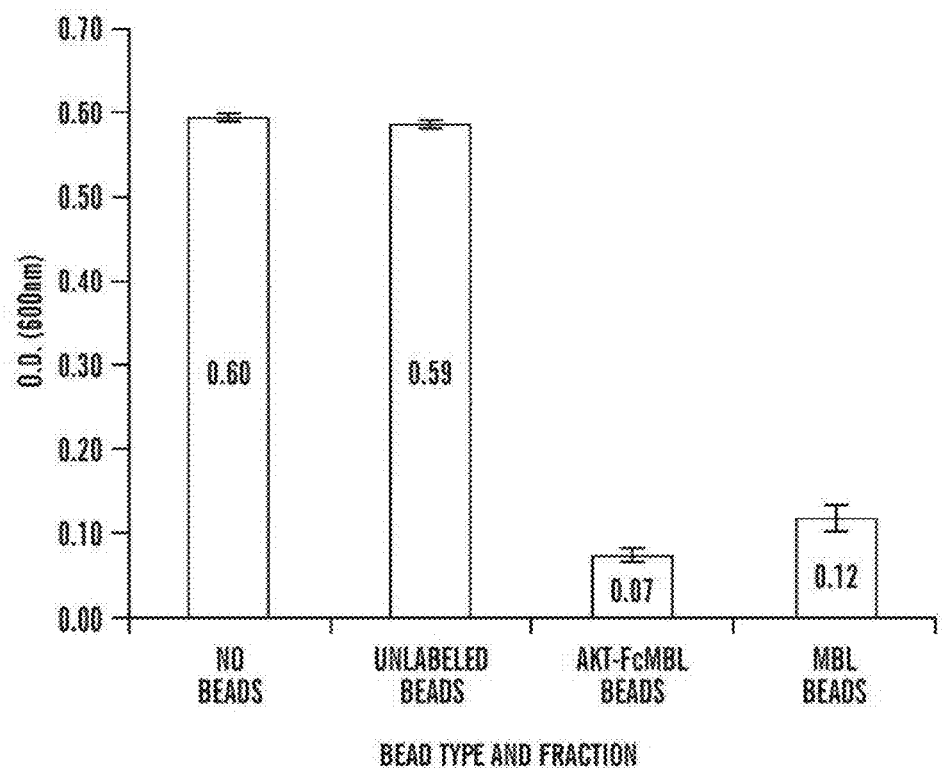
Figure 7:
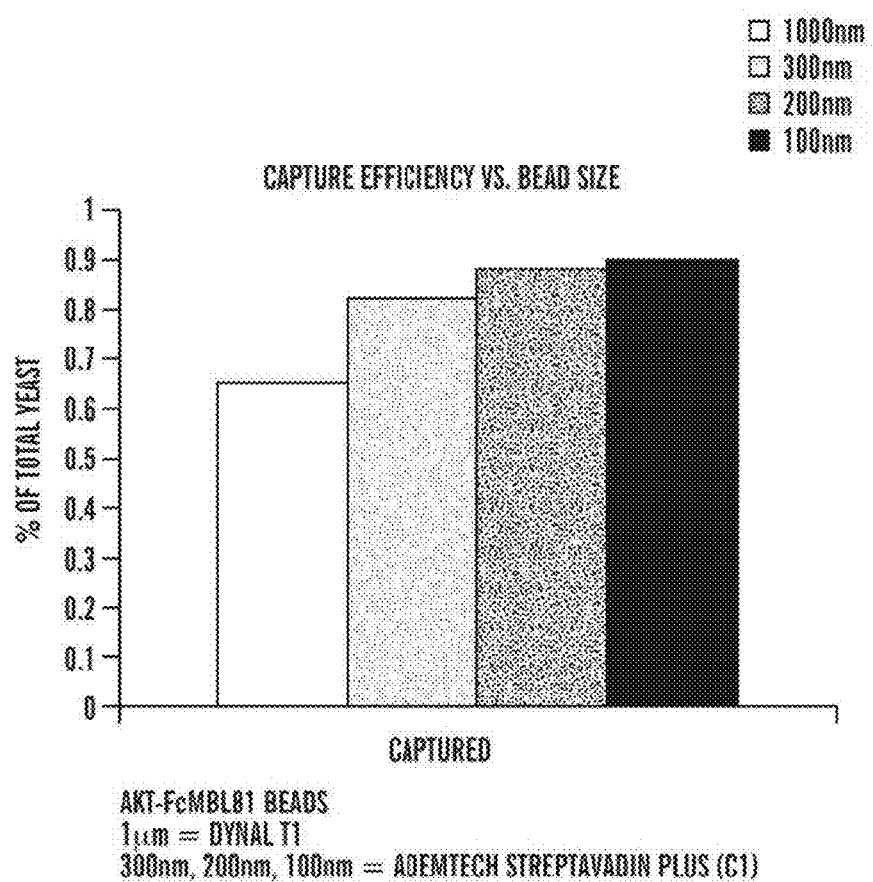
FIG. 7 shows the size effect of one or more embodiments of the microbe-targeting substrates (e.g., microbe-targeting magnetic microbeads such as AKT-FcMBL.81 magnetic microbeads, wherein the size of the microbeads were varied from about 100 nm to about 1000 nm diameter) on the efficiency of capturing microbes or pathogens, e.g., Candida.

The oriented AKT-FcMBL.81 microbeads demonstrated significantly better binding performance than (sino) WT MBL microbeads in pull-down binding assays using the MYONE™ Streptavidin 1 micron beads (FIG. 6B). Thus, the finding indicates that the AKT-FcMBL.81 microbeads have a higher binding capacity than WT MBL microbeads.

Example 6: Effect of Magnetic Microbead Sizes on Efficiency of Pathogen Capture

To determine the optimal microbead size for capturing both fungi and bacteria, the binding of *Candida* to microbeads (with a size ranging between ~1 µm and ~128 nm) coated with AKT Fc MBL was evaluated using the Pull-down assay described in Example 5. Surprisingly, the capture efficiency increases with decreasing sizes of magnetic microbeads. This reverses the hypothesis that the larger microbeads were better for fungi and that the ~100 nm were better for bacteria but would be sub-optimal for fungi. Thus, in some embodiments, the ~100 nm-microbeads (e.g., ~128 nm) can be used for both bacteria and fungal capture.

Example 7: Binding Performance of Engineered MBL Magnetic Microbeads in Saturated vs Log Phase Growth *Candida* Cultures As shown in Example 5, static cultures of *Candida* were bound strongly by the engineered MBL microbeads. Next, it was sought to determine if there was any difference in microbead performance using *Candida* in log-phase growth.

First, *C. albicans* 2-day old overnight culture and log-phase culture (OD600=~0.5) were washed 2 times with PBS. The final pellet of *C. albicans* was resuspended in T-TBS w/Calcium [TBS, 0.1% Tween-20, 5 mM $CaCl_2$] with a reading of OD600 around 0.3-0.5. The unlabeled MYONE™ T1 streptavidin microbeads were washed 2 times in PBS 0.1% BSA and diluted in original volume of PBS 0.1% BSA. To a 1.5 mL tube, about 1 mL of above *C. albicans* mixture was first added, followed by either 2 µl of unlabeled microbeads, 2 µl of FcMBL labeled microbeads, or 2 µl of WT MBL labeled microbeads. A *C. albicans* mixture was used as a no-bead control. All the mixtures were then mixed on a Hula mixer for about 10 minutes, followed by capturing the microbeads on a magnet for 2 minutes. The OD of unbound fraction (supernatant) was measured at 600 nm.

Figure 8:
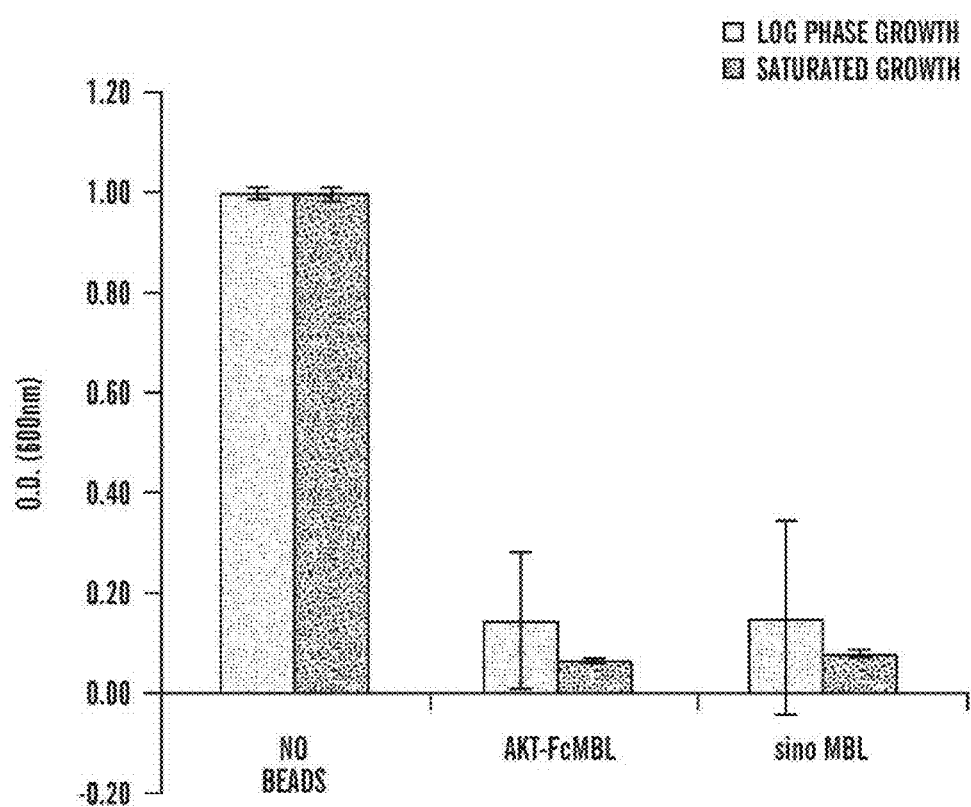
FIG. 8 shows the amount of unbound microbes remained in the microbe samples after treatment with different magnetic microbeads (including the engineered microbe-targeting magnetic microbeads) when the microbes (e.g., Candida) are growing in a log phase vs. in a saturated phase.
Figure 9:
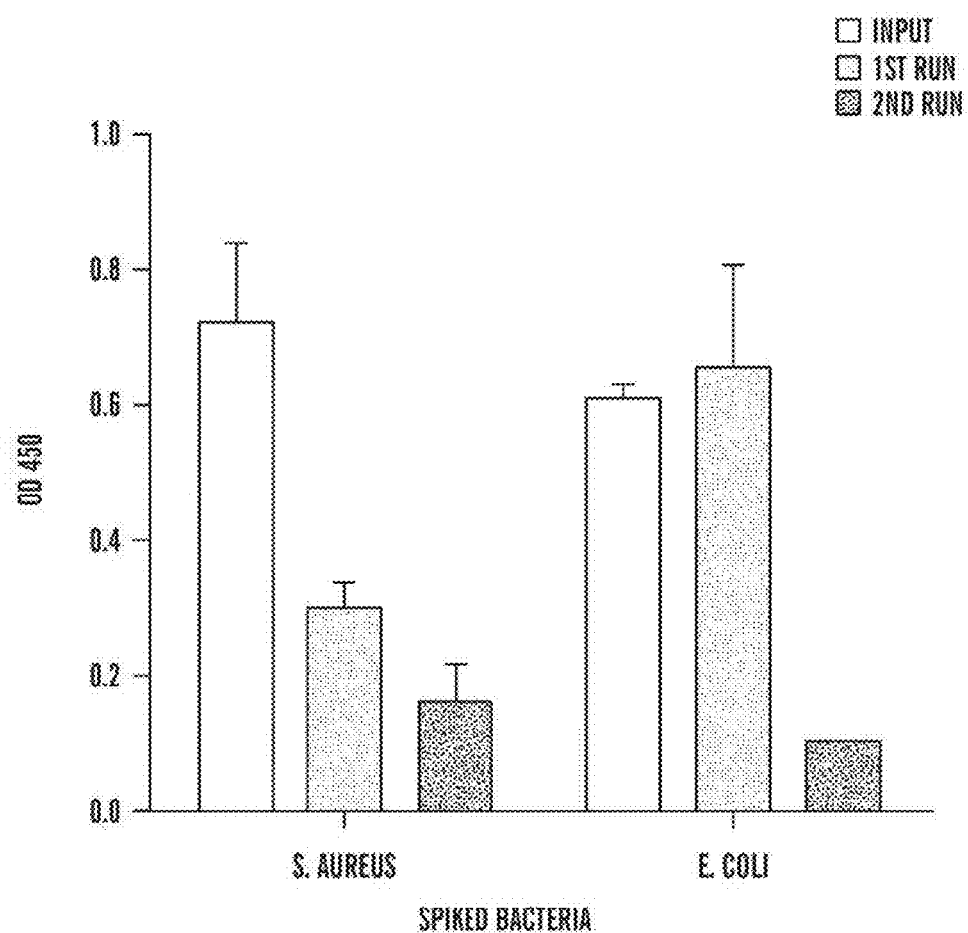
FIG. 9 shows the depletion of microbe/microbial matter from a blood sample from a human donor as measured using FcMBL ELISA. In the figure, "input" corresponds to undiluted EDTA donor blood spiked with S. aureus or E. coli, and supplemented with $Ca^{2+}$ (final $[Ca^{2+}]$=5 mM) and heparin (4 mg/ml), before addition of any FcMBL microbeads. "$1^{st}$ run" corresponds to the "input" blood sample incubated with 20 µl/mL MYONE™ FcMBL microbeads for microbe capture (with mixing on a HULAMIXER™ 20'), followed by FcMBL-based ELISA analysis. "$2^{nd}$ run" corresponds to the "input" blood sample incubated with 20 µl/ml MYONE™ FcMBL microbeads for microbe capture (with mixing on a shaker 10'), followed by FcMBL-based ELISA analysis.

FIG. 8 indicates that there may be a difference in AKT-FcMBL and WT MBL capacity to pull down *C. albicans* depending on the growth state of the yeast, but the variance in the log phase growth is relatively noisy. One of skill in the art can determine the pathogen capture efficiency of different embodiments of engineered microbe-targeting magnetic microbeads described herein with varying pathogen densities, e.g., using the methods described herein.

Example 8: Evaluation of the Engineered MBL Magnetic Microbead Performance in Human Blood Samples Blood samples containing bacteria and bacterial debris can be efficiently cleansed/captured using engineered MBL magnetic microbeads. The amount of bacteria and bacterial debris present in blood can be reliably determined using the FcMBL ELISA (see FIG. 10, Example 9). The blood samples spiked with either *E. coli* or *S. aureus* were complemented with 5 mM calcium (final concentration) and with 4 mg/ml heparin followed by binding/clearing with the engineered MBL magnetic microbeads. The performance of the engineered MBL magnetic microbeads in spike-in blood was assessed by FcMBL ELISA as described later.

The clearing of bacteria/bacterial fragments from a blood sample improved when iterative captures were performed, e.g., due to saturation of the FcMBL engineered beads in the first binding run.

Example 9: Colorimetric ELISA for Detecting Pathogen

Presented herein is a colorimetric ELISA (Enzyme linked Immunosorbent Assay) kit developed for detecting pathogens, which can integrate into the existing workflow and capabilities of a typical laboratory (e.g., a pathology laboratory). In some embodiments, the ELISA kit can comprise engineered microbe-targeting magnetic microbeads (e.g., Fc MBL or AKTFc MBL-coated magnetic microbeads), HRP-labeled Fc MBL or AKTFc MBL. Other secondary reagents (e.g. HRP (Horse Radish Peroxidase) labeled antibodies) can also be included in the ELISA kit described herein. The HRP labeled proteins & antibodies can diffuse into the clumps of pathogen and magnetic microbeads. The HRP enzyme can amplify the detection signal, thus improving the sensitivity of the assay. Such ELISA kit can be used with typical laboratory experiments that work with magnetic microbeads in a microtiter plate, e.g., KingFisher 96-well magnetic bead washer.

Figure 10:
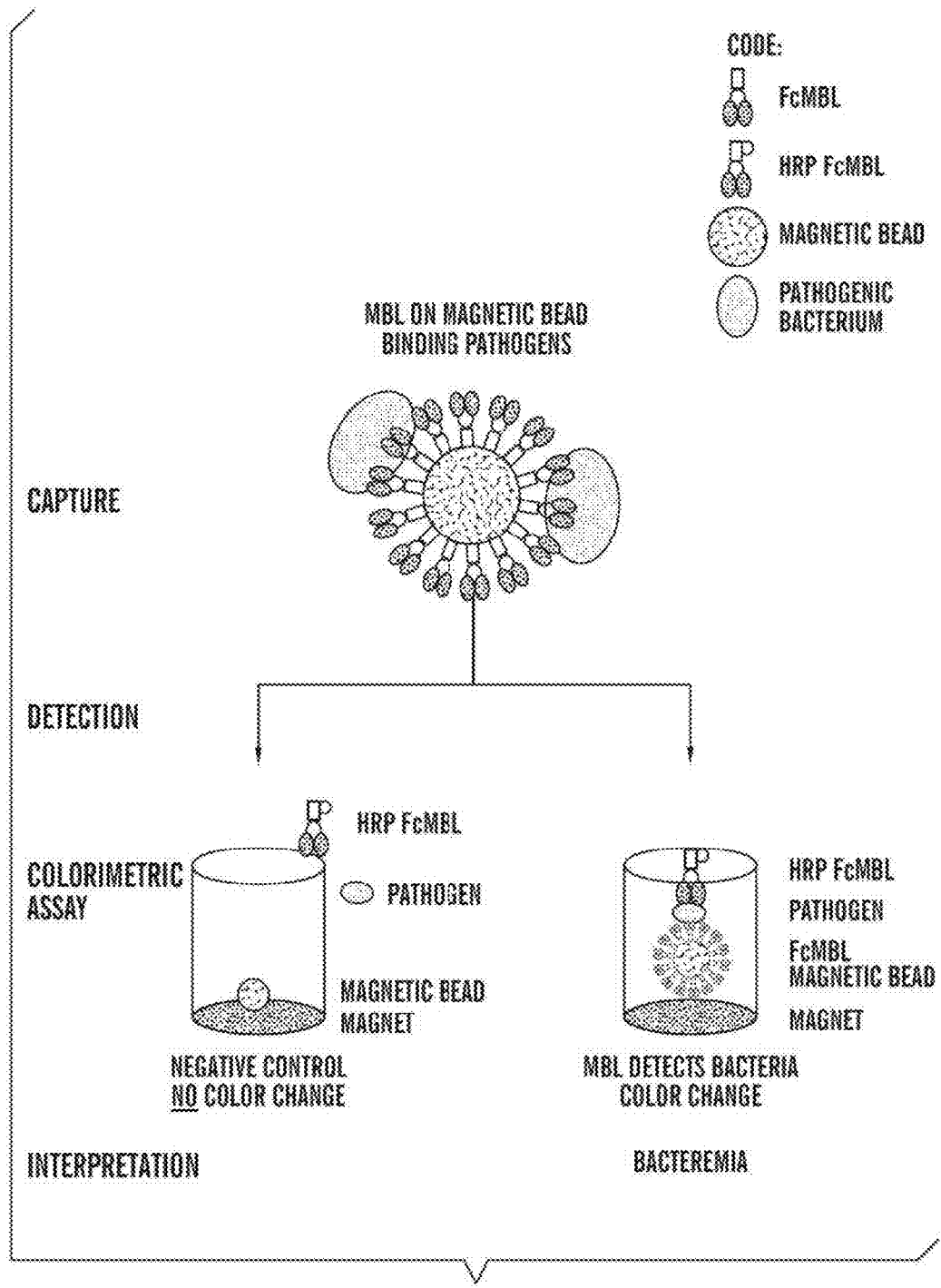
FIG. 10 is a schematic diagram of an exemplary ELISA assay comprising engineered microbe-targeting magnetic microbeads according to one or more embodiments. The ELISA assay can be used for any diagnostic applications, e.g., for sepsis tests.

In some embodiments of the ELISA assays described herein, the microbe-targeting magnetic microbeads, e.g., FcMBL magnetic microbeads, can capture microbes or pathogens in a sample, followed by detection with microbe-targeting HRP (e.g., FcMBL-HRP or Wheat Germ Agglutinin (WGA)-HRP). Such assays can be used to determine the presence of an unidentified pathogen. A schematic diagram showing one or more embodiments of the ELISA assays comprising microbe-targeting magnetic microbeads is shown in FIG. 10.

In other embodiments of the ELISA assays described herein, the microbe-targeting magnetic microbeads, e.g., Fc MBL magnetic microbeads, can capture microbes or pathogens in a sample, followed by detection with specific antibodies depending on various pathogen tests. For example, anti-gram positive or anti-gram negative antibodies can be used in a rapid Gram test, or specific anti-Salmonella antibodies can be used in a typhoid test.

The ELISA assays provided herein can be automated, e.g., by employing the existing capabilities of typical laboratory equipments, e.g., a 96-well assay system coupled with a KINGFISHER™ magnetic bead wash system.

An exemplary protocol for determining the limit of detection (LOD) of such ELISA assay is described below:

a. Capture a microbe solution (e.g., *E. coli* dilutions) with engineered microbe-targeting magnetic microbeads described herein (e.g., FcMBL.81 magnetic microbeads) for about 15-minute incubation b. Isolate the magnetic microbeads on a magnet for about 2 minutes, followed by four washes with a detergent, e.g., TBS-T 5 mM $Ca^{2+}$ c. Detect the bound microbes with a microbe-targeting HRP reagent, e.g., FcMBL.81 HRP, reagent (for about 20 mins) in a blocking buffer, e.g., a 6% BSA block d. Perform a detection assay with addition of a HRP substrate, e.g., TMB (3,3',5,5'-tetramethylbenzidine) chromogen (incubation for about 5 min).

e. Stop the reaction with an acid, e.g., 4 N $H_2SO_4$
f. Measure O.D. at a certain wavelength depending on the enzyme substrate used (e.g., 450 nm for TMB chromogen)

Figure 12:
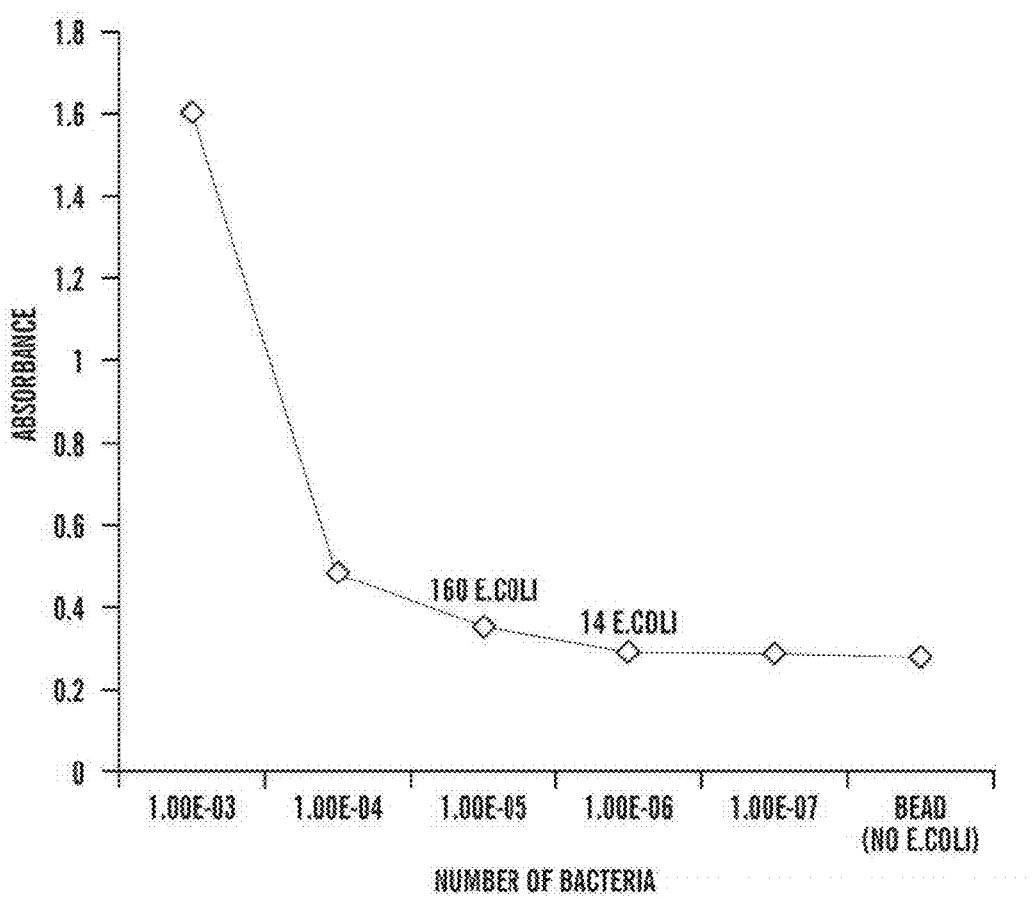
FIG. 12 is a graph showing bacterial detection sensitivity of one or more embodiments of the FcMBL-based ELISA assay. Serial dilutions of E. coli were spiked into a buffer, captured by AKT-FcMBL magnetic microbeads (about 128 nm in size) and detected by an ELISA method using HRP-labeled FcMBL. In some embodiments, the limit of detection (LOD) of the FcMBL-based ELISA colorimetric assay is about or below 160 E. coli bacteria.

An exemplary graph of O.D. against varying concentrations of microbes or pathogens can be plotted for data analysis (FIG. 12). It should be clear that any other ELISA protocols established in the art can be adapted herein for use with the engineered microbe-targeting magnetic microbeads.

Example 10: Exemplary Rapid Pathogen Detection Methods Based on Colorimetic Assays Sepsis or "blood poisoning" by bacterial and fungal infection produces 18 million cases per year worldwide resulting in over 6 million deaths. A particularly vulnerable group is the newborn population in developing countries. Of the approximately 3.6 million newborn deaths each year, worldwide infections are responsible for 30% of these deaths, of which 15% are attributed to sepsis. Of the 3.6 million deaths, 98% of these are present in developing countries where the medical facilities are limited.

When physicians suspect that a patient is suffering from bacteremia they must act quickly: since bacteria can divide very rapidly, every hour lost before a correct treatment is administered can make a crucial difference in patient outcome (Garnacho-Montero et al 2006 *Critical Care* 10:R111). Speed is especially important for neonates as up to 50% of neonatal deaths occur in the first 24 hours. Consequently, physicians must quickly establish whether the patient indeed has bacteremia, and if so, what antibiotics to prescribe. The current gold standard for identification of infection is blood culture, which generally takes days and fails to identify a causative agent in more than 50% of cases. Therefore, there is a strong need, e.g., in developing countries, for a point-of-care diagnostic assay/device that is portable, requires no electricity, is easily read, is low cost, and/or is rapid.

Further, in studies from developing countries the majority of blood stream infections have been caused by *Staphylococci, Klebsiella* and *Acinetobacter*, which together comprise more than 85% of the pathogens isolated. In studies in Boston, the major pathogens are *Staphylococci, Enterococci, Klebsiella, Escherichia* and *Pseudomonas*, which make up more than 85% of the pathogens isolated. Therefore, there is a need for a rapid test that can detect and quantify bacteria or fungi infection of body fluids that are normally sterile and free of pathogens. In addition, it would be advantageous to be able to classify the microbe or pathogen into Gram-positive or Gram-negative microbe in order to choose the correct broad spectrum treatment option speedily.

Pathogen Extraction and Concentration:

As presented herein, magnetic microbeads that are coated with engineered mannose binding lectin (MBL) can be used for extraction and/or concentration of pathogens or microbes from blood. MBL is an innate-immune-system protein that can adhere to most blood-borne pathogens, thus enabling the magnetic microbeads suitably selective for extracting and purifying bacterial and fungal pathogens from large samples of body fluids, e.g., blood, CSF, synovial fluid and urine. Some embodiments of the engineered microbe-targeting molecules, e.g., engineered MBL (Fc linked to mannose binding region of MBL) can be 1000-fold lower in cost of production and do not activate complement/coagulation. Other alternatives to MBL include, but are not limited to, antibodies, and other lectins. In some embodiments, engineered MBL-coated magnetic microbeads can be used for capturing one or more microbes and/or pathogens in a test sample.

Exemplary Colorimetric ELISA Assay for Detecting and Quantifying Infection:

FIG. 10 shows an exemplary scheme of an ELISA method for detection and quantification of blood borne pathogens using one or more embodiments of the engineered microbe-targeting molecules or substrates (e.g., FcMBL-coated magnetic microbeads). A patient sample is mixed with magnetic microbeads coated with a suitable capture agent, e.g., 1 μm or 128 nm magnetic microbeads coated with FcMBL molecules (including AKT-FcMBL molecules), and a suitable buffer, e.g., Tris buffered saline with 5 mM calcium ions and Tween 20 detergent. In some embodiments, a suitable buffer can be Tris-buffered saline containing Tween 20, but without 5 mM calcium ions. Following a suitable incubation and/or mixing period, e.g., about 10 minutes or about 20 minutes on a mixer (e.g., a HULAMIXER™ from Invitrogen), the FcMBL-coated magnetic microbeads with captured pathogens can be collected using a magnetic stand (Invitrogen) and washed in, e.g., Tris buffered saline with 5 mM calcium with or without Tween 20 detergent, to remove blood products. The captured pathogens can be detected and quantified by any methods known in the art and/or described herein, e.g., using chromogenic reagents such as Horseradish Peroxidase (HRP)-labeled FcMBL (which can detect the infection caused by any microbes, e.g., bacterial or fungal microbes) or specific antibodies against Gram-Positive bacteria, e.g., anti-LTA antibodies, or against Gram-Negative bacteria, e.g. anti-LPS antibodies, or against *Candida* fungi, e.g., anti-*Candida* antibodies.

Figure 20A:
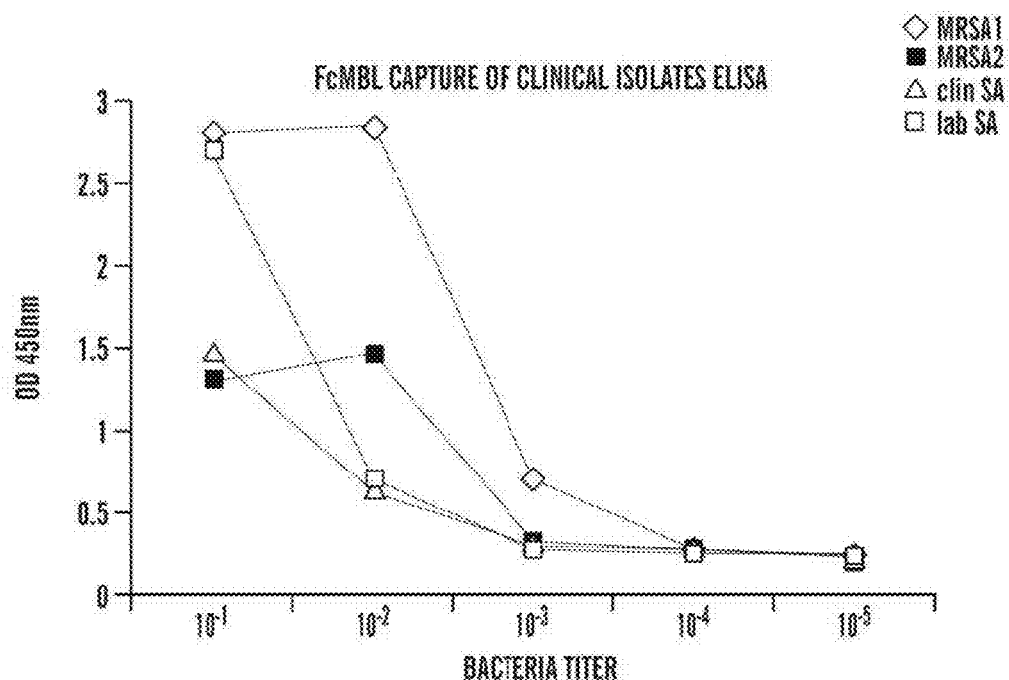
FIGS. 20A and 20B are line graphs showing capture efficiency of engineered microbe-targeting or microbe-binding molecules (e.g., FcMBL) in clinical isolates of different microbial species.
Figure 20B:
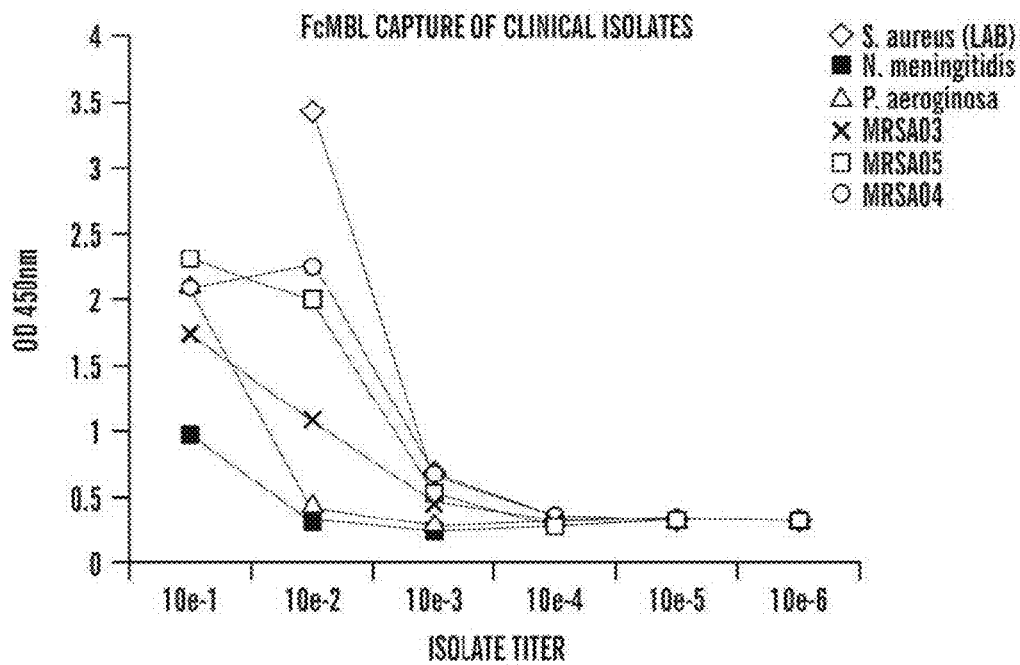

The level of infection or the amount of microbes captured on FcMBL-coated magnetic microbeads can be quantified, for example, by comparing the test samples against standard curves of reference (e.g., laboratory strains of bacteria or fungi) run in parallel. For example, FIGS. 20A-20B show data for capture efficiency of clinical isolates assessed by FcMBL ELISA as described herein. Briefly, about 10 μg FcMBL magnetic microbeads (~1 μM) was added to about 10 μL of bacteria in the presence of calcium ions (e.g., 1 mL TBST-$Ca^{2+}$). The capture was agitated at about 900 rpm for about 10 mins at about 25° C., and ELISA was performed on, e.g., THERMO-LAB SYSTEM KINGFISHER™ Magnetic Particle Processor, using HRP-labeled FcMBL reagents.

Figure 11:
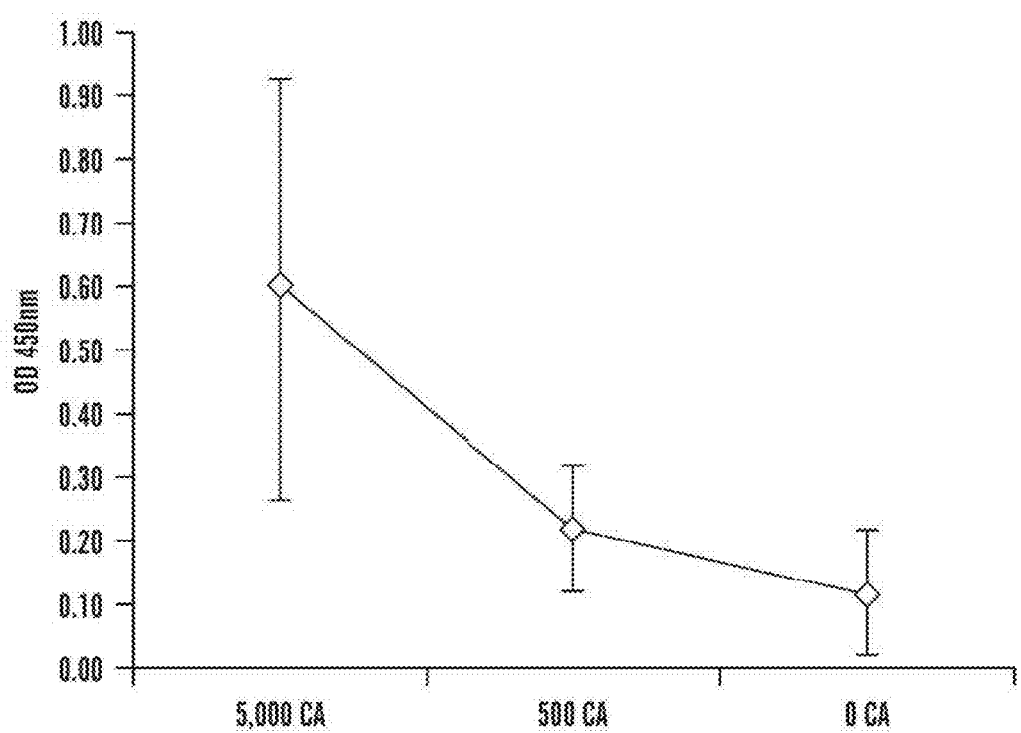
FIG. 11 is a graph showing results of detecting C. albicans in blood. Serial dilutions of C. albicans were spiked into blood, captured by AKT-FcMBL magnetic microbeads (1 µm) and detected by an ELISA method using HRP-labeled FcMBL.

An example of FcMBL-based ELISA detecting *C. albicans* captured from blood is shown in FIG. 11, which shows that less than 500 *Candida* fungi cells in blood can be detected using an embodiment of the FcMBL-based ELISA.

Figure 21A:
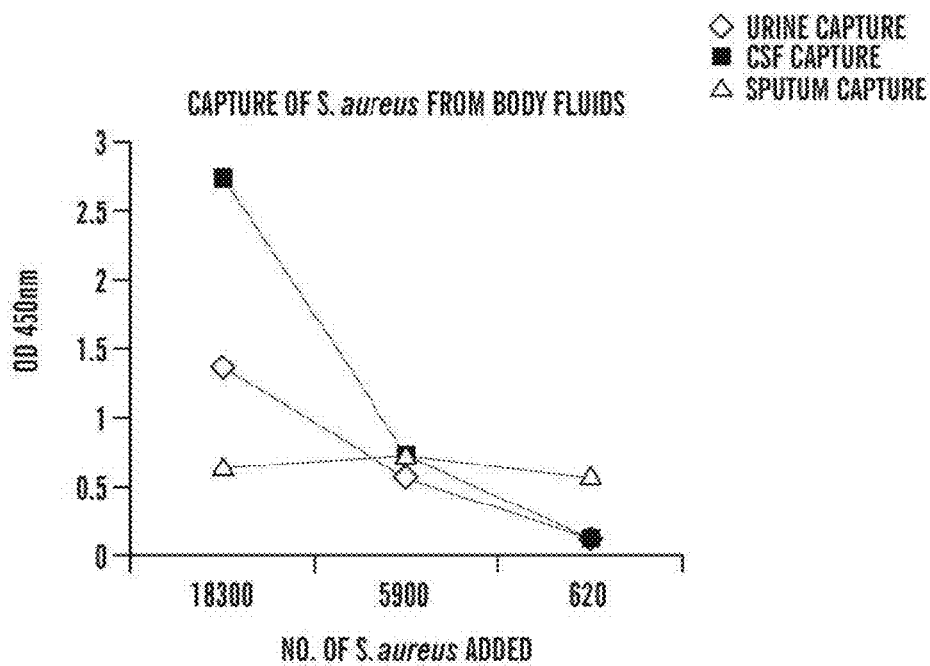
FIGS. 21A-21B are line graphs showing capture efficiency of engineered microbe-targeting or microbe-binding molecules (e.g., FcMBL) in clinical isolates obtained from different types of fluids.
Figure 21B:
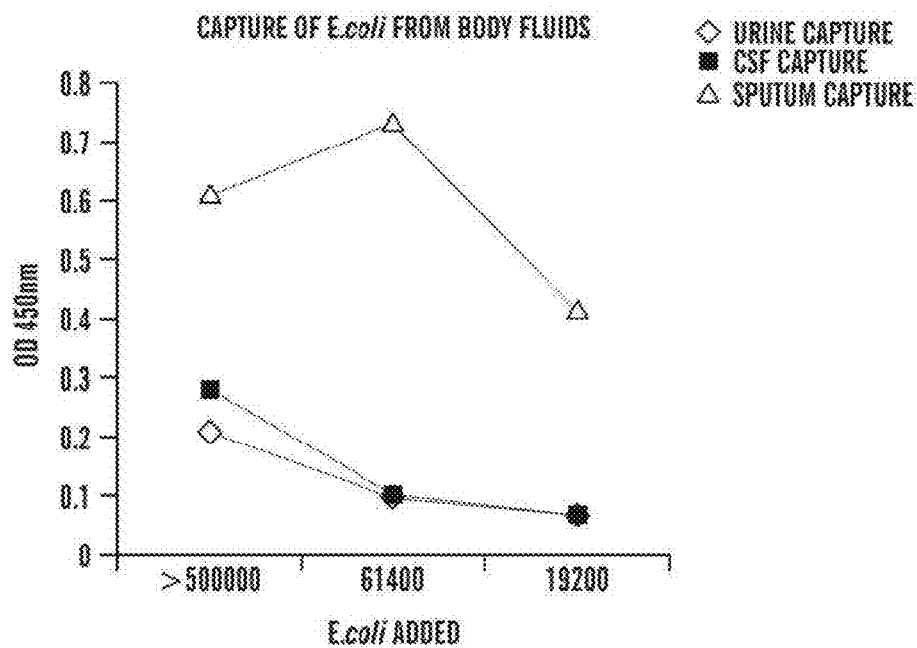

The sensitivity of the MBL sandwich ELISA for detecting *E. coli* in suitable buffers was evaluated and shown in FIG. 12. The limit of detection (LOD) for *E. coli* in one embodiment of the FcMBL-based ELISA assay was about or below 160 bacteria. Additionally, the capture efficiency of clinical isolates from different body fluids was assessed by FcMBL ELISA described herein (FIG. 21A). Briefly, about 10 μg FcMBL magnetic microbeads (~1 μM) was added to about 10 μL of bacteria spiked in a ~1 mL to ~2 mL mixture of fluid sample (e.g., blood, urine, CSF, sputum) and TBST-$Ca^{2+}$ at a 1:1 volume ratio. The capture was agitated at about 900 rpm for about 20 mins at about 25° C., and ELISA was performed on, e.g., THERMO-LAB SYSTEM KING-FISHER™ Magnetic Particle Processor, using HRP-labeled FcMBL reagents. FIG. 21A shows that laboratory strains and clinical methicillin-resistant *S. aureus* (MRSA) can be isolated from blood, while *N. meningitidis* appears to produce high background signal using one embodiment of the FcMBL ELISA described herein. FIGS. 21A-21B shows that *S. aureus* and *E. coli* spiked into different body fluids such as blood, CSF, and urine can be detected using one or more embodiments of the FcMBL ELISA described herein, while sputum appears to produce high background signal using one embodiment of the FcMBL ELISA described herein.

In some embodiments, the ELISA assay can comprise capture of a microbe or pathogen from blood with one or more embodiments of the FcMBL-coated magnetic microbeads (128 nm or 1 micron sized magnetic microbeads coated with one or more embodiments of FcMBL proteins) and detection either with labeled-FcMBL (e.g., HRP-labeled FcMBL) for non-specific detection of bacteria, or with labeled antibodies for specific detection of, e.g., but not limited to, Gram-positive bacteria, Gram-negative bacteria, or fungi.

In one embodiment, the FcMBL-HRP or FcMBL-AP construct was generated using LIGHTNING-LINK™ HRP Conjugation Kit or LIGHTNING-LINK™ AP Conjugation Kit (Innova Biosciences), which is a lyophilized HRP or AP mixture for directional coupling to antibodies and other proteins. The creation of FcMBL-HRP or FcMBL-AP can use any other commercially-available kits as any labeling procedures for antibodies well known in the art can be used.

Exemplary Manual Dipstick or ELISA Test:

Two exemplary forms of a rapid diagnostic assay, e.g., for a point of care diagnostic, were developed and assessed. These rapid diagnostic assays can be used in developing countries as they are portable, easily read, low cost, rapid, and require no electricity. The exemplary schematics of the two diagnostic assays are shown in FIGS. 13-14. FIG. 13 shows an exemplary schematic of a manual dipstick assay for pathogen detection, and FIG. 14 shows an exemplary schematic of a manual ELISA test for pathogen detection.

In one embodiment, the dipstick test requires capture of the pathogen to a membrane upon which the colorimetric readout is determined from. The attachment of the FcMBL to the membrane can be performed with multiple approaches, for example, by direct cross-linking FcMBL to the membrane, cross-linking FcMBL to the membrane via a nucleic acid matrix (e.g., DNA matrix) for orientation and concentration (in a manner similar to FcMBL-coated magnetic microbeads), using FcMBL-coated magnetic microbeads in combination with a focused magnetic field gradient applied to the membrane, or any other art-recognized methods.

Figure 15:
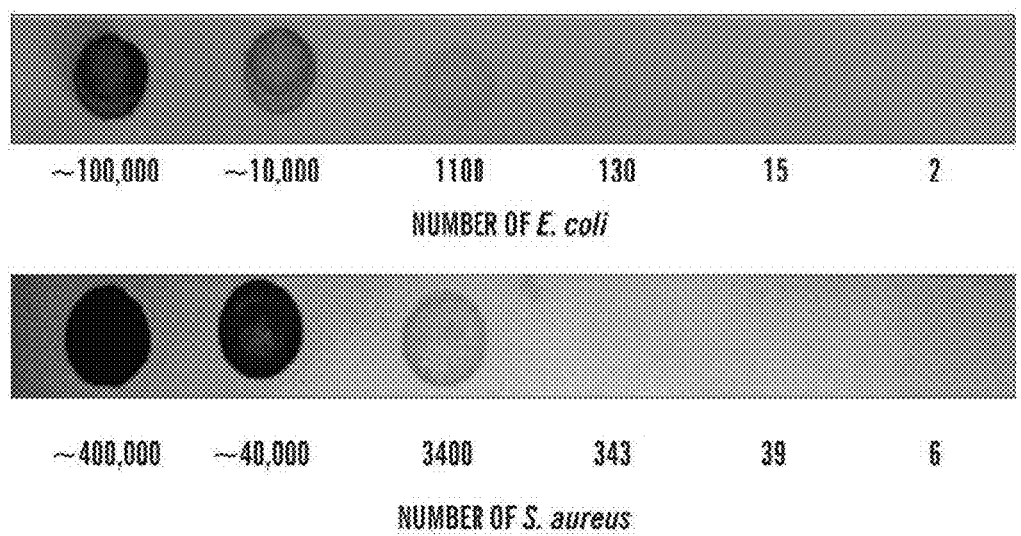
FIG. 15 is an image showing direct detection of bacteria on a membrane by AP-labeled FcMBL. Serial dilutions of E. coli and S. aureus ($10^{-1}$ to $10^{-6}$) were spotted directly onto a Biodyne membrane, blocked for about 30 mins in 1% casein, washed twice in TBST containing $Ca^{2+}$ (5 mM), incubated with AP-labeled FcMBL (1:10,000 dilution) in 3% BSA 1×TBST containing $Ca^{2+}$ (for about 20 min), washed twice in TBST containing $Ca^{2+}$ (5 mM) and once in TBS containing $Ca^{2+}$ (5 mM), and reacted with BCIP/NBT for about 20 mins to develop a colorimetric readout. In this example, maximum dilution allowed for detection of both species was $10^{-4}$ after 30 min development (corresponding to detection of 130 E. coli and 343 S. aureus cells).

FIG. 15 shows results for a general dot blot detection of bacteria on a membrane. Serial dilutions of either *E. coli* or *S. aureus* were attached directly to a Biodyne membrane, which was then blocked in 1% casein, incubated for 20 min with alkaline phosphatase (AP)-labeled FcMBL, washed, and detected colorimetrically with a BCIP/NBT reagent. The sensitivity of the assay was about 200 cfu/ml to about 300 cfu/ml.

Figure 16:
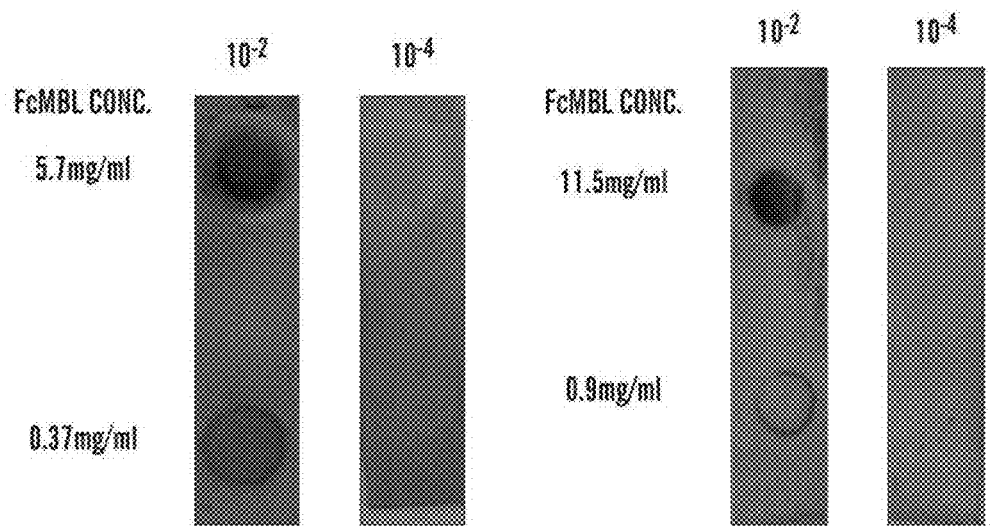
FIG. 16 is an image showing capture and detection of S. aureus by dot blot using a membrane coupled with FcMBL. Dilutions of S. aureus ($10^{-2}$ and $10^{-4}$) were captured by FcMBL immobilized on a Biodyne membrane. For example, 5 μL of two indicated concentrations of FcMBL were spotted onto a Biodyne membrane, allowed to dry, blocked in 1% casein, and washed twice in TBST containing $Ca^{2+}$ (5 mM). Each FcMBL concentration was assessed for capture (~10 min) of serial dilutions of *S. aureus*, washed, and detected with 1:10,000 dilution of AP-labeled FcMBL in 3% BSA 1×TBST containing $Ca^{2+}$ (~20 min). Excess AP-labeled FcMBL was removed by washes (e.g., washing three times with TBST containing $Ca^{2+}$ (5 mM) and once with TBS containing $Ca^{2+}$ (5 mM)). Colorimetric detection was developed with BCIP/NBT for ~20 min.

FIG. 16 shows results for a dot blot detection of bacteria on a membrane coupled with FcMBL. In one embodiment, a membrane (e.g., Biodyne membrane) is attached with FcMBL molecules at a certain concentration. Bacteria (e.g., *S. aureus*) was added to the FcMBL-Biodyne membranes, which were then blocked in 1% casein, incubated for 20 min with alkaline phosphatase (AP)-labeled FcMBL, washed, and detected colorimetrically with a BCIP/NBT reagent. As shown in FIG. 16, the capture and detection of the bacteria is FcMBL concentration dependent. As described earlier, in some embodiments, FcMBL can be directly immobilized on a membrane. In other embodiments, FcMBL can be coupled to a membrane by a nucleic acid matrix (e.g., DNA matrix). In alternative embodiments, FcMBL can be couple to any surface other than a membrane, e.g., a paper substrate, for the dipstick assay.

Any existing ELISA protocol can be used in combination with the engineered microbe-targeting molecules or substrates as described herein for microbe detection. Below shows an example of a protocol for an ELISA-based microbe detection method carried out in a blood collection tube (e.g., a modified blood VACUTAINER® optionally containing one or more anti-coagulants such as citrate, phosphate, and dextrose (CPD) as shown in FIG. 14. The numeric steps below correspond to the numeric values indicated in FIG. 14.

1. Add a test sample, e.g., blood, to one or more embodiments of the microbe-targeting molecules or substrates (e.g., FcMBL-coated magnetic microbeads). For example, about 10 µg of FcMBL magnetic microbeads (e.g., at a concentration of about 2 mg/mL) can be added to a test sample.
2. Resuspend the microbe-targeting molecules substrates (e.g., FcMBL-coated magnetic microbeads) in the test sample, e.g., blood.
3. Add TBST (e.g., Tris buffered saline (TB S) with 0.05% Tween 80) containing $Ca^{2+}$ at ~5 mM (e.g., ~5 mM $CaCl_2$)
4. Incubate the mixture (optionally with gentle agitation) for about 10 mins to capture microbes
5. Collect the microbe-targeting molecules or substrates. For example, if the microbe-targeting molecules or substrates are FcMBL-coated magnetic microbeads, the microbeads can be collected with a magnet, e.g., placing a magnet around the tube.
6. Add TBST wash until a desired level (e.g., a wash fill line) Collect the FcMBL-coated magnetic microbeads—remove wash—repeat steps 5 and 6 at least two times
8. Add resuspended FcMBL-HRP (e.g., resuspending FcMBL-HRP lyophilized in about 6% BSA buffer in ddH2O) or other desired detection agent to the collected FcMBL-coated magnetic microbeads and incubate for about 10 mins
9. Collect the FcMBL-coated magnetic microbeads
10. Add TBST wash to a desired level (e.g., a wash fill line)
11. Collect the FcMBL-coated magnetic microbeads—remove wash—repeat steps 9 and 10
12. Add a substrate suitable for the detection agent (e.g., a chromogenic substrate such as TMB for HRP-based detection) and allow the reaction to develop for about 10 mins
13. Collect the FcMBL-coated magnetic microbeads, e.g., with a magnet.
14. Transfer the reaction solution to a readout tube and compare the color of the reaction solution to a reference (e.g., a reference strip).

The reagents and steps as shown above are illustrated as an example and are not meant to be limiting. Thus, appropriate modifications to reagents and/or steps by a person having ordinary skill in the art are also within the scope described herein. For example, different wash buffers, detection agents, and/or chromogenic substrates can be used. The number of wash steps can be increased or decreased, depending on the volume of wash buffer used and/or incubation time. Some reagents (e.g., FcMBL magnetic microbeads) for the assay can be supplied as lyophilized and/or in sterile bottles. The readout of the assay can be based upon comparison to a reference (e.g., a laminated color strip). In one embodiment, the total assay time of the assay is approximately 1 hour.

In contrast to blood culture, some embodiments of the pathogen detection assays or diagnostic assays described herein can detect bacteria and/or fungi in short times, e.g., as little as 1 hour. Further, additional advantages of some embodiments of the diagnostic assays (e.g., point-of-care dipstick and ELISA assays as shown in FIGS. 13-14) can include, e.g., Portable: half of neonatal deaths occur in home childbirth settings;
No electricity needed: manual operation;
Easy to read: colorimetric readout;
Low cost: no expensive instrument needed to read result;
Easy disposal: incinerate biohazard waste; or
any combinations thereof.

Accordingly, some embodiments of the pathogen detection assays or diagnostic assays described herein can enhance clinically-based diagnosis in regions without lab access, thus reducing inappropriate use of antibiotics. Further, some aspects described herein can reduce patient loss to follow-up by enabling the diagnostic test and treatment administration/prescription in same encounter. Additionally, some aspects described herein can reduce exposure of neonates to clinical setting.

Example 11: Regeneration of Engineered MBL Molecules (FcMBL) Using Sodium Phosphate Buffers and/or Acidic Buffers FcMBL described herein can be used to capture a wide range of microbes from environmental and biological samples. In situations where continuous cleaning or monitoring is required it would be useful to be able to use the same substrate (e.g., microbeads) throughout the process. This would require releasing captured microbes so the substrate (e.g., microbeads) could be reused. However, releasing captured microbes from the FcMBL microbeads can be difficult. While the initial binding of FcMBL microbeads to microbes is calcium-dependent, after the microbes are bound, transferring the microbe/microbead mixture to a solution lacking calcium generally does not lead to the release of the captured microbe—presumably because of the high avidity between the microbeads and microbes makes FcMBLs affinity for calcium too high to overcome by simple dilution in a reasonable amount of time. Therefore, mechanisms for actively removing the calcium from the FcMBL-microbe interaction were evaluated herein.

The most common strategy used in the art for removing calcium is the use of calcium chelating agents (e.g. EDTA or EGTA). Unfortunately, chelating agents such as EDTA and EGTA can be harsh or dangerous to biological samples, so additional mechanisms to actively remove calcium were investigated. Two alternative strategies that were evaluated includes (i) the use of low pH buffers (acids) that can protonate the negatively charged carboxyl groups (glutamate side chains) on FcMBL that are responsible for binding calcium (protonating these side chains can remove their negative charge, which can remove their ability to bind to positively charged calcium ions) and (ii) the use of buffers in that calcium is not soluble such that the introduction of such buffers can lead to the precipitation of the calcium ions, making them unavailable for the necessary interaction with the FcMBL-microbe interface. Specifically, 0.2M glycine buffer at pH 2.8 and 0.1M Sodium Phosphate Buffer at pH 6.0 (the solubility of calcium in phosphate buffer is extremely low) have been used and compared to 0.1M EDTA in Tris Buffered Salt. These conditions have been assessed on FcMBL microbeads bound to the bacteria, E. coli, using an FcMBL-based ELISA.

Figure 18A:
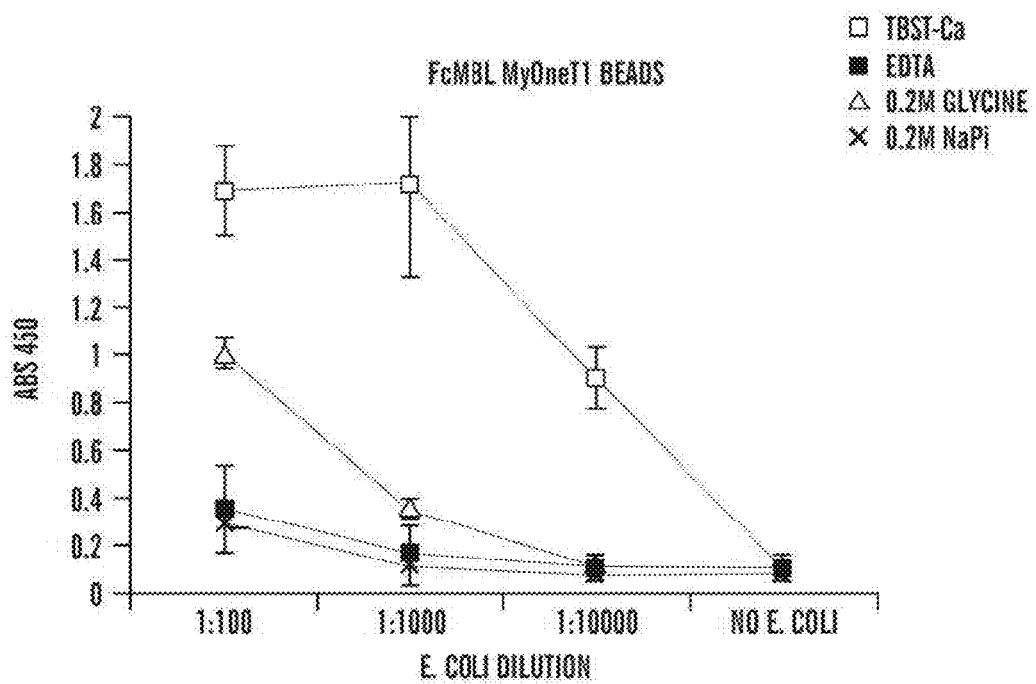
FIGS. 18A and 18B are line graphs showing ELISA of *E. coli* on two different FcMBL microbead formats.
Figure 18B:
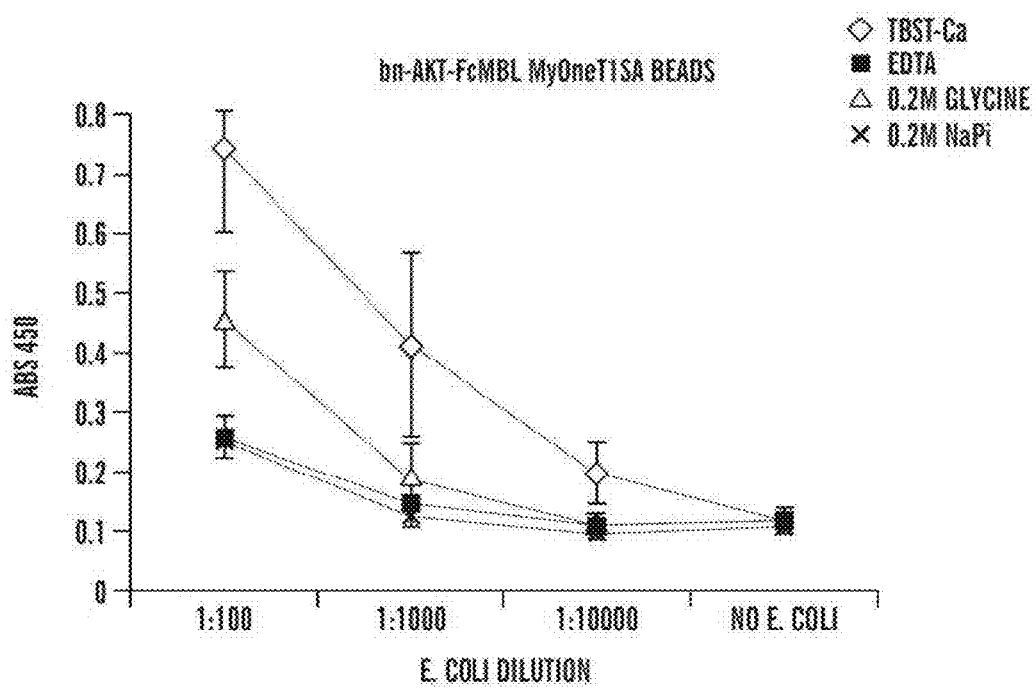

Three different dilutions of an E. coli overnight culture were captured on FcMBL microbeads, washed with one of four elution buffers including a TBST control, EDTA, 0.2M glycine (pH 2.8) and 0.1M sodium phosphate (pH 6.0), and then run through a standard ELISA protocol. A decrease in signal corresponds to less E. coli bound to the FcMBL microbeads prior to the ELISA assau. As seen in FIGS. 18A and 18B, in addition to EDTA, both the low pH buffer (e.g., 0.2M glycine, pH 2.8) and the sodium phosphate buffer were able to release bound E. coli from the FcMBL microbeads. Amount of released microbe can be increased by increasing the incubation time or by combining the phosphate and acid conditions (i.e. phosphate buffer at a low pH).

Example 12: Use of the FcMBL as an Antibiotic or Antiseptic

S. aureus is the major cause of sepsis in wounds, burns and orthopedic surgery. To determine whether the binding of S. aureus to FcMBL microbeads reduced the number and growth of bacterial colonies on agar plate culture, two equal aliquots of a $10^{-4}$ dilution of S. aureus were plated onto identical LB agar plates and cultured overnight. One of the aliquots was mixed with FcMBL microbeads, and the mixture of microbeads and pathogens was plated. The control aliquot was plated without any FcMBL microbeads.

Figure 19:
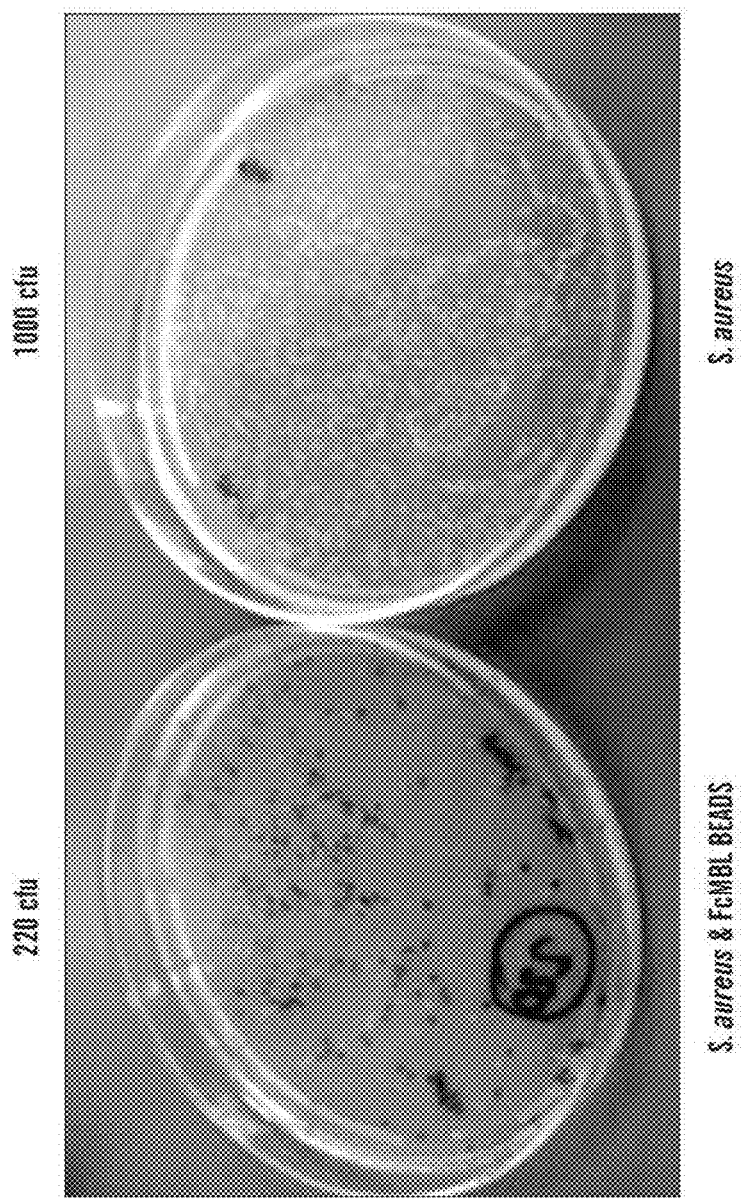
FIG. 19 is an image showing plating out of equal titers of *S. aureus* either mixed with FcMBL microbeads or control without FcMBL microbeads.

As shown in FIG. 19, the plate with the S. aureus mixed with FcMBL microbeads grew 220 colonies whereas the control grew more than 1000 colonies.

Binding of the FcMBL microbeads with S. aureus reduces the number of colonies on overnight plating ~5-fold, indicating that a wound dressing attached with FcMBL microbeads can enable the binding of S. aureus to FcMBL microbeads, thus reducing and localizing pathogen load. As such, the movement of the S. aureus deeper into the wound can be reduced. Localized pathogens attached to dressings can be easily removed during regular dressing changes. In other embodiments, the FcMBL localization treatment can be combined with other wound dressing protocols e.g., but not limited to, silver nanoparticles, negative pressure treatment, vacuum-assisted debridement. In alternative embodiments, FcMBL microbeads can be used to debride a fluid.

In some embodiments, FcMBL molecules are assessed as a therapeutic in an animal model of sepsis, including, e.g., MBL knockout mouse model (See, e.g., U.S. Pat. No. 7,491,868, the content of which is incorporated herein by reference), S. aureus model, and/or the rat sepsis model (See, e.g., Onderdonk A B et al., (1984) Rev Infect Dis; 6 Suppl 1:S91-5). A surrogate molecule with mouse Fc g2a and human MBL as the human IgG1Fc are made immunogenic in mice. Fully mouse versions with mouse MBL-A and -C which work in both mice and rats are constructed.

Example 13: Elution of Bacteria Bound to FcMBL Molecules with Various Chelation, pH and Salt Buffers A series of buffers with different chelating agents, pH, salt content were assessed in the 96 well ELISA assay to determine which buffer could elute S. aureus or E. coli off the FcMBL microbeads. An exemplary ELISA assay for detection of S. aureus or E. coli is described herein, and is not construed to be limiting. Any other detection methods known in the art can be also used to detect readout signals of the target bacteria.

Figure 23:
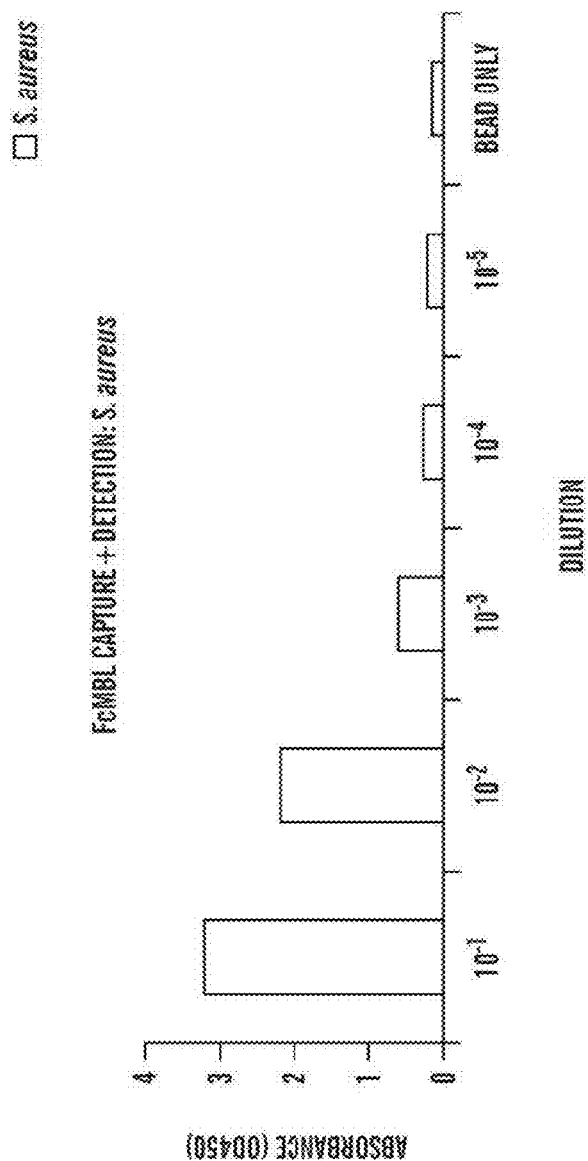
FIG. 23 is a bar graph showing detection signals of various concentrations of *S. aureus* captured by AKT-Fc-MBL 1 μM magnetic microbeads and detected by FcMBL-HRP ELISA. Sensitivity of this embodiment of the assay was about 149 CFU/mL.

As described in Example 10, FIG. 10 shows the exemplary basis of the ELISA assay using FcMBL-coated magnetic microbeads. The level of infection or the amount of microbes captured on FcMBL-coated magnetic microbeads can be quantified by comparing the test samples against standard curves, e.g., of laboratory strains of bacteria or fungi run in parallel. As shown in FIG. 23, using HRP-labeled FcMBL molecules as a detection agent in the ELISA assay can detect as few as 149 bacteria (e.g., S. aureus) in buffers. In some embodiments, the ELISA assay can be performed in less than 1 hour.

Figure 24:
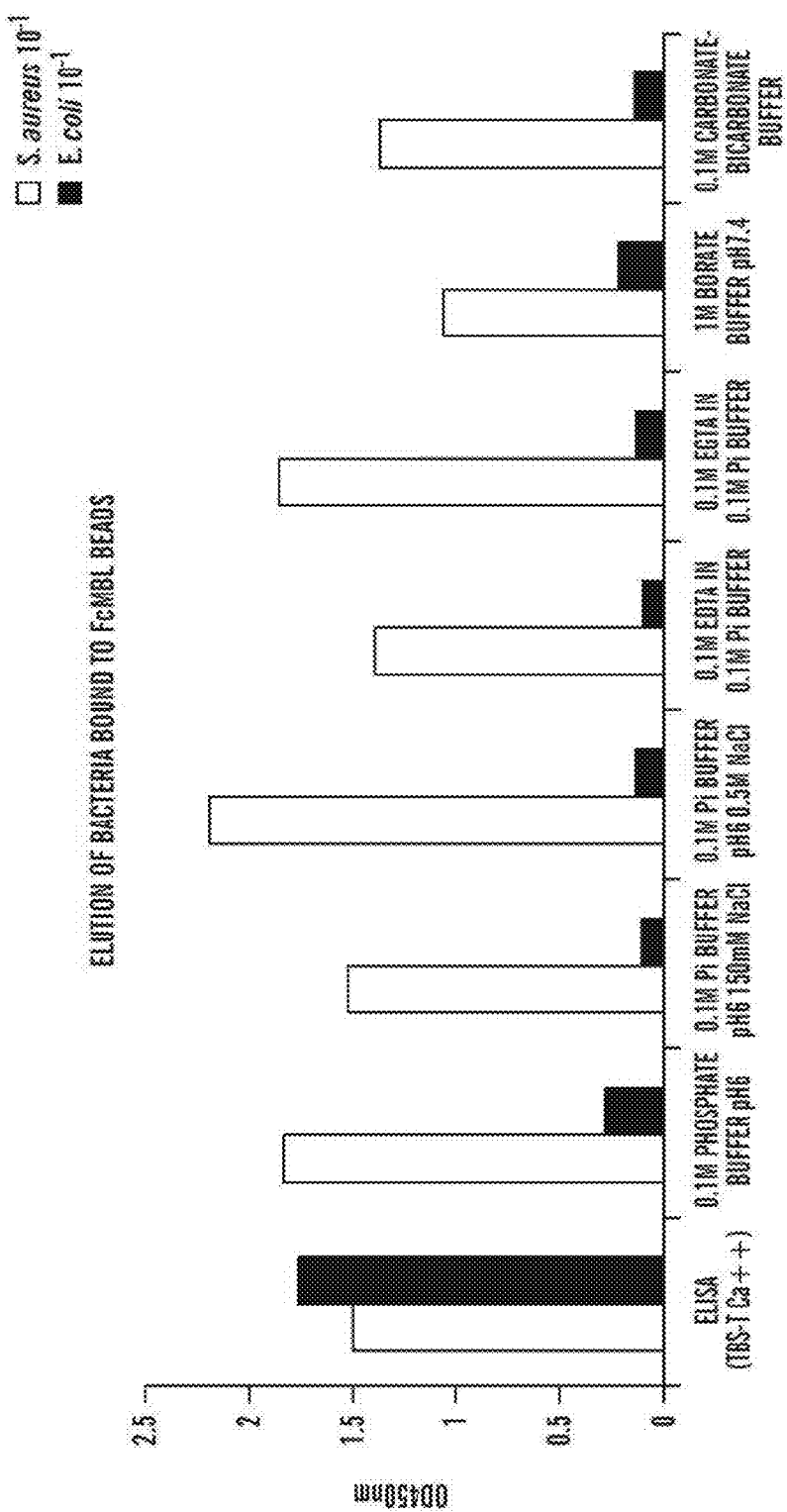
FIG. 24 is a bar graph showing elution of *S. aureus* and *E. coli* bacteria bound onto FcMBL-coated substrates (e.g., magnetic microbeads) with different treatments, including chelation, pH and salt washes.

The buffers that were assessed included, but were not limited to, 0.1M phosphate buffer (pH 6); 0.1M phosphate buffer (pH 6) containing about 150 mM NaCl; 0.1 M phosphate buffer (pH 6) containing 500 mM NaCl; 0.1 M EDTA in 0.1M phosphate buffer; 0.1 M EGTA in 0.1M phosphate buffer; 1M borate buffer (pH 7.4); and 0.1 M carbonate-bicarbonate buffer. A buffer of TBST containing $Ca^{2+}$ at a concentration greater than 1 mM was used as a control. Without wishing to be bound by theory, $Ca^{2+}$ is generally required for binding of microbes to MBL portion of the FcMBL molecule. After incubation for about 10-20 mins at room temperature (or up to 37° C.), elution of microbes bound to FcMBL magnetic microbeads was analyzed. As shown in FIG. 24, all the assessed buffers, except the ones containing $Ca^{2+}$, were able to elute greater than 85% of the E. coli bound to the FcMBL molecules and/or magnetic microbeads, but they had little or no effect on S. aureus. However, the borate buffer at 1M and pH 7.4 could elute about 33% of the S. aureus.

Figure 25A:
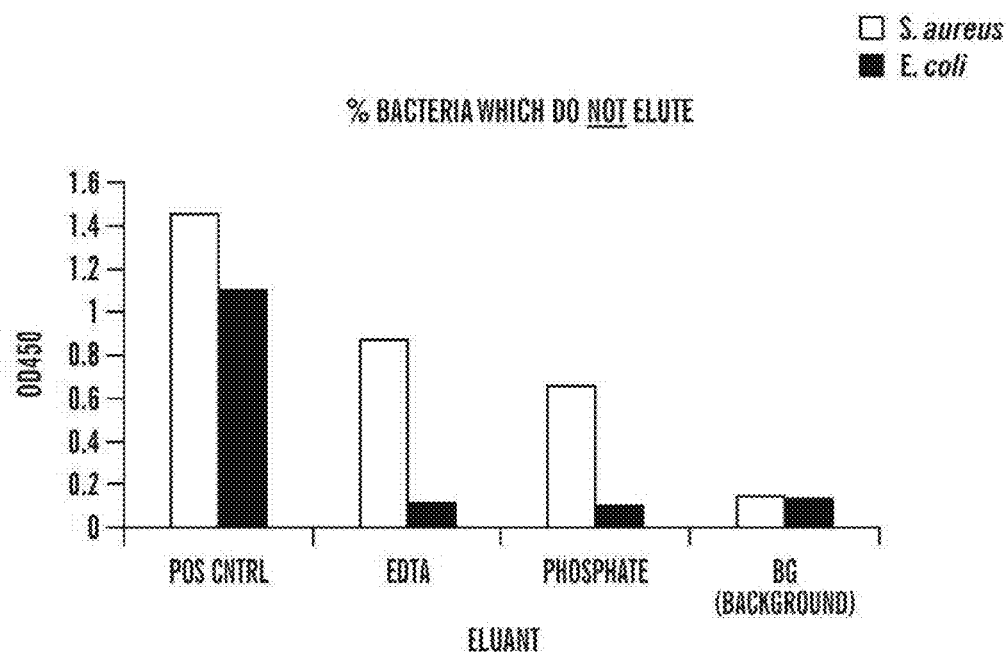
FIGS. 25A and 25B are bar graphs showing elution of *E. coli* and *S. aureus* off FcMBL-coated substrates (e.g., magnetic microbeads) using chelators.
Figure 25B:
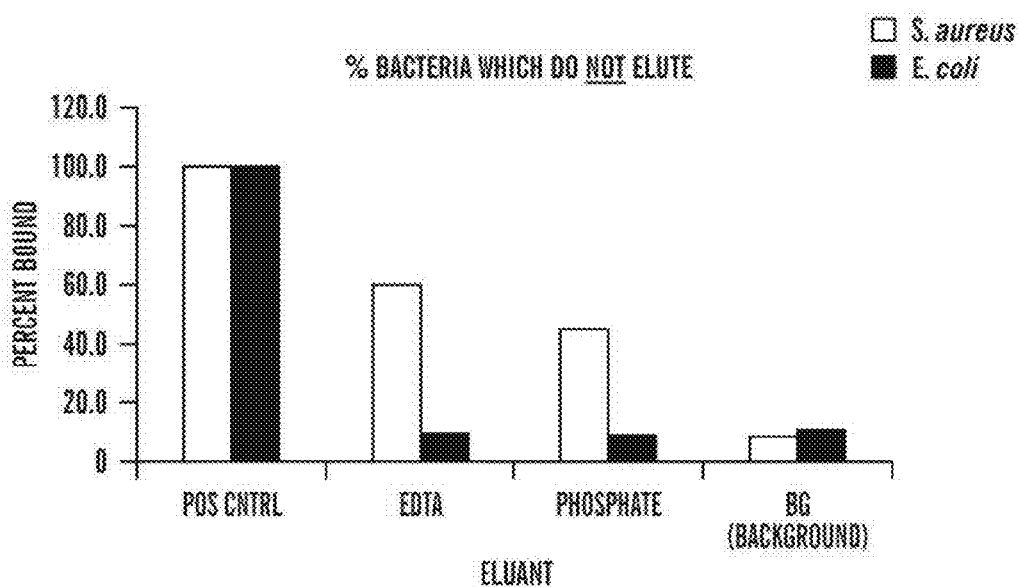

The elution of S. aureus and E. coli bacteria from FcMBL-coated magnetic microbeads were also assessed using 0.1M EDTA or 0.1M phosphate buffer (pH 7.4) containing about 150 mM NaCl. The results are shown in FIG. 25A and FIG. 25B as the OD450 and as a percent of bound bacteria, respectively. FIG. 25B shows that the EDTA and phosphate buffer can elute only 40% and 53% of the S. aureus off the FcMBL-coated magnetic microbeads, whereas both the EDTA and phosphate buffer can remove greater than 90% of the E coli bacteria off the FcMBL-coated magnetic microbeads and reduce the signal to about background level, indicating that the S. aureus can be bound more tightly to Fc portion of the FcMBL molecules/magnetic microbeads than the gram-negative E. coli bacteria.

Example 14: Single Tube Assay for Detecting and/or Distinguishing S. aureus from E. coli Any existing ELISA protocol can be used in combination with the microbe-targeting substrates as described herein for microbe detection. For example, an exemplary protocol for an ELISA-based microbe detection method carried out in a modified blood collection tube (e.g., a modified blood VACUTAINER® optionally containing one or more anticoagulants such as citrate, phosphate and dextrose (CPD)) is described earlier in Example 10 and shown in FIG. 14 and can be used to detect and/or distinguish S. aureus from E. coli.

In some embodiments, the step 3 of the above-described exemplary protocol can employ TBST without calcium salts or calcium ions. In other embodiments, the step 3 of the protocol can include a chelating agent (e.g., 50 mM EDTA or EGTA) in the TBST buffer with or without calcium ions. In these embodiments, the absence of free calcium ions in the TBST buffer (e.g., either by addition of a chelating agent or absence of calcium ions into the TBST buffer) can reduce the likelihood of at least E. coli, but not S. aureus substantially, binding to the microbe-targeting substrates. Thus, S. aureus, but not E. coli, is preferentially captured on the microbe-targeting substrates in the absence of free calcium ions. In some embodiments, the step 3 of the above-described exemplary protocol can employ TBST with calcium salts or calcium ions, which allows at least both E. coli and S. aureus to be captured on the microbe-targeting substrates.

In some embodiments, the washes involved in steps 6, 7, and 10 can include calcium salts (e.g., ~5 mM $CaCl_2$) or calcium ions in the wash buffer, e.g., TBST. Thus, at least both E. coli and S. aureus can remain binding to the microbe-targeting substrates. In other embodiments where the captured E. coli is desirable to be removed from the microbe-targeting substrates, the washes involved in steps 6, 7, and 10 can exclude calcium salts or calcium ions, and/or include a chelating agent (e.g., ~50 mM EDTA and EGTA) in the wash buffer.

As noted earlier, the reagents and steps as shown in Example 10 and FIG. 14 are illustrated as an example and are not meant to be limiting. Thus, appropriate modifications to reagents and/or steps by a person having ordinary skill in the art are also within the scope described herein. For example, different wash buffers, detection agents, and/or chromogenic substrates can be used. The number of wash steps can be increased or decreased, depending on the volume of wash buffer used and/or incubation time. Some reagents (e.g., FcMBL magnetic microbeads and/or FcMBL-HRP) for the assay can be supplied as lyophilized and/or in sterile bottles. The readout of the assay can be based upon comparison to a reference (e.g., a laminated color strip). In one embodiment, the total assay time of the assay is approximately 1 hour to 1.5 hours.

Using the exemplary ELISA assay protocol described above, FIGS. 26A-26B show the results of tube-based colorimetric ELISA assay for S. aureus and E. coli binding to FcMBL-coated magnetic microbeads in the presence or absence of EDTA chelation. S. aureus and E. coli ($10^{-1}$ dilution approximately corresponding to about $10^8$ bacteria) were captured by FcMBL-coated magnetic microbeads in the presence or absence of calcium ions and/or EDTA. For example, in some embodiments, after resuspension of the FcMBL-coated magnetic microbeads in a test sample, e.g., blood, a TBST buffer (e.g., Tris buffered saline (TBS) with 0.05% Tween) with calcium salts (e.g., ~5 mM $CaCl_2$) can be added. In such embodiments, both E. coli and S. aureus can be captured on the FcMBL-coated magnetic microbeads in the presence of calcium ions. In order to remove the captured E. coli from the FcMBL-coated magnetic microbeads, the FcMBL-coated magnetic microbeads with bacteria can be washed with TBST without sufficient free calcium ions (e.g., TBST without a calcium salt, e.g., $CaCl_2$; a solution of a calcium salt (e.g., ~5 mM $CaCl_2$) with excess EDTA (e.g., ~50 mM EDTA); or a EDTA solution (e.g., ~50 mM EDTA)). In alternative embodiments, E. coli can be prevented from binding to the FcMBL-coated magnetic microbeads when a test sample is in contact with FcMBL-coated magnetic microbeads, e.g., by using TBST without sufficient free calcium ions to enable E. coli binding to the FcMBL-coated magnetic microbeads.

Figure 26A:
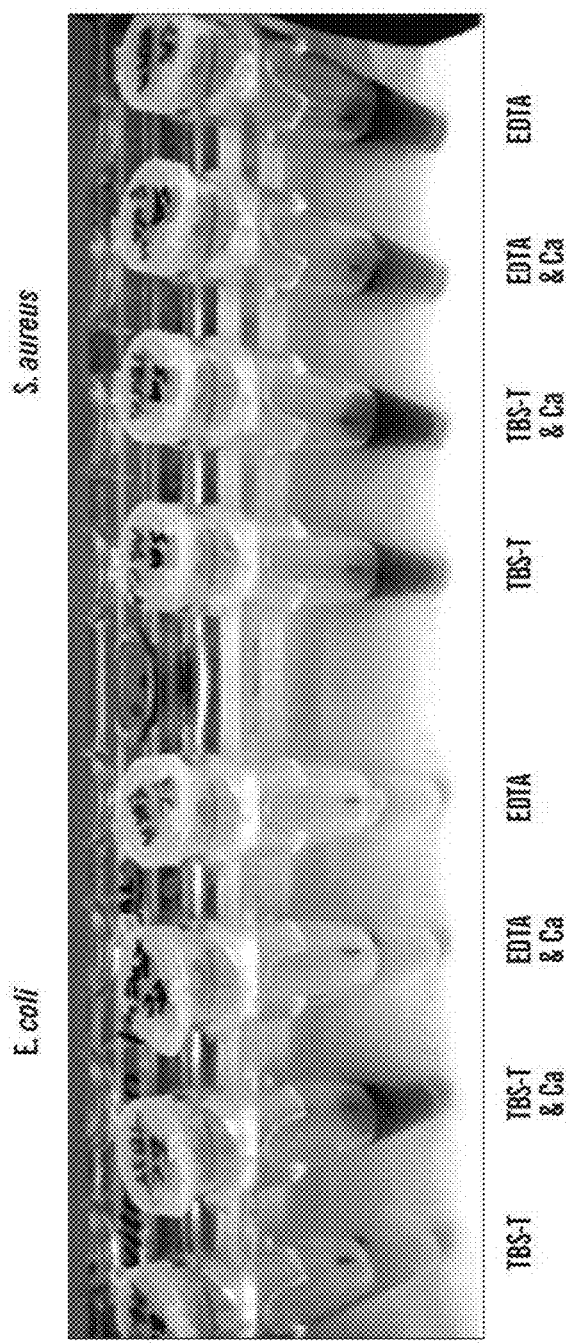
FIGS. 26A and 26B show results of tube-based ELISA for *S. aureus* and *E. coli* binding to FcMBL-coated substrates (e.g., magnetic microbeads) in the presence of a chelating agent (e.g., EDTA).
Figure 26B:
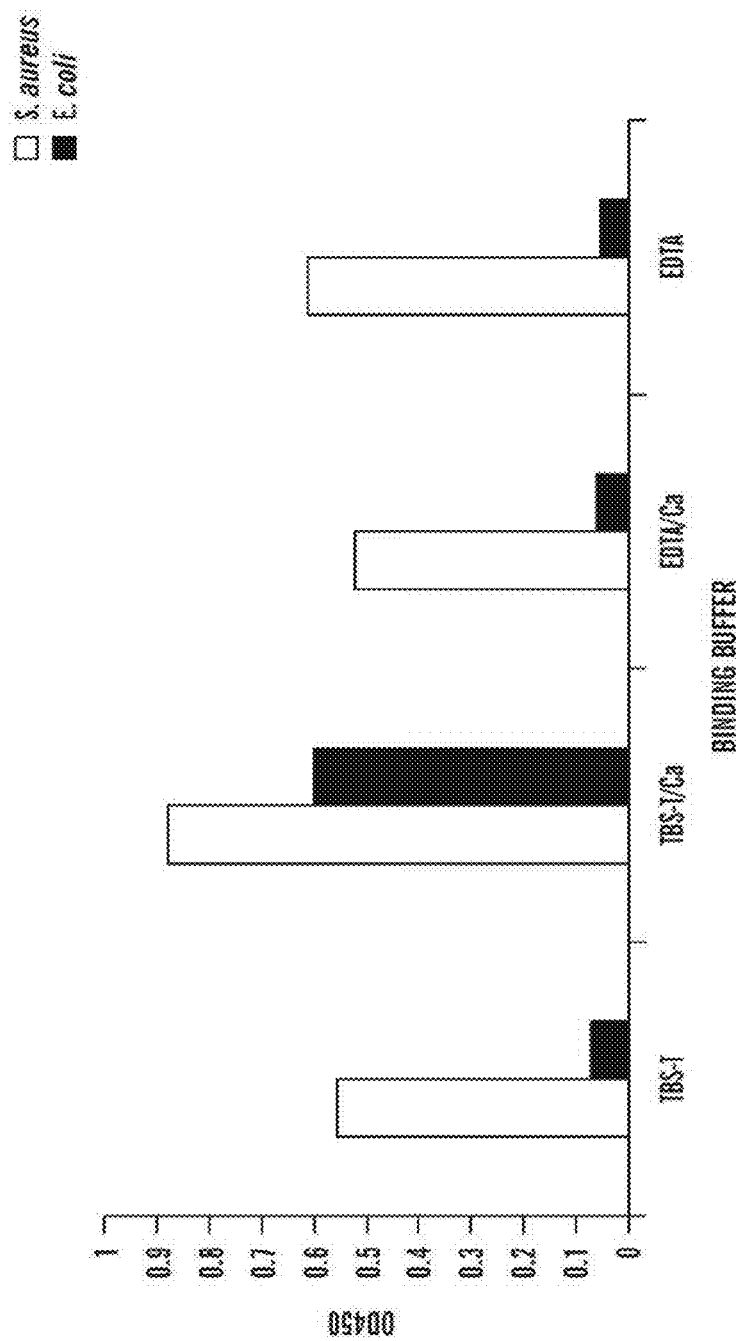

After microbe capture and washes, any remaining bacteria bound on the FcMBL-coated magnetic microbeads were then detected, e.g., by FcMBL-HRP and TMB colorimetric detection. The total assay time was about 40 minutes. FIGS. 26A-26B show that unlike E. coli, S. aureus can bind to the FcMBL in the presence of a chelating agent, e.g., EDTA, indicating that other than MBL-mediated binding, Fc-mediated binding can be involved. However, there can be additive binding of S. aureus to the FcMBL in the presence of calcium ions, as the binding of S. aureus to the FcMBL in the presence of calcium ions is almost twice as strong as that in the absence of calcium ions. This indicates that both the Fc binding and the MBL binding can be responsible for the stable binding between FcMBL and S. aureus. The kinetics of binding between FcMBL and S. aureus can be determined, e.g., on a BiaCore system, or KinExA.

Figure 27:
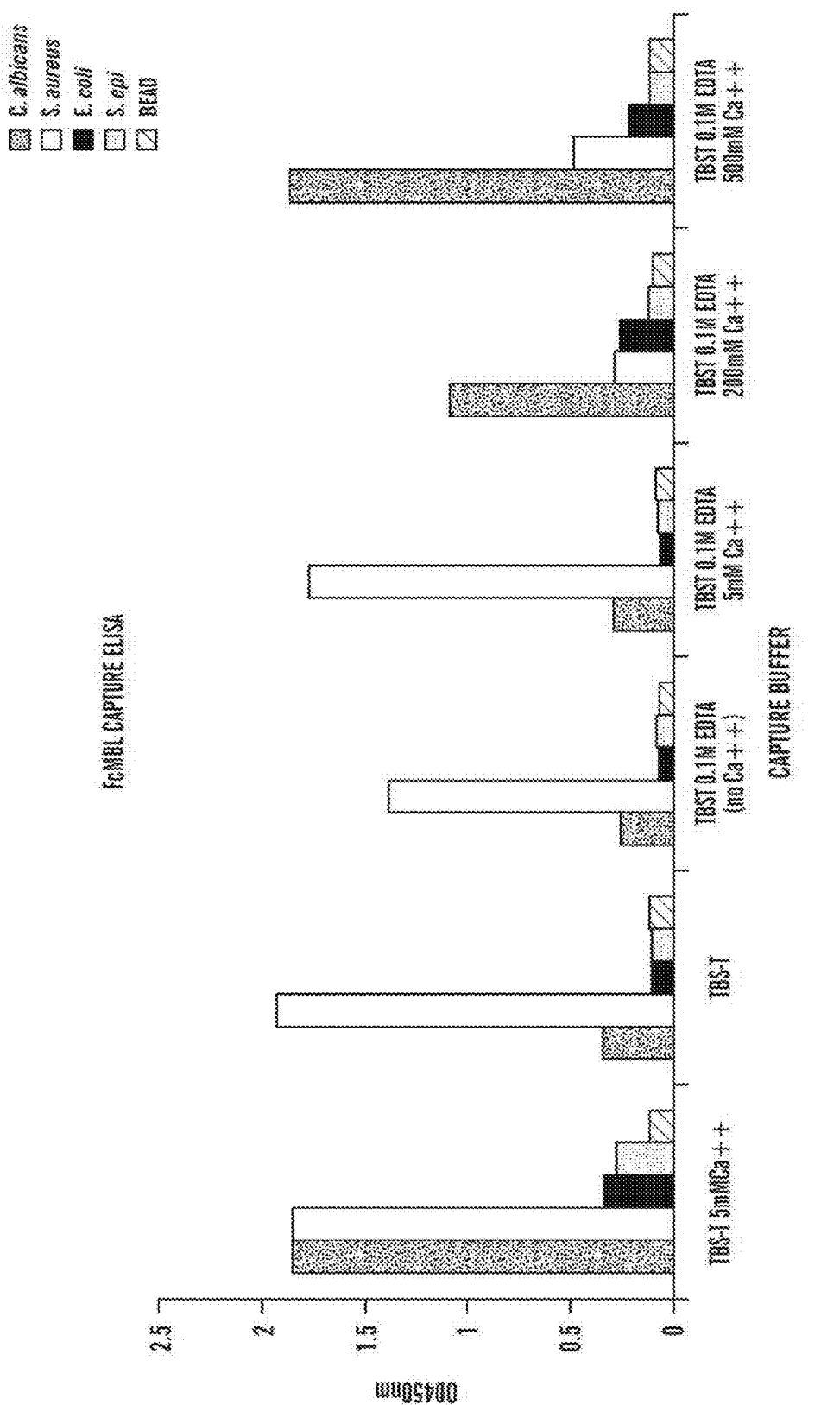
FIG. 27 is a bar graph comparing different microbial or pathogenic species captured on FcMBL-coated substrates (e.g., magnetic microbeads) in the presence or absence of a chelating agent (e.g., EDTA) and various $Ca^{2+}$ concentrations.

It was next sought to determine if capture of S. aureus in the presence of a chelating agent, e.g., EDTA, is selective. Accordingly, capture of four pathogenic species, e.g., E. coli, S. aureus, S. epidermidis and C. albicans, were compared in the presence or absence of a chelating agent, e.g., EDTA, and variable $Ca^{2+}$ concentrations. FIG. 27 shows that S. aureus can be captured by FcMBL-coated magnetic microbeads in the presence of a chelating agent, e.g., EDTA, while the other pathogenic species, e.g., E. coli, S. epidermidis and C. albicans requires calcium ions for binding to the FcMBL-coated magnetic microbeads. In some embodiments, replacement of $Ca^{2+}$ at high concentrations appears to reduce S. aureus capture on the FcMBL-coated magnetic microbeads. It is noted that S. epidermidis, unlike S. aureus, requires calcium ions for binding to the FcMBL-coated magnetic microbeads. Thus, capture and/or wash in the presence of a chelating agent, e.g., EDTA, can not only be used to distinguish S. aureus from E. coli, but can also be used to distinguish between S. aureus and S. epidermidis.

Figure 28:
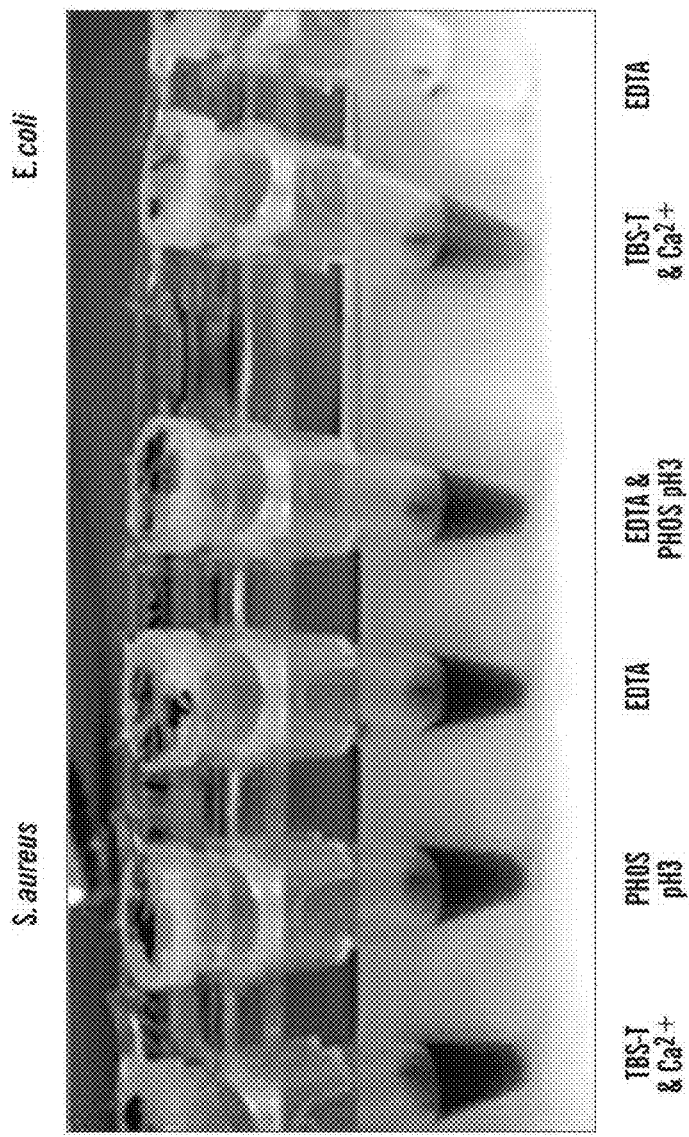
FIG. 28 is an image showing colorimetric outcomes of the tube-based ELISA assay for *S. aureus* and *E. coli* binding to FcMBL-coated substrates (e.g., magnetic microbeads) in the presence or absence of a chelating agent (e.g., EDTA) and/or a low pH buffer.

As S. aureus generally expresses protein A, which can contribute to the Fc-mediated binding with the FcMBL, it was next sought to determine if disruption of Fc-mediated binding can cause S. aureus to elute off the FcMBL. Without wishing to be bound by theory, to disrupt Fc binding with protein A, a low pH buffer can generally be used, e.g., pH 3 buffer containing about 100 mM phosphate and 150 mM NaCl can be used; whereas chelation, e.g., using 50 mM EDTA, can generally be used to disrupt MBL-mediated binding. However, as shown in FIG. 28, while E coli, as shown herein, can be eluted off the FcMBL-coated magnetic microbeads with 50 mM EDTA pH 8, the S. aureus is not significantly eluted by EDTA pH 8 nor by a pH 3 buffer containing 0.1M Phosphate/0.15M $Na^+$ pH 3 nor by sequential washing with EDTA followed by the low pH phosphate buffer. As EDTA precipitates phosphate, the EDTA and low pH phosphate buffer were not be able to be used together to determine if S. aureus could be eluted off FcMBL by disruption of both MBL-mediated and Fc-mediated binding. Nevertheless, the findings that S. aureus could not be eluted off FcMBL by chelation or by reducing the pH indicate that there can be at least two independent mechanisms of binding the S. aureus to the FcMBL-coated magnetic microbeads. Without wishing to be bound by theory, chelation (which removes MBL—dependent binding) is not sufficient to cause S. aureus eluting off FcMBL because the Fc-dependent binding to Staphylococcal protein A is not affected and the low pH elution of protein A binding does not disrupt the MBL specific binding. (This can be further assessed by using controls such as Fc-coated and wild-type MBL-coated magnetic microbeads.) Accordingly, in some embodiments, it is contemplated that concurrent disruption of both Fc-mediated and MBL-mediated binding between S. aureus and FcMBL can prevent S. aureus from binding to FcMBL. An exemplary low pH buffer that can work in concert with EDTA chelation is 2M arginine at pH 4.4 (Arakawa et al. 2004 *Protein Expr Purif.;* 36(2):244-2488). In one embodiment, 2 M arginine at pH 4.4 can be used to elute S. aureus off FcMBL and/or prevent S. aureus from binding to FcMBL.

The findings herein indicate that protein A present in the cell wall of S. aureus can at least partly contribute to the ability of capturing S. aureus, rather than E. coli, in the presence of a chelating agent (e.g., EDTA) due to the Fc-mediated binding. Thus, it is contemplated that protein A-expressing microbe can be captured on FcMBL in the presence of a chelating agent (e.g., EDTA), and thus be distinguishable from protein A-negative microbes, e.g., E. coli.

Example 15: Dot Blot/Dipstick Assays for Detecting and/or Distinguishing S. aureus from E. coli Dot blot and/or dipstick assays can be developed to capture microbe on a substrate surface crosslinked with FcMBL upon which the colorimetric readout is determined from. In some embodiments, the dot blot and/or dipstick assays can be used to distinguish S. aureus from E. coli.

The attachment of the FcMBL to the a substrate surface (e.g., membrane surface, glass surface, tubing surface) can be performed with multiple approaches, for example, by direct cross-linking FcMBL to the substrate surface; cross-linking FcMBL to the substrate surface via a nucleic acid matrix (e.g., DNA matrix or DNA/oligonucleotide origami structures) for orientation and concentration (in a manner similar to FcMBL-coated magnetic microbeads) to increase detection sensitivity; cross-linking FcMBL to the substrate surface via a dendrimer-like structure (e.g., PEG/Chitin-structure) to increase detection sensitivity; attracting FcMBL-coated magnetic microbeads to the substrate surface with a focused magnetic field gradient applied to the substrate surface, or any other art-recognized methods. In some embodiments, the substrate surface can be "oiled". Without wishing to be bound by theory, the treating of a substrate surface with an omniphobic layer can allow the binding to a microbe by FcMBL without a subsequent hydrophobic binding between the microbe and the substrate surface. This can allow chelation to remove the microbe when required. See, e.g., Wong T S et al., "Bioinspired self-repairing slippery surfaces with pressure-stable omniphobicity." (2011) *Nature* 477(7365): 443-447, and International Application No.: PCT/US12/21928, the content of which is incorporated herein by reference, for methods to produce a slippery substrate surface. In some embodiments, the substrate surface can be further treated with a blocking agent (e.g., treatment with ~1% casein for about 30 mins) to reduce any non-specific binding.

In some embodiments, the dipsticks attached with FcMBL can be added to a test sample, e.g., a blood sample, followed by one or more washes with TBST and incubation with alkaline phosphatase (AP)-labeled FcMBL (e.g., ~20 mins of incubation with 1:10,000 dilution of AP-labeled FcMBL in TBST containing 3% BSA). After incubation with alkaline phosphatase, the dipsticks can be washed once or a plurality of times (e.g., at least 3 washes with TBST followed by at least one wash with TBS) before addition of a BCIP/NBT reagent for colorimetric development (e.g., ~20 mins). In some embodiments, the wash buffers (e.g., TBST or TBS) can contain calcium ions or calcium salt (e.g., ~5 mM $CalC1_2$) such that any microbe including E. coli and S. aureus can be captured on the dipsticks. In alternative embodiments, the wash buffers (e.g., TBST or TBS) can contain no calcium ions or calcium salts. In some embodiments, the wash buffers (e.g., TBST or TBS) containing calcium ions or calcium salt (e.g., ~5 mM $CaCl_2$) can contain a chelating agent (e.g., ~50 mM EDTA or EGTA) in excess to chelate free calcium ions. As shown herein, *S. aureus* can remain bound onto FcMBL in the presence of a chelating agent or no calcium ions. Accordingly, when the dipsticks after contact with a test sample, e.g., blood, are washed with buffers containing no free calcium ions and/or a chelating agent, any bacteria on the dipsticks detected afterward is likely *S. aureus* (as *E. coli* generally requires calcium ions for MBL-mediated binding).

FIG. 15 shows results for a general dot blot/dipstick detection of bacteria on a Biodyne membrane. Serial dilutions of either *E. coli* or *S. aureus* ($10^{-1}$ to $10^{-6}$ dilutions) were spotted directly onto a Biodyne membrane, which was then blocked in 1% casein, washed with TBST containing ~5 mM $CaCl_2$ once or at least two times, incubated for 20 min with alkaline phosphatase (AP)-labeled FcMBL (1:10,000 dilution in TBST containing 3% BSA and 5 mM $CaCl_2$, washed with TBST containing 5 mM $CaCl_2$ at least three times followed by at least one wash with TBS containing 5 mM $CaCl_2$, and detected colorimetrically with a BCIP/NBT reagent. FIG. 15 shows that as low as 130 *E. coli* or 343 *S. aureus* can be detected after 30-min development using AP-labeled FcMBL and BCIP/NBT detection system. To distinguish *S. aureus* from *E. coli* in a test sample, the dot blots spotted with the test sample, e.g., blood, can be washed in the presence of a chelating agent, e.g., EDTA. A microbe detected in the presence of a chelating agent, e.g., EDTA, is likely *S. aureus*, rather than *E. coli*.

As described earlier, FIG. 16 shows results for a dot blot detection of *S. aureus* bacteria on a membrane coupled with FcMBL. In one embodiment, a membrane (e.g., Biodyne membrane) is attached with FcMBL molecules at a certain concentration. Bacteria (e.g., *S. aureus*) was captured by FcMBL immobilized on the Biodyne membrane, which were then blocked in 1% casein (e.g., for about 30 mins), incubated for 20 min with alkaline phosphatase (AP)-labeled FcMBL, washed, and detected colorimetrically with a BCIP/NBT reagent. As shown in FIG. 16, the capture and detection of the bacteria is FcMBL concentration dependent. As described earlier, in some embodiments, FcMBL can be directly immobilized on a membrane. For example, about 1 µg to about 1 mg FcMBL, about 2 µg to about 500 µg FcMBL, about 5 µg to about 250 µg FcMBL, or about 10 µg to about 100 µg FcMBL can be spotted onto a Biodyne membrane and allowed to dry. In one embodiment, the concentration of the FcMBL solution used for spotting on the membrane can be about 0.1 mg/mL to about 25 mg/mL, about 0.5 mg/mL to about 20 mg/mL, about 5 mg/mL to about 15 mg/mL. In one embodiment, the concentration of the FcMBL solution used for spotting on the membrane can be about ~11.5 mg/mL. In other embodiments, FcMBL can be coupled to a membrane by a nucleic acid matrix (e.g., DNA matrix). In alternative embodiments, FcMBL can be coupled to any surface other than a membrane, e.g., a paper substrate, for the dipstick assay. In some embodiments, the substrate surface (e.g., Biodyne membrane) after coupling with FcMBL can be further treated with a blocking agent (e.g., incubation with 1% casein for about 30 mins) to reduce any non-specific binding. In some embodiments, the blocked substrate surface can be washed with one or more washes, e.g., with TBST with or without calcium ions (e.g., from a calcium salt such as $CaCl_2$). In some embodiments, the blocked substrate surface can be washed with at least two washes, e.g., with TBST containing calcium ions (e.g., from a calcium salt such as $CaCl_2$).

An exemplary protocol for dot blot determination of *E. coli* and/or *S. aureus* is provided below:

Provide a Biodyne membrane spotted with about 1-100 µg (or about 3-15 µg) of FcMBL, which has been optionally blocked with about 1% casein for about 1 hour and washed at least two times in TBST containing ~5 mM $Ca^{2+}$.

Dip the FcMBL-spotted membrane in a test sample, e.g., blood sample

Add in TBST containing ~5 mM calcium ions, and/or a chelating agent (e.g., ~100 mM EDTA), and incubate for about 20 mins to allow bacteria captured by FcMBL. Addition of a chelating agent (e.g., EDTA) can cause chelation of calcium ions, which can in turn prevent/disrupt MBL-mediated binding, but not Fc-mediated binding. In some embodiments, TBST containing ~5 mM calcium ions can be used to capture both *E. coli* and *S. aureus*, and *E. coli* can then be eluted off with a TBST wash buffer containing a chelating agent (e.g., EDTA).

Wash at least two times in TBST containing ~5 mM calcium ions, and/or ~100 mM EDTA, and each wash can last for about 10 mins. Addition of EDTA in the capture or wash buffer can cause chelation of calcium ions, which can in turn prevent/disrupt MBL-mediated binding, but not Fc-mediated binding. Thus, *E. coli* cannot bind to FcMBL in the presence of a chelating agent, e.g., EDTA.

Optionally wash at least two times in TBST containing ~5 mM calcium ions.

Incubate, e.g., for about 30 mins, in alkaline phosphatase (AP)-labeled FcMBL (e.g., 1:5000 dilution) diluted in TBST containing about 3% BSA and ~5 mM calcium ions Wash at least three times with TBST containing ~5 mM calcium ions Wash one or more times with TBS containing ~5 mM calcium ions.

Develop with NBT/BCIP, e.g., for 4 min, for colorimetric detection.

Any modifications to the exemplary protocol within one of skill in the art are also within the scope of different aspects and/or embodiments described herein. For examples, the number of washes can be increased or decreased based on, e.g., the volume of a wash buffer used, how long each wash takes, and/or binding affinity strength of bacteria to FcMBL. Further, different detection enzymes and corresponding enzyme substrates, other than AP and NBT/BCIP, can be used, including, but not limited to HRP and/or chromogenic substrates (e.g., TMB, DAB, and ABTS). In some embodiments, any chelating agent that can chelate calcium ions (e.g., EGTA, and EDTA) can be used. In some embodiments, any sources of calcium ions (e.g., different calcium salts such as calcium fluoride) that are compatible with the ELISA assay and binding of bacteria to FcMBL can also be used.

FIG. 29 shows that, using the exemplary protocol described above, *S. aureus* can be captured on FcMBL-spotted dot blots in the presence of a chelating agent, e.g., EDTA, while *E. coli* cannot, because *S. aureus* express protein A, which can contribute to Fc-mediated binding, but *E. coli* do not. Thus, *S. aureus* can be distinguished from *E. coli* based on the difference in binding behavior of *S. aureus* and *E. coli* to FcMBL in the presence of a chelating agent, and in calcium ions.

Without wishing to be bound by theory, as protein G can generally bind to Fc of IgG, in some embodiments, the methods described herein can be used to detect protein G-expressing microbes (e.g., streptococci) and distinguish them from protein G-negative microbes, e.g., *E. coli*.

Example 16: Rapid Identification of Microbes from FcMBL Bound Microbial Matter or Component(s)

The diagnosis of infection relies on indirect or direct evidence. The indirect evidence relies on the detection of an adapted and specific host response directed against the pathogen. The direct evidence relies on the culture of the microorganism from the infected site, amplification and detection of pathogen-specific nucleic acids or the detection of a specific antigen in blood or urine.

Specific antigen detection is widely used for a variety of infectious diseases, most commonly for legionellosis (*Legionella pneumophila* serotype 1 in urine), malaria (*Plasmodium falciparum* in blood) and with less success with *Streptococcus pneumonia* infection (in urine). However, direct antigen detection can only be used to rule in or rule out a specific etiology and cannot identify most bacteria.

As described herein, engineered microbe-binding molecules or substrates (e.g., FcMBL-bound paramagnetic microbeads) can be capable of binding the surface of a wide array of microbes including pathogens, e.g., but not limited to, bacterial, fungal, parasitic or viral. For example, in some embodiments, blood or urine or any other biological fluid can be subjected to microbial capture by FcMBL coated magnetic microbeads and adequate controls (e.g., non-specific binding control by non-relevant protein coated magnetic microbeads). Accordingly, engineered microbe-binding molecules or substrates (e.g., FcMBL) can be used to bind microbes such as bacteria for diagnostic or therapeutic applications.

Not only can the engineered microbe-binding molecules or substrates bind to at least a portion of a cell surface of a microbe, the engineered microbe-binding molecules can also capture circulating microbe-originating cell fragments or matter derived from microbes found in biological fluids, e.g., in the course of an infection, even in the absence of bacteremia. The presence of such elements can be used for diagnostic applications, e.g., the presence of pathogen-originating cell fragments or matter derived from pathogens can be diagnostic of an infectious disease. Moreover, the biochemical/proteomic (MALDI-TOF, multiple mass spectrometry (e.g., MSn) or specific antibody or aptamer based) analysis of the bound products can allow the recognition of elements pathognomonic for the most important pathogens. Accordingly, provided herein are also methods for diagnosis of infection occurring in any organ in the body of a subject (including blood, normally sterile fluids or virtual cavities) by capture of non-viable microbial matter or particles circulating in blood, or found in other fluids such as urine, or in any other organ sampled by any appropriate means (e.g., but not limited to, biopsy, puncture, aspiration, and lavage).

Binding of microbes or fragments thereof (including matter derived from microbes) can not only be used for infection of a sampled organ or tissue or cell(s) (blood or otherwise) but also to any major infectious process ongoing anywhere in the body where sufficient bacterial destruction or catabolism results in the presence of microbial matter in the bloodstream, urine or any other conveniently accessed fluid.

The wide spectrum of FcMBL can enable the capture of most clinically relevant bacterial species. As the presence of microbial matter or fragments of microbes can reflect deep tissue infection as they generally find its way into the bloodstream and most likely the urine, the capture and characterization of this microbial matter or fragments of microbes can be used as evidence markers specific for a given microbial species, thus allowing the diagnosis and/or identification of a microbe causing infection anywhere in an organism.

Figure 30A:
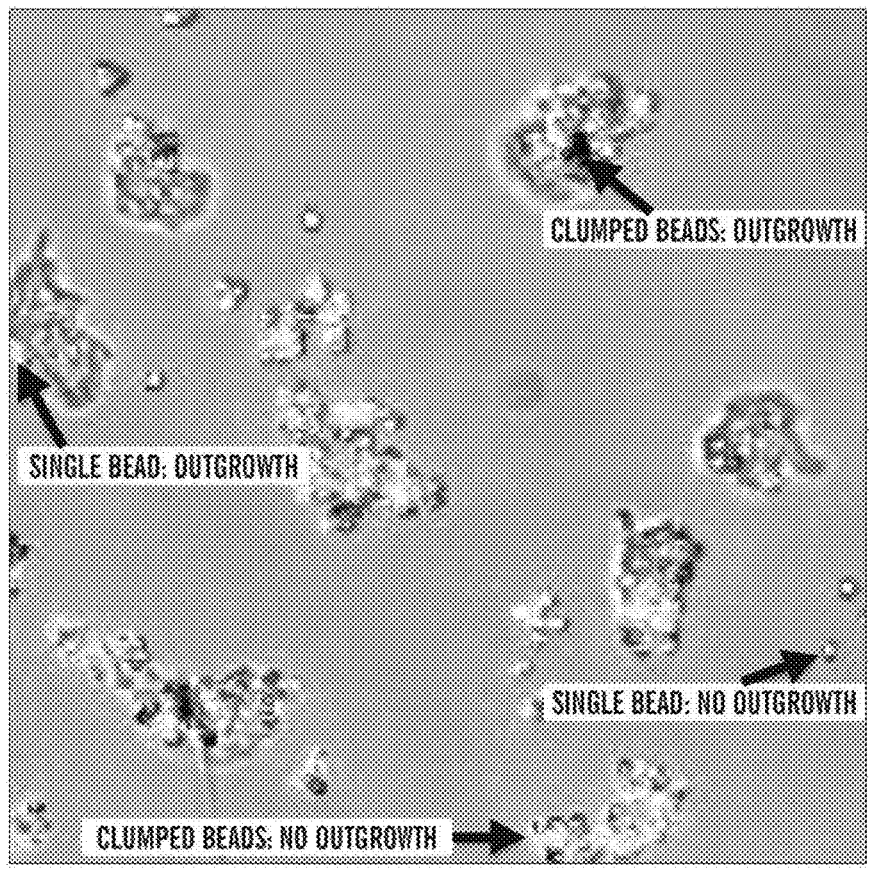
FIGS. 30A-30B are images showing binding of one or more embodiments of microbe-targeting substrates to microbial matter, including live microbes and/or fragments or matter derived from microbes.
Figure 30B:
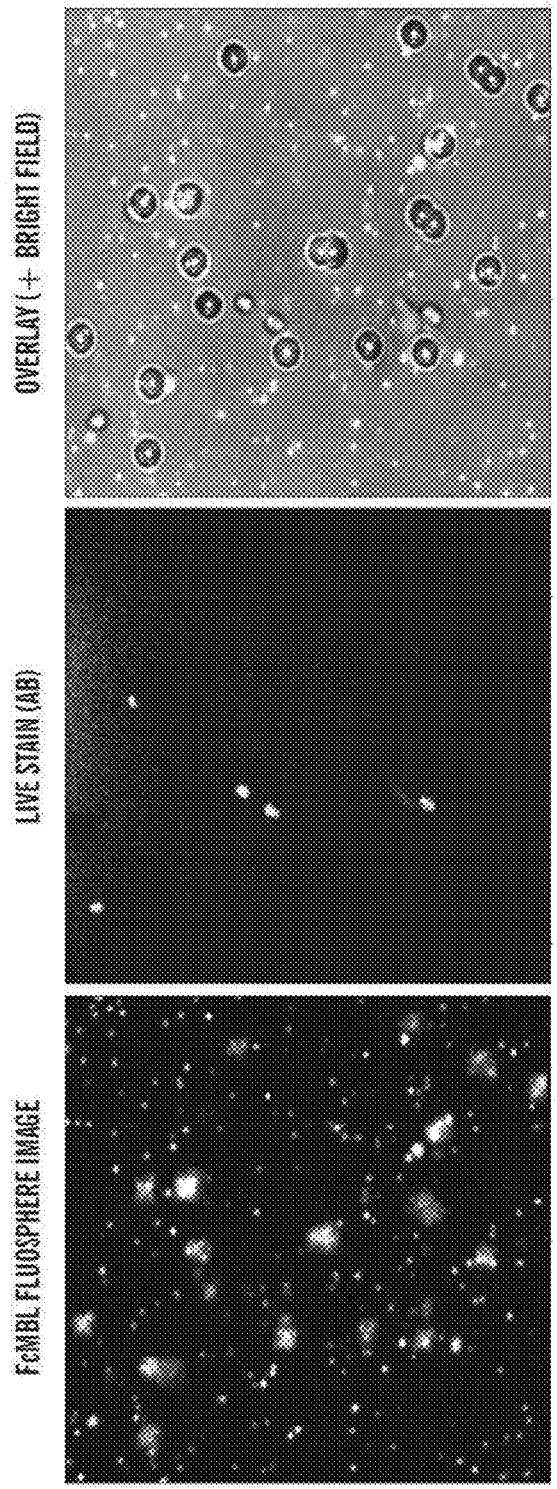

To this end, it was sought to determine if FcMBL could bind to microbial matter including non-viable fragments or matter derived from a microbe, including endotoxin. The FcMBL-coated microbeads (e.g., FcMBL-coated magnetic or fluorescent microbeads) were incubated with bacterial cultures and later detected under a microscope. Specifically, the paramagnetic microbeads (1 μm diameter, MYONE™, Invitrogen) coated with FcMBL were used to capture *E. coli* and/or bacterial fragments thereof diluted in TBST $Ca^{2+}$ 5 mM for about 10 mins, followed by about 3 washes (the number of washes can be fewer or more, depending on the sample processing conditions). The FcMBL-coated paramagnetic microbeads were observed under bright field. The captured *E. coli* and/or bacterial fragments could be also labeled with FcMBL-coated FluoroSpheres (e.g., 1:100 in TBST containing 5 mM $Ca^{2+}$ and 3% BSA: incubation for about 2 hours). All FcMBL binding matter was imaged using FcMBL coated fluorospheres (Invitrogen). It was readily visible that both intact microbes and fragments thereof were captured by FcMBL-coated microbeads, as evidenced by observed outgrowth from bound intact microbes, as compared to no outgrowth from bound fragments of a microbe (FIG. 30A). Further, the FcMBL-coated microbeads were incubated, e.g., for about 1 hour, in the presence of Alamar Blue (AB) stain for detection of live cells and were imaged with an appropriate photo-excitation wavelength (e.g., SPS: yellow/green-FluoroSpheres; Red-AB). As shown in FIG. 30B, matter or material bound to FcMBL-coated fluorospheres and/or magnetic microbeads can contain both live microbes (middle panel) and non-viable matter derived from microbes, e.g., *E. coli* (left panel).

Figure 31A:
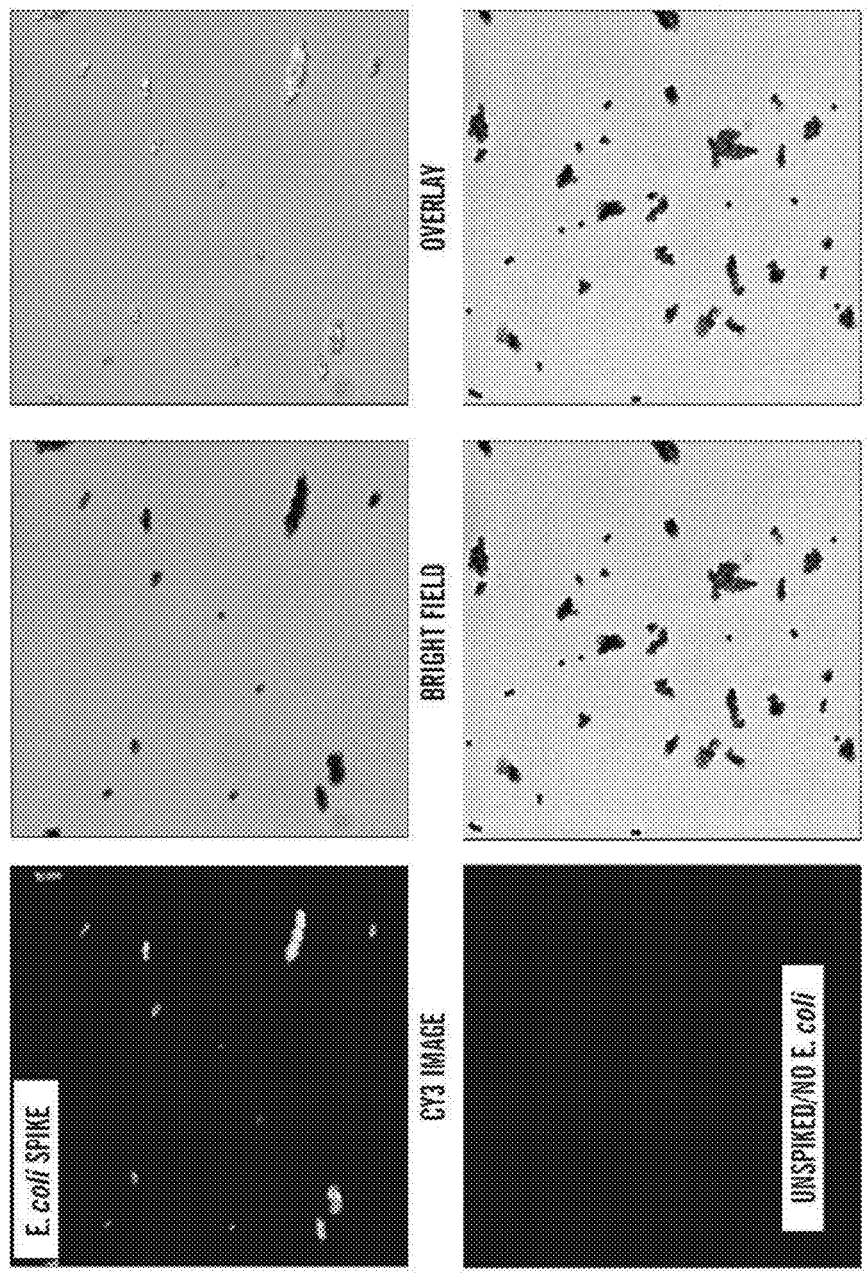
FIGS. 31A-31B are images showing capture of microbes or fragments thereof on one or more embodiments of microbe-targeting substrates from fluid samples, followed by antibody characterization.
Figure 31B:
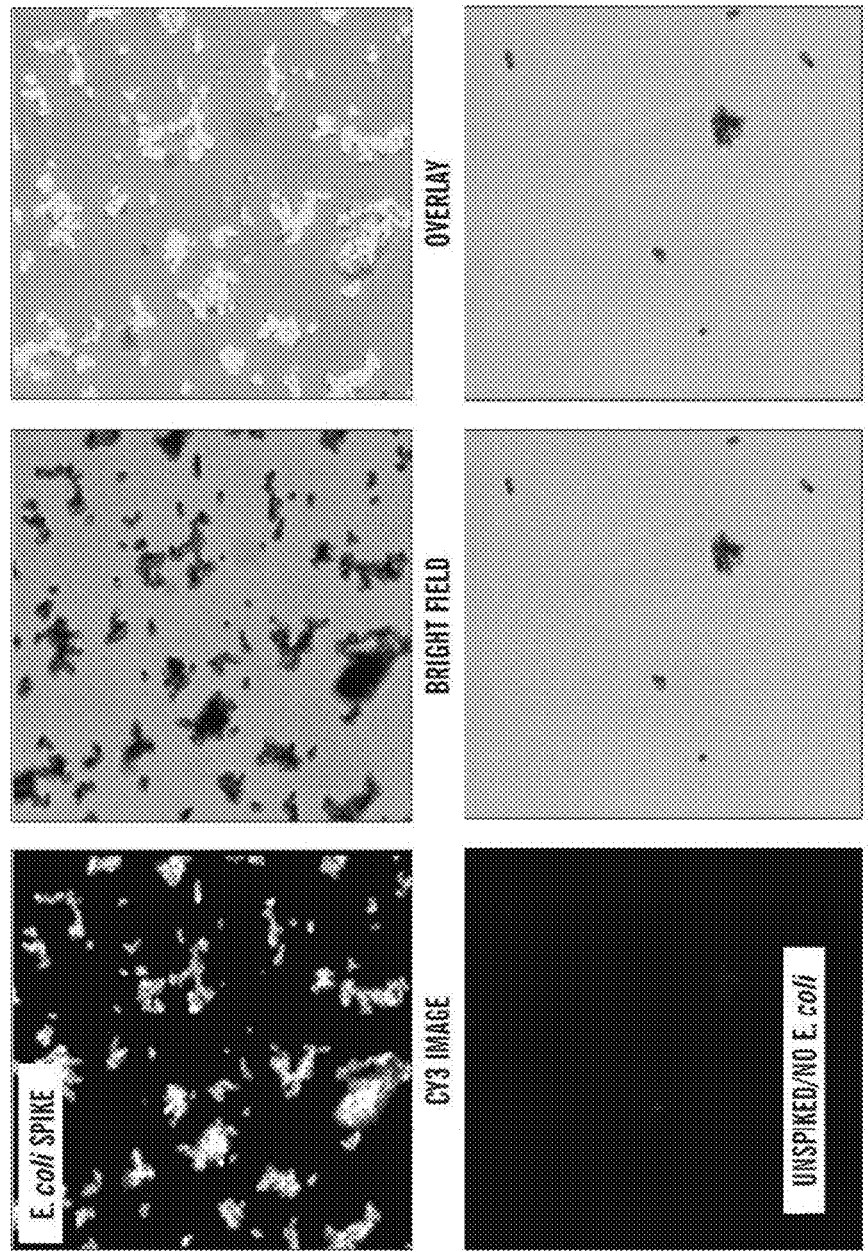

The use of specific antibodies allows the characterization of the nature and/or nature of the microbial material bound to FcMBL. Without to be limiting, a specific antibody raised against *Escherichia coli* lipopolysaccharide Lipid A (anti-LPS Lipid A antibody) or other antibodies specific to a pathogen of interest was used in this Example. The *E. coli* was captured with 1 μm FcMBL microbeads as described herein, followed by incubation with a primary antibody specific to *E. coli* and optionally a labeled secondary antibody that binds to the primary antibody for imaging (if the primary antibody does not contain a detectable label). In one embodiment, the captured *E. coli* bound on the FcMBL microbeads was incubated with an anti-LPS lipid A antibody (e.g., polyclonal antibody), for example, diluted by about 500-fold in TBST containing $Ca^{2+}$ 5 mM and 3% BSA for about 20 minutes, followed by incubation with an anti-goat IgG Cy3-labeled antibody, for example, diluted by about 2000-fold in TBST containing $Ca^{2+}$ 5 mM and 3% BSA for about 20 minutes. The labeled *E. coli* bound on FcMBL-coated microbeads were then imaged by a fluorescent microscope. As shown in FIGS. 31A-31B, the *E. coli*-specific antibody (e.g., anti-LPS Lipid A antibody) was shown to successfully bound to *E. coli* bound to FcMBL-coated substrates (e.g., magnetic microbeads or fluorescent microbeads). This binding was observed whether the capture of *E. coli* on FcMBL-coated magnetic beads (e.g., AKT-FcMBL-coated MYONE™ magnetic microbeads) was performed in buffer or in blood with anti-coagulation agents such as heparin (FIG. 31A) or EDTA (FIG. 31B). Microbeads incubated in blood or buffer without *E. coli* (e.g., not spiked with

*E. coli*) were not found to be bound by the anti-LPS Lipid A antibody. In addition, other antibodies (for example anti-LTA antibodies) that are not reactive to *E. coli* strain did not bind to the microbeads. Accordingly, characterization and/or identification of microbes or fragments thereof bound onto engineered microbe-binding molecules or substrates (e.g., FcMBL or FcMBL-coated microbeads) can be achieved, e.g., by use of antibodies specific to the microbe of interest.

In a rat sepsis model, samples (e.g., 200 μL) of blood and pleural fluid collected from the animal after 24-hr infection were incubated with 1 μm FcMBL microbeads as described herein. In some embodiments, the blood was treated with EDTA before the incubation with FcMBL microbeads.

In some embodiments, the FcMBL microbeads after incubation with a biological fluid sample (e.g., blood or pleural fluid) were further incubated with FcMBL-HRP for an ELISA assay as shown in FIG. 10. The blood-EDTA sample collected from a rat after 24-hour infection produced an ELISA signal of OD450 nm at ~0.8, while the pleural fluid sample collected at the same time point produced an ELISA signal overflow. Similar trends were observed in results obtained from 72-hr samples.

Figure 32A:
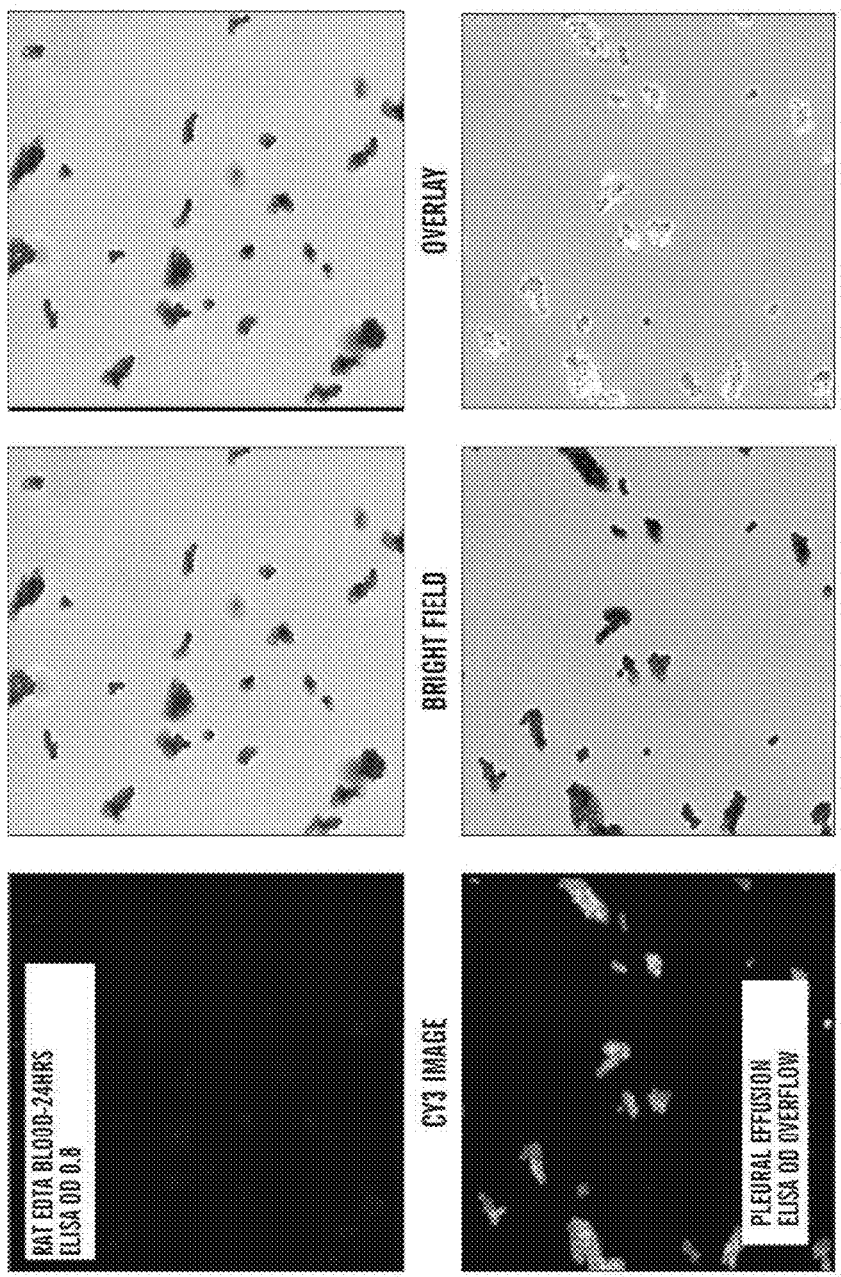
FIGS. 32A-32B are images showing capture of microbes on one or more embodiments of microbe-targeting substrates from samples of a rat sepsis model, followed by antibody characterization.
Figure 32B:
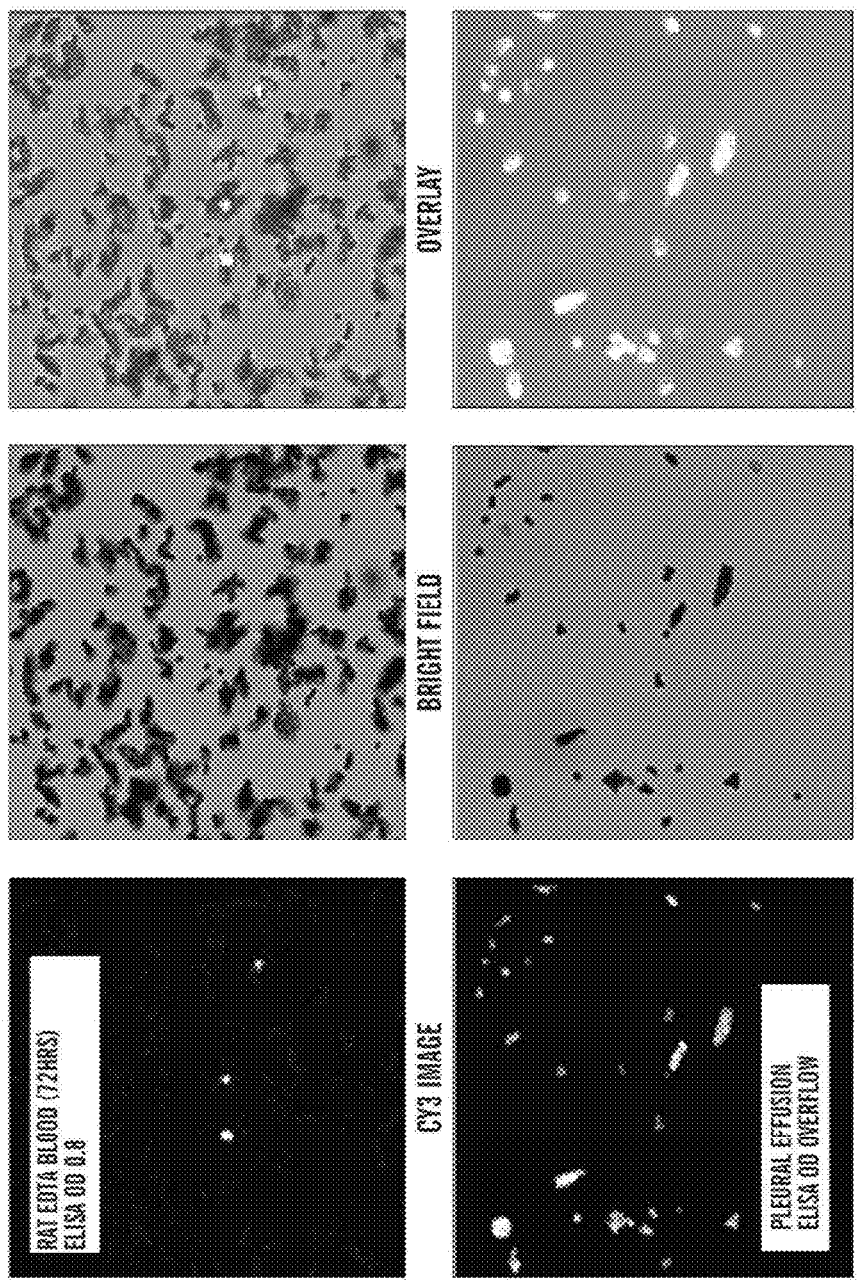

In other embodiments, the FcMBL microbeads after incubation with a biological fluid sample (e.g., blood or pleural fluid) was further subjected to an antibody-based characterization as described above. For example, the captured microbes bound on the FcMBL microbeads was incubated with an anti-LPS lipid A antibody (e.g., polyclonal antibody), for example, diluted by about 500-fold in TBST containing $Ca^{2+}$ 5 mM and 3% BSA for about 20 minutes, followed by incubation with an anti-goat IgG Cy3-labeled antibody, for example, diluted by about 2000-fold in TBST containing $Ca^{2+}$ 5 mM and 3% BSA for about 20 minutes. The labeled *E. coli* bound on FcMBL-coated microbeads were then imaged by a fluorescent microscope. The samples from a rat sepsis model were characterized for the presence of LPS on the FcMBL-coated microbeads (see FIGS. 32A-32B). The pleural effusion (ELISA OD—overflow) had widespread binding of anti-LPS antibodies whereas the blood sample from the rat (ELISA OD—0.8) had some of defined signals (FIGS. 32A-32B), which can be representative of intact *E. coli*.

Figure 33:
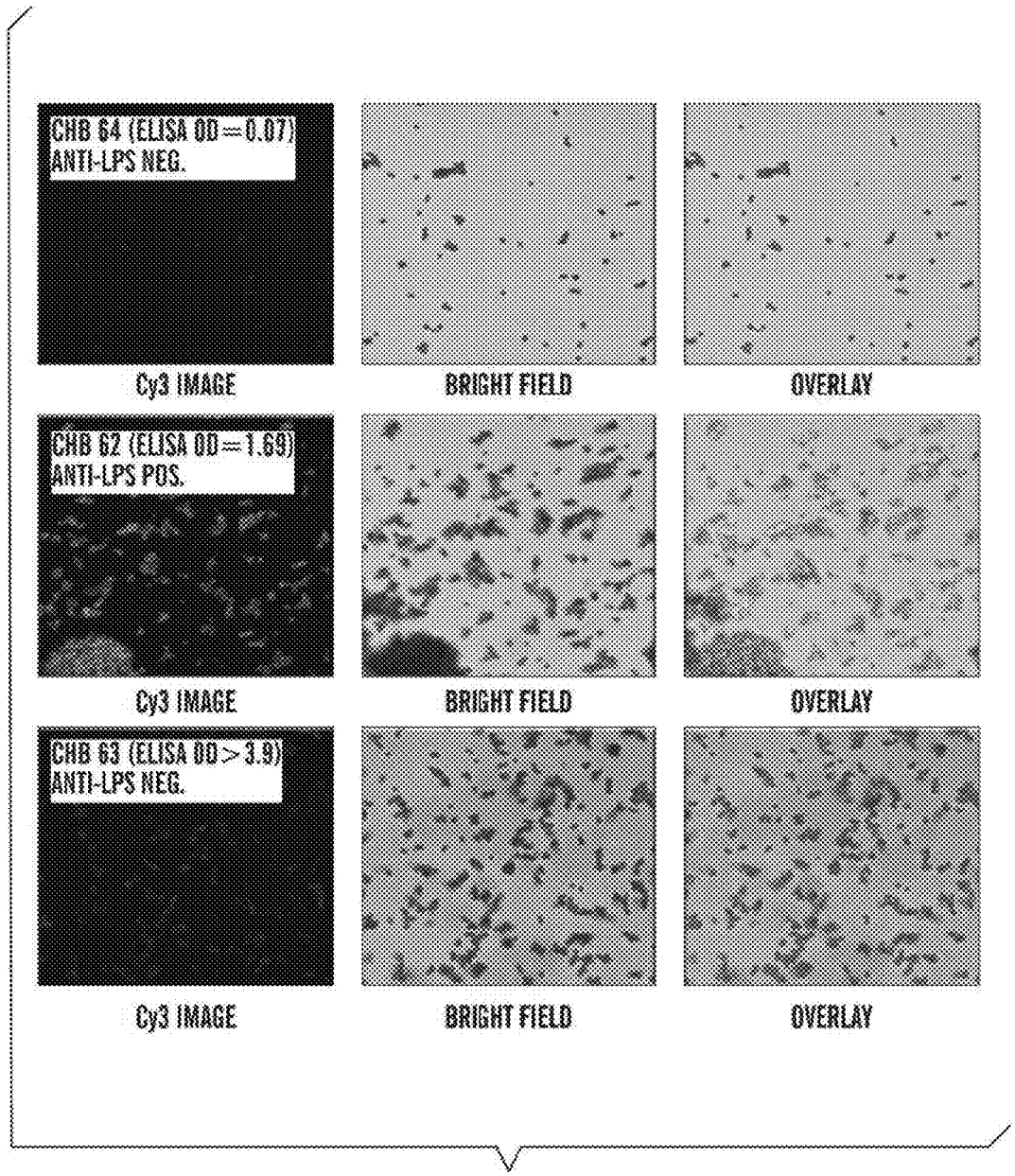
FIG. 33 is a set of images showing the use of specific antibodies to microbes to allow further discrimination or identification of samples that indicate positive signals with one or more embodiments of microbe-targeting substrates. De-identified clinical blood samples were screened by FcMBL ELISA described herein and the captured microbial matters (including intact cells and fragments thereof) on the FcMBL-coated microbeads were further screened by using an anti-LPS lipid A antibody. The top panel indicates that no detection of anti-LPS lipid A antibody signal was observed in clinical samples with substantially negative or negligible signal from FcMBL ELISA, indicative of no microbial infection detected in the clinical samples. The middle panel indicates that the microbial matter producing positive signal (OD=~1.69) in FcMBL ELISA bound to anti-LPS lipid A antibody, which indicates that the microbial matter could be derived from E. coli, and that the corresponding clinical samples had a gram-negative infection (e.g., E. coli infection). In contrast, the bottom panel indicates that the microbial matter producing positive signal (OD>3.9) did not bind to anti-LPS lipid A antibody, which indicates that the microbial matter could be derived from microbes other than E. coli, e.g., when the clinical samples were infected with a gram-positive microbe.

When applied to the clinical samples that are positive by FcMBL ELISA, the specific detection of certain molecules (e.g., proteins, carbohydrates, lipids) present on a microbe surface such as Lipid A can allow further discrimination of positive samples or identification of microbes present in the positive samples. In this regard, samples of de-identified blood samples from a hospital were incubated with 1 μm FcMBL microbeads as described herein. The FcMBL microbeads after incubation with the blood were first screened by further incubating with FcMBL-HRP for an ELISA assay as shown in FIG. 10. The FcMBL microbeads were then further subjected to an antibody-based characterization as described above. For example, in order to identify *E. coli*, the captured microbes bound on the FcMBL microbeads was incubated with an anti-LPS lipid A antibody (e.g., polyclonal antibody), for example, diluted by about 500-fold in TBST containing $Ca^{2+}$ 5 mM and 3% BSA for about 20 minutes, followed by incubation with an anti-goat IgG Cy3-labeled antibody, for example, diluted by about 2000-fold in TBST containing $Ca^{2+}$ 5 mM and 3% BSA for about 20 minutes. The labeled *E. coli* bound on FcMBL-coated microbeads were then imaged by a fluorescent microscope as shown in FIG. 33.

It was demonstrated herein that specific detection of LPS in FcMBL microbead bound microbes or microbial fragments was present in some positive samples but none in FcMBL ELISA samples generating negative or negligible signals (FIG. 33): this indicates that the use of a microbe family-specific antibody allows the discrimination of the microbe from which the captured material originates. For example, the sample (bottom panel) with a positive FcMBL ELISA signal did not demonstrate any binding of anti-LPS antibodies to the FcMBL-coated microbeads, indicating that the microbes and/or microbial fragments bound to the FcMBL-coated microbeads were not associated with *E. coli*. (e.g., when the sample was infected with a gram-positive microbe). In contrast, the sample (middle panel) with a positive FcMBL ELISA signal demonstrated substantial binding of anti-LPS antibodies to the FcMBL-coated microbeads, indicating that the microbes and/or microbial fragments bound to the FcMBL-coated microbeads were associated with *E. coli* or a gram-negative microbe. Accordingly, such sample was determined to be infected with *E. coli* and/or a gram-negative microbial infection. More importantly, it should be noted that each of these de-identified samples were determined to be culture negative using traditional methods in patients with clinical evidence of infection but no microbiological documentation. Accordingly, the use of engineered microbe-binding molecules or substrates (e.g., FcMBL or FcMBL-coated microbeads) is more sensitive and reliable than culture methods for diagnosis of an infection.

The screening of a library of antibodies directed against the most common microbes (including pathogens) can allow direct diagnosis of microbe-specific infections anywhere in the body by a simple blood or urine test available in less than three hours in any microbiology laboratory equipped for magnetic separation.

In a different embodiment, a rapid test could be performed using a "dipstick" format. For example, a membrane spotted with lines of microbial species-specific antibodies (instead of FcMBL molecules as shown in FIG. 13) can be incubated with the FcMBL-coated microbeads previously incubated with the fluid tested. The FcMBL-coated microbeads captured by the proper antibodies can form a detectable band (e.g., rust-colored for FcMBL-coated magnetic microbeads) on the membrane, indicating the species (one or many) of which microbial matter or microbes was captured.

Without wishing to be bound, while the Example demonstrates the use of specific antibodies to characterize and/or identify microbes present in a sample, other characterization methods such as mass spectrometric characterization methods can also be used. In some embodiments, the FcMBL microbeads with captured microbes and/or microbial matter/fragments can be washed prior to any characterization methods such as mass spectrometric characterization methods.

In some embodiments, the FcMBL-coated microbeads with captured microbes and/or microbial matter/fragments can be subjected to direct MALDI-TOF analysis for characterization and/or identification of species of microbes and/or microbial matter bound to the FcMBL-coated microbeads. For example, the FcMBL-coated microbeads with captured microbial materials can be directly subjected to MALDI-TOF analysis. Alternatively, any art-recognized protocols can be applied on the FcMBL-coated microbeads to recover bound microbes and/or microbial compounds/fragments prior to MALDI-TOF analysis. Exemplary methods to recover bound microbes and/or microbial compounds/fragments prior to MALDI-TOF analysis include, but are not limited to, $Ca^{2+}$ chelation of FcMBL-coated microbeads to release MBL bound material; lowering pH to release Fcbound protein A; protein extraction using formic acid and acetonitrile, and any combinations thereof. The control microbeads (e.g., non-FcMBL-coated microbeads) can be treated similarly for baseline determination.

Extracted captured material from FcMBL-coated microbeads and/or non-specific control-bound material can be subjected to mass spectrometric analysis, including but not limited to, MALDI-TOF or MALDI-TOF-TOF. The non-specific control-bound material can establish a baseline for the composition of the medium tested. This profile can be used as reference for the analysis of the FcMBL-bound material. Peaks present in the control-bound samples can be subtracted from the profile obtained from FcMBL-bound material.

The specific FcMBL bound material profile (e.g., after subtraction of the reference profile) can constitute the microbe signature. Both positive and/or negative charge analysis can be performed to identify informative peaks.

The microbe signature recognition can be analyzed by comparing the specific FcMBL bound material profiles to microbe signature libraries, e.g., using algorithms based on the previously accumulated profiles such as matching comparison algorithms.

For identification of microbe species, depending on origins of microbes, a microbe signature library can be established by in vivo or in situ samples such as clinical-trial derived samples and/or environment derived samples (e.g., samples collected from a clinical setting, culture medium, food processing plant, water source). For example, blood (or other biological fluids) of patients infected with known microbes, e.g., pathogens, can be analyzed and a microbial material signature can be characterized. Recognition of the signature in the same clinical context can establish the family/genus/species diagnosis.

Additionally or alternatively, another microbe library can be established from in vitro analysis of FcMBL binding moieties of microbes submitted to mechanical or chemical or antibiotic lysis or autolysis. The microbial material can be captured in different media, buffer, urine, blood or any appropriate medium.

The diagnostic profiles can be matched to any reference profiles, e.g., specific in vivo or in situ derived microbe profiles and/or specific in-vitro derived microbes profiles for identification with a probability score for generic infection, clades level, family level, genus level or species level identification.

Example 17: Performance Comparison of Colorimetric ELISA Using FcMBL Magnetic Microbeads and Conventional Blood Cultures An animal model simulating intra-abdominal sepsis was produced by implanting large bowel or cecal contents in the pelvic region of rats. The bowel or cecal contents were harvested from rats fed on a beef diet for 2 weeks. Based on MALDI-TOF analysis, the cecal contents contained different pathogens including *Clostridium perfringiens*, *Enterobacteria*, *Enterococcus avium/raffinosus*, and *Enterococcus* spp. Additional details on creation of an animal model (e.g., a rat) with an intra-adominal sepsis can be found in Weinstein et al (1974) *Infection and Immunity*. 10: 1250-1255 and Onderdonk et al. (1974) *Infection and Immunity*. 10: 1256-1259.

In one experiment, the cecal contents ($10^9$ bacterial cells) were implanted in the pelvic region of five rats. Rats were scarified at different time points according to their morbidity after the implantation and their morbidity ranking is shown in Table 1.

TABLE 1

Morbidity ranking of rats after implantation of cecal contents pelvic region of rats.

|  | Morbidity ranking (scale 1-5) | Sacrifice time point (hrs after implantation) |
| --- | --- | --- |
| Rat #1 | 1 (sickest) | 10 hours |
| Rat #2 | 2 | 18 hours |
| Rat #3 | 3 | 48 hours |
| Rat #4 | 5 (the least sickest) | 48 hours |
| Rat #5 | 4 | 48 hours |

The rats were sacrificed and blood was collected for further analysis. In order to compare the performance of the conventional blood cultures and colorimetric ELISA using FcMBL magnetic microbeads described herein (e.g., in Example 10), blood collected from the rats was analyzed by the two different methods. For conventional blood culture methods, the rat blood was cultured anaerobically for 4 days in different bacterial culture media (e.g., chocolate agar, sheep blood agar (SBA), Luria Broth (LB) and colistin Nalidixic Acid Agar (CNA) that is generally used for selective isolation of Gram-positive cocci). For FcMBL-based ELISA methods, the rat blood was diluted and subjected to FcMBL-based colorimetric ELISA described in Example 10, where the FcMBL magnetic beads captured both live and dead pathogens directly from the diluted rat blood, and the captured matter was then incubated with HRP-FcMBL detection reagent followed by a colorimetric readout of OD450 with TMB substrate. The FcMBL-based colorimetric ELISA was performed in less than 1 hour.

Figure 34A:
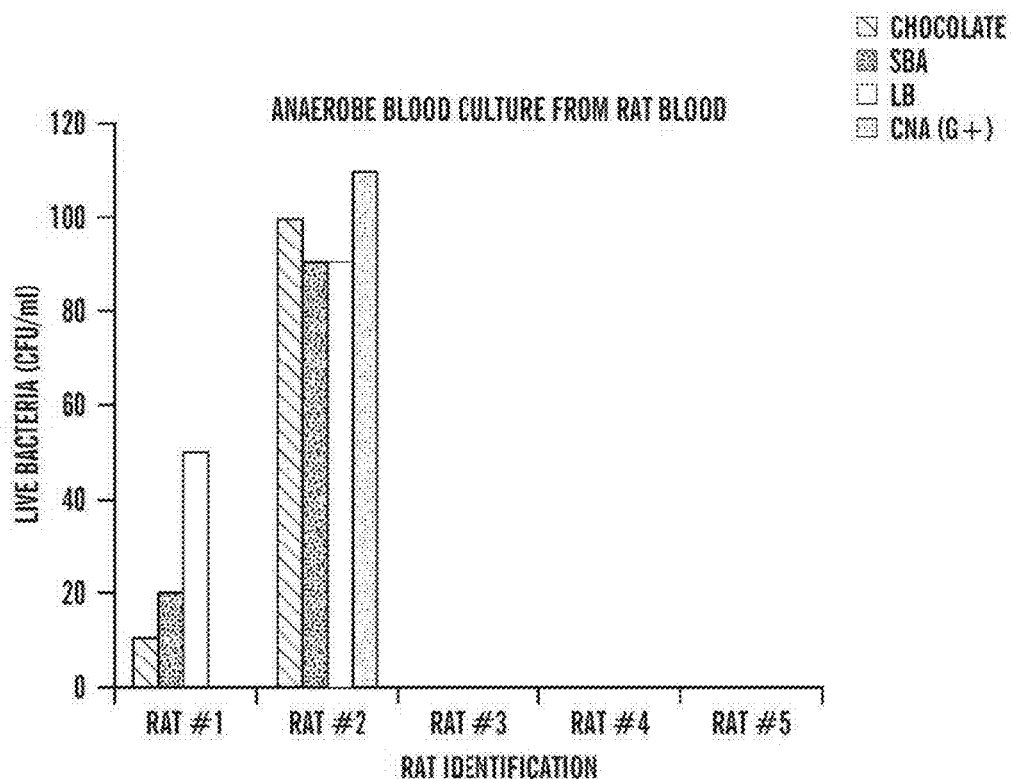
FIGS. 34A-34D are data graphs showing that use of FcMBL magnetic microbeads is a more sensitive and reliable measure of blood-borne pathogens (including live and non-viable pathogens such as dead pathogens and endotoxins) than conventional blood cultures.

FIG. 34A shows results of anaerobe cultures at Day 4 of the blood collected from the five rats developed with intra-abdominal abscesses. While Rat #1 appeared to be sicker than Rat #2 and needed to be sacrificed the first, the blood culture indicated that there were more bacteria present in the blood of Rat #2 than in Rat #1. Further, the blood culture method was not sensitive enough to detect bacteria present in Rat #3, even though Rat #3 appeared to be sick 48 hours after the implantation.

Figure 34B:
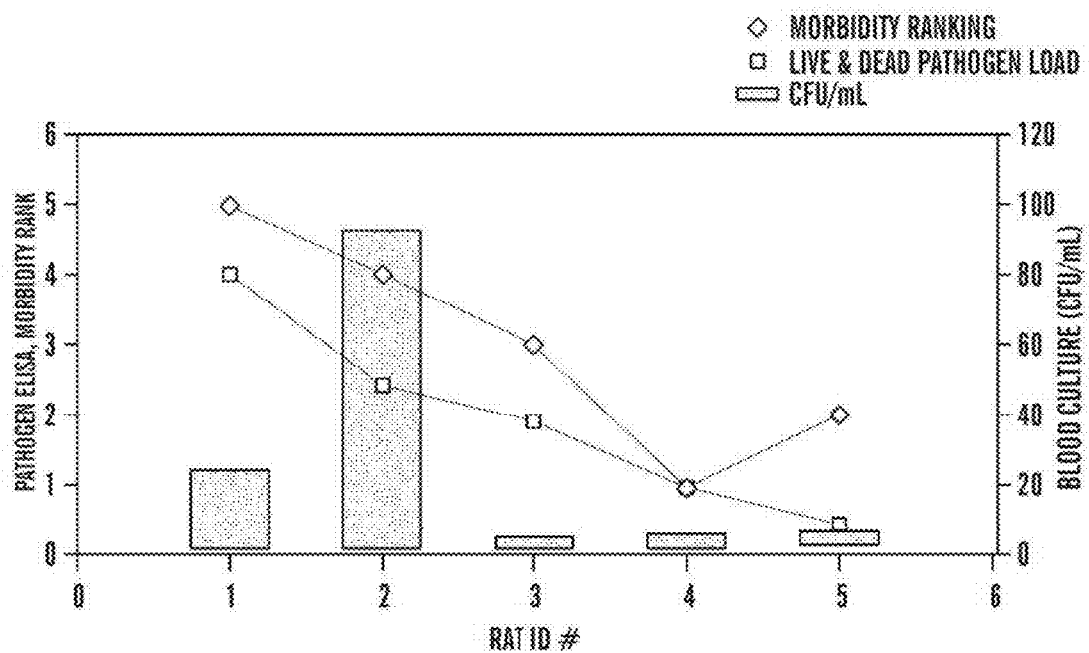
Figure 34C:
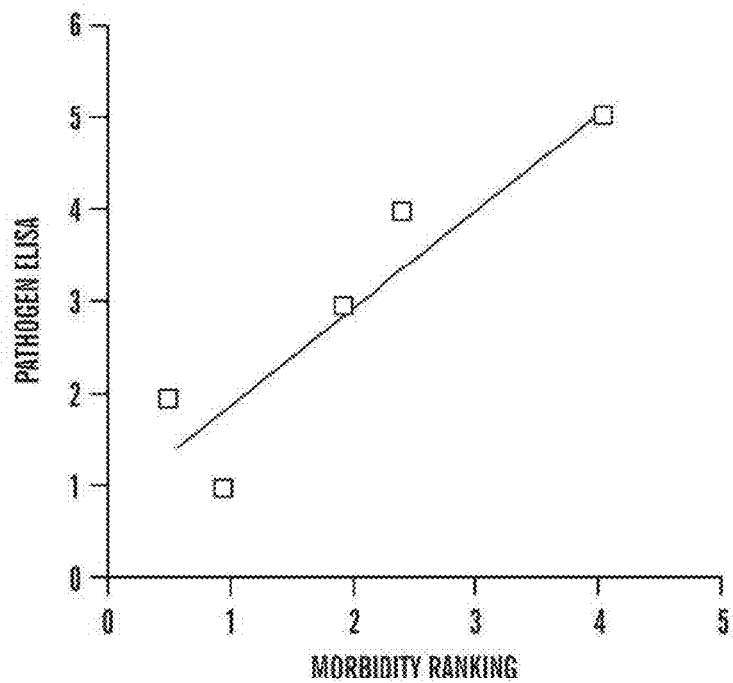

In contrast, as shown in FIG. 34B, the FcMBL-based ELISA assay provided a better correlation of the pathogen load (including live and dead pathogens/microbial matter) with morbidity ranking than what was indicated by blood cultures. FIG. 34C shows a substantially linear correlation of pathogen load determined by the ELISA using FcMBL magnetic microbeads with morbidity ranking. Further, the FcMBL-based ELISA assay was more sensitive than the blood culture method, as evidenced by detectable levels of pathogen loads using FcMBL-based ELISA assay, as compared to undetectable levels in blood cultures, even after 4 days of culturing (FIG. 34B).

A similar rat animal study was performed separately, as described above. Rats were scarified at different time points according to their morbidity after the implantation and their morbidity ranking is shown in Table 2.

TABLE 2

Morbidity ranking of rats after implantation of cecal contents pelvic region of rats.

|  | Morbidity ranking (scale 1-5) | Sacrifice time point (time after implantation) |
|---|---|---|
| Rat #21 | 4-5 (with 5 the least sickest) | 5 days |
| Rat #22 | 4-5 | 5 days |
| Rat #23 | 1 (the most sickest) | 11 hours |
| Rat #24 | 4-5 | 5 days |
| Rat #25 | 2 | 11 hours |

Figure 34D:
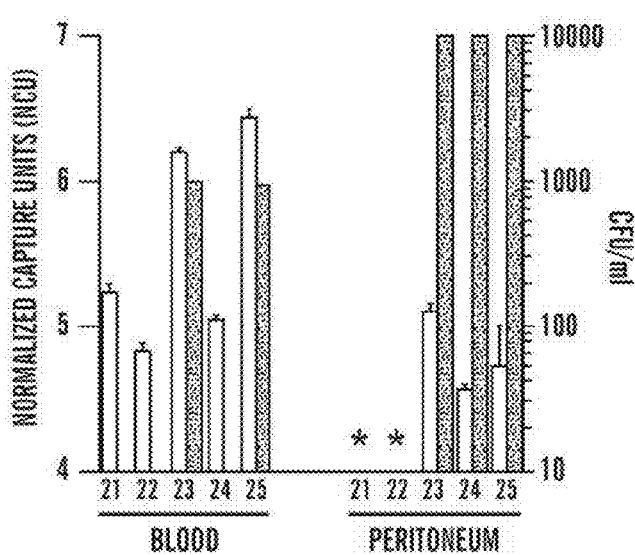

Similar to the previous experiment, as shown in FIG. 34D, rats with positive blood culture died of sepsis and they also had high levels of microbes (live and dead) and microbial matter (e.g., endotoxin and microbial debris) detected by FcMBL-based ELISA. Based on FIGS. 34B and 34D, the surviving rats had about 2 logs less microbes (live and dead) and microbial matter (e.g., endotoxin and microbial debris) in the blood than the rats which died from sepsis. The FcMBL-based ELISA was sensitive enough to detect such low levels of microbes and microbial matter in surviving rat blood, which was usually not detectable by blood cultures.

Accordingly, this Example shows that FcMBL microbeads can bind cecal microbes used in the intraabdominal sepsis model. Further, an ELISA using FcMBL reagents can be used to rapidly detect live microbes and/or non-viable microbial matter (including dead microbes and endotoxins) in a blood sample (e.g., 1-hour ELISA assay vs. 4-day blood culture). Further, the ELISA using FcMBL reagents is demonstrated to be more sensitive than blood cultures.

Figure 35:
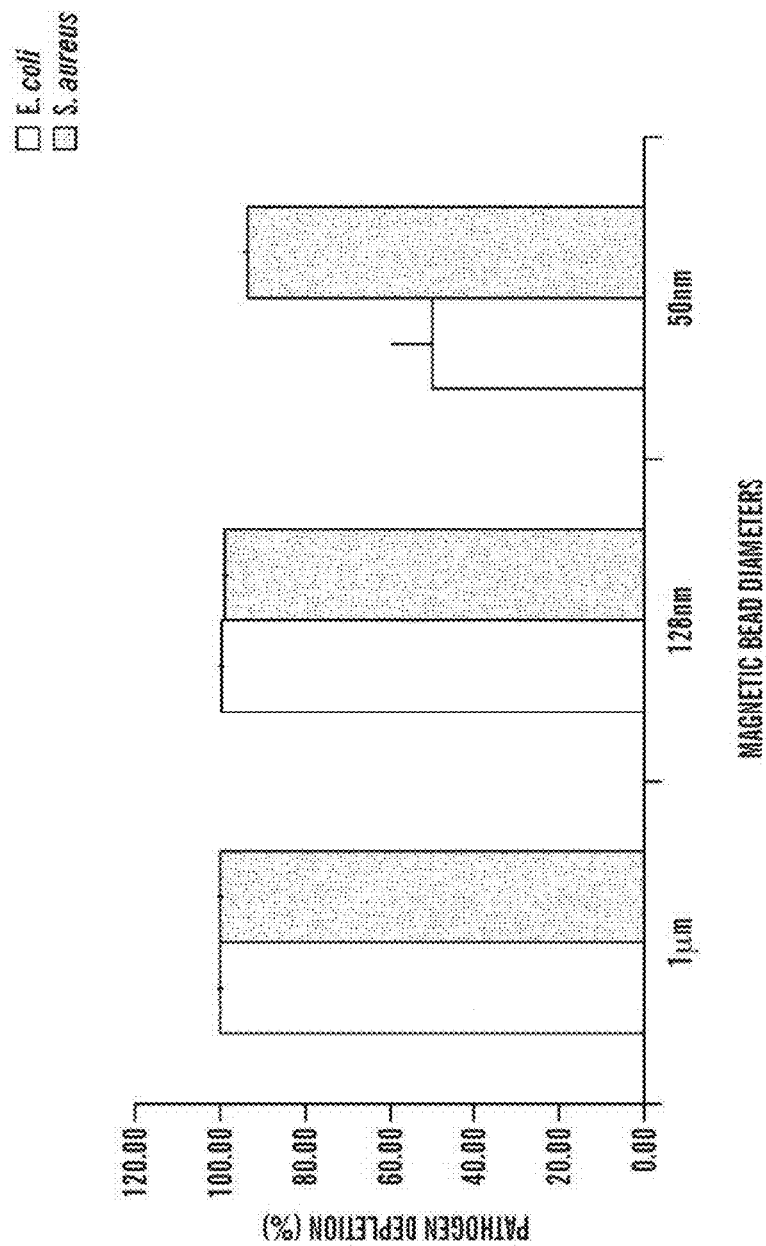
FIG. 35 is a bar graph showing percentages of microbe depletion by one or more embodiments of the microbe-targeting magnetic microbeads. FcMBL-coated magnetic microbeads of different sizes (~1 μm, ~128 nm, and ~50 nm) were used to capture E. coli and S. aureus that were initially spiked into a buffered solution. The microbe-bound FcMBL-coated magnetic microbeads were then removed from the buffered solution. After removal of the magnetic microbeads, the buffered solution was used for inoculaton on LB plates to determine the level of microbe depletion by FcMBL-coated magnetic microbeads of different sizes.

Example 18: Microbe Depletion Using FcMBL-Coated Magnetic Microbeads of Different Sizes To assess the performance of FcMBL-coated magnetic microbeads of different sizes to capture a microbe in a test sample, FcMBL-coated magnetic microbeads were produced by conjugating a saturating amount of biotinylated FcMBL molecules to magnetic microbeads of different sizes: (1) 1 µm MYONE™ T1 Streptavidin microbeads; (2) 128 nm Ademtech microbeads coated with streptavidin; and (3) 50 nm Miltenyi microbeads coated with anti-biotin IgG. Appropriate volumes (e.g., ~20 µL) of different sized FcMBL-coated magnetic microbeads were then added to aliquots of a sample (e.g., ~1 mL) containing *E. coli* or *S. aureus* cells. The mixture was then mixed for about 10 mins (e.g., using a HULAMIXER™ sample mixer), followed by magnetic separation of the microbeads. The supernatant after removal of the microbeads was then plated on LB agar, which was then incubated overnight at ~37° C. Any microbes that were not captured by the FcMBL-coated magnetic microbeads will grow on LB agar overnight. FIG. 35 indicates successful depletion of microbes (e.g., *E. coli* or *S. aureus*) present in a test sample using FcMBL-coated magnetic microbeads of different sizes.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

```
                                                        (SEQ ID NO. 1)
MSLFPSLPLL  LLSMVAASYS  ETVTCEDAQK  TCPAVIACSS  PGINGFPGKD  GRDGTKGEKG

EPGQGLRGLQ  GPPGKLGPPG  NPGPSGSPGP  KGQKGDPGKS  PDGDSSLAAS  ERKALQTEMA

RIKKWLTFSL  GKQVGNKFFL  TNGEIMTFEK  VKALCVKFQA  SVATPRNAAE  NGAIQNLIKE

EAFLGITDEK  TEGQFVDLTG  NRLTYTNWNE  GEPNNAGSDE  DCVLLLKNGQ  WNDVPCSTSH

LAVCEFPI (SEQ ID NO. 2)
ETVTCEDAQK  TCPAVIACSS  PGINGFPGKD  GRDGTKGEKG  EPGQGLRGLQ  GPPGKLGPPG

NPGPSGSPGP  KGQKGDPGKS  PDGDSSLAAS  ERKALQTEMA  RIKKWLTFSL  GKQVGNKFFL

TNGEIMTFEK  VKALCVKFQA  SVATPRNAAE  NGAIQNLIKE  EAFLGITDEK  TEGQFVDLTG

NRLTYTNWNE  GEPNNAGSDE  DCVLLLKNGQ  WNDVPCSTSH  LAVCEFPI (SEQ ID NO. 3)
AASERKALQT  EMARIKKWLT  FSLGKQVGNK  FFLTNGEIMT  FEKVKALCVK  FQASVATPRN

AAENGAIQNL  IKEEAFLGIT  DEKTEGQFVD  LTGNRLTYTN  WNEGEPNNAG  SDEDCVLLLK

NGQWNDVPCS  TSHLAVCEFP  I (SEQ ID NO. 4)
VGNKFFLTNG  EIMTFEKVKA  LCVKFQASVA  TPRNAAENGA  IQNLIKEEAF  LGITDEKTEG

QFVDLTGNRL  TYTNWNEGEP  NNAGSDEDCV  LLLKNGQWND  VPCSTSHLAV  CEFPI
```

-continued (SEQ ID NO. 5)
PDGDSSLAAS ERKALQTEMA RIKKWLTFSL GKQVGNKFFL TNGEIMTFEK VKALCVKFQA

SVATPRNAAE NGAIQNLIKE EAFLGITDEK TEGQFVDLTG NRLTYTNWNE GEPNNAGSDE

DCVLLLKNGQ WNDVPCSTSH LAVCEFPI (SEQ ID NO. 6)
EPKSSDKTHT CPPCPAPELL GGPSVFLFPP KPKDTLMISR TPEVTCVVVD VSHEDPEVKF

NWYVDGVEVH NAKTKPREEQ YNSTYRVVSV LTVLHQDWLN GKEYKCKVSN KALPAPIEKT

ISKAKGQPRE PQVYTLPPSR DELTKNQVSL TCLVKGFYPS DIAVEWESNG QPENNYKTTP

PVLDSDGSFF LYSKLTVDKS RWQQGNVFSC SVMHEALHNH YTQKSLSLSP GAPDGDSSLA

ASERKALQTE MARIKKWLTF SLGKQVGNKF FLTNGEIMTF EKVKALCVKF QASVATPRNA

AENGAIQNLI KEEAFLGITD EKTEGQFVDL TGNRLTYTNW NEGEPNNAGS DEDCVLLLKN

GQWNDVPCST SHLAVCEFPI (SEQ ID NO. 7)
AKTEPKSSDKTHT CPPCPAPELL GGPSVFLFPP KPKDTLMISR TPEVTCVVVD VSHEDPEVKF

NWYVDGVEVH NAKTKPREEQ YNSTYRVVSV LTVLHQDWLN GKEYKCKVSN KALPAPIEKT

ISKAKGQPRE PQVYTLPPSR DELTKNQVSL TCLVKGFYPS DIAVEWESNG QPENNYKTTP

PVLDSDGSFF LYSKLTVDKS RWQQGNVFSC SVMHEALHNH YTQKSLSLSP GAPDGDSSLA

ASERKALQTE MARIKKWLTF SLGKQVGNKF FLTNGEIMTF EKVKALCVKF QASVATPRNA

AENGAIQNLI KEEAFLGITD EKTEGQFVDL TGNRLTYTNW NEGEPNNAGS DEDCVLLLKN

GQWNDVPCST SHLAVCEFPI (SEQ ID NO. 8)
EPKSSDKTHT CPPCPAPELL GGPSVFLFPP KPKDTLMISR TPEVTCVVVD VSHEDPEVKF

NWYVDGVEVH NAKTKPREEQ YNSTYRVVSV LTVLHQDWLN GKEYKCKVSN KALPAPIEKT

ISKAKGQPRE PQVYTLPPSR DELTKNQVSL TCLVKGFYPS DIAVEWESNG QPENNYKTTP

PVLDSDGSFF LYSKLTVDKS RWQQGNVFSC SVMHEALHNH YTQKSLSLSP GATSKQVGNKF

FLTNGEIMTF EKVKALCVKF QASVATPRNA AENGAIQNLI KEEAFLGITD EKTEGQFVDL

TGNRLTYTNW NEGEPNNAGS DEDCVLLLKN GQWNDVPCST SHLAVCEFPI (SEQ ID NO. 9)
EPKSSDKTHT CPPCPAPELL GGPSVFLFPP KPKDTLMISR TPEVTCVVVD VSHEDPEVKF

NWYVDGVEVH NAKTKPREEQ YNSTYRVVSV LTVLHQDWLN GKEYKCKVSN KALPAPIEKT

ISKAKGQPRE PQVYTLPPSR DELTKNQVSL TCLVKGFYPS DIAVEWESNG QPENNYKTTP

PVLDSDGSFF LYSKLTVDKS RWQQGNVFSC SVMHEALHNH YTQKSLSLSP GA

---

What is claimed is:

1. An engineered microbe-targeting molecule comprising:
   a) at least one microbe surface-binding domain that comprises a carbohydrate recognition domain or fragment thereof of mannose-binding lectin;
   b) a substrate-binding domain comprising an AKT tripeptide adapted for orienting the microbe surface-binding domain away from a substrate; and
   c) at least one linker comprising an Fc region of an immunoglobulin, the linker positioned between the microbe surface-binding domain and the substrate-binding domain, wherein the AKT tripeptide is inserted at an N-terminus of the Fc region.

2. The engineered molecule of claim 1, wherein the immunoglobulin is selected from the group consisting of IgA, IgD, IgE, IgG, and IgM.

3. A kit comprising:
   a) one or more containers containing a population of engineered microbe-targeting molecules comprising:
      i. at least one microbe surface-binding domain that comprises a carbohydrate recognition domain (CRD) or fragment thereof of mannose-binding lectin;
      ii. a substrate-binding domain comprising an AKT tripeptide adapted for orienting the microbe surface-binding domain away from a substrate; and
      iii. at least one linker comprising an Fc region of an immunoglobulin, the linker positioned between the microbe surface-binding domain and the substrate-binding domain, wherein the AKT tripeptide is inserted at an N-terminus of the Fc region; and
   b) a blocking reagent, a microbe lysing reagent, or a degradative enzyme reagent.

4. The kit of claim 3, further comprising one or more substrates to which the engineered microbe-targeting molecules are conjugated.

5. The kit of claim 4, wherein the substrates are selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a spiral mixer, and a hollow-fiber reactor.

6. The kit of claim 5, wherein the substrates include a population of the microbeads.

* * * * *

SEQUENCE LISTING

<160> NUMBER OF SEQ ID NOS: 21

<210> SEQ ID NO 1
<211> LENGTH: 248
<212> TYPE: PRT
<213> ORGANISM: Homo sapiens

<400> SEQUENCE: 1

Met Ser Leu Phe Pro Ser Leu Pro Leu Leu Leu Ser Met Val Ala
1               5                   10                  15

Ala Ser Tyr Ser Glu Thr Val Thr Cys Glu Asp Ala Gln Lys Thr Cys
            20                  25                  30

```
Pro Ala Val Ile Ala Cys Ser Ser Pro Gly Ile Asn Gly Phe Pro Gly
            35                  40                  45
Lys Asp Gly Arg Asp Gly Thr Lys Gly Glu Lys Gly Glu Pro Gly Gln
 50                  55                  60
Gly Leu Arg Gly Leu Gln Gly Pro Pro Gly Lys Leu Gly Pro Pro Gly
 65                  70                  75                  80
Asn Pro Gly Pro Ser Gly Ser Pro Gly Pro Lys Gly Gln Lys Gly Asp
                 85                  90                  95
Pro Gly Lys Ser Pro Asp Gly Asp Ser Ser Leu Ala Ala Ser Glu Arg
            100                 105                 110
Lys Ala Leu Gln Thr Glu Met Ala Arg Ile Lys Lys Trp Leu Thr Phe
            115                 120                 125
Ser Leu Gly Lys Gln Val Gly Asn Lys Phe Phe Leu Thr Asn Gly Glu
130                 135                 140
Ile Met Thr Phe Glu Lys Val Lys Ala Leu Cys Val Lys Phe Gln Ala
145                 150                 155                 160
Ser Val Ala Thr Pro Arg Asn Ala Ala Glu Asn Gly Ala Ile Gln Asn
                165                 170                 175
Leu Ile Lys Glu Glu Ala Phe Leu Gly Ile Thr Asp Glu Lys Thr Glu
            180                 185                 190
Gly Gln Phe Val Asp Leu Thr Gly Asn Arg Leu Thr Tyr Thr Asn Trp
            195                 200                 205
Asn Glu Gly Glu Pro Asn Asn Ala Gly Ser Asp Glu Asp Cys Val Leu
            210                 215                 220
Leu Leu Lys Asn Gly Gln Trp Asn Asp Val Pro Cys Ser Thr Ser His
225                 230                 235                 240
Leu Ala Val Cys Glu Phe Pro Ile
                245

<210> SEQ ID NO 2
<211> LENGTH: 228
<212> TYPE: PRT
<213> ORGANISM: Homo sapiens

<400> SEQUENCE: 2

Glu Thr Val Thr Cys Glu Asp Ala Gln Lys Thr Cys Pro Ala Val Ile
 1               5                  10                  15
Ala Cys Ser Ser Pro Gly Ile Asn Gly Phe Pro Gly Lys Asp Gly Arg
                 20                  25                  30
Asp Gly Thr Lys Gly Glu Lys Gly Glu Pro Gly Gln Gly Leu Arg Gly
             35                  40                  45
Leu Gln Gly Pro Pro Gly Lys Leu Gly Pro Pro Gly Asn Pro Gly Pro
 50                  55                  60
Ser Gly Ser Pro Gly Pro Lys Gly Gln Lys Gly Asp Pro Gly Lys Ser
 65                  70                  75                  80
Pro Asp Gly Asp Ser Ser Leu Ala Ala Ser Glu Arg Lys Ala Leu Gln
                 85                  90                  95
Thr Glu Met Ala Arg Ile Lys Lys Trp Leu Thr Phe Ser Leu Gly Lys
            100                 105                 110
Gln Val Gly Asn Lys Phe Phe Leu Thr Asn Gly Glu Ile Met Thr Phe
            115                 120                 125
Glu Lys Val Lys Ala Leu Cys Val Lys Phe Gln Ala Ser Val Ala Thr
            130                 135                 140
Pro Arg Asn Ala Ala Glu Asn Gly Ala Ile Gln Asn Leu Ile Lys Glu
145                 150                 155                 160
```

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190

Pro Asn Asn Ala Gly Ser Asp Glu Asp Cys Val Leu Leu Lys Asn
        195                 200                 205

Gly Gln Trp Asn Asp Val Pro Cys Ser Thr Ser His Leu Ala Val Cys
    210                 215                 220

Glu Phe Pro Ile
225

<210> SEQ ID NO 3
<211> LENGTH: 141
<212> TYPE: PRT
<213> ORGANISM: Homo sapiens

<400> SEQUENCE: 3

Ala Ala Ser Glu Arg Lys Ala Leu Gln Thr Glu Met Ala Arg Ile Lys
1               5                   10                  15

Lys Trp Leu Thr Phe Ser Leu Gly Lys Gln Val Gly Asn Lys Phe Phe
            20                  25                  30

Leu Thr Asn Gly Glu Ile Met Thr Phe Glu Lys Val Lys Ala Leu Cys
        35                  40                  45

Val Lys Phe Gln Ala Ser Val Ala Thr Pro Arg Asn Ala Ala Glu Asn
    50                  55                  60

Gly Ala Ile Gln Asn Leu Ile Lys Glu Glu Ala Phe Leu Gly Ile Thr
65                  70                  75                  80

Asp Glu Lys Thr Glu Gly Gln Phe Val Asp Leu Thr Gly Asn Arg Leu
                85                  90                  95

Thr Tyr Thr Asn Trp Asn Glu Gly Glu Pro Asn Asn Ala Gly Ser Asp
            100                 105                 110

Glu Asp Cys Val Leu Leu Lys Asn Gly Gln Trp Asn Asp Val Pro
        115                 120                 125

Cys Ser Thr Ser His Leu Ala Val Cys Glu Phe Pro Ile
    130                 135                 140

<210> SEQ ID NO 4
<211> LENGTH: 115
<212> TYPE: PRT
<213> ORGANISM: Homo sapiens

<400> SEQUENCE: 4

Val Gly Asn Lys Phe Phe Leu Thr Asn Gly Glu Ile Met Thr Phe Glu
1               5                   10                  15

Lys Val Lys Ala Leu Cys Val Lys Phe Gln Ala Ser Val Ala Thr Pro
            20                  25                  30

Arg Asn Ala Ala Glu Asn Gly Ala Ile Gln Asn Leu Ile Lys Glu Glu
        35                  40                  45

Ala Phe Leu Gly Ile Thr Asp Glu Lys Thr Glu Gly Gln Phe Val Asp
    50                  55                  60

Leu Thr Gly Asn Arg Leu Thr Tyr Thr Asn Trp Asn Glu Gly Glu Pro
65                  70                  75                  80

Asn Asn Ala Gly Ser Asp Glu Asp Cys Val Leu Leu Lys Asn Gly
                85                  90                  95

Gln Trp Asn Asp Val Pro Cys Ser Thr Ser His Leu Ala Val Cys Glu
            100                 105                 110

Phe Pro Ile
        115

<210> SEQ ID NO 5
<211> LENGTH: 148
<212> TYPE: PRT
<213> ORGANISM: Homo sapiens

<400> SEQUENCE: 5

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
        35                  40                  45

Glu Lys Val Lys Ala Leu Cys Val Lys Phe Gln Ala Ser Val Ala Thr
    50                  55                  60

Pro Arg Asn Ala Ala Glu Asn Gly Ala Ile Gln Asn Leu Ile Lys Glu
65                  70                  75                  80

Glu Ala Phe Leu Gly Ile Thr Asp Glu Lys Thr Glu Gly Gln Phe Val
                85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Leu Lys Asn
        115                 120                 125

Gly Gln Trp Asn Asp Val Pro Cys Ser Thr Ser His Leu Ala Val Cys
    130                 135                 140

Glu Phe Pro Ile
145

<210> SEQ ID NO 6
<211> LENGTH: 380
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr

```
            130                 135                 140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

Thr Asn Gly Glu Ile Met Thr Phe Glu Lys Val Lys Ala Leu Cys Val
        275                 280                 285

Lys Phe Gln Ala Ser Val Ala Thr Pro Arg Asn Ala Ala Glu Asn Gly
    290                 295                 300

Ala Ile Gln Asn Leu Ile Lys Glu Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Leu Lys Asn Gly Gln Trp Asn Asp Val Pro Cys
        355                 360                 365

Ser Thr Ser His Leu Ala Val Cys Glu Phe Pro Ile
    370                 375                 380

<210> SEQ ID NO 7
<211> LENGTH: 383
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
                20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Lys Phe Asn
        50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110
```

Asn Lys Ala Leu Pro Ala Pro Ile Glu Lys Thr Ile Ser Lys Ala Lys
            115                 120                 125

Gly Gln Pro Arg Glu Pro Gln Val Tyr Thr Leu Pro Pro Ser Arg Asp
        130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
                245                 250                 255

Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
        275                 280                 285

Leu Cys Val Lys Phe Gln Ala Ser Val Ala Thr Pro Arg Asn Ala Ala
290                 295                 300

Glu Asn Gly Ala Ile Gln Asn Leu Ile Lys Glu Ala Phe Leu Gly
305                 310                 315                 320

Ile Thr Asp Glu Lys Thr Glu Gly Gln Phe Val Asp Leu Thr Gly Asn
                325                 330                 335

Arg Leu Thr Tyr Thr Asn Trp Asn Glu Gly Glu Pro Asn Asn Ala Gly
            340                 345                 350

Ser Asp Glu Asp Cys Val Leu Leu Leu Lys Asn Gly Gln Trp Asn Asp
        355                 360                 365

Val Pro Cys Ser Thr Ser His Leu Ala Val Cys Glu Phe Pro Ile
370                 375                 380

<210> SEQ ID NO 8
<211> LENGTH: 351
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Thr Ser Lys Gln Val Gly Asn Lys
225                 230                 235                 240

Phe Phe Leu Thr Asn Gly Glu Ile Met Thr Phe Glu Lys Val Lys Ala
                245                 250                 255

Leu Cys Val Lys Phe Gln Ala Ser Val Ala Thr Pro Arg Asn Ala Ala
            260                 265                 270

Glu Asn Gly Ala Ile Gln Asn Leu Ile Lys Glu Glu Ala Phe Leu Gly
        275                 280                 285

Ile Thr Asp Glu Lys Thr Glu Gly Gln Phe Val Asp Leu Thr Gly Asn
    290                 295                 300

Arg Leu Thr Tyr Thr Asn Trp Asn Glu Gly Glu Pro Asn Asn Ala Gly
305                 310                 315                 320

Ser Asp Glu Asp Cys Val Leu Leu Leu Lys Asn Gly Gln Trp Asn Asp
                325                 330                 335

Val Pro Cys Ser Thr Ser His Leu Ala Val Cys Glu Phe Pro Ile
            340                 345                 350

<210> SEQ ID NO 9
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
```

```
                    85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
            115                 120                 125
Arg Glu Pro Gln Val Tyr Thr Leu Pro Pro Ser Arg Asp Glu Leu Thr
        130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
210                 215                 220
Ser Leu Ser Leu Ser Pro Gly Ala
225                 230

<210> SEQ ID NO 10
<211> LENGTH: 2
<212> TYPE: PRT
<213> ORGANISM: Homo sapiens

<400> SEQUENCE: 10

Asn Asp
1

<210> SEQ ID NO 11
<211> LENGTH: 3
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any amino acid

<400> SEQUENCE: 11

Glu Xaa Asn
1

<210> SEQ ID NO 12
<211> LENGTH: 10
<212> TYPE: PRT
<213> ORGANISM: Homo sapiens

<400> SEQUENCE: 12

Asn Glu Gly Glu Pro Asn Asn Ala Gly Ser
1               5                   10

<210> SEQ ID NO 13
<211> LENGTH: 9
<212> TYPE: PRT
<213> ORGANISM: Homo sapiens

<400> SEQUENCE: 13

Gly Ser Asp Glu Asp Cys Val Leu Leu
1               5

<210> SEQ ID NO 14
```

```
<211> LENGTH: 15
<212> TYPE: PRT
<213> ORGANISM: Homo sapiens

<400> SEQUENCE: 14

Leu Leu Leu Lys Asn Gly Gln Trp Asn Asp Val Pro Cys Ser Thr
1               5                   10                  15

<210> SEQ ID NO 15
<211> LENGTH: 33
<212> TYPE: PRT
<213> ORGANISM: Homo sapiens

<400> SEQUENCE: 15

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
                20                  25                  30

Gln

<210> SEQ ID NO 16
<211> LENGTH: 27
<212> TYPE: PRT
<213> ORGANISM: Homo sapiens

<400> SEQUENCE: 16

Glu Pro Gly Gln Gly Leu Arg Gly Leu Gln Gly Pro Pro Gly Lys Leu
1               5                   10                  15

Gly Pro Pro Gly Asn Pro Gly Pro Ser Gly Ser
                20                  25

<210> SEQ ID NO 17
<211> LENGTH: 4
<212> TYPE: PRT
<213> ORGANISM: Homo sapiens

<400> SEQUENCE: 17

Gly Lys Leu Gly
1

<210> SEQ ID NO 18
<211> LENGTH: 11
<212> TYPE: PRT
<213> ORGANISM: Homo sapiens

<400> SEQUENCE: 18

Gly Pro Pro Gly Lys Leu Gly Pro Pro Gly Asn
1               5                   10

<210> SEQ ID NO 19
<211> LENGTH: 10
<212> TYPE: PRT
<213> ORGANISM: Homo sapiens

<400> SEQUENCE: 19

Arg Gly Leu Gln Gly Pro Pro Gly Lys Leu
1               5                   10

<210> SEQ ID NO 20
<211> LENGTH: 14
<212> TYPE: PRT
<213> ORGANISM: Homo sapiens

<400> SEQUENCE: 20
```

```
Gly Lys Leu Gly Pro Pro Gly Asn Pro Gly Pro Ser Gly Ser
1               5                   10

<210> SEQ ID NO 21
<211> LENGTH: 20
<212> TYPE: PRT
<213> ORGANISM: Homo sapiens

<400> SEQUENCE: 21

Gly Leu Arg Gly Leu Gln Gly Pro Pro Gly Lys Leu Gly Pro Pro Gly
1               5                   10                  15

Asn Pro Gly Pro
            20
```